US012258381B2

United States Patent
Seow et al.

(10) Patent No.: US 12,258,381 B2
(45) Date of Patent: Mar. 25, 2025

(54) ACTIVATING CHIMERIC RECEPTORS AND USES THEREOF IN NATURAL KILLER CELL IMMUNOTHERAPY

(71) Applicant: National University of Singapore, Singapore (SG)

(72) Inventors: See Voon Seow, Singapore (SG); Dario Campana, Singapore (SG)

(73) Assignee: National University of Singapore, Singapore (SG)

( * ) Notice: Subject to any disclaimer, the term of this patent is extended or adjusted under 35 U.S.C. 154(b) by 1267 days.

(21) Appl. No.: 16/967,881

(22) PCT Filed: Feb. 7, 2019

(86) PCT No.: PCT/IB2019/000181
§ 371 (c)(1),
(2) Date: Aug. 6, 2020

(87) PCT Pub. No.: WO2019/155288
PCT Pub. Date: Aug. 15, 2019

(65) Prior Publication Data
US 2021/0046115 A1   Feb. 18, 2021

Related U.S. Application Data

(60) Provisional application No. 62/736,879, filed on Sep. 26, 2018, provisional application No. 62/628,788, filed on Feb. 9, 2018.

(51) Int. Cl.
| C07K 14/705 | (2006.01) |
| A61K 39/00 | (2006.01) |
| A61P 35/00 | (2006.01) |
| C07K 14/725 | (2006.01) |
| C12N 5/0783 | (2010.01) |
| C12N 15/113 | (2010.01) |
| C12N 15/62 | (2006.01) |

(52) U.S. Cl.
CPC .... *C07K 14/70517* (2013.01); *A61K 39/4613* (2023.05); *A61K 39/4631* (2023.05); *A61K 39/464402* (2023.05); *A61P 35/00* (2018.01); *C07K 14/7051* (2013.01); *C07K 14/7056* (2013.01); *C07K 14/70578* (2013.01); *C12N 5/0646* (2013.01); *C12N 15/113* (2013.01); *C12N 15/62* (2013.01); *A61K 2239/38* (2023.05); *A61K 2239/50* (2023.05); *C07K 2319/03* (2013.01); *C07K 2319/33* (2013.01); *C12N 2310/14* (2013.01); *C12N 2310/531* (2013.01)

(58) Field of Classification Search
CPC ..... A61K 35/17; A61P 35/00; C07K 14/7051; C07K 14/70517; C07K 14/7056; C07K 14/70578; C07K 2319/03; C07K 2319/33; C07K 2319/00; C12N 5/0646; C12N 15/113; C12N 15/62; C12N 2310/14; C12N 2310/531
See application file for complete search history.

(56) References Cited

U.S. PATENT DOCUMENTS

| 4,650,764 A | 3/1987 | Temin et al. |
| 4,690,915 A | 9/1987 | Rosenberg |
| 4,844,893 A | 7/1989 | Honsik et al. |
| 4,980,289 A | 12/1990 | Temin et al. |
| 5,124,263 A | 6/1992 | Temin et al. |
| 5,359,046 A | 10/1994 | Capon |
| 5,399,346 A | 3/1995 | Anderson et al. |
| 5,653,977 A | 8/1997 | Saleh |
| 5,674,704 A | 10/1997 | Goodwin et al. |
| 5,686,281 A | 11/1997 | Roberts |
| 5,712,149 A | 1/1998 | Roberts |
| 6,103,521 A | 8/2000 | Capon et al. |
| 6,303,121 B1 | 10/2001 | Kwon |
| 6,319,494 B1 | 11/2001 | Capon et al. |
| 6,355,476 B1 | 3/2002 | Kwon et al. |

(Continued)

FOREIGN PATENT DOCUMENTS

| CN | 101684456 A | 3/2010 |
| CN | 103113470 A | 5/2013 |

(Continued)

OTHER PUBLICATIONS

Kaiser BK, Pizarro JC, Kerns J, Strong RK. Structural basis for NKG2A/CD94 recognition of HLA-E. Proc Natl Acad Sci U S A. May 6, 2008; 105(18):6696-701. doi: 10.1073/pnas.0802736105. (Year: 2008).*
Qin L, Lai Y, Zhao R, Wei X, Weng J, Lai P, Li B, Lin S, Wang S, Wu Q, Liang Q, Li Y, Zhang X, Wu Y, Liu P, Yao Y, Pei D, Du X, Li P. Incorporation of a hinge domain improves the expansion of chimeric antigen receptor T cells. J Hematol Oncol. Mar. 13, 2017; 10(1):68. (Year: 2017).*
Figueiredo C, Seltsam A, Blasczyk R. Permanent silencing of NKG2A expression for cell-based therapeutics. J Mol Med (Berl). Feb. 2009;87(2):199-210. (Year: 2009).*

(Continued)

*Primary Examiner* — Hong Sang
*Assistant Examiner* — Carol Ann Chase
(74) *Attorney, Agent, or Firm* — Hamilton, Brook, Smith & Reynolds, P.C.

(57) ABSTRACT

Current invention relates to a polynucleotide encoding activating chimeric receptors comprising engineered Natural Killer Group 2 member C (NKG2C) having enhanced affinity for HLA class I histocompatibility antigen alpha chain E (HLA-E)/peptide complex or an extracellular receptor domain of NKG2A coupled to an effector domain. It also relates to NK cells expressing such constructs and the use of these NK cells to induce cytotoxicity. It further exemplifies that the NK cells expressing polynucleotide encoding NKG2C (SIIS)/CD94/DAP12 or NKG2C/CD94/4-1 BB/CD3z showed enhanced NK cytotoxicity against cancer cells.

17 Claims, 42 Drawing Sheets

Specification includes a Sequence Listing.

(56) References Cited

U.S. PATENT DOCUMENTS

| | | | |
|---|---|---|---|
| 6,361,998 B1 | 3/2002 | Bell et al. | |
| 6,410,319 B1 | 6/2002 | Raubitschek et al. | |
| 6,797,514 B2 | 9/2004 | Berenson et al. | |
| 7,052,906 B1 | 5/2006 | Lawson et al. | |
| 7,070,995 B2 | 7/2006 | Jensen | |
| 7,435,596 B2 | 10/2008 | Campana et al. | |
| 7,446,179 B2 | 11/2008 | Jensen et al. | |
| 7,446,190 B2 | 11/2008 | Sadelain et al. | |
| 7,763,243 B2 | 7/2010 | Lum et al. | |
| 7,932,055 B2 | 4/2011 | Spee et al. | |
| 7,994,298 B2 | 8/2011 | Zhang et al. | |
| 8,026,097 B2 | 9/2011 | Campana et al. | |
| 8,399,645 B2 | 3/2013 | Campana et al. | |
| 9,487,800 B2 | 11/2016 | Schonfeld et al. | |
| 9,511,092 B2 | 12/2016 | Campana et al. | |
| 9,605,049 B2 | 3/2017 | Campana et al. | |
| 9,834,590 B2 | 12/2017 | Campana et al. | |
| 9,856,322 B2 | 1/2018 | Campana et al. | |
| 10,428,305 B2 | 10/2019 | Campana et al. | |
| 10,538,739 B2 | 1/2020 | Campana et al. | |
| 10,736,920 B2 | 8/2020 | Yu et al. | |
| 10,774,309 B2 | 9/2020 | Campana et al. | |
| 10,774,311 B2 | 9/2020 | Campana et al. | |
| 10,801,012 B2 | 10/2020 | Campana et al. | |
| 10,829,737 B2 | 11/2020 | Campana et al. | |
| 10,836,999 B2 | 11/2020 | Campana et al. | |
| 11,141,436 B2 | 10/2021 | Trager et al. | |
| 11,154,575 B2 | 10/2021 | Trager et al. | |
| 11,253,547 B2 | 2/2022 | Trager et al. | |
| 11,365,236 B2 | 6/2022 | Leong et al. | |
| 11,560,548 B2 | 1/2023 | Campana et al. | |
| 11,673,937 B2 | 6/2023 | Campana et al. | |
| 11,873,512 B2 | 1/2024 | Campana et al. | |
| 11,896,616 B2 | 2/2024 | Kamiya et al. | |
| 2002/0018783 A1 | 2/2002 | Sadelain et al. | |
| 2003/0129649 A1* | 7/2003 | Kobilka | C07K 14/70571 435/7.1 |
| 2003/0147869 A1 | 8/2003 | Riley | |
| 2003/0215427 A1 | 11/2003 | Jensen | |
| 2004/0038886 A1 | 2/2004 | Finney et al. | |
| 2004/0043401 A1 | 3/2004 | Sadelain et al. | |
| 2004/0126363 A1 | 7/2004 | Jensen et al. | |
| 2005/0042208 A1 | 2/2005 | Sagawa et al. | |
| 2005/0048549 A1 | 3/2005 | Cao et al. | |
| 2005/0113564 A1 | 5/2005 | Campana et al. | |
| 2006/0093605 A1 | 5/2006 | Campana et al. | |
| 2006/0247191 A1 | 11/2006 | Finney et al. | |
| 2007/0160578 A1 | 7/2007 | Waldmann et al. | |
| 2007/0166327 A1 | 7/2007 | Cooper et al. | |
| 2008/0177047 A1 | 7/2008 | Fujita-Yamaguchi | |
| 2008/0247990 A1 | 10/2008 | Campbell | |
| 2008/0299137 A1* | 12/2008 | Svendsen | A61P 37/04 435/69.7 |
| 2009/0281035 A1* | 11/2009 | Spee | A61P 37/04 530/391.7 |
| 2010/0029749 A1* | 2/2010 | Zhang | A61K 38/10 536/23.4 |
| 2012/0015434 A1 | 1/2012 | Campana et al. | |
| 2012/0148552 A1 | 6/2012 | Jensen | |
| 2012/0282256 A1 | 11/2012 | Campana et al. | |
| 2012/0321666 A1 | 12/2012 | Copper et al. | |
| 2013/0072401 A1* | 3/2013 | Ye | C12Q 1/6886 506/9 |
| 2013/0266551 A1 | 10/2013 | Campana et al. | |
| 2013/0280221 A1 | 10/2013 | Schonfeld et al. | |
| 2013/0288368 A1 | 10/2013 | June et al. | |
| 2014/0023626 A1 | 1/2014 | Peled et al. | |
| 2014/0271635 A1 | 9/2014 | Brogdon et al. | |
| 2014/0286973 A1 | 9/2014 | Powell, Jr. | |
| 2014/0302608 A1 | 10/2014 | Dominici et al. | |
| 2015/0139943 A1 | 5/2015 | Campana et al. | |
| 2015/0190471 A1 | 7/2015 | Copik et al. | |
| 2015/0218649 A1 | 8/2015 | Saenger et al. | |
| 2016/0000828 A1 | 1/2016 | Campana et al. | |
| 2016/0362472 A1 | 1/2016 | Bitter et al. | |
| 2016/0152723 A1 | 6/2016 | Chen et al. | |
| 2016/0158285 A1 | 6/2016 | Cooper et al. | |
| 2017/0044227 A1 | 2/2017 | Schonfeld | |
| 2017/0073423 A1 | 3/2017 | Juillerat et al. | |
| 2017/0073638 A1* | 3/2017 | Campana | C07K 14/5443 |
| 2017/0129967 A1 | 5/2017 | Wels et al. | |
| 2017/0283482 A1 | 10/2017 | Campana et al. | |
| 2017/0355957 A1 | 12/2017 | Biondi et al. | |
| 2017/0368098 A1 | 12/2017 | Chen et al. | |
| 2018/0002397 A1 | 1/2018 | Shah et al. | |
| 2018/0044391 A1 | 2/2018 | Gundram et al. | |
| 2018/0044417 A1 | 2/2018 | Pule et al. | |
| 2018/0046571 A1 | 2/2018 | Magill et al. | |
| 2018/0086831 A1 | 3/2018 | Pule et al. | |
| 2018/0104278 A1 | 4/2018 | Zhang et al. | |
| 2018/0117146 A1 | 5/2018 | Yu et al. | |
| 2018/0134765 A1 | 5/2018 | Landgraf et al. | |
| 2018/0371052 A1 | 12/2018 | Ma et al. | |
| 2019/0038733 A1 | 2/2019 | Campana et al. | |
| 2019/0046571 A1 | 2/2019 | Campana et al. | |
| 2019/0062430 A1 | 2/2019 | Wu et al. | |
| 2019/0290693 A1 | 9/2019 | Qi et al. | |
| 2019/0336533 A1 | 11/2019 | Hwang et al. | |
| 2019/0376037 A1 | 12/2019 | Campana et al. | |
| 2020/0016208 A1 | 1/2020 | Kamiya et al. | |
| 2020/0116208 A1 | 1/2020 | Kamiya et al. | |
| 2020/0131244 A1 | 4/2020 | Leong et al. | |
| 2020/0255803 A1 | 8/2020 | Zhang et al. | |
| 2020/0340995 A1 | 10/2020 | Campana et al. | |
| 2020/0407686 A1 | 12/2020 | Campana et al. | |
| 2021/0009951 A1 | 1/2021 | Hu et al. | |
| 2021/0017271 A1 | 1/2021 | Tan et al. | |
| 2021/0054409 A1 | 2/2021 | Zhu et al. | |
| 2021/0324388 A1 | 10/2021 | Vinanica et al. | |
| 2021/0338727 A1 | 11/2021 | Trager et al. | |
| 2021/0363218 A1* | 11/2021 | Fan | C07K 14/7056 |
| 2022/0002424 A1 | 1/2022 | Trager et al. | |
| 2022/0047635 A1 | 2/2022 | Liu et al. | |
| 2022/0233590 A1 | 7/2022 | Trager et al. | |
| 2022/0233593 A1 | 7/2022 | Trager et al. | |
| 2022/0281971 A1 | 9/2022 | Shimasaki et al. | |
| 2022/0411754 A1 | 12/2022 | Trager et al. | |
| 2023/0002471 A1 | 1/2023 | Leong et al. | |
| 2023/0028399 A1 | 1/2023 | Rajangam et al. | |
| 2023/0220343 A1 | 7/2023 | Campana et al. | |
| 2023/0265390 A1 | 8/2023 | Trager et al. | |
| 2023/0390392 A1 | 12/2023 | Trager et al. | |

FOREIGN PATENT DOCUMENTS

| | | |
|---|---|---|
| CN | 105838677 A | 8/2016 |
| CN | 105985931 A | 10/2016 |
| CN | 107109363 A | 8/2017 |
| CN | 107636015 A | 1/2018 |
| CN | 107827990 A | 3/2018 |
| CN | 108840930 A | 11/2018 |
| EP | 0 952 213 A2 | 3/1999 |
| EP | 0 830 599 B1 | 4/2000 |
| EP | 1 231 262 A1 | 8/2002 |
| EP | 1 306 427 A1 | 5/2003 |
| EP | 1 053 301 B1 | 4/2004 |
| EP | 1 820 017 | 6/2006 |
| EP | 1 233 058 B1 | 12/2006 |
| EP | 1 036 327 B1 | 7/2009 |
| EP | 2 411 507 | 9/2010 |
| EP | 2 493 485 | 5/2011 |
| EP | 2 493 486 | 5/2011 |
| EP | 2 593 542 | 1/2012 |
| EP | 2 141 997 B1 | 10/2012 |
| EP | 2 614 151 | 10/2012 |
| EP | 2 756 521 | 3/2013 |
| EP | 2 866 834 | 1/2014 |
| EP | 2 903 637 | 4/2014 |
| EP | 2 904 106 | 4/2014 |
| EP | 2 948 544 | 7/2014 |
| EP | 2 956 175 | 8/2014 |
| EP | 2 961 831 | 9/2014 |
| EP | 2 964 753 | 9/2014 |

(56) References Cited

FOREIGN PATENT DOCUMENTS

| | | |
|---|---|---|
| EP | 2 970 426 | 9/2014 |
| EP | 2 968 601 | 10/2014 |
| EP | 2 986 636 | 10/2014 |
| EP | 2 537 416 B1 | 11/2014 |
| EP | 3 008 173 | 12/2014 |
| EP | 2 856 876 A1 | 4/2015 |
| EP | 3 057 986 | 4/2015 |
| EP | 3 063 175 | 5/2015 |
| EP | 3 071 221 | 5/2015 |
| EP | 3 071 222 | 5/2015 |
| EP | 3 071 223 | 5/2015 |
| EP | 3 083 671 | 6/2015 |
| EP | 3 083 691 | 6/2015 |
| EP | 3 094 653 | 7/2015 |
| EP | 3 105 318 | 8/2015 |
| EP | 3 105 335 | 8/2015 |
| EP | 2 968 492 | 9/2015 |
| EP | 3 119 425 | 9/2015 |
| EP | 3 126 380 | 10/2015 |
| EP | 3 134 432 | 10/2015 |
| EP | 3 180 359 | 2/2016 |
| EP | 3 189 132 | 3/2016 |
| EP | 3 012 268 A1 | 4/2016 |
| EP | 2 614 077 B1 | 8/2016 |
| EP | 3 115 373 A1 | 1/2017 |
| EP | 3 567 049 A2 | 11/2019 |
| EP | 3690033 A1 | 8/2020 |
| JP | 2017-112982 A | 6/2017 |
| WO | WO 92/17198 A1 | 10/1992 |
| WO | WO 95/007358 A1 | 3/1995 |
| WO | WO 96/023814 A1 | 8/1996 |
| WO | WO 96/024671 A1 | 8/1996 |
| WO | WO 96/41163 A1 | 12/1996 |
| WO | WO 97/023613 A2 | 7/1997 |
| WO | WO 98/026061 A2 | 6/1998 |
| WO | WO 99/000494 A2 | 1/1999 |
| WO | WO 99/06557 A2 | 2/1999 |
| WO | WO 99/38954 A1 | 8/1999 |
| WO | WO 99/057268 A1 | 11/1999 |
| WO | WO 2000/014257 A1 | 3/2000 |
| WO | WO 00/23573 A2 | 4/2000 |
| WO | WO 2001/29191 A1 | 4/2001 |
| WO | WO 2001/38494 A1 | 5/2001 |
| WO | WO 2002/10350 A1 | 2/2002 |
| WO | WO 2002/033101 A1 | 4/2002 |
| WO | WO 02/077029 A2 | 10/2002 |
| WO | WO 2003/089616 A2 | 10/2003 |
| WO | WO 2004/027036 A2 | 4/2004 |
| WO | WO 2004/039840 A1 | 5/2004 |
| WO | 2005/000890 A1 | 1/2005 |
| WO | WO 2005/044996 A2 | 5/2005 |
| WO | WO 2005/118788 A2 | 12/2005 |
| WO | WO 2006/036445 A2 | 4/2006 |
| WO | WO 2006/052534 A2 | 5/2006 |
| WO | WO 2006/061626 A2 | 6/2006 |
| WO | 2006/119115 A2 | 11/2006 |
| WO | WO 2007/046006 A2 | 4/2007 |
| WO | WO 2008/121420 A1 | 10/2008 |
| WO | WO 2009/117566 A1 | 9/2009 |
| WO | WO 2010/071836 A1 | 6/2010 |
| WO | WO 2010/110734 A1 | 9/2010 |
| WO | WO 2011/020047 A1 | 2/2011 |
| WO | WO 2011/053321 A1 | 5/2011 |
| WO | WO 2011/053322 A1 | 5/2011 |
| WO | WO 2011/069019 A2 | 6/2011 |
| WO | WO 2011/080740 A1 | 7/2011 |
| WO | WO 2011/150976 A1 | 12/2011 |
| WO | WO 2012/009422 A1 | 1/2012 |
| WO | WO 2012/031744 A1 | 3/2012 |
| WO | WO 2012/040323 A2 | 3/2012 |
| WO | WO 2012/071411 A2 | 5/2012 |
| WO | WO 2012/079000 A1 | 6/2012 |
| WO | WO 2012/136231 A1 | 10/2012 |
| WO | 2013/043196 A1 | 3/2013 |
| WO | WO 2013/040371 A2 | 3/2013 |
| WO | WO 2013/040557 A2 | 3/2013 |
| WO | WO 2013/123720 A2 | 8/2013 |
| WO | WO 2013/123726 A1 | 8/2013 |
| WO | WO 2014/005072 A1 | 1/2014 |
| WO | WO 2014/011993 A2 | 1/2014 |
| WO | WO 2014/055413 A2 | 4/2014 |
| WO | WO 2014/055442 A1 | 4/2014 |
| WO | WO 2014/055657 A1 | 4/2014 |
| WO | WO 2014/055668 A1 | 4/2014 |
| WO | WO 2014/099671 A1 | 6/2014 |
| WO | WO 2014/117121 A1 | 7/2014 |
| WO | WO 2014/127261 A1 | 8/2014 |
| WO | WO 2014/134165 A1 | 9/2014 |
| WO | WO 2014/138704 A1 | 9/2014 |
| WO | WO 2014/145252 A2 | 9/2014 |
| WO | WO 2014/164554 A1 | 10/2014 |
| WO | WO 2014/172584 A1 | 10/2014 |
| WO | WO 2014/186469 A2 | 11/2014 |
| WO | WO 2014/201021 A2 | 12/2014 |
| WO | WO 2015/058018 A1 | 4/2015 |
| WO | WO 2015/066551 A2 | 5/2015 |
| WO | WO 2015/075468 A1 | 5/2015 |
| WO | WO 2015/075469 A1 | 5/2015 |
| WO | WO 2015/075470 A1 | 5/2015 |
| WO | WO 2015/092024 A2 | 6/2015 |
| WO | WO 2015/095895 A1 | 6/2015 |
| WO | WO 2015/105522 A1 | 7/2015 |
| WO | WO 2015/120421 A1 | 8/2015 |
| WO | WO 2015/123642 A1 | 8/2015 |
| WO | WO 2015/142314 A1 | 9/2015 |
| WO | WO 2015/142661 A1 | 9/2015 |
| WO | WO 2015/150771 A1 | 10/2015 |
| WO | WO 2015/154012 A1 | 10/2015 |
| WO | WO 2015/154012 A8 | 10/2015 |
| WO | WO 2015/164759 A2 | 10/2015 |
| WO | WO 2015/174928 A1 | 11/2015 |
| WO | 2015/188119 A1 | 12/2015 |
| WO | WO 2015/193411 A1 | 12/2015 |
| WO | 2016/014576 A1 | 1/2016 |
| WO | WO 2016/011210 A2 | 1/2016 |
| WO | WO 2016/030691 A1 | 3/2016 |
| WO | WO 2016/033331 A1 | 3/2016 |
| WO | WO 2016/040441 A1 | 3/2016 |
| WO | WO 2016/042041 A1 | 3/2016 |
| WO | WO 2016/042461 A1 | 3/2016 |
| WO | WO 2016/061574 A1 | 4/2016 |
| WO | 2016/073755 A9 | 5/2016 |
| WO | WO 2016/069607 A1 | 5/2016 |
| WO | WO 2016/073602 A2 | 5/2016 |
| WO | WO 2016/073629 A1 | 5/2016 |
| WO | WO 2016/073755 A2 | 5/2016 |
| WO | WO 2016/075612 A1 | 5/2016 |
| WO | WO 2016/100985 A2 | 6/2016 |
| WO | 2016/118857 A1 | 7/2016 |
| WO | WO 2016/109661 A1 | 7/2016 |
| WO | WO 2016/109668 A1 | 7/2016 |
| WO | WO 2016/115482 A1 | 7/2016 |
| WO | 2016/126213 A1 | 8/2016 |
| WO | 2017/040324 A1 | 8/2016 |
| WO | WO 2016/123122 A1 | 8/2016 |
| WO | WO 2016/123333 A1 | 8/2016 |
| WO | WO 2016/124765 A1 | 8/2016 |
| WO | WO 2016/124930 A1 | 8/2016 |
| WO | WO 2016/126608 A1 | 8/2016 |
| WO | 2016/139487 A1 | 9/2016 |
| WO | WO 2016/141357 A1 | 9/2016 |
| WO | WO 2016/142314 A1 | 9/2016 |
| WO | WO 2016/149254 A1 | 9/2016 |
| WO | WO 2016/151315 A1 | 9/2016 |
| WO | WO 2016/154055 A1 | 9/2016 |
| WO | WO 2016/154585 A1 | 9/2016 |
| WO | WO 2016/172537 A1 | 10/2016 |
| WO | WO 2016/172583 A1 | 10/2016 |
| WO | WO 2016/174405 A1 | 11/2016 |
| WO | WO 2016/174406 A1 | 11/2016 |
| WO | WO 2016/174407 A1 | 11/2016 |
| WO | WO 2016/174408 A1 | 11/2016 |
| WO | WO 2016/174409 A1 | 11/2016 |
| WO | WO 2016/174461 A1 | 11/2016 |

(56) References Cited

FOREIGN PATENT DOCUMENTS

| | | |
|---|---|---|
| WO | WO 2016/174652 A1 | 11/2016 |
| WO | WO 2016/179684 A1 | 11/2016 |
| WO | WO 2016/191587 A1 | 12/2016 |
| WO | WO 2016/191755 A1 | 12/2016 |
| WO | WO 2016/196388 A1 | 12/2016 |
| WO | WO 2016/197108 A1 | 12/2016 |
| WO | WO 2016/201304 A1 | 12/2016 |
| WO | WO 2016/210293 A1 | 12/2016 |
| WO | WO 2017/004150 A1 | 1/2017 |
| WO | WO 2017/011804 A1 | 1/2017 |
| WO | WO 2017/021701 A1 | 2/2017 |
| WO | WO 2017/023859 A1 | 2/2017 |
| WO | WO 2017/024131 A1 | 2/2017 |
| WO | WO 2017/027325 A1 | 2/2017 |
| WO | WO 2017/029511 A1 | 2/2017 |
| WO | WO 2017/032777 A1 | 3/2017 |
| WO | WO 2017/034615 A1 | 3/2017 |
| WO | WO 2017/037083 A1 | 3/2017 |
| WO | WO 2017/058752 A1 | 4/2017 |
| WO | WO 2017/058753 A1 | 4/2017 |
| WO | WO 2017/079694 A2 | 5/2017 |
| WO | WO 2017/079705 A1 | 5/2017 |
| WO | WO 2017/079881 A1 | 5/2017 |
| WO | WO 2017/096329 A1 | 6/2017 |
| WO | WO 2017/127729 A1 | 7/2017 |
| WO | 2017/172981 A2 | 10/2017 |
| WO | 2017/186928 A1 | 11/2017 |
| WO | 2017/222593 A1 | 12/2017 |
| WO | WO 2018/022646 A1 | 2/2018 |
| WO | 2018/057915 A1 | 3/2018 |
| WO | 2018106732 A1 | 6/2018 |
| WO | WO 2018/103503 A1 | 6/2018 |
| WO | 2018/124766 A2 | 7/2018 |
| WO | WO 2018/182511 A1 | 10/2018 |
| WO | WO 2018/183385 A1 | 10/2018 |
| WO | 2019/028051 A1 | 2/2019 |
| WO | WO 2019/062817 A1 | 4/2019 |
| WO | WO 2019/077037 A1 | 4/2019 |
| WO | 2019/091478 A1 | 5/2019 |
| WO | 2019/112899 A2 | 6/2019 |
| WO | 2019/129220 A1 | 7/2019 |
| WO | WO 2019/129002 A1 | 7/2019 |
| WO | WO 2019/155286 A2 | 8/2019 |
| WO | WO 2019/155288 A1 | 8/2019 |
| WO | 2019/169290 A1 | 9/2019 |
| WO | 2019/199689 A1 | 10/2019 |
| WO | WO 2019/193476 A1 | 10/2019 |
| WO | WO 2020/044239 A1 | 3/2020 |
| WO | WO 2020/083282 A1 | 4/2020 |
| WO | WO 2021/009694 A1 | 1/2021 |

OTHER PUBLICATIONS

Call ME, Wucherpfennig KW, Chou JJ. The structural basis for intramembrane assembly of an activating immunoreceptor complex. Nat Immunol. Nov. 2010;11(11):1023-9. (Year: 2010).*

Lanier LL. DAP10- and DAP12-associated receptors in innate immunity. Immunol Rev. Jan. 2009;227(1):150-60. doi: 10.1111/j.1600-065X.2008.00720.x. PMID: 19120482; PMCID: PMC2794881. (Year: 2009).*

UniProt P26717 NKG2C_HUMAN. Integrated into UniProtKB/Swiss-Prot Aug. 1, 1992. https://www.uniprot.org/uniprotkb/P26717/entry. Accessed Jul. 17, 2024 (Year: 1992).*

Caratelli et al., "FCγ Chimeric Receptor-Engineered T Cells: Methodology, Advantages, Limitations, and Clinical Relevance," Front Immunol., vol. 8, Article 457, 8 pages (Apr. 27, 2017).

Hombach, A.A., et al., "Costimulation by chimeric antigen receptors revisited: the T cell antitumor response benefits from combined CD28-OX40 signalling", Int. J. Cancer, 129, 2935-2944 (2011).

Hurton, L.V. et al., "Tethered IL-15 augments antitumor activity and promotes a stem-cell memory subset in tumor-specific T cells," PCNAS, USA, 113(48): E7788-E7797 (Nov. 2016).

Kober, J., et al. "The capacity of the TNF family members 4-1BBL, OX40L, CD70, GITRL, CD30L and Light to costimulate human T cells," Eur J Immuno, vol. 38, No. 10, pp. 2678-2688 (Oct. 28, 2008).

NCIthesaurus, Bicistronic chimeric antigen reeptor vector, retrieved online from: https://ncit.nci.nih.gov/ncitbrowser/pages/home.jsf.jsessionid=12B0F7AF71E9A4035C38B5E4F6C055B0, retrieved on: Jan. 21, 2021.

Abakushina, E.V., "Immunotherapy With Natural Killer Cells In The Treatment Of Cancer," Russian Journal of Immunology, vol. 10, No. 2, pp. 131-142 (2016) (Abstract only).

Pakula, A.A. et al., "Genetic analysis of protein stability and function," Annual Review of Genetics, V. 23, N. 1, p. 289-310, c. 305-306 (1989).

Ye et al. "Effects of target cell overexpression of IL-15, 4-1 BBL and IL-18 1-102 combine with IL-2 on NK cell activation and cytotoxicity during ex vivo expansion" Chin J Cancer Biother, Oct. 31, 2014, vol. 21, No. 5, pp. 537-542 (Non-English, Search Report for PCT/SG2018/050138 attached).

Gacerez, A, et al., "How Chimeric Antigen Receptor Design Affects Adoptive T Cell Therapy," Journal of Cellular Physiology, vol. 231, No. 12, pp. 2590-2598; Jun. 2, 2016.

Sadelain, M. et al., "The Basic Principles of Chimeric Antigen Receptor Design," Cancer Discovery, vol. 3, No. 4, pp. 388-398 (Apr. 1, 2013).

Wang, W., "NK cell-mediated antibody-dependent cellular cytotoxicity in cancer immunotherapy," Frontiers in Immunology, 2015, 6, 368.

Ren, P.-P. et al., Anti-EGFRvIII Chimeric Antigen Receptor-Modified T Cells for Adoptive Cell Therapy of Glioblastoma, Current Pharmaceutical Design, 23(14), 2113-2116 (2017).

Morgan, R.A. et. al., Recognition of Glioma Stem Cells by Genetically Modified T Cells Targeting EGFRvIII and Development of Adoptive Cell Therapy for Glioma, Human Gene Therapy, 23(10), 1043-1053 (2012).

Dalal, A.-R. et al., Third-Generation Human Epidermal Growth Factor Receptor 2 Chimeric Antigen Receptor Expression on Human T Cells Improves with Two-Signal Activation, Human Gene Therapy, 845-852 (2018) (Abstract).

Choi, B. D. et al., Chimeric antigen receptor T-cell immunotherapy for glioblastoma: practical insights for neurosurgeons, Neurosurg Focus, 44(6):E13, 1-6 (2018).

Mirzaei, H.R., et al., "Construction and functional characterization of a fully human anti-CD19 chimeric antigen receptor (huCAR)-expressing primary human T cells," J Cell Physiol. Jun. 2019; 234(6):9207-9215. doi: 10.1002/jcp.27599. Epub Oct. 26, 2018. PMID: 30362586 (Abstract).

Chen, F., "Construction of Anti-CD20 Single-Chain Antibody-CD28-CD137-TCR Recombinant Genetic Modified T Cells and its Treatment Effect on B Cell Lymphoma," Med Sci Monit 2015; 21:2110-2115 (Jul. 21, 2015).

Kohrt, H.E., "Immunomodulation of NK Cells through 4-1BB (CD137) to Improve the Anti-Lymphoma Activity of Rituximab: Antibody-Based Anti-Lymphoma Snergy," Blood, 2010, 116(21), 422 (Abstract).

Robak, T., New Anti-CD20 Monoclonal Antibodies for the Treatment of B-Cell Lymphoid Malignancies, BioDrugs 25, 13-25 (2011) (Abstract).

Kochenderfer, J.N., "Eradication of B-lineage and regression of lymphoma in a patient treated with autologous T cells genetically engineered to recognize CD19," Blood, 2010, 116(20), 4099-4102.

Schmohl J.U., et al., Tetraspecific scFv construct provides NK cell mediated ADCC and self-sustaining stimuli via Insertion of IL-15 as a cross-linker. Oncotarget. 2016; 7: 73830-73844.

Vinanica, N., et al., "Specific stimulation of T lymphocytes with erythropoietin for adoptive immunotherapy", Blood, 135(9): 668-679 (Feb. 27, 2020).

Zuther, "Generation of the Plasmid pMT/BiP SCA431scFv-Fc-IL 15 (#1118)," Chapter 4.1.8 of An Anti-CD30 Immunocytokine with Combined IL-2 and IL-12 Domains Enhances Anti-Tumor Immunity, p. 70 (Oct. 1, 2009).

(56) References Cited

OTHER PUBLICATIONS

Imamura, M. et al., "Autonomous growth and increased cytotoxicity of natural killer cells expressing membrane-bound Interleukin-15," Blood, 124(7): 1081-1088 (2014).
Suarez, et al., "Chimeric Antigen Receptor T Cells Secreting Anti-PD-L1 Antibodies More Effectively Regress Renal Cell Carcinoma in a Humanized Mouse Model," Oncotarget, vol. 7, No. 23, Apr. 29, 2016.
Li, et al., "Therapeutically Targeting Glypican-2 via Single-Domain Antibody-Based Chimeric Antigen Receptors and Immunotoxins in Neuroblasoma," PNAS, pp. E6623-E6631 (Jul. 24, 2017).
Abken et al., "Chimeric T-cell receptors: highly specific tools to target cytotoxic T-lymphocytes to tumour cells," Cancer Treat Rev., 23(2): 97-112, Mar. 1997.
Abken, H., et al., "Tuning tumor-specific T-cell activation: a matter of costimulation?" Trends in Immunol. 23: 240-245 (2002).
Aguera-Gonzalez et al., "Palmitoylation of MICA, a ligand for NKG2D, mediates its recruitment to membrane microdomains and promotes its shedding," Eur. J. Immunol. vol. 41, pp. 3667-3676 (2011).
Alderson et al., "Molecular and Biological Characterization of Human 4-1BB and its Ligand," Eur. J. Immunol., 1994, 24: 2219-2227.
Allison et al., "Structure, function, and serology of the T-cell antigen receptor complex," Ann. Rev. Immunol., 1987, 5:503-540.
Alvarez-Vallina, L. and Hawkins, R.E., "Antigen-specific targeting of CD28-mediated T cell co-stimulation using chimeric single-chain antibody variable fragment-CD28 receptors," Eur. J. Immunol., 26: 2304-2309 (1996).
Ang, S.O. et al, "Avoiding the need for clinical-grade OKT3: ex vivo expansion of T cells using artificial antigen presenting cells genetically modified to crosslink CD3" Biology of Blood and Marrow Transplantation, Jan. 9, 2012, vol. 8, No. 2, pp. S258.
Annenkov, A., et al., "Engineering mouse T lymphocytes specific to type II collagen by transduction with a chimeric receptor consisting of a single chain Fv and TCR zeta," Gene Therapy, 7: 714-722 (2000).
Antony, G.K., et al., "Interleukin 2 in cancer therapy," Current Medicinal Chemistry,17(29): 3297-3302 (2010).
Aoudjit and Vuori, "Integrin Signaling in Cancer Cell Survival and Chemoresistance," Chemotherapy Research and Practice, 2012(Article ID 283181), 1-16, 2012.
Appelbaum, "Haematopoietic cell transplantation as immunotherapy," Nature, 2001, 411(6835): 385-389.
Aruffo, A., et al., "Molecular cloning of a CD28 cDNA by a high-efficiency COS cell expression system," Proc. Natl. Acad. Sci., 1987, 84:8573-8577.
ATCC No. CCL-243, 1975, 19 pages.
Azuma, M, et al., "Functional Expression of B7/BB1 on Activated T Lymphocytes," J. Exp. Med. 177: 845-850 (1993).
Baek, H.J. et al., "Ex vivo expansion of natural killer cells using cryopreserved irradiated feeder cells," *Anticancer Research*, 33: 2011-2020 (2013).
Barber et al., "Chimeric NKG2D Expressing T Cells Eliminate Immunosuppression and Activate Immunity within the Ovarian Tumor Microenvironment," J. Immunol, vol. 183, pp. 6939-6947 (2009).
Barber et al., "Chimeric NKG2D Receptor-Bearing T Cells as Immunotherapy for Ovarian Cancer," American Association for Cancer, vol. 67, No. 10, pp. 5003-5008, (May 15, 2007).
Barber et al., "Chimeric NKG2D receptor-expressing T cells as an immunotherapy for multiple myeloma," Experimental Hematology, vol. 36, pp. 1318-1328, (2008).
Barber et al., "Chimeric NKG2D T Cells Require Both T Cell- and Host-Derived Cytokine Secretion and Perforin Expression to Increase Tumor Antigen Presentation and Systemic Immunity," J. Immunol, vol. 183, pp. 2365-2372 (2009).

Barber et al., "Immunotherapy with Chimeric NKG2D Receptors Leads to Long-Term Tumor-Free Survival and Development of Host Antitumor Immunity in Murine Ovarian Cancer," J. Immunol., vol. 180, pp. 72-78, (2008).
Barber et al., "Treatment of multiple myeloma with adoptively transferred chimeric NKG2D receptor-expressing T cells," Gene Therapy, vol. 18, pp. 509-516, (2011).
Barrett, D.M., et al., "Chimeric Antigen Receptor Therapy for Cancer," Annu Rev. Med. 65: 333-347 (2014).
Bartholomew et al., "Mesenchymal stem cells suppress lymphocyte proliferation in vitro and prolong skin graft survival in vivo," Exp Hematol, Jan. 2002, 30(1): 42-48.
Batlevi, C.L., et al. "Novel immunotherapies in lymphoid malignancies," Nature Rev. Clin. Oncol.13:25-40 (2016).
Baum et al., "Side effects of retroviral gene transfer into hematopoietic stem cells," Blood, Mar. 2003, 101(6): 2099-2114.
Bejcek et al., "Development and Characterization of Three Recombinant Single Chain Antibody Fragments (scFvs) Directed against the CD19 Antigen," Cancer Res., 1995, 55:2346-2351.
Berger, C. et al., "Safety and immunologic effects of IL-15 administration in nonhuman primates," *Blood*, 114(12): 2417-2426 (2009).
Besser, M.J., et al., "Adoptive Transfer of Tumor-Infiltrating Lymphocytes in Patients with Metastatic Melanoma: Intent-to-Treat Analysis and Efficacy after Failure to Prior Immunotherapies," Clin. Cancer Res. 19: 4792-4800 (2013).
Better et al., "Manufacturing and Characterization of KTE-C19 in a Multicenter Trial of Subjects with Refractory Aggressive Non-Hodgkin Lymphoma (NHL) (ZUMA-1)," Poster session presented at the American Association for Cancer Research Annual Meeting, New Orleans, Louisiana (2016).
Billadeau et al., "NKG2D-DAP10 triggers human NK cell-mediated killing via a Syk-independent regulatory pathway," Nat Immunol, Jun. 2003, 4(6): 557-564.
Bischof et al., "Autonomous induction of proliferation, JNK and NF-xB activation in primary resting T cells by mobilized CD28," Eur J Immunol., 30(3):876-882, Mar. 2000.
Bork et al., "The immunoglobulin fold. Structural classification, sequence patterns and common core," J Mol Biol., 242(4):309-320, Sep. 30, 1994.
Boyman, O., et al., "The role of interleukin-2 during homeostasis and activation of the immune system," *Nat Rev Immunol.*, 12: 180-190 (2012).
Brand, L.J. et al., "Abstract LB-185: A PSMA-directed natural killer cell approach for prostate cancer immunotherapy," Cancer Research, 77(13 Supplement): Abstract No. LB-185, 1-4 (Jul. 2017).
Brentjens et al., "Eradication of Systemic B-Cell Tumors by Genetically Targeted Human T Lymphocytes Co-Stimulated By CD80 and Interleukin-15," Nature Medicine, 2003, 9: 279-286.
Brentjens, R.J., et al., "CD19-Targeted T Cells Rapidly Induce Molecular Remissions in Adults with Chemotherapy-Refractory Acute Lymphoblastic Leukemia," Sci. Trans. Med. 5: 1-9 (2013).
Brentjens, R.J., et al., "Safety and persistence of adoptively transferred autologous CD19-targeted T cells in patients with relapsed or chemotherapy refractory B-cell leukemias," Blood 119(18): 4817-4828 (2011).
Bridgeman, J.S., et al., "Building Better Chimeric Antigen Receptors for Adoptive T Cell Therapy," Current Gene Therapy 10: 77-90 (2010).
Bridgeman, J.S. et al., "The Optimal Antigen Response of Chimeric Antigen Receptors Harboring the CD3ζ Transmembrane Domain is Dependent upon Incorporation of the Receptor into the Endogenous TCR/CD3 Complex," *J Immunol*, 184(12): 6938-6949 (May 2010).
Brocker et al., "New simplified molecular design for functional T cell receptor," Eur J Immunol., 23(7):1435-1439, Jul. 1993.
Bromley et al., "The immunological synapse and CD28-CD80 interactions," Nat Immunol., 2(12):1159-1166, Dec. 2001.
Bronte, V., and Mocellin, S., "Suppressive Influences in the Immune Response to Cancer," J. Immunother . 32: 1-11 (2009).
Budagian, V. et al., "IL-15/IL-15 receptor biology: A guided tour through an expanding universe," *Cytokine & Growth Factor Reviews*, 17: 259-280 (2006).
Bukczynski et al., "Costimulation of Human CD28⁻ T Cells by 4-1BB Ligand," Eur. J. Immunol., 2003, 33: 446-454.

(56) References Cited

OTHER PUBLICATIONS

Burkett, P.R. et al., "Coordinate expression and trans presentation of interleukin (IL)-15Rα and IL-15 supports natural killer cell and memory CD8+ T cell homeostasis," *J Exp Med.*, 200(7): 825-834 (2004).

Caligiuri et al., "Immunotherapeutic approaches for hematologic malignancies," Hematology Am Soc Hematol Educ Program, 2004, 37-53.

Campana et al., "Immunophenotyping of Leukemia," Journal of Immunol Methods, 2000, 243: 59-75.

Cardoso AA, et al., "Pre-B acute lymphoblastic leukemia cells may induce T-cell anergy to alloantigen," Blood 88:41-48 (1996).

Carson, W.E. et al., "A potential role for interleukin-15 in the regulation of human natural killer cell survival," J Clin Invest., 99(5): 937-943 (1997).

Carter, P., et al., "Identification and validation of cell surface antigens for antibody targeting in oncology," Endocrine-Related Cancer 11: 659-687 (2004).

Cesano, A., et al. "Reversal of Acute Myelogenous Leukemia in Humanized SCID Mice Using a Novel Adoptive Transfer Approach," J. Clin. Invest. 94: 1076-1084 (1994).

Chambers, C.A., "The expanding world of co-stimulation: the two-signal model revisited," Trends in Immunol., 2001, 22(4):217-223.

Champlin R. "T-cell depletion to prevent graft-versus-host disease after bone marrow transplantation," Hematol Oncol Clin North Am. Jun. 1990;4(3):687-698.

Chang et al., "Five Different Anti-Prostate-specific Membrane Antigen (PSMA) Antibodies Confirm PSMA Expression in Tumor-associated Neovasculature," Cancer Res., 59: 3192-3198 (1999).

Chang, Y.H. et al., "A chimeric receptor with NKG2D specificity enhances natural killer cell activation and killing of tumor cells," Cancer Res., 73(6): 1777-1786 (2013).

Chao, D.T. et al., "BCL-2 family: regulators of cell death," Annu Rev Immunol., 16: 395-419 (1998).

Cheresh et al., "Disialogangliosides GD2 and GD3 Are Involved in the Attachment of Human Melanoma and Neuroblastoma Cells to Extracellular Matrix Proteins," J Cell Biol. 1986, 102(3):688-696.

Chertova, E. et al., "Characterization and favorable in vivo properties of heterodimeric soluble IL-15:IL-15Rα cytokine compared to IL-15 monomer," J Biol Chem., 288(25): 18093-18103 (2013).

Cheung et al., "Anti-Idiotypic Antibody Facilitates scFv Chimeric Immune Receptor-Gene Transduction and Clonal Expansion of Human Lymphocytes for Tumor Therapy," Hybridoma and Hybridomics, 2003, 24(4): 209-218.

Chiorean and Miller, "The biology of natural killer cells and implications for therapy of human disease," J Hematother Stem Cell Res, Aug. 2001, 10(4): 451-463.

Cho, D., and D. Campana, "Expansion and activation of natural killer cells for cancer immunotherapy," The Korean Journal of Laboratory Medicine, 29(2): 89-96 (2009).

Clarke et al., "Folding studies of immunoglobulin-like β-sandwich proteins suggest that they share a common folding pathway," Structure, 7(9):1145-1153, Sep. 15, 1999.

ClinicalTrials.gov, "A Multi-Center Study Evaluating KTE-C19 in Pediatric and Adolescent Subjects With Relapsed/Refractory B-precursor Acute Lymphoblastic Leukemia (ZUMA-4)," available at https://clinicaltrials.gov/show/NCT02625480, NCT02625480 (Retrieved from the Internet on Jun. 21, 2016).

ClinicalTrials.gov, "A Phase 1-2 Multi-Center Study Evaluating KTE-C19 in Subjects With Refractory Aggressive Non-Hodgkin Lymphoma (ZUMA-1) (ZUMA-1)," available at https://clinicaltrials.gov/show/NCT02348216, NCT02348216 (Retrieved from the Internet on Jun. 21, 2016).

ClinicalTrials.gov, "A Phase 2 Multicenter Study Evaluating Subjects With Relapsed/Refractory Mantle Cell Lymphoma (ZUMA-2)," available at https://clinicaltrials.gov/show/NCT02601313, NCT02601313 (Retrieved from the Internet on Jun. 21, 2016).

ClinicalTrials.gov, "A Study Evaluating KTE-C19 in Adult Subjects With Relapsed/Refractory B-precursor Acute Lymphoblastic Leukemia (r/r ALL) (ZUMA-3) (ZUMA-3)," available at https://clinicaltrials.gov/show/NCT02614066, NCT02614066 (Retrieved from the Internet on Jun. 21, 2016).

ClinicalTrials.gov, "Administration of Anti-CD19-chimeric-antigen-receptor-transduced T Cells From the Original Transplant Donor to Patients With Recurrent or Persistent B-cell Malignancies After Allogenic Stem Cell Transplantation," available at https://clinicaltrials.gov/show/NCT01087294, NCT01087294 (Retrieved from the Internet on Jun. 21, 2016).

ClinicalTrials.gov, "Anti-CD19 White Blood Cells for Children and Young Adults With B Cell Leukemia or Lymphoma," available at https://clinicaltrials.gov/show/NCT01593696, NCT01593696 (Retrieved from the Internet on Jun. 21, 2016).

ClinicalTrials.gov, "CAR T Cell Receptor Immunotherapy for Patients With B-cell Lymphoma," available at https://clinicaltrials.gov/show/NCT00924326, NCT00924326 (Retrieved from the Internet on Jun. 21, 2016).

ClinicalTrials.gov, "CD19 CAR T Cells for B Cell Malignancies After Allogencic Transplant," available at https://clinicaltrials.gov/show/NCT01475058, NCT01475058 (Retrieved from the Internet on Jun. 21, 2016).

ClinicalTrials.gov, "CD19 Chimeric Receptor Expressing T Lymphocytes In B-Cell Non Hodgkin's Lymphoma, ALL & CLL (CRETI-NH)," available at https://clinicaltrials.gov/show/NCT00586391, NCT00586391 (Retrieved from the Internet on Jun. 21, 2016).

ClinicalTrials.gov, "CD19+ CAR T Cells for Lymphoid Malignancies," available at https://clinicaltrials.gov/show/NCT02529813, NCT02529813 (Retrieved from the Internet on Jun. 21, 2016).

ClinicalTrials.gov, "Consolidation Therapy With Autologous T Cells Genetically Targeted to the B Cell Specific Antigen CD19 in Patients With Chronic Lymphocytic Leukemia Following Upfront Chemotherapy With Pentostatin, Cyclophosphamide and Rituximab," available at https://clinicaltrials.gov/show/NCT01416974, NCT01416974 (Retrieved from the Internet on Jun. 21, 2016).

ClinicalTrials.gov, "Genetically Engineered Lymphocyte Therapy in Treating Patients With B-Cell Leukemia or Lymphoma That is Resistant or Refractory to Chemotherapy," available at https://clinicaltrials.gov/show/NCT01029366, NCT01029366 (Retrieved from the Internet on Jun. 21, 2016).

ClinicalTrials.gov, "High Dose Therapy and Autologous Stem Cell Transplantation Followed by Infusion of Chimeric Antigen Receptor (CAR) Modified T-Cells Directed Against CD19+ B-Cells for Relapsed and Refractory Aggressive B Cell Non-Hodgkin Lymphoma," available at https://clinicaltrials.gov/show/NCT01840566, NCT01840566 (Retrieved from the Internet on Jun. 21, 2016).

ClinicalTrials.gov, "In Vitro Expanded Allogeneic Epstein-Barr Virus Specific Cytotoxic T-Lymphocytes (EBV-CTLs) Genetically Targeted to the CD19 Antigen in B-cell Malignancies," available at https://clinicaltrials.gov/show/NCT01430390, NCT01430390 (Retrieved from the Internet on Jun. 21, 2016).

ClinicalTrials.gov, "Precursor B Cell Acute Lymphoblastic Leukemia (B-ALL) Treated With Autologous T Cells Genetically Targeted to the B Cell Specific Antigen CD19," available at https://clinicaltrials.gov/show/NCT01044069, NCT01044069 (Retrieved from the Internet on Jun. 21, 2016).

ClinicalTrials.gov, "Study Evaluating the Efficacy and Safety of JCAR015 in Adult B-cell Acute Lymphoblastic Leukemia (B-ALL) (ROCKET)," available at https://clinicaltrials.gov/show/NCT02535364, NCT02535364 (Retrieved from the Internet on Jun. 21, 2016).

ClinicalTrials.gov, "T Cells Expressing a Fully-human AntiCD19 Chimeric Antigen Receptor for Treating B-cell Malignancies," available at https://clinicaltrials.gov/show/NCT02659943, NCT02659943(Retrieved from the Internet on Jun. 21, 2016).

ClinicalTrials.gov, "T-Lymphocytes Genetically Targeted to the B-Cell Specific Antigen CD19 in Pediatric and Young Adult Patients With Relapsed B-Cell Acute Lymphoblastic Leukemia," available at https://clinicaltrials.gov/show/NCT01860937, NCT01860937(Retrieved from the Internet on Jun. 21, 2016).

ClinicalTrials.gov, "Treatment of Relapsed or Chemotherapy Refractory Chronic Lymphocytic Leukemia or Indolent B Cell Lymphoma Using Autologous T Cells Genetically Targeted to the B Cell

(56) References Cited

OTHER PUBLICATIONS

Specific Antigen CD19", Available at: https://clinicaltrials.gov/show/NCT00466531, NCT00466531(Retrieved from the Internet on Jun. 21, 2016).

Cochran et al., "Receptor clustering and transmembrane signaling in T cells," Trends Biochem Sci., 26(5):304-310, May 2001.

Collins et al., "Donor leukocyte infusions in 140 patients with relapsed malignancy after allogeneic bone marrow transplantation," J. Clin. Oncol., Feb. 1997, 15(2): 433-444.

Collins et al., "Donor leukocyte infusions in acute lymphocytic leukemia," Bone Marrow Transplantation, 2000, 26: 511-516.

Cooley, S. et al., "Donor selection for natural killer cell receptor genes leads to superior survival after unrelated transplantation for acute myelogenous leukemia," Blood, 116(14): 2411-2419 (2010).

Cooper et al., "T-Cell Clones can be Rendered Specific for CD19: Toward the Selective Augmentation Of the Graft-Versus-B Lineage Leukemia Effect," Blood, 2003, pp. 1637-1644, vol. 101.

Cooper, M.A. et al., "In vivo evidence for a dependence on interleukin 15 for survival of natural killer cells," *Blood*, 100(10): 3633-3638 (2002).

Cruz et al., "Infusion of donor-derived CD19-redirected virus-specific T cells for B-cell malignancies relapsed after allogeneic stem cell transplant: a phase 1 study," Blood 122(17):2965-2973 (2013).

Curti, A. et al., "Successful transfer of alloreactive haploidentical KIR ligand-mismatched natural killer cells after infusion in elderly high risk acute myeloid leukemia patients," Blood, 118(12):3273-3279 (2011).

Damle et al., "Differential regulatory signals delivered by antibody binding to the CD28 (Tp44) molecule during the activation of human T lymphocytes," J Immunol., 140(6):1753-1761, Mar. 15, 1988.

Darcy, P.K., et al., "Expression in cytotoxic T lymphocytes of a single-chain anti-carcinoembryonic antigen antibody. Redirected Fas ligand-mediated lysis of colon carcinoma," Eur. J. Immunol. 28: 1663-1672 (1998).

Davila, M.L., et al., "Efficacy and Toxicity Management of 19-28z CAR T Cell Therapy in B Cell Acute Lymphoblastic Leukemia," Science Translat. Med. 6(24) (2014).

De La Chapelle, A. et al., "Truncated erythropoietin receptor causes dominantly inherited benign human erythrocytosis," Proc Natl Acad Sci USA., vol. 90, No. 10, pp. 4495-4499 (May 1993).

DeBenedette et al., "Role of 4-1BB ligand in costimulation of T lymphocyte growth and its upregulation on M12 B lymphomas by cAMP," J Exp Med, Mar. 1995, 181(3): 985-992.

DeBenedette, MA, et al.. "Costimulation of CD28" T Lymphocytes by 4-1 BB Ligand, J. Immunol., 1997, pp. 551-559, vol. 158.

Delahaye, N.F. et al., "Alternatively spliced NKp30 isoforms affect the prognosis of gastrointestinal stromal tumors," *Nat Med.*, 17(6): 700-707 (2011).

Diefenbach et al., "Selective associations with signaling proteins determine stimulatory versus costimulatory activity of NKG2D," Nature Publishing Group, vol. 3, No. 12, pp. 1142-1149, (Dec. 2002).

Dotti et al., "Design and Development of Therapies using Chimeric Antigen Receptor-Expressing T cells," Immunol Rev., 257(1), 35 pages, Jan. 2014.

Doubrovina, et al., "Evasion from NK Cell Immunity by MHC Class I Chain-Related Molecules Expressing Colon Adenocarcinoma," Journal of Immunology, vol. 171, pp. 6889-6899, (2003).

Dubois et al., "IL-15Rα recycles and presents IL-15 In trans to neighboring cells," Immunity, Nov. 2002, 17(5): 537-547.

Dubois, S., et al., "Preassociation of IL-15 with IL-15Rα-IgG1-Fc enhances its activity on proliferation of NK and CD8+/CD44$^{high}$ T cells and its antitumor action," Journal of Immunology, 180(4):2099-2106 (2008).

Dudley, M.E., et al., "Adoptive Transfer of Cloned Melanoma-Reactive T Lymphocytes for the Treatment of Patients with Metastatic Melanoma," J. Immunother. 24: 363-373 (2001).

Ellis et al., "Interactions of CD80 and CD86 with CD28 and CTLA4," J Immunol., 156(8):2700-2709, Apr. 15, 1996.

Eshhar et al., "Specific activation and targeting of cytotoxic lymphocytes through chimeric single chains consisting of antibody-binding domains and the γ or ζ subunits of the immunoglobulin and T-cell receptors," Proc. Natl. Acad. Sci. USA, 1993, 90:720-724.

Eshhar, Z, et al . "Functional Expression of Chimeric Receptor Genes in Human T Cells," J. Immunol. Methods, 2001, 248(1-2):67-76.

Eshhar, Z., "Tumor-specific T-bodies: towards clinical application," Cancer Immunol. Immunother. 45: 131-136 (1997).

Fagan, E.A., and Eddleston, A.L.W.F., "Immunotherapy for cancer: the use of lymphokine activated killer (LAK) cells," Gut 28: 113-116 (1987).

Farag et al., "Natural killer cell receptors: new biology and insights into the Graft-versus-leukemia effect," Blood, 2002, 100(6):1935-1947.

Fehniger TA, et al.; "Ontogeny and expansion of human natural killer cells: clinical implications", Int Rev Immunol. Jun. 2001; 20(3-4):503-534.

Fehniger, T.A., et al., "Interleukin 15: biology and relevance to human disease," Blood, 97(1): 14-32 (2001).

Ferlazzo, G. et al., "Distinct roles of IL-12 and IL-15 in human natural killer cell activation by dendritic cells from secondary lymphoid organs," PNAS, 101(47): 16606-16611 (2004).

Fernandez-Messina et al., "Human NKG2D-ligands: cell biology strategies ensure immune recognition," Frontiers in Immunology, vol. 3, Article 299, 9 Pages, (Sep. 2012).

Ferris, R.L. et al., "Tumor antigen-targeted, monoclonal antibody-based immunotherapy: clinical response, cellular immunity, and immunoescape," *J Clin Oncol*, 28(28): 4390-4399 (2010).

Finney et al., "Activation of resting human primary T cells with chimeric receptors: costimulation from CD28, inducible costimulator, CD134, and CD137 in series with signals from the TCR ζ chain", J Immunol. Jan. 1, 2004; 172(1):104-113.

Finney et al., "Chimeric receptors providing both primary and costimulatory signaling in T cells from a single gene product," J Immunol. Sep. 15, 1998;161(6):2791-2797.

Foon et al., "Clinical and immune responses in advanced melanoma patients immunized with an anti-idiotype antibody mimicking disialoganglioside GD2," J. Clin. Oncol.., 18(2):376-384, Jan. 2000.

Freshney, Animal Cell Culture, Cancer Research Campaign, IRL Press, 1986, 248 pages [Table of Contents Only].

Fujisaki, H. et al., "Expansion of highly cytotoxic human natural killer cells for cancer cell therapy," Cancer Res., 69(9): 4010-4017 (2009).

Fujisaki, H. et al., "Replicative potential of human natural killer cells," Br J Haematol, 145: 606-613 (2009).

Galustian, C. et al., "MP84-07A Tale of Tails—A Novel Approach to Immunotherapy of Prostate Cancer," J Urol, 195(4S): e1092 (May 2016).

Gardner, R., et al., "Acquisition of a CD19 negative myeloid phenotype allows immune escape of MLL-rearranged B-ALL from CD19 CAR-T cell therapy," Blood, vol. 127, No. 20 (May 2016), 2406-2410.

Garrity et al., "The activating NKG2D receptor assembles in the membrane with two signaling dimers into a hexameric structure," PNAS, vol. 102, No. 21, pp. 7641-7646, May 24, 2005.

Geiger and Jyothi, "Development and application for receptor-modified T lymphocytes for adoptive immunotherapy," Transfus Med Rev, Jan. 2001, 15(1): 21-34.

Geiger et al., "Integrated src kinase and costimulatory activity enhances signal transduction through single-chain chimeric receptors in T lymphocytes", Blood. Oct. 15, 2001; 98(8):2364-2371.

GenBank Accession No. NM 007360 GI:315221123, *Homo sapiens* killer cell lectin like receptor K1 (KLRK1), mRNA, dated May 29, 2017, 4 pages.

GenBank Accession No. NM_000734 GI: 37595563, *Homo sapiens* CD3Z antigen, ζ polypeptide (TiT3 complex) (CD3Z), transcript variant 2, mRNA, dated Oct. 27, 2004, 6 pages.

GenBank Accession No. NM_001768 GI: 27886640, *Homo sapiens* CD8 antigen, α polypeptide (p32) (CD8A), transcript variant 1, mRNA, dated Oct. 27, 2004, 5 pages.

(56) References Cited

OTHER PUBLICATIONS

GenBank Accession No. NM_011612 GI: 6755830, Mus musculus tumor necrosis factor receptor superfamily, member 9 (Tnfrsf9), mRNA, dated Oct. 26, 2004, 8 pages.
Germain et al., "T-cell signaling: the importance of receptor clustering," Curr Biol., 7(10):R640-R644, Oct. 1, 1997.
Ghobadi, et al., "Updated Phase 1 Results from ZUMA-1: A Phase 1-2 Multicenter Study Evaluating the Safety and Efficacy of KTE-C19 (Anti-CD19 CAR T Cells) in Subjects With Refractory Aggressive Non-Hodgkin Lymphoma," Slides accompanying oral presentation at the American Association for Cancer Research Annual Meeting, New Orleans, Louisiana (2016).
Ghorashian, S., et al., "CD19 chimeric antigen receptor T cell therapy for haematological malignancies," Br. J. Haematol. 169:463-478 (2015).
Giebel, S. et al., "Survival advantage with KIR ligand incompatibility in hematopoietic stem cell transplantation from unrelated donors," *Blood*, 102(3): 814-819 (2003).
Gilfillan et al., "NKG2D recruits two distinct adapters to trigger NK cell activation and costimulation," Nature Publishing Group, Nature Immunology, vol. 3, No. 12, pp. 1150-1155, Dec. 2002.
Gill, S., et al., "Chimeric antigen receptor T cell therapy: 25 years in the making," Blood Rev. 11 pages, (2015).
Ginaldi, L., et al., "Levels of expression of CD19 and CD20 in chronic B cell leukacmias," J. Clin. Pathol. 51: 364-369 (1998).
Giuliani, M. et al., "Generation of a novel regulatory NK cell subset from peripheral blood CD34+progenitors promoted by membrane-bound IL-15," PLos One, 3(5): e2241 (2008).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia, 1999, 1(2): 123-127.
Goodier and Londei, "CD28 is not directly involved in the response of human $CD3^{-\ CD56+}$ natural killer cells to lipopolysaccharide: a role for T cells," Immunology, Apr. 2004, 111(4): 384-390.
Goodwin et al., "Molecular cloning of a ligand for the inducible T cell gene 4-1BB: a member of an emerging family of cytokines with homology to tumor necrosis factor", Eur J Immunol. Oct. 1993; 23(10):2631-2641.
Grauer et al., "Identification, Purification, and Subcellular Localization of Prostate-specific Membrane Antigen PSM' Protein in the LNCaP Prostatic Carcinoma Cell Line," Cancer Res., 58: 4787-4789 (1998).
Greene et al., "Covalent dimerization of CD28/CTLA-4 and oligomerization of CD80/CD86 regulate T cell costimulatory interactions," J Biol Chem., 271(43):26762-26771, Oct. 25, 1996.
Greenfield, E.A., et al., "CD28/B7 Costimulation: A Review," Crit. Rev. Immunol. 18: 389-418 (1998).
Greenwald et al., "The B7 Family Revisited," Annu. Rev. Immunol., 2005, 23: 515-548.
Grillo-López, A., "Rituximab: An Insider's Historical Perspective," Seminars in Oncology 27(6 Suppl 12): 9-16 (2012).
Gross et al., "Endowing T cells with antibody specificity using chimeric T cell receptors," FASEB J. Dec. 1992;6(15):3370-3378.
Grupp et al., "Chimeric antigen receptor-modified T cells for acute lymphoid leukemia," N Engl J Med. Apr. 18, 2013; 368 (16):1509-1518.
Handgretinger, R., et al., "A phase I study of neuroblastoma with the anti-ganglioside GD2 antibody 14.G2a," Cancer Immunol. Immunother. 35: 199-204 (1992).
Hara et al., "NKG2D gene polymorphisms are associated with disease control of chronic myeloid leukemia by dasatinib," Int. J. Hematol., 9 pages, Aug. 9, 2017.
Harada H, et al., "Selective expansion of human natural killer cells from peripheral blood mononuclear cells by the cell line, HFWT", Jpn J Cancer Res. Mar. 2002; 93(3):313-319.
Harada H, et al.; "A Wilms tumor cell line, HFWT, can greatly stimulate proliferation of CD56+human natural killer cells and their novel precursors in blood mononuclear cells", Exp Hematol. Jul. 2004; 32(7):614-621.

Harding et al., "CD28-mediated signalling co-stimulates murine T cells and prevents induction of anergy in T-cell clones," Nature, 356(6370):607-609, Apr. 16, 1992.
Harmon et al., "Dexamethasone induces irreversible $G_1$ arrest and death of a human lymphoid cell line," J Cell Physiol, Feb. 1979, 98(2): 267-278.
Haynes NM, et al., "Rejection of syngeneic colon carcinoma by CTLs expressing single-chain antibody receptors codelivering CD28 costimulation", J Immunol., Nov. 15, 2002; 169(10):5780-5786.
Haynes NM, et al., "Single-chain antigen recognition receptors that costimulate potent rejection of established experimental tumors", Blood, Nov. 1, 2002; 100(9):3155-3163.
Haynes, N.M., et al., "Redirecting Mouse CTL Against Colon Carcinoma: Superior Signaling Efficacy of Single-Chain Variable Domain Chimeras Containing TCR-ζ vs FcεRI-γ," J. Immunol. 166: 182-187 (2001).
Heuser, C., et al., "T-cell activation by recombinant immunoreceptors: Impact of the intracellular signalling domain on the stability of receptor expression and antigen-specific activation of grafted T cells," Gene Therapy 10: 1408-1419 (2003).
Hoffmann, S.C. et al. "2B4 Engagement Mediates Rapid LFA-1 and Actin-Dependent NK Cell Adhesion to Tumor Cells as Measured by Single Cell Force Spectroscopy," J. Immunol, 186(5): 2757-2764 (Jan. 2011).
Hollyman, D., et al., "Manufacturing Validation of Biologically Functional T Cells Targeted to CD19 Antigen for Autologous Adoptive T cell Therapy," J. Immunother. 32: 169-180 (2009).
Hombach, et al., "Tumor-specific T cell activation by recombinant immunoreceptors: CD3 ζ signaling and CD28 costimulation are simultaneously required for efficient IL-2 secretion and can be integrated into one combined CD28/CD3 ζ signaling receptor molecule", J Immunol., Dec. 1, 2001; 167(11 ):6123-6131.
Hombach et al., "T-Cell Activation by Recombinant Receptors: CD28 Costimulation Is Required for Interleukin 2 Secretion and Receptor-mediated T-Cell Proliferation but Does Not Affect Receptor-mediated Target Cell Lysis," Cancer Res., Mar. 1, 2001, 61:1976-1982.
Hombach et al., "The recombinant T cell receptor strategy: insights into structure and function of recombinant immunoreceptors on the way towards an optimal receptor design for cellular immunotherapy," Curr Gene Ther. 2002 2(2):211-226.
Hombach, A., et al., "Adoptive immunotherapy with genetically engineered T cells: modification of the IgG1 Fc 'spacer' domain in the extracellular moiety of chimeric antigen receptors avoids 'off-target' activation and unintended initiation of an innate immune response," Gene Therapy 17: 1206-1213 (2010).
Hombach, A., et al., "T cell activation by recombinant FcεRI γ-chain immune receptors: an extracellular spacer domain impairs antigen-dependent T cell activation but not antigen recognition," Gene Therapy 7: 1067-1075 (2000).
Horng et al., "NKG2D signaling is coupled to the interleukin 15 receptor signaling pathway," Nature Immunology, vol. 8, No. 12, pp. 1345-1352, Dec. 2007.
Hsu, C. et al., "Cytokine-independent growth and clonal expansion of a primary human $CD8^+$T-cell clone following retroviral transduction with the IL-15 gene," *Blood*, 109(12): 5168-5177 (2007).
Hsu, K.C. et al., "Improved outcome in HLA-identical sibling hematopoietic stem-cell transplantation for acute myelogenous leukemia predicted by KIR and HLA genotypes," Blood, 105(12): 4878-4884 (2005).
Huang Q.S. et al, "Expansion of human natural killer cells ex vivo," Chine J Cell Mol Immunol, Dec. 31, 2008, vol. 24, No. 12, pp. 1167-1170.
Hurtado et al., "Potential role of 4-1BB in T cell activation. Comparison with the costimulatory molecule CD28," J Immunol, Oct. 1995, 155(7): 3360-3367.
Imai C et al. "Genetic modification of primary natural killer cells overcomes inhibitory signals and induces specific killing of leukemic cells," Blood. 2005;106:376-383.
Imai C, et al., "Chimeric receptors with 4-1BB signaling capacity provoke potent cytotoxicity against acute lymphoblastic leukemia", Leukemia., Feb. 12, 2004; 18(4):676-684.

(56) References Cited

OTHER PUBLICATIONS

Imai C, et al., "T-cell immunotherapy for B-lineage acute lymphoblastic leukemia using chimeric antigen receptors that deliver 4-1 BB-mediated costimulatory signals", Blood. Nov. 16, 2003; 102(11):66a-67a. (Abstract #223).
Imai et al. "Genetic Modification of T cells for cancer therapy," Journal of Biological Regulators and Homeostatic Agents, 18 (1): 62-71; Jan. 2004.
Imai, C., et al; "A novel method for propagating primary natural killer (NK) cells allows highly Efficient expression of anti-CD19 chimeric receptors and generation of powerful cytotoxicity Against NK-resistant acute lymphoblastic leukemia cells." Abstract# 306 Blood 104 (Nov. 16, 2004).
Imamura, M. et al., "Autonomous growth and increased cytotoxicity of natural killer cells expressing membrane-bound interleukin-15," *Blood*, 124(7): 1081-1088 (Jul. 8, 2014).
Inaguma et al., "Expression of neural cell adhesion molecule L1 (CD171) in neuroectodermal and other tumors. An immunohistochemical study of 5155 tumors and critical evaluation of CD171 prognostic value in gastrointestinal stromal tumors," Oncotarge., 7(34):55276-55289, Jul. 11, 2016.
Ishii, H. et al., "Monocytes enhance cell proliferation and LMP1 expression of nasal natural killer/T-cell lymphoma cells by cell contact-dependent interaction through membrane-bound IL-15," International Journal of Cancer, 130: 48-58 (2012).
Ishiwata I, et al., "Carcinoembryonic proteins produced by Wilms' tumor cells in vitro and in vivo", Exp Pathol. 1991; 41(1):1-9.
Israeli, R.S., et al., "Expression of the Prostate-specific Membrane Antigen," Cancer Res., 1994, 54:1807-1811.
Ito et al., "Hyperdiploid acute lymphoblastic leukemia with 51 to 65 chromosomes: a distinct biological entity with a marked propensity to undergo apoptosis," Blood, Jan. 1999, 93(1): 315-320.
Jena et al., "Redirecting T-cell specificity by introducing a tumor-specific chimeric antigen receptor," Blood, 2010, 116(7):1035-1044.
Jenkins et al., "Inhibition of antigen-specific proliferation of type 1 murine T cell clones after stimulation with immobilized anti-CD3 monoclonal antibody," J Immunol., 144(1):16-22, Jan. 1, 1990.
Jensen, M., et al., "CD20 is a molecular target for scFvFc:ζ receptor redirected T cells: implications for cellular immunotherapy of CD20⁻malignancy," Biol. Blood and Marrow Transplantation 4: 75-83 (1998).
Jensen, M.C., et al., "Anti-transgene Rejection Responses Contribute to Attenuated Persistence of Adoptively Transferred CD20/CD19-Specific Chimeric Antigen Receptor Redirected T Cells in Humans," Biol. Blood Marrow Transplant 16: 1245-1256 (2010).
Jiang, E., "Functional characterization of interleukin-15 gene transduction into the human natural killer cell line NKL," Cytother. 10(3):265-274, 2008.
Jiang, W. et al., "hIL-15 gene-modified human natural killer cells (NKL-IL15) augments the anti-human hepatocellular carcinoma effect in vivo," Immunobiology, 219: 547-553 (Mar. 12, 2014).
Johnson and Jenkins, "The role of anergy in peripheral T cell unresponsiveness," Life Sci, 1994, 55(23): 1767-1780.
June et al., "The B7 and CD28 receptor families," Immunol Today, Jul. 1994, 15(7): 321-331.
Kabalak et al., "Association of an NKG2D gene variant with systemic lupus erythematosus in two populations," Human Immunology, vol. 71, pp. 74-78, 2010.
Kaiser, B.K. et al., "Structural basis for NKG2A/CD94 Recognition of HLA-E," Proc Nat'l Acad Sci USA, 105(18): 6696-6701 (Apr. 2008).
Kalos et al, "T Cells with Chimeric Antigen Receptors Have Potent Antitumor Effects and Can Establish Memory in Patients with Advanced Leukemia," Sci Transl Med. Aug. 10, 2011;3(95):95ra73.
Kariv, I., et al., "Analysis of the Site of Interaction of CD28 with Its Counter-Receptors CD80 and CD86 and Correlation with Function," J. of Immunol. 157: 29-38 (1996).

Kershaw, M.H., et al., "A Phase I Study on Adoptive Immunotherapy Using Gene-Modified T Cells for Ovarian Cancer," Clin. Cancer Res. 12: 6106-6115 (2006).
Khammari, A., et al., "Long-term follow-up of patients treated by adoptive transfer of melanoma tumor-infiltrating lymphocytes as adjuvant therapy for stage III melanoma," Cancer Immunol. Immunother. 56: 1853-1860 (2007).
Kim Y J, et al., "Human 4-1 BB regulates CD28 co-stimulation to promote Th1 cell responses. Eur J. Immunol", Mar. 1998; 28(3): 881-890.
Kim Y J, et al., "Novel T cell antigen 4-1 BB associates with the protein tyrosine kinase p56lck1", J Immunol. Aug. 1, 1993; 151(3): 1255-1262.
Kitaya, K. et al., "IL-15 expression at human endometrium and decidua," Biology of Reproduction, 63(3): 683-687 (2000).
Kitaya, K., et al., "Regulatory role of membrane-bound form interleukin-15 on human uterine microvascular endothelial cells in circulating CD16(−) natural killer cell extravasation into human endometrium," Biology of Reproduction, 89(3): 70, 1-7, (2013).
Klein E, et al., "Properties of the K562 cell line, derived from a patient with chronic myeloid leukemia", Int J Cancer. Oct. 15, 1976; 18(4):421-431.
Klingemann HG, et al., "Ex vivo expansion of natural killer cells for clinical applications", Cytotherapy. 2004; 6(1):15-22.
Kobayashi et al., "Role of trans-cellular IL-15 presentation in the activation of NK cell-mediated killing, which leads to enhanced tumor immunosurveillance," Blood, Jan. 2005, 105(2): 721-727.
Kochenderfer, J.N. et al. "Construction and Pre-clinical Evaluation of an Anti-CD19 Chimeric Antigen Receptor," J. Immunother. 32(7):689-702 (2009).
Kochenderfer, J.N., et al. "Chemotherapy-Refractory Diffuse Large B-Cell Lymphoma and Indolent B-Cell Malignancies Can be Effectively Treated With Autologous T Cells Expressing an Anti-CD19 Chimeric Antigen Receptor," J. Clin. Oncol. 33:540-549 (2014).
Kochenderfer, J.N., et al. "Donor-derived CD19-targeted T cells cause regression of malignancy persisting after allogeneic hematopoietic stem cell transplantation," Blood 122(25): 4129-4139 (2013).
Kochenderfer, J.N., et al., "B-cell depletion and remissions of malignancy along with cytokine-associated toxicity in a clinical trial of anti-CD19 chimeric-antigen-receptor-transduced T cells," Blood 119(12):2709-2720 (2012).
Kochenderfer, J.N., et al., "Eradication of B-lineage cells and regression of lymphoma in a patient treated with autologous T cells genetically-engineered to recognize CD19," Blood 116(20):4099-4102 (2010).
Koeffler and Golde, "Acute myelogenous leukemia: a human cell line responsive to colony-stimulating activity," Science, Jun. 1978, 200(4337): 1153-1154.
Koehler et al. "Engineered T Cells for the Adoptive Therapy of B-Cell Chronic Lymphocytic Leukaemia," Advances in Hematology, vol. 2012, Article ID 595060, 13 pages; doi:10.1155/2012/595060 (2012).
Kohn et al., "CARs on track in the clinic," Mol Ther. Mar. 2011; 19(3):432-438.
Koka, R. et al., "Cutting edge: murine dendritic cells require IL-15R α to prime NK cells," *J Immunol.*, 173(6): 3594-3598 (2004).
Kolb HJ, et al., "Graft-Versus-Leukemia Effect of Donor Lymphocyte Transfusions in Marrow Grafted Patients," Blood, 1995, 86(5):2041-2050.
Kowolik, C.M., "CD28 Costimulation Provided through a CD19-Specific Chimeric Antigen Receptor Enhances In vivo Persistence and Antitumor Efficacy of Adoptively Transferred T Cells," Cancer Research 66(22): 10995-11004 (2006).
Krampera et al., "Bone marrow mesenchymal stem cells inhibit the response of naïve and memory antigen-specific T cells to their cognate peptide," Blood, May 2003, 101(9): 3722-3729.
Krause et al., "Antigen-dependent CD28 Signaling Selectively Enhances Survival and Proliferation in Genetically Modified Activated Human Primary T Lymphocytes," J. Exp. Med., 1998, 188(4): 619-626.

(56) References Cited

OTHER PUBLICATIONS

Krug, C., et al., "Stability and activity of MCSP-specific chimeric antigen receptors (CARs) depend on the scFv antigen-binding domain and the protein backbone," Cancer Immunol. Immunother. 64:1623-1635 (2015).
Kuo et al., "Efficient gene transfer into primary murine lymphocytes obviating the need for drug selection," Blood, Aug. 1993, 82(3): 845-852.
Kurokawa, M., et al., "Caspases and kinases in a death grip," Cell, 138(5): 838-854 (2009).
Kwon, BS, et al., "cDNA sequences of two inducible T-cell genes", Proc Natl Acad Sci U SA. Mar. 1989; 86(6):1963-1967.
LaBonte, M.L. et al., "Molecular Determinants Regulating the Pairing of NKG2 Molecules with CD94 for Cell Surface Heterodimer Expression," J Immunol, 172(11): 6902-6912 (May 2004).
Lafreniere, R., et al.., "Successful Immunotherapy of Murine Experimental Hepatic Metastases with Lymphokine-activated Killer Cells and Recombinant Interleukin 2," Cancer Res. 45: 3735-3741 (1985).
Lamers, C.H.J., et al., "Treatment of Metastatic Renal Cell Carcinoma With Autologous T-Lymphocytes Genetically Retargeted Against Carbonic Anhydrase IX: First Clinical Experience," J. Clin. Oncol. vol. 24, No. 13: e20-e22 (May 1, 2006).
Lang et al., "Absence of B7.1-CD28/CTLA-4-mediated co-stimulation in human NK cells," Eur. J. Immunol, Mar. 1998, 28: 780-786.
Langer et al., "Comparative Evaluation of Peripheral Blood T Cells and Resultant Engineered Anti-CD19 CAR T-Cell Products From Patients With Relapsed/Refractory Non-Hodgkin Lymphoma (NHL)," Abstract 2305, Proceedings: AACR 107th Annual Meeting 2016; Apr. 16- 20, 2016, New Orleans, Louisiana.
Lanzavecchia et al., "Antigen decoding by T lymphocytes: from synapses to fate determination," Nat Immunol., vol. 2, No. 6:487-492, Jun. 2001.
Lapteva, N. et al., "Large-scale ex vivo expansion and characterization of natural killer cells for clinical applications," Cytotherapy, 14(9): 1131-1143 (2012).
Le Blanc et al., "Mesenchymal stem cells inhibit and stimulate mixed lymphocyte cultures and mitogenic responses independently of the major histocompatability complex," Scand J Immunol, Jan. 2003, 57(1): 11-20.
Lee, D.W., et al., "T cells expressing CD19 chimeric antigen receptors for acute lymphoblastic leukaemia in children and young adults: a phase 1 dose-escalation trial," Lancet 385:517-528 (2015).
Lehner et al., "Redirecting T Cells to Ewing's Sarcoma Family of Tumors by a Chimeric NKG2D Receptor Expressed by Lentiviral Transduction of MRNA Transfection," PLoS One, vol. 7, Issue 2; e31210, Feb. 2012.
Leung, W. et al., "Determinants of antileukemia effects of allogeneic NK cells," J Immunol., 172(1): 644-650 (2004).
Li et al., "Costimulation by CD48 and B7-1 induces immunity against poorly immunogenic tumors," J Exp Med, Feb. 1996, 183(2): 639-644.
Li et al., "Polarization Effects of 4-1BB during CD28 Costimulation in Generating Tumor-reactive T Cells for Cancer Immunotherapy," Cancer Research, vol. 63, pp. 2546-2552, May 15, 2003.
Li, Q., et al., "Bifacial effects of engineering tumour cell-derived exosomes on human natural killer cells" Experimental Cell Research, Dec. 19, 2017, vol. 363, No. 2, pp. 141-150.
Liao, W., et al., "Interleukin-2 at the crossroads of effector responses, tolerance, and immunotherapy," Immunity, 38(1): 13-25 (2013).
Liebowitz et al., "Costimulatory approaches to adoptive immunotherapy," Curr Opin Oncol, Nov. 1998, 10(6): 533-541.
Linsley et al., "The role of CD28 receptor during T cell responses to antigen," Annu. Rev. Immunol., 1993, 191-212.
Liu, H., et al., "Monoclonal Antibodies to the Extracellular Domain of Prostate-specific Membrane Antigen Also React with Tumor Vascular Endothelium," Cancer Res. 57: 3629-3634 (1997).
Liu, L, et al. "Novel CD4-Based Bispecific Chimeric Antigen Receptor Designed for Enhanced Anti-HIV Potency and Absence of HIV Entry Receptor Activity," J. Virol. 89(13):6685-6694 (2015).

Lode et al., "Targeted cytokines for cancer immunotherapy," Immunol Res., 21(2-3):279-288, (2000).
López-Requena et al., "Gangliosides, Ab1 and Ab2 antibodies III. The idiotype of anti-ganglioside mAb P3 is immunogenic in a T cell-dependent manner," Mol Immunol., 2007, 44(11):2915-2922.
López-Requena et al., "Gangliosides, Ab1 and Ab2 antibodies IV. Dominance of VH domain in the induction of anti-idiotypic antibodies by Jene gun immunization," Mol Immunol. Apr. 2007;44(11):3070-3075. Epub Mar. 2, 2007.
Lozzio CB, et al., "Human chronic myelogenous leukemia cell-line with positive Philadelphia chromosome", Blood. Mar. 1975; 45(3):321-334.
Lozzio et al., "Properties and Usefulness of the Original K-562 Human Myelogenous Leukemia Cell Line," Leukemia Research, vol. 3, No. 6, pp. 363-370, 1979.
Lugli, E. et al., "Transient and persistent effects of IL-15 on lymphocyte homeostasis in nonhuman primates," Blood, 116(17): 3238-3248 (2010).
Ma et al., "Chapter 15: Genetically engineered T cells as adoptive immunotherapy of cancer," Cancer Chemotherapy and Biological Response Modifiers Annual 20, Ch. 15, 315-341, Giaccone et al. (Eds.), Elsevier, 2002.
Maher J., et al., "Human T-lymphocyte cytotoxicity and proliferation directed by a single chimeric TCRζ/CD28 receptor", Nat Biotechnol. Jan. 2002; 20(1):70-75.
Maloney, D.G., "Newer Treatments for Non-Hodgkin's Lymphoma: Monoclonal Antibodies," Oncology 12(10): 63-76 (1998).
Manabe et al., "Interleukin-4 induces programmed cell death (apoptosis) in cases of high-risk acute lymphoblastic leukemia," Blood, Apr. 1994, 83(7): 1731-1737.
Mann et al., "Construction of a retrovirus packaging mutant and its use to produce helper-free defective retrovirus," Cell, May 1983, 33(1): 153-159.
Manzke et al., "Immunotherapeutic strategies in neuroblastoma: antitumoral activity of deglycosylated Ricin A conjugated anti-GD2 antibodies and anti-CD3xanti-GD2 bispecific antibodies," Med Pediatr Oncol., 36(1):185-189, Jan. 2001.
Manzke et al., "Locoregional treatment of low-grade B-cell lymphoma with CD3xCD19 bispecific antibodies and CD28 costimulation. I. Clinical phase I evaluation," Int J Cancer., 91(4):508-515, Feb. 15, 2001.
Manzke et al., "Locoregional treatment of low-grade B-cell lymphoma with CD3xCD19 bispecific antibodies and CD28 costimulation. II. Assessment of cellular immune responses," Int J Cancer., 91(4):516-522, Feb. 15, 2001.
Marincola, F.M., et al., "Escape of Human Solid Tumors from T-Cell Recognition: Molecular Mechanisms and Functional Significance," Adv. Immunol. 74: 181-273 (2000).
Markowitz et al., "A safe packaging line for gene transfer: separating viral genes on two different plasmids," J Virol, Apr. 1988, 62(4): 1120-1124.
Marktel et al., "Immunologic potential of donor lymphocytes expressing a suicide gene for early immune reconstitution after hematopoietic T-cell-depleted stem cell transplantation," Blood, Feb. 2003, 101(4): 1290-1298.
Martinet O., et al., T cell activation with systemic agonistic antibody versus local 4-1 BB ligand gene delivery combined with interleukin-12 eradicate liver metastases of breast cancer, Gene Ther. Jun. 2002; 9(12):786-792.
Martinez, E., et al., "Cutting Edge: NKG2D-Dependent Cytotoxicity Is Controlled by Ligand Distribution in the Target Cell Membrane", The Journal of Immunology, 2011, 186:5538-5542.
Maude et al., "Chimeric antigen receptor T cells for sustained remissions in leukemia," N Engl J Med., 371(16):1507-1517, Oct. 16, 2014.
Maus MV, et al., "Ex vivo expansion of polyclonal and antigen-specific cytotoxic T lymphocytes by artificial APCs expressing ligands for the T-cell receptor, CD28 and 4-1BB", Nat Biotechnol. Feb. 2002; 20(2): 143-148.
May KF, Jr, et al., "Anti-4-1 BB monoclonal antibody enhances rejection of large tumor burden by promoting survival but not clonal expansion of tumor-specific CDS+ T cells," Cancer Res. 2002, 62(12):3459-3465.

(56) References Cited

OTHER PUBLICATIONS

McLaughlin et al., "Adoptive T-cell therapies for refractory/relapsed leukemia and lymphoma: current strategies and recent advances," Ther Adv Hematol., 6(6):295-307, Dec. 2015.
Melero I, et al., "Amplification of tumor immunity by gene transfer of the co-stimulatory 4-1 BB ligand: synergy with the CD28 co-stimulatory pathway," Eur J Immunol., 1998, 28(3):1116-1121.
Melero I, et al., "NK1.1 cells express 4-1BB (CDw137) costimulatory molecule and are required for tumor immunity elicited by anti-4-1 BB monoclonal antibodies," Cell Immunol., 1998, 190(2): 167-172.
Melero, I. et al, "Monoclonal antibodies against the 4-1BB T-cell activation molecule eradicate established tumors," Nature Med., 1997, 3:682-685.
Mihara et al., "Development and functional characterization of human bone marrow mesenchymal cells immortalized by enforced expression of telomerase," Br J Haematol, Mar. 2003, 120(5):846-849.
Miller et al., "Role of monocytes in the expansion of human activated natural killer cells," Blood, Nov. 1992, 80(9): 2221-2229.
Miller et al., "Successful adoptive transfer and in vivo expansion of human haploidentical NK cells in patients with cancer," Blood, Apr. 2005, 105(8): 3051-3057.
Miller, J.S., "Therapeutic applications: natural killer cells in the clinic," *Hematology Am Soc Hematol Educ Program* 2013: 247-253 (2013).
Milone MC, et al., "Chimeric receptors containing CD137 signal transduction domains mediate enhanced survival of T cells and increased antileukemic efficacy in vivo", Mol Ther. Apr. 21, 2009; 17(8):1453-1464.
Minamoto, S. et al., "Acquired Erythropoietin Responsiveness of Interleukin-2-dependent T lymphocytes Retrovirally Transduced with Genes Encoding Chimeric Erythropoietin/Interleukin-2 Receptors," Blood, vol. 86, No. 6, pp. 2281-2287 (1995).
Mishra, A. et al., "Aberrant overexpression of IL-15 initiates large granular lymphocyte leukemia through chromosomal instability and DNA hypermethylation," *Cancer Cell*, 22(5): 645-655 (2012).
Mogi et al., "Tumour rejection by gene transfer of 4-1BB ligand and into a CD80(+) murine squamous cell carcinoma and the requirements of co-stimulatory molecules on tumour and host cells," Immunology, Dec. 2000, 101(4): 541-547.
Mohammed, S. et al., "Improving Chimeric Antigen Receptor-Modified T Cell Function by Reversing the Immunosuppressive Tumor Microenvironment of Pancreatic Cancer," Mol. Ther. 4, vol. 25, No. 1, pp. 249-258 (2017).
Mondino et al., "Surface proteins involved in T cell costimulation," J Leukoc Biol, Jun. 1994, 55(6): 805-815.
Mora, "Dinutuximab for the treatment of pediatric patients with high-risk neuroblastoma," Expert Rev Clin Pharmacol., 9(5):647-653, Epub Mar. 21, 2016.
Morandi, B. et al., "NK cells provide helper signal for CD8+ T cells by inducing the expression of membrane-bound IL-15 on DCs," International Immunology, 21(5): 599-606 (2009).
Moretta L, et al., "Unravelling natural killer cell function: triggering and inhibitory human NK receptors," Embo J., 2004, 23(2):255-259.
Moritz et al., "A spacer region between the single chain antibody- and the CD3 ζ-chain domain of chimeric T cell receptor components is required for efficient ligand binding and signaling activity," Gene Ther. Oct. 1995; 2(8):539-546.
Moritz, D., et al., "Cytotoxic T lymphocytes with a grafted recognition specificity for ERBB2-expressing tumor cells," Proc. Natl. Acad. Sci. USA 91:4318-4322 (1994).
Mortier, E., et al., "IL-15Rα chaperones IL-15 to stable dendritic cell membrane complexes that activate NK cells via trans presentation," *The Journal of Experimental Medicine*, 205(5): 1213-1225 (2008).
Musso, T. et al., "Human monocytes constitutively express membrane-bound, biologically active, and interferon-γ -upregulated interlocukin-15," *Blood*, 93(10): 3531-3539 (1999).

Nadler et al., "B4, a human B lymphocyte-associated antigen expressed on normal, mitogen-activated, and malignant B lymphocytes," J Immunol, Jul. 1983, 131(1): 244-250.
Nagashima et al., "Stable transduction of the interleukin-2 gene into human natural killer cell lines and their phenotypic and functional characterization in vitro and in vivo," Blood, May 1998, 91(10): 3850-3861.
Nakamura et al., "Chimeric anti-ganglioside $G_{M2}$ antibody with antitumor activity," Cancer Res. Mar. 15, 1994; 54(6):1511-1516.
Naume et al., "A comparative study of IL-12 (cytotoxic lymphocyte maturation factor)-, IL-2-, and IL-7-induced effects on immunomagnetically purified CD56+ NK cells," J Immunol, Apr. 1992, 148(8): 2429-2436.
Neepalu et al., "Phase 1 Biomarker Analysis of the ZUMA-1 Study: A Phase 1-2 Multi-Center Study Evaluating the Safety and Efficacy of Anti-CD19 CAR T Cells (KTE-C19) in Subjects with Refractory Aggressive Non-Hodgkin Lymphoma," Poster session presented at the American Society of Hematology Annual Meeting, Orlando, Florida (Dec. 5-8, 2015).
Negrini, S. et al., "Membrane-bound IL-15 stimulation of peripheral blood natural killer progenitors leads to the generation of an adherent subset co-expressing dendritic cells and natural killer functional markers," *Haematologica*, 96(5): 762-766 (2011).
Nicholson et al., "Construction and characterisation of a functional CD19 specific single chain Fv fragment for immunotherapy of B lineage leukaemia and lymphoma," Mol Immunol., 34(16-17):1157-1165, Nov.-Dec. 1997.
Nishigaki et al., "Prevalence and growth characteristics of malignant stem cells in B-lineage acute lymphoblastic leukemia," Blood, May 1997, 89(10): 3735-3744.
Nunès et al., "The role of $p21^{ras}$ in CD28 signal transduction: triggering of CD28 with antibodies, but not the ligand B7-1, activates $p21^{ras}$," J Exp Med., 180(3):1067-1076, Sep. 1, 1994.
Oelke, M. et al., "Ex vivo induction and expansion of antigen-specific cytotoxic T cells by HLA-Ig-coated artificial antigen-presenting cells," Nat Med., 2003, 9(5):619-624.
Olsen, S.K. et al., "Crystal structure of the interleukin-15 interleukin-15 receptor α complex Insights into trans and cis presentation," The Journal of Biological Chemistry, 282(51): 37191-37204 (2007).
Ozkaynak, M.F. et al., "Phase I Study of Chimeric Human/Murine Anti-Ganglioside $G_{D2}$ Monoclonal Antibody (ch14.18) With Granulocyte-Macrophage Colony-Stimulating Factor in Children With Neuroblastoma Immediately After Hematopoietic Stem-Cell Transplantation: A Children's Cancer Group Study," J. Clinical Oncol. 18: 4077-4085 (2000).
Pan et al., "Regulation of dendritic cell function by NK cells: mechanisms underlying the synergism in the combination therapy of IL-12 and 4-1BB activation," J Immunol, Apr. 2004, 172(8): 4779-4789.
Park, J.H., et al., "Are All Chimeric Antigen Receptors Created Equal?" J. Clin. Oncol. 33: 651-653 (2015).
Park, J.H., et al., "CD19-Targeted 19-28z CAR Modified Autologous T Cells Induce High Rates of Complete Remission and Durable Responses in Adult Patients with Relapsed, Refractory B-Cell ALL," Abstract presented at the American Society of Hematology Annual Meeting, San Francisco, California, available at https://ash.confex.com/ash/2014/webprogram/Paper76573.html (Dec. 6-9, 2014).
Park, J.H., et al., Abstract, "682 Implications of Minimal Residual Disease Negative Complete Remission (MRD-CR) and Allogeneic Stem Cell Transplant on Safety and Clinical Outcome of CD19-Targeted 19-28z CAR Modified T cells in Adult Patients with Relapsed, Refractory B-Cell ALL," Am. Soc'y Hematol., available at https://ash.confex.com/ash/2015/webprogram/Paper86688.html (Dec. 5-8, 2015).
Park, Y.P., et al., "Complex Regulation of Human NKG2D-DAP10 Cell Surface Expression: Opposing Roles of the γc Cytokines and TGF-β1", Blood, Sep. 15, 2011, vol. 118, No. 11, pp. 3019-3027.
Parkhurst, M.R. et al., "Adoptive transfer of autologous natural killer cells leads to high levels of circulating natural killer cells but does not mediate tumor regression," Clin Cancer Res., 17(19): 6287-6297 (2011).

(56) References Cited

OTHER PUBLICATIONS

Patel, S.D., et al., "Impact of chimeric immune receptor extracellular protein domains on T cell function," Gene Therapy 6: 412-419 (1999).

Paul, W.E., Fundamental Immunology, Third Edition, Chs. 1, 13 and 32 (pp. 1-20, 467-504, and 1143-1178), Raven Press, New York (1993).

Peach, R.J., et al., "Complementarity Determining Region 1 (CDR1)- and CDR3-analogous Regions in CTLA-4 and CD28 Determine the Binding to B7-1," J. Exp. Med. 180: 2049-2058 (1994).

Perussia et al., "Preferential proliferation of natural killer cells among peripheral blood mononuclear cells cocultured with B lymphoblastoid cell lines," Nat Immun Cell Growth Regul, 1987, 6(4): 171-188.

Pollok et al., "Regulation of 4-1BB expression by cell-cell interactions and the cytokines, interleukin-2 and interleukin-4*," Eur J Immunol, Feb. 1995, 25(2): 488-494.

Pollok KE, et al., "Inducible T cell antigen 4-1 BB Analysis of expression and function," J Immunol., 1993, 150(3):771-781.

Porter et al., "The graft-versus-leukemia of allogencic cell therapy," Annu Rev Med, 1999, 50:369-386.

Porter DL et al., "Chimeric Antigen Receptor-Modified T Cells in Chronic Lymphoid Leukemia", N. Eng. J. Med. Aug. 25, 2011; 365(8):725-733.

Porter et al., "Induction of graft-versus-host disease as immunotherapy for relapsed chronic myeloid leukemia," N Engl J Med, Jan. 1994, 330(2): 100-106.

Pui et al., "Childhood acute lymphoblastic leukaemia—current status and future perspectives," Lancet Oncol, Oct. 2001, 2(10): 597-607.

Pule et al. "Virus-specific T cells engineered to coexpress tumor-specific receptors: persistence and antitumor activity in individuals with neuroblastoma," Nature Med., 2008, 14(11):1264-1270.

Qi L. et al., "Multiple effects of IL-21 on the ex vivo expansion of human primary NK cells," Immunology, Nov. 28, 2014, vol. 143, No. S2, p. 62-176, Poster Abstract 708.

Qian, L. et al., "Construction of a plasmid for co-expression of mouse membrane-bound form of IL-15 and RAE-18 and its biological activity," *Plasmid*, 65(3): 239-245 (2011).

Rajagopalan et al., Found: a cellular activating ligand for N Kp44, Blood, 122(17):2921-2922, Oct. 2013.

Ramos et al., "Chimeric antigen receptor (CAR)-engineered lymphocytes for cancer therapy," Expert Opin Biol Ther., 2011, 11(7):855-873.

Ramos, C.A., et al., "CD19-CAR Trials," The Cancer J. 20: 112-118 (2014).

Riddell, S.R., et al., "T-Cell Therapy of Leukemia," Cancer Control 9: 114-122 (2002).

Riley et al., "The CD28 family: a T-cell rheostat for therapeutic control of T-cell activation," Blood, 2005, 105:13-21.

Roberts et al., "Antigen-specific cytolysis by neutrophils and NK cells expressing chimeric immune receptors bearing $\zeta$ or $\gamma'$ signaling domains," J Immunol, Jul. 1998, 161(1): 375-384.

Robertson MJ, et al.; "Costimulation of human natural killer cell proliferation: role of accessory cytokines and cell contact-dependent signals", Nat Immun. 1996-1997; 15(5):213-226.

Rooney et al., "Use of gene-modified virus-specific T lymphocytes to control Epstein-Barr-virus-related lymphoproliferation," Lancet, Jan. 1995, 345(8941): 9-13.

Rosenberg et al., "Special Report: Use of tumor-infiltrating lymphocytes and interleukin-2 in the immunotherapy of patients with metastatic melanoma," N. Engl. J. Med., 1988, 319:1676-1680.

Rosenberg, S.A., et al., "Adoptive cell therapy for the treatment of patients with metastatic melanoma," Curr. Opin. Immunol. 21: 233-240 (2009).

Rosenfeld et al., "Phenotypic characterization of a unique non-T, non-B acute lymphoblastic leukaemia cell line," Nature, Jun. 1977, 267(5614): 841-843.

Rosenstein, M. et al., "Extravasation of intravascular fluid mediated by the systemic administration of recombinant interleukin 2," J Immunol, 137(5): 1735-1742 (1986).

Ross et al., "Classification of pediatric acute lymphoblastic leukemia by gene expression profiling," Blood, Oct. 2003, 102(8): 2951-2959.

Rossi, J.M., et al., "Phase 1 Biomarker Analysis of ZUMA-1 (KTEC19-101) Study: A Phase 1-2 Multi-Center Study Evaluating the Safety and Efficacy of Anti-CD19 CAR T cells (KTE-C19) in Subjects with Refractory Aggressive Non-Hodgkin Lymphoma (NHL)," Abstracted presented at the American Society of Hematology Annual Meeting, Orlando, Florida, available at https://ash.confex.com/ash/2015/webprogram/Paper80339.html. (Dec. 5-8, 2015).

Rossig C, et al., "Epstein-Barr virus-specific human T lymphocytes expressing antitumor chimeric T-cell receptors: potential for improved immunotherapy," Blood, 2002, 99:2009-2016.

Rossig et al., "Targeting of $G^{D2}$-positive tumor cells by human T lymphocytes engineered to express chimeric T-cell receptor genes," Int J Cancer, Oct. 2001, 94(2): 228-236.

Rowley, J. et al., "Expression of IL-15RA or an IL-15/IL-15RA fusion on CD8+ T cells modifies adoptively transferred T-cell function in cis," *European Journal of Immunology*, 39: 491-506 (2009).

Rubnitz, J.E. et al., "NKAML: a pilot study to determine the safety and feasibility of haploidentical natural killer cell transplantation in childhood acute myeloid leukemia," J Clin Oncol, 28(6): 955-959 (2010).

Ruggeri, L. et al., "Effectiveness of donor natural killer cell alloreactivity in mismatched hematopoietic transplants," Science, 295(5562): 2097-2100 (2002).

Sadelain et al., "The promise and potential pitfalls of chimeric antigen receptors," Curr Opin Immunol., 2009, 21(2):215-223.

Sadelain et al., "Targeting tumours with genetically enhanced T lymphocytes," Nat Rev Cancer. Jan. 2003;3(1):35-45.

Sadelain, M., "CAR Therapy: the CD19 Paradigm," J. Clin. Investigation 125: 3392-3400 (2015).

Sahm et al., "Expression of IL-15 in N K cells results in rapid enrichment and selective cytotoxicity of gene-modified effectors that carry a tumor-specific antigen receptor," Cancer Immunol. Immunother., 61 (9): 1451-1461, Feb. 2012.

Salih, H.R., et al., "Cutting Edge: Down-Regulation of MICA on Human Tumors by Proteolytic Shedding", The Journal of Immunology, 2002, 169:4098-4102.

Salomon and Bluestone, "Complexities of CD28/B7: CTLA-4 costimulatory pathways in autoimmunity and transplantation," Annu Rev Immunol, 2001, 19: 225-252.

Sambrook et al., "Molecular Cloning: A Laboratory Manual," (1989) [Table of Contents and Preface Only].

Sankhla, S.K., et al., "Adoptive immunotherapy using lymphokine-activated killer (LAK) cells and interleukin-2 for recurrent malignant primary brain tumors," J Neurooncol. 27: 133-140 (1995).

Santegoets, S.J. et al., "IL-21 promotes the expansion of CD27+ CD28+ tumor infiltrating lymphocytes with high cytotoxic potential and low collateral expansion of regulatory T cells," Journal of Translational Medicine, Feb. 12, 2013, vol. 11, No. 37, pages e1-e10.

Savoldo, B., et al., "CD28 costimulation improves expansion and persistence of chimeric antigen receptor modified T cells in lymphoma patients," J. Clin. Invest. 121(5):1822-1826 (2011).

Schmaltz et al., "T cells require TRAIL for optimal graft-versus-tumor activity," Nat Med, Dec. 2002, 8(12): 1433-7.

Schneider et al., "Characterization of EBV-genome negative "null" and "T" cell lines derived from children with acute lymphoblastic leukemia and leukemic transformed non-Hodgkin lymphoma," Int J Cancer, May 1977, 19(5): 621-626.

Schroers et al., "Gene transfer into human T lymphocytes and natural killer cells by Ad5/F35 chimeric adenoviral vectors," Exp Hematol, Jun. 2004, 32(6): 536-546.

Schulz, G., et al., "Detection of Ganglioside $G_{D2}$ in Tumor Tissues and Sera of Neuroblastoma Patients," Cancer Research 44: 5914-5920 (1984).

Schumacher, "T-cell-receptor gene therapy," Nat Rev Immunol, Jul. 2002, 2(7): 512-519.

(56) References Cited

OTHER PUBLICATIONS

Schwartz et al., "Structural basis for co-stimulation by the human CTLA-4/B7-2 complex," Nature, 410(6828):604-608, Mar. 29, 2001.
Schwarz et al., "ILA, the human 4-1BB homologue, is inducible in lymphoid and other cell lineages," Blood, Feb. 1995, 85(4): 1043-1052.
Scott, A.M. et al., "Antibody therapy of cancer," *Nat Rev Cancer*, 12(4): 278-287 (2012).
Sentman, C.L., et al., "NK Cell Receptors as Tools in Cancer Immunotherapy", Advances in Cancer Research, 2006, pp. 249-292.
Sentman, C.L., et al., "NKG2D CARs as Cell Therapy for Cancer", The Cancer Journal, vol. 20, No. 2, Mar./Apr. 2014, pp. 156-159.
Sheard, M.A. et al., "Membrane-bound TRAIL supplements natural killer cell cytotoxicity against neuroblastoma cells," Journal of Immunotherapy, 36(5): 319-329 (2013).
Shimasaki, N. et al., "A clinically adaptable method to enhance the cytotoxicity of natural killer cells against B-cell malignancies," Cytotherapy, 14(7): 830-840 (2012).
Shook et al., "Natural Killer Cell Engineering for Cellular Therapy of Cancer," National Institutes of Health, Tissue Antigens, vol. 78, No. 6, pp. 409-415, Dec. 2011.
Shuford, WW, et al., "4-1 BB costimulatory signals preferentially induce CD8+ T cell proliferation and lead to the amplification in vivo of cytotoxic T cell responses", J Exp Med. Jul. 7, 1997; 186(1): 47-55.
Shum et al., "Conservation and Variation in Human and Common Chimpanzee CD94 and NKG2 Genes," The American Association of Immunologists, The Journal of Immunology, pp. 240-252, Downloaded on Jun. 18, 2017.
Sica G, et al., "Modulation of the immune response through 4-1BB." In: Habib N, ed. Cancer gene therapy: past achievements and future challenges. New York: Kluwer Academic/Plenum Publishers; 355-362 (2000) [Book].
Slavik et al., "CD28/CTLA-4 and CD80/CD86 families: signaling and function," Immunol Res., 19(1):1-24, 1999.
Slavin et al., "Allogeneic cell therapy with donor peripheral blood cells and recombinant human interleukin-2 to treat leukemia relapse after allogeneic bone marrow transplantation," Blood, Mar. 1996, 87(6): 2195-2204.
Sneller, M.C. et al., "IL-15 administered by continuous infusion to rhesus macaques induces massive expansion of CD8+ T effector memory population in peripheral blood," Blood, 118(26): 6845-6848 (2011).
Somanchi, S.S. et al., "Expansion, purification, and functional assessment of human peripheral blood NK cells," Journal of Visualized Experiments, 48A: 2540 (2011).
Song et al., "Chimeric NKG2D CAR-Expressing T Cell-Mediated Attack of Human Ovarian Cancer is Enhanced by Histone Deacetylase Inhibition," Human Gene Therapy, vol. 24, pp. 295-305, Mar. 2013.
Spear et al., "Chimeric Antigen Receptor T Cells Shape Myeloid Cell Function within the Tumor Microenvironment through IFN-γ and GM-CSF," The Journal of Immunology, pp. 6389-6399, 2014.
Spear et al., "Collaboration of chimeric antigen receptor (CAR)-expressing T cells and host T cells for optimal elimination of established ovarian tumors," OncoImmunology, vol. 2, No. 2, 12 pages, Apr. 2013.
Spear et al., "NKG2D CAR T-cell therapy inhibits the growth of NKG2D ligand heterogeneous tumors," Immunology and Cell Biology, vol. 91, pp. 435-440, 2013.
Srinivasan et al., "A retro-inverso peptide mimic of CD28 encompassing the MYPPPY motif adopts a polyproline type II helix and inhibits encephalitogenic T cells in vitro," J Immunol., 167(1):578-585, Jul. 1, 2001.
Srivannaboon et al., "Interleukin-4 variant (BAY 36-1677) selectively induces apoptosis in acute lymphoblastic leukemia cells," Blood, Feb. 2001, 97(3): 752-758.
Stamper et al., "Crystal structure of the B7-1/CTLA-4 complex that inhibits human immune responses," Nature, 410(6828):608-611, Mar. 29, 2001.

Steel et al., "Interleukin-15 biology and its therapeutic implications in cancer," Trends Pharmacol. Sci. 33(1) :35-41, Jan. 2012.
Stein, P.H., et al., "The Cytoplasmic Domain of CD28 is both Necessary and Sufficient for Costimulation of Interleukin-2 Secretion and Association with Phosphatidylinositol 3'-Kinase," Mol. Cell. Biol. 14: 3392-3402 (1994).
Stong RC, et al., "Human acute leukemia cell line with the t(4;11) chromosomal rearrangement exhibits B lineage and monocytic characteristics," Blood, 1985,65:21-31.
Sullivan, L.C. et al., "The Heterodimeric Assembly of the CD94-NKG2 Receptor Family and Implications for Human Leukocyte Antigen-E Recognition," Immunity, 27(6): 900-911 (Dec. 2007).
Sun, J., et al., "Early transduction produces highly functional chimeric antigen receptor-modified virus-specific T-cells with central memory markers: a Production Assistant for Cell Therapy (PACT) translational application," J. Immunother. Cancer (2015).
Sundstrom and Nilsson, "Establishment and characterization of a human histiocytic lymphoma cell line (U-937)," Int J Cancer, May 1976, 17(5): 565-577.
Sussman et al., "Protein Data Bank (PDB): database of three-dimensional structural information of biological macromolecules," Acta Crystallogr D Biol Crystallogr., 54(Pt 6 Pt 1):1078-1084, Nov. 1, 1998.
Swerdlow, S.H. et al., eds., "WHO Classification of Tumours of Haematopoietic and Lymphoid Tissues," International Agency for Research on Cancer (IARC) (4th ed. 2008) (Excerpts).
Tacke et al., "CD28-mediated induction of proliferation in resting T cells in vitro and in vivo without engagement of the T cell receptor: evidence for functionally distinct forms of CD28," Eur J Immunol., 27(1):239-247, Jan. 1997.
Tagaya, Y. et al., "IL-15: a pleiotropic cytokine with diverse receptor/signaling pathways whose expression is controlled at multiple levels," Immunity, 4(4): 329-336 (1996).
Takahashi, C, et al., "Cutting edge: 4-1 BB is a bona fide CD8 T cell survival signal", J Immunol. May 1, 1999; 162(9):5037-5040.
Thomas et al., "Monoclonal antibody therapy with rituximab for acute lymphoblastic leukemia," Hematol Oncol Clin North Am., 23(5):949-971, Oct. 2009.
Topp, M.S., et al., "Universal chimeric immunoreceptors for targeting B-cell malignancies with engineered CTL: combining CD19-specific TCR ζ signaling with engineered CD28-mediated co-stimulation," Mol. Ther. 3(5)(part 2 of 2): S21 (2001).
Trinchieri et al., "Response of resting human peripheral blood natural killer cells to interleukin 2," J Exp Med, Oct. 1984, 160(4): 1147-1169.
Trompeter ct al., "Rapid and highly efficient genc transfer into natural killer cells by nucelofection," J Immunol Methods, Mar. 2003, 274(1-2): 245-256.
Tsukamoto, K. et al., "Juxtacrine function of interleukin-15/interleukin-15 receptor system in tumour derived human B-cell lines," *Clinical and Experimental Immunology*, 146(3): 559-566 (2006).
Turtle, "Therapy of B Cell Malignancies with CD19-Specific Chimeric Antigen Receptor Modified T Cells of Defined Subset Composition," Blood 124(21): 384, 6 pages, 2014.
Turtle, C.J., et al., Abstract, "A Phase I/II Clinical Trial of Immunotherapy for CD19+ B Cell Malignancies With Defined Composition of CD4+ and CD8+ Central Memory T Cells Lentivirally Engineered To Express a CD19-Specific Chimeric Antigen Receptor" Mol. Ther., 2014, 22(Supp.1):296.
Upshaw et al., "NKG2D-mediated signaling requires a DAP10-bound Grb2-Vav! intermediate and hosphatidylinositol-3-kinase in human natural killer cells," Nature Immunology, vol. 7, No. 5, pp. 524-532, May 2006.
Verdonck et al., "Donor leukocyte infusions for recurrent hematologic malignancies after allogeneic bone marrow transplantation: impact of infused and residual donor T cells," Bone Marrow Transplant, Dec. 1998, 22(11): 1057-1063.
Verma and Stock, "Management of adult acute lymphoblastic leukemia: moving toward a risk-adapted approach," Curr Opin Oncol, Jan. 2001, 13(1): 14-20.
Vinay, DS et al., "Role of 4-1 BB in immune responses", Seminars in Immunol. Dec. 1998; 10(6):481-489.

(56) References Cited

OTHER PUBLICATIONS

Viola, "The amplification of TCR signaling by dynamic membrane microdomains," Trends Immunol., 22(6):322-327, Jun. 2001.
Vivier, E. et al., "Innate or adaptive immunity? The example of natural killer cells," Science, 331(6013): 44-49 (2011).
Voss et al., "Targeting p53, hdm2, and CD19: vaccination and immunologic strategies," Bone Marrow Transplant., 25 Suppl 2:S43-S45, May 2000.
Vujanovic, L. et al., "Virally infected and matured human dendritic cells activate natural killer cells via cooperative activity of plasma membrane-bound TNF and IL-15," Blood, 116(4): 575-583 (2010).
Waldmann, T.A. et al., "Safety (toxicity), pharmacokinetics, immunogenicity, and impact on elements of the normal immune system of recombinant human IL-15 in rhesus macaques," *Blood*, 117(18): 4787-4795 (2011).
Walter et al., "Reconstitution of cellular immunity against cytomegalovirus in recipients of allogeneic bone marrow by transfer of T-cell clones from the donor," N Engl J Med, Oct. 1995, 333(16): 1038-1044.
Wang, et al., "Phase I Studies of central-memory-derived CD19 CAR T cell therapy following autologous HSCT in patients with B-Cell NHL," Blood (forthcoming 2016).
Warrens AN, et al., "Splicing by overlap extension by PCR using asymmetric amplification: an improved technique for the generation of hybrid proteins of immunological interest," Gene 20;186: 29-35 (1997).
Watzl, C., et al., "Signal Transduction During Activation and Inhibition of Natural Killer Cells", Curr Protoc Immunol., Aug. 2010, pp. 1-19.
Weijtens, M.E.M., et al., "Functional balance between T cell chimeric receptor density and tumor associated antigen density: CTL mediated cytolysis and lymphokine production," Gene Ther. 7: 35-42 (2000).
Weissman et al., "Molecular cloning and chromosomal localization of the human T-cell receptor ζ chain: Distinction from the molecular CD3 complex," PNAS USA, 1988, 85:9709-9713.
Westwood, J.A., et al., "Adoptive transfer of T cells modified with a humanized chimeric receptor gene inhibits growth of Lewis-Y expressing tumors in mice," PNAS 102(52): 19051-19056 (2005).
WHO, "WHO Classification of Tumours of Haematopoietic and Lymphoid Tissues," International Agency for Research on Cancer (IARC), 4th Edition, 40 pages, 2008.
Wilkie, S. et al., "Selective Expansion of Chimeric Antigen Receptor-targeted T-cells with Potent Effector Function Using Interleukin-4," J Biol Chem., vol. 295, No. 33, pp. 25538-25544 (2010).
Willimsky, G. and Blankenstein, T., "Sporadic immunogenic tumours avoid destruction by inducing T-cell tolerance," Nature 437: 141-146 (2005).
Wittnebel, S. et al., "Membrane-bound interleukin (IL)-15 on renal tumor cells rescues natural killer cells from IL-2 starvation-induced apoptosis," Cancer Research, 67(12): 5594-5599 (2007).
Wu and Lanier, "Natural killer cells and cancer," Adv Cancer Res, 2003, 90: 127-156.
Wu, et al. "An Activating Immunoreceptor Complex Formed by NKG2D and DAP10," Science, vol. 285, pp. 730-732, Jul. 30, 1999.
Wyss-Coray, T., et al., "The B7 adhesion molecule is expressed on activated human T cells: functional involvement in T-T cell interactions," Eur. J. Immunol., 23: 2175-2180 (1993).
Xu, Y., et al., "Closely related T-memory stem cells correlate with in vivo expansion of CAR.CD19-T cells and are preserved by IL-7 and IL-15," Blood 123(24):3750-3759 (2014).
Yan et al., "Murine CD8 lymphocyte expansion in vitro by artificial antigen-presenting cells expressing CD137L (4-1 BBL) is superior to CD28, and CD137L expressed on neuroblastoma expands CD8 tumour-reactive effector cells in vivo," Immunology, 2004, 112(1):105-116.
Ye et al., "Gene therapy for cancer using single-chain Fv fragments specific for 4-1BB," Nat Med, Apr. 2002, 8(4): 343-348.

Yeoh et al., "Classification, subtype discovery, and prediction of outcome in pediatric acute lymphoblastic leukemia by gene expression profiling," Cancer Cell, Mar. 2002, 1(2): 133-143.
Yoshida et al., "A novel adenovirus expressing human 4-1BB ligand enhances antitumor immunity," Cancer Immunol Immunother, Feb. 2003, 52(2): 97-106.
Zah, E. et al., "T Cells Expressing CD19/CD20 Bispecific Chimeric Antigen Receptors Prevent Antigen Escape by Malignant B Cells," Cancer Immunol Res, 4(6): 498-508 (Apr. 2016).
Zanoni, I. et al., "IL-15 cis presentation is required for optimal NK cell activation in lipopolysaccharide-mediated inflammatory conditions," *Cell Reports*, 4: 1235-1249 (2013).
Zeis, M. et al., "Allogeneic MHC-Mismatched Activated Natural Killer Cells Administered After Bone Marrow Transplantation Provide a Strong Graft-Versus-Leukemia Effect in Mice," BrJ Haematol, 1997, pp. 757-761, vol. 96.
Zhang et al., "Chimeric NKG2D-Modified T Cells Inhibit Systemic T-Cell Lymphoma Growth in a Manner Involving Multiple Cytokines and Cytotoxic Pathways," Cancer Research, vol. 67, No. 22, pp. 11029-11036, Nov. 15, 2007.
Zhang et al., "Chimeric NK-receptor-bearing T cells mediate antitumor immunotherapy," Gene Therapy, Blood, vol. 106, No. 5, pp. 1544-1551, Sep. 2005.
Zhang et al., "Generation of Antitumor Responses by Genetic Modification of Primary Human T Cells with a Chimeric NKG2D Receptor," Cancer Research, vol. 66, No. 11, pp. 5927-5933, Jun. 1, 2006.
Zhang et al., "Mouse Tumor Vasculature Expresses NKG2D Ligands and Can Be Targeted by Chimeric NKG2D-Modified T Cells," The Journal of Immunology, pp. 2455-2463, (2013) Downloaded Feb. 20, 2018.
Zhang, J. et al., "Characterization of interleukin-15-gene-modified human natural killer cells: implications for adoptive cellular immunotherapy," Haematologica, 89(3): 338-347 (2004).
International Search Report and Written Opinion for Int'l Application No. PCT/IB2019/000181, titled: Activating Chimeric Receptors and Uses Thereof in Natural Killer Cell Immunotherapy, Date Mailed: Jun. 28, 2019.
International Preliminary Report on Patentability for Int'l Application No. PCT/IB2019/000181, titled: Activating Chimeric Receptors and Uses Thereof in Natural Killer Cell Immunotherapy, Dated: Aug. 11, 2020.
U.S. Appl. No. 60/383,872, filed May 28, 2002 by Saidelain, et al.
Gillet et al., Selectable Markers for Gene Therapy. Chapter 26 of Gene and Cell Therapy:Therapeutic Mechanisms and Strategies, 3rd Ed. N .S. Templeton Ed, (CRC Press:Bpca Ratpm. FL), pp. 555 and 558, 2009.
Suerth et al., "Efficient Generation of Gene-Modified Human Natural Killer Cells via Alpharetroviral Vectors," J. Mol. Med. 94:83-93, 2016, published online Aug. 25, 2015.
Sokolic et al., "A Selectable Bicistronic Retroviral Vector Corrects the Molecular Defect in a Cell Line Derived from a Patient with Leukocyte Adhesion Deficiency," Biol. Blood Marrow Transpl. 12(2) Suppl 1: 20-21, Feb. 2006.
Abken, H. et al., "Antigen-specific T-cell activation independently of the MHC: chimeric antigen receptor-redirected T cells," Frontiers in Immunology, V. 4, Article 371, c. 4 (2013).
Calabrese, et al., "IL-6 biology: implications for clinical targeting in rheumatic disease," S. Nat. Rev. Rheumatol, 10, 720-727 (2014); published online Aug. 19, 2014 (corrected online Sep. 19, 2014).
Cordoba, S.P. et al., "The large ectodomains of CD45 and CD148 regulate their segregation from and inhibition of ligated T-cell receptor," Blood, The Journal of the American Society of Hematology, V. 121, N. 21, p. 4295-4302, c. 4301 (2013).
Culpepper, D.J. et al., "Systematic mutation and thermodynamic analysis of central tyrosine pairs in polyspecific NKG2D receptor interactions," Molecular Immunology, V. 48, N. 4, p. 516-523, c. 521-522 (2011).
de Felipe, P., "Polycistronic Viral Vectors," Current Gene Therapy, V. 2, N. 3, p. 355-378, c. 360 (2002).
Lanier, Lewis L., "NK Cell Recognition," Annual Review of Immunology, vol. 23, No. 1, pp. 225-274 (2005).

(56) References Cited

OTHER PUBLICATIONS

Lima, et al., "Interleukin-6 Neutralization by Antibodies Immobilized at the Surface of Polymeric Nanoparticles as a Therapeutic Strategy for Arthritic Diseases," ACS Appl. Mater. Interfaces 2018, 10, 13839-13850.
Zhao, Y. et al., "A Herceptin-Based Chimeric Antigen Receptor with Modified Signaling Domains Leads to Enhanced Survival of Transduced T Lymphocytes and Antitumor Activity," The Journal of Immunology, V. 183, N. 9, p. 5563-5574, c. 5568, 5571 (2009).
Denman et al., "Membrane-Bound IL-21 Promotes Sustained Ex Vivo Proliferation of Human Natural Killer Cells," PLoS One, vol. 7, Issue 1, Jan. 2012.
Dowell, A. C., "Studies of Human T cell Costimulation:Potential for the Immunotherapy of Cancer," A thesis submitted to The University of Birmingham for the degree of Doctor of Philosophy, CRUK Institute for Cancer Studies, 2010.
GenBank Accession No. NM_172175.2, *Homo sapiens* interleukin 15 (IL15), transcript variant 2, mRNA, dated Feb. 12, 2011, 4 pages.
Hasan, A.N., "Soluble and membrane-bound interleukin (IL)-15 Ra/IL-15 complexesmediate proliferation of high-avidity central memory CD81T cells foradoptive immunotherapy of cancer and infections," Clinical and Experimental Immunology, 186: 249-265, 2016.
Leitner et al., "T cell stimulator cells, an efficient and versatile cellular system to assess the role of costimulatory ligands in the activation of human T cells," Journal of Immunological Methods, 362, 131-141, 2010.
Oyer et al., "Natural killer cells stimulated with PM21 particles expand and biodistribute in vivo: Clinical implications for cancer treatment," Cytotherapy, 18: 653-663, 2016.
Wang et al., "Human NK cells maintain licensing status and are subject to killer immunoglobulin-like receptor (KIR) and KIR-ligand inhibition following ex vivo expansion," Cancer Immunol Immunother, 65:1047-1059, 2016.
Zhang et al., "Improving Adoptive T Cell Therapy by Targeting and Controlling IL-12 Expression to the Tumor Environment," The American Society of Gene & Cell Therapy Molecular Therapy, vol. 19, No. 4, 751-759, 2011.
Eyquem et al., "Targeting a CAR to the TRAC locus with CRISPR/Cas9 enchances tumour rejction" Nature, 2017, 543 (7643): 113-117.
Seif et al., "The role of JAK-STAT signaling pathway and its regulators in the fate of T helper cells" Cell Communication and Signaling (2017) 15:23.
Themeli et al., "Generation of tumor-targeted human T lympocytes from Induced pluripotent stem cells for cancer therapy", Nat Biotechnol., 2013; 31(10): 028-933.
Watowich et al., "The Erythropoietin Receptor: Molecular Structure and Hematopoietic Signaling Pathways," J. Investig Med. 2011, 59(7): 1067-1072.
AASEQ1_05172022_135256_pep_vs_AASEQ2_05172022_135256_pep_align_4-1 BBL, May 17, 2022.
Atreya, et al., "Blockade of interleukin 6 trans signaling suppresses T-cell resistance against apoptosis in chronic intestinal inflammation: Evidence in Crohn disease and experimental colitis in vivo" Nature Medicine, vol. 6, No. 5, May 2000; pp. 583-588.
Barrett, et al., "Interleukin 6 Is Not Made By Chimeric Antigen Receptor T Cells and Does Not Impact Their Function" Blood (2016) 128(22):654.
Bedouelle, et al., "Diversity and junction residues as hotspots of binding energy in an antibody neutralizing the dengue virus" FEBS Journal 273 (2006) 34-46.
Berger, C. et al., "CD28 costimulation and immunoaffinity-based selection efficiently gernate primary gene-modified T cells for adoptive immunotherapy," Blood, 101:: 476-484 (2003).
Brentjens, et al., "Eradication of systemic B-cell tumors by genetically targeted human T lymphocytes co-stimulated by CD80 and interleukin-15" Nat. Med. 2003; 9(3):279-286.
Brown, et al., "Tolerance to Single, but Not Multiple, Amino Acid Replacements in Antibody VH CDR2" J. Immunol. May 1, 1996; 156(9):3285-91.
Colman, "Effects of amino acid sequence changes on antibody-antigen interactions" Research in Immunology 145:33-36 (1994).
Frankel et al., "Characterization of diphtheria fusion proteins targeted to the human interleukin-3 receptor" Protein Eng., 2000, v.13, n.8, p. 575-581.
Gillet et al., "Selectable markers for gene therapy," Chapter 27 of Gene and Cell Therapy: Therapeutic Mechanisms and Strategies, 3rd Ed. N .S. Templeton Ed, (CRC Press:Boca Raton, FL), pp. 701-738 (2009).
Hong, et al., "Interleukin-6 expands homeostatic space for peripheral T cells" Cytokine 64 (2013) pp. 532-540.
Hopp et al., "A Short Polypeptide Marker Sequence Useful for Recombinant Protein Identification and Purification" Bio/ Technology, vol. 6, pp. 1204-1210 (Oct. 1988).
Iacobucci et al., Truncating Erythropoietin Receptor Rearrangements in Acute Lymphoblastic Leukemia, Cancer Cell, vol. 29, No. 2, pp. 186-200, published on Feb. 8, 2016.
Jiang, Z., et al., "IL-6 trans-signaling promotes the expansion and anti-tumor activity of CAR T cells" Leukemia (2021) 35; pp. 1380-1391.
Kontermann, et al., "Bispecific antibodies," Drug Discovery Today, 2015, v. 7, n. 20, p. 838-847, Fig. 1.
Lee, et al., "Current concepts in the diagnosis and management of cytokine release syndrome" Blood, Jul. 10, 2014, vol. 124, No. 2, 188-195.
Li, et al., "IL-6 Promotes T Cell Prolif era ti on and Expansion under Inflammatory Conditions in Association with Low-Level ROR-yt Expression" J. Immunol (2018) 201(10); pp. 2934-2946.
Morgan, et al., "Case Report of a Serious Adverse Event Following the Administration of T Cells Transduced With a Chimeric Antigen Receptor Recognizing ERBB2" Molecular Therapy, vol. 18, No. 4, 843-851, Apr. 2010.
Nish, et al., "T cell-intrinsic role of IL-6 signaling in primary and memory responses" eLife 2014;3:e01949.
Pelechas et al., "Sirukumab: a promising therapy for rheumatoid arthritis" Expert Opinion On Biological Therapy, 2017, vol. 17, No. 6, 755-763.
Rochman, et al., "IL-6 Increases Primed Cell Expansion and Survival" The Journal of Immunology (2005) 174(8); pp. 4761-4767.
Rudikoff, et al., "Single amino acid substitution altering antigen-binding specificity" Proc. Natl Acad. Sci. USA, vol. 79, pp. 1979-1983, Mar. 1982.
Teachey, et al., "Identification of Predictive Biomarkers for Cytokine Release Syndrome after Chimeric Antigen Receptor T-cell Therapy for Acute Lymphoblastic Leukemia" Cancer Discovery, Jun. 2016, pp. 664-679.
Vajdos, et al., "Comprehensive Functional Maps of the Antige••binding Site of an Anti-Erb82 Antibody Obtained with Shotgun Scanning Mutagenesis" J. Mol. Biol. (2002) 320, 415-428.

\* cited by examiner

MSCV-DAP12-P2A-NKG2C(165-168 SIIS)-T2A-CD94-IRES-GFP

FIG. 1B

HLA - E Signal Peptide
(21 aa - SEQ ID. NO. 69)
MVDGTLLLLLSEALALTQTWA

HLA - G Signal Peptide
(21 aa - SEQ ID. NO.70)
MVVMAPRTLFLLLSGALTLTETWA    + HLA - E Mature Protein

MSCV-NKG2A-CD8tm-41BB-CD3ζ-IRES-GFP

MSCV-CD94-CD8tm-41BB-CD3ζ-IRES-GFP

FIG. 6B

| SEQ ID NO. 1 | Full Length NKG2D DNA |
| --- | --- |
| SEQ ID NO. 2 | Truncated NKG2D DNA |
| SEQ ID NO. 3 | Codon Optimized Truncated NKG2D DNA |
| SEQ ID NO. 4 | CD8 Signaling Sequence DNA |
| SEQ ID NO. 5 | CD8 Alpha Hinge DNA |
| SEQ ID NO. 6 | CD8 Beta DNA |
| SEQ ID NO. 7 | CD16 Alpha DNA |
| SEQ ID NO. 8 | CD16 Beta DNA |
| SEQ ID NO. 9 | 2B4 PROTEIN |
| SEQ ID NO. 10 | DAP 10 DNA |
| SEQ ID NO. 11 | DAP 12 DNA |
| SEQ ID NO. 12 | 4-1BB DNA |
| SEQ ID NO. 13 | CD3-Zeta DNA |
| SEQ ID NO. 14 | Canonical Hemi-tam PROTEIN |
| SEQ ID NO. 15 | ITSM Motif PROTEIN |
| SEQ ID NO. 16 | Membrane-Bound IL 15 DNA |
| SEQ ID NO. 17 | Membrane-Bound IL 15 PROTEIN |
| SEQ ID NO. 18 | NKG2D/CD8a/4-1BB/CD3z DNA |
| SEQ ID NO. 19 | NKG2D/CD8a/4-1BB/CD3z PROTEIN |
| SEQ ID NO. 20 | NCR1 TM/IC Domains PROTEIN |
| SEQ ID NO. 21 | Full Length NCR2 PROTEIN |
| SEQ ID NO. 22 | NCR3 TM/IC Domains PROTEIN |
| SEQ ID NO. 23 | NKG2D/CD16 DNA |
| SEQ ID NO. 24 | NKG2D/CD16 PROTEIN |
| SEQ ID NO. 25 | CD8 Sig Seq/NKG2D Cod Opt ECD/CD8a Hinge/CD16 Tm/CD16 ICR/4-1BB ICR DNA |
| SEQ ID NO. 26 | CD8 Sig Seq/NKG2D Cod Opt ECD/CD8a Hinge/CD16 Tm/CD16 ICR/4-1BB ICR PROTEIN |
| SEQ ID NO. 27 | NKG2D/NCR1 DNA |
| SEQ ID NO. 28 | NKG2D/NCR1 PROTEIN |
| SEQ ID NO. 29 | NKG2D/NCR3 DNA |
| SEQ ID NO. 30 | NKG2D/NCR3 PROTEIN |
| SEQ ID NO. 31 | Motif for GS Linker PROTEIN |
| SEQ ID NO. 32 | $GS_3$/CD8a Hinge PROTEIN |
| SEQ ID NO. 33 | GS9 PROTEIN |

FIG. 9

| | |
|---|---|
| SEQ ID NO. 34 | GS3 PROTEIN |
| SEQ ID NO. 35 | 2B4 ICR PROTEIN |
| SEQ ID NO. 36 | 2B4 ICR DNA |
| SEQ ID NO. 37 | NKp80 ICR PROTEIN |
| SEQ ID NO. 38 | NKp80 ICR DNA |
| SEQ ID NO. 39 | B2Ad N-Term ECD PROTEIN |
| SEQ ID NO. 40 | B2 AdR N-Term ECD DNA |
| SEQ ID NO. 41 | B2 AdR First TM Helix PROTEIN |
| SEQ ID NO. 42 | B2 AdR First TM Helix DNA |
| SEQ ID NO. 43 | NK15_1 c/ CD8a Hinge Increase-CD8a Signal Seq/NKG2D Cod Opt/GS3/CD8a Hinge/CD16 TM/CD16 ICR/4-1BB ICR DNA |
| SEQ ID NO. 44 | NK15_2 c/ CD8a Hinge Decrease-CD8a Sig Seq/NKG2D Cod Opt/GS3/CD16 TM/CD16 ICR/4-1BB ICR DNA |
| SEQ ID NO. 45 | NK15_3 c/ CD8a Hinge Decrease-CD8a/NKG2D Cod Opt/CD16 TM/CD16 ICR/4-1BB ICR DNA |
| SEQ ID NO. 46 | CD8a/NKG2D/CD8a Hinge/CD8a TM/4-1BB ICR/2B4 ICR DNA |
| SEQ ID NO. 47 | CD8a/NKG2D/ADRB2 N-Term ECD/ADRB2 First Tm/4-1BB ICR/2B4 ICR DNA |
| SEQ ID NO. 48 | CD8a/NKG2D/CD8a Hinge/CD8a Tm/4-1BB ICR/2B4 ICR/GS/NKp80 ICR DNA |
| SEQ ID NO. 49 | CD8a/NKG2D/CD8a Hinge/CD8a Tm/4-1BB ICR/ NKp80 ICR DNA |
| SEQ ID NO. 50 | CD8a/NKG2D Cod Opt/GS3/NKG2D ECD/ADRB2 EC/ADRB2 Tm/4-1 BB ICR/NKp80 ICR DNA |
| SEQ ID NO. 51 | CD8a/NKG2D Cod Opt/GS3/NKG2D ECD/CD8a Hinge/CD8a Tm/4-1 BB ICR/NKp80 ICR DNA |
| SEQ ID NO. 52 | CD8a Signal Seq/NKG2D Cod Opt ECD/GS3/NKG2D ECD/CD8a Hinge/CD16 TM/CD16 ICR/4-1BB ICR DNA |
| SEQ ID NO. 53 | CD8a Signal Seq/NKG2D Cod Opt ECD/CD8a Hinge/CD16 TM/CD16 ICR/4-1BB ICR/2B4 ICR DNA |
| SEQ ID NO. 54 | CD8a Signal Seq/NKG2D Cod Opt ECD/CD8a Hinge/CD16 TM/CD16 ICR/4-1BB ICR/NKp80 ICR DNA |
| SEQ ID NO. 55 | FLAG Tag PROTEIN |
| SEQ ID NO. 56 | His Tag PROTEIN |
| SEQ ID NO. 57 | Myc Tag PROTEIN |

FIG. 9
(Continued)

ACTIVATING CHIMERIC RECEPTORS AND USES THEREOF IN NATURAL KILLER CELL IMMUNOTHERAPY

RELATED APPLICATIONS

This application is the U.S. National Stage of International Application No. PCT/IB2019/000181, filed Feb. 7, 2019, which designates the U.S., published in English, and claims the benefit of U.S. Provisional Application No. 62/628,788, filed Feb. 9, 2018 and U.S. Provisional Application No. 62/736,879, filed Sep. 26, 2018. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
  a. File name: 4459_1147_002 Seq_List.txt; created Feb. 6, 2019, 86.4 KB in size.

BACKGROUND

The emergence and persistence of many diseases is characterized by an insufficient immune response to aberrant cells, including malignant and virally infected cells. Immunotherapy is the use and manipulation of the patient's immune system for treatment of various diseases.

SUMMARY

Immunotherapy presents a new technological advancement in the treatment of disease, wherein immune cells are engineered to express certain targeting and/or effector molecules that specifically identify and react to diseased or damaged cells. This represents a promising advance due, at least in part, to the potential for specifically targeting diseased or damaged cells, as opposed to more traditional approaches, such as chemotherapy, where all cells are impacted, and the desired outcome is that sufficient healthy cells survive to allow the patient to live. One immunotherapy approach is the recombinant expression of activating chimeric receptors in immune cells to achieve the targeted recognition and destruction of aberrant cells of interest.

To address this need for specifically targeting and destroying, disabling or otherwise rendering inert diseased or infected cells, there are provided for herein polynucleotides, amino acids, and vectors that encode activating chimeric receptors that impart enhanced targeting and cytotoxicity to cells, such as natural killer cells. Also provided for are methods for producing the cells, and methods of using the cells to target and destroy diseased or damaged cells. In several embodiments, there is provided a polynucleotide encoding an activating chimeric receptor comprising an extracellular receptor domain and an effector domain comprising a transmembrane region and an intracellular signaling domain, wherein the extracellular receptor domain comprises a peptide that binds an immune antigen with high affinity.

For example, in several embodiments, there is provided a polynucleotide encoding an activating chimeric receptor that comprises an extracellular receptor domain that comprises an engineered variant of Natural Killer Group 2 member C (NKG2C) having higher affinity for an immune ligand of NKG2C. In several embodiments, the polynucleotide is designed to impart to the encoded NKG2C variant an enhanced binding affinity for an immune ligand, such as the HLA-E/peptide complex, relative to native NKG2C, whereas a non-engineered NKG2C has lower binding affinity for HLA-E/peptide complex. In several embodiments, an engineered NKG2C variant is used in the absence of a native or engineered NKG2A variant. In several embodiments, full length, or other native truncated form of, NKG2C is not used.

In several embodiments, there is provided a polynucleotide encoding an activating chimeric receptor that comprises or an extracellular receptor domain that comprises a fragment of Natural Killer Group 2 member A (NKG2A), the fragment engineered to transduce activation signals, rather than inhibitory signals, upon binding of an immune ligand, such as the HLA-E/peptide complex. In several embodiments, an engineered NKG2A variant is used in the absence of a native or engineered NKG2C variant. In several embodiments, full length, or other native truncated form of, NKG2A is not used.

In several embodiments, the activating chimeric receptor encoded by the polynucleotide comprises an effector domain that comprises a transmembrane region and an intracellular signaling domain, those domains serving to transduces activation and/or costimulatory signals following binding of the chimeric receptor (with enhanced affinity) to an immune antigen, such as the HLA-E/peptide complex. In several embodiments, the extracellular receptor domain comprises an engineered NKG2C variant coupled to an effector domain comprising a transmembrane region and an intracellular signaling domain. In several embodiments, the engineered NKG2C variant extracellular domain is coupled to a native NKG2C transmembrane region and/or a native NKG2C intracellular signaling domain. In several embodiments, the engineered NKG2C variant comprises the amino acid sequence of SEQ ID NO. 58. In several embodiments, the engineered NKG2C variant is encoded by the nucleic acid sequence of SEQ ID NO: 63, or a fragment thereof. In some embodiments, the NKG2C variant has at least about 70%, about 75%, about 80%, about 85%, about 90%, about 95%, about 98%, or about 99% homology as compared to SEQ ID NO: 63.

In several embodiments, the activating chimeric receptor comprises a fragment of NKG2A coupled to an effector domain comprising a transmembrane region and an intracellular signaling domain. In several embodiments, the NKG2A fragment is coupled to a native NKG2A transmembrane region and/or a native NKG2A intracellular signaling domain. In several embodiments, the NKG2A fragment is coupled to a native NKG2C transmembrane region and/or a native NKG2C intracellular signaling domain. In several embodiments, the NKG2A fragment has the sequence of SEQ ID NO: 65. In several embodiments, the fragment of NKG2A has at least about 70%, about 75%, about 80%, about 85%, about 90%, about 95%, about 98%, or about 99% homology as compared to SEQ ID NO: 65. In one embodiment, the NKG2A fragment is coupled to a CD8a transmembrane domain and an effector domain comprising one or more of 4-1BB and CD3zeta. In several embodiments, such an activating chimeric receptor construct is encoded by the nucleic acid sequence of SEQ ID NO: 61 or comprises the amino acid sequence of SEQ ID NO: 62.

In several embodiments, other signaling moieties are used within the effector domain. For example, in several embodiments, the polynucleotide further encodes DNAX-activating protein 12 (DAP12) or DAP10. In several embodiments, however, DAP10 is not included in the activating receptor construct and/or is not included in another engineered construct expressed by cells. Likewise, in several embodiments, DAP12 is not included in the activating receptor construct and/or is not included in another engineered construct expressed by cells. In several embodiments, the polynucleotide encodes native CD94 or a chimeric CD94. In several embodiments, the chimeric CD94 comprises an extracellular receptor domain comprising a fragment of CD94 and an effector domain comprising a transmembrane region and an intracellular signaling domain. In additional embodiments, a chimeric CD94 receptor comprises a fragment of CD94 coupled a CD8a transmembrane domain and an effector domain comprising one or more of 4-1BB and CD3zeta. In several embodiments, the chimeric CD94 is encoded by the nucleic acid sequence of SEQ ID NO: 59. In several embodiments, the chimeric CD94 comprises the amino acid sequence of SEQ ID NO: 60. Variants, fragments, or truncations of CD94 are also used in some embodiments. For example, in several embodiments, a CD94 variant having at least about 70%, about 75%, about 80%, about 85%, about 90%, about 95%, about 98%, or about 99% homology as compared to SEQ ID NO: 59 or 60 is used. In one embodiment the fragment of CD94 has at least 80% homology to SEQ ID NO: 67. In one embodiment the fragment of CD94 has at least 80% homology to SEQ ID NO: 68.

In several embodiments, the effector domain comprises one or more of CD16, NCR1, NCR2, NCR3, 4-1BB, NKp80, DAP10, CD3zeta, 2B4. Actively signaling fragments of any of these signaling moieties are also useful, according to some embodiments.

In several embodiments, the activating chimeric receptor further comprises a linker and/or a hinge region. In several embodiments, these regions (if included) can function to space apart other portions of the molecule, for example to reduce steric hindrance of the receptor, and/or to reduce or eliminate functional issues that may result upon formation of tertiary structures. In several embodiments, the activating chimeric receptor comprises a GS linker that can optionally be repeated two or more times. For example, in several embodiments the GS linker is repeated 3, 4, 5, 6 or more times. In several embodiments, the hinge region comprises a glycine-serine repeating motif having the amino acid sequence of SEQ ID NO: 31. Repeats need not be in a "head to tail" format serially, but can be spaced apart from one another. In several embodiments, the chimeric receptor comprises a hinge region. Some embodiments employ hinges encoded by nucleic acid sequence of SEQ ID NO: 5. Additional embodiments employ a hinge region encoded by a fragment of the nucleic acid sequence of SEQ ID NO: 5. In several embodiments, the hinge region comprises the amino acid sequence of SEQ ID NO: 32 or SEQ ID NO: 33. In several embodiments, the hinge region is encoded by the nucleic acid sequence of SEQ ID NO: 34. Some embodiments employ portions of the beta-adrenergic receptor as a hinge region. Some embodiments employ a hinge region is encoded by the nucleic acid sequence of SEQ ID NO: 40 or of SEQ ID NO: 42.

In several embodiments, a signal peptide is also provided. Thus, in several embodiments, the extracellular receptor domain further comprises a CD8a signal peptide, wherein the signal peptide comprises the nucleic acid sequence of SEQ ID NO. 4.

In order to facilitate and, in some embodiments, enhance activating signaling by the chimeric receptors disclosed, the effector domain is configured to include one or more hemi-ITAM sequences. In several embodiments, the hemi-ITAM comprises either the amino acid sequence of SEQ ID NO. 14 or the amino acid sequence of SEQ ID NO. 37. In some embodiments, wherein more than one sequence of hemi-ITAM (or other transmembrane or signaling component) is provided, the ultimate construct encoded by the polynucleotide may utilize a mixture of the sequences (e.g., hetero-tandem signaling domains). In several embodiments, the effector domain comprises one or more ITSM sequences. For example, the ITSM, in several embodiments, comprises the amino acid sequence of SEQ ID NO. 15 and/or the amino acid sequence of SEQ ID NO. 35

In several embodiments, the polynucleotide further encodes a chimeric receptor comprising an extracellular receptor domain that binds native ligands of Natural Killer Group 2 member D (NKG2D) and an effector domain comprising a transmembrane region and an intracellular signaling domain that serve to transduce signals to a cell expressing the chimeric receptor upon binding of an NKG2D ligand. In several embodiments, the chimeric receptor does not employ full-length or wild-type NKG2D, but rather a fragment of NKG2D that retains the ability to bind one or more ligands of NKG2D. In several embodiments, the chimeric receptor that binds NKG2D is provided on a separate polynucleotide from that encoding the activating receptor (yet ultimately both can be co-expressed in a single cell).

In several embodiments, the polynucleotide also encodes a short hairpin RNA (shRNA) that specifically inhibits transcription or translation of native NKG2A. In such embodiment, the shRNA that inhibits transcription or translation of native NKG2A results in a reduced, if not eliminated, expression of NKG2A on cells expressing the polynucleotide. In some embodiments, this reduces the competition for an immune antigen between the higher affinity NKG2A and NKG2C. As a result, the relatively lower affinity NKG2C receptor is able to bind an immune antigen (such as the HLA-E/peptide complex) and transduce activating signals to the cell (such as an NK cell). In one embodiment, the shRNA comprises a nucleotide sequence that hybridizes under stringent conditions to the native NKG2A gene and comprises a sense fragment being substantially identical to a target sequence in the NKG2A gene (that target sequence being absent from the NKG2A fragment), and an antisense fragment, wherein the sense and antisense fragments are separated by a loop fragment. Other mechanisms to reduce native NKG2A receptor expression can also be employed, depending on the embodiment. For example, a separate vector could be used that comprises antisense sequences to disrupt native NKG2A receptor production (but spares production of engineered NKG2A fragments/constructs as disclosed herein). Gene editing techniques can also be employed to selective trim one or more regions of DNA encoding native NKG2A receptors. Immune or mechanical separation techniques (affinity immobilization) can also be used to selectively deplete cell populations, such as immune cells like NK or T cells, of cells expressing NKG2A receptors.

In several embodiments, the provided polynucleotide encodes, or is co-expressed with an additional construct that encodes, membrane-bound interleukin 15 (mbIL15). Membrane-bound IL15 facilitates, in several embodiments, the expansion of cells expressing the activating chimeric receptors disclosed herein.

In some embodiments, the polynucleotide is an mRNA. In several embodiments, the polynucleotide is operably linked to at least one regulatory element for the expression of the activating chimeric receptors.

In addition to polynucleotides, there are provided herein vectors that comprise the polynucleotides, the vectors configured to deliver and facilitate the expression of the protein encoded by the polynucleotide in a cell, such as an immune cell (e.g., a NK cell). In several embodiments, the vector is a retrovirus, such as a lentivirus or HIV. Additional embodiments provide for other vectors, such as adenovirus, adeno-associated virus and even non-viral vectors (e.g., liposomes).

Additionally provided for herein are genetically engineered cells, such as immune cells, that comprise the polynucleotide(s) disclosed herein and express the activating chimeric receptor(s). Various immune cells are employed depending on the embodiment. In several embodiments, NK cells are used. In some embodiments, autologous cells (e.g., NK cells) engineered to express the activating chimeric receptors are provided. Additional embodiments provide for allogeneic cells (e.g., NK cells) engineered to express the activating chimeric receptors disclosed herein. In several embodiments, the cell populations are enriched for high affinity activating chimeric receptors. In one embodiment, enrichment comprises converting (e.g., by expressing the polynucleotides disclosed herein) inhibitory NKG2A receptors into activating NKG2A receptors. Additionally, this conversion can be coupled with expression of engineered NKG2C receptors having increased affinity for ligands that result in NKG2C transmitting activating signals. Moreover, cell populations can be configured to lack surface expression of native NKG2A, either through genetic modulation of the nucleic acids encoding native NKG2A and/or by selective depletion of cells expressing native NKG2A from a population.

Also provide for herein is a genetically engineered immune cells, such as a NK cell, comprising an activating chimeric receptor that is either an engineered NKG2C receptor having increased affinity for antigens or an NKG2A variant that has been converted from an inhibitory receptor to an activating receptor. In several embodiments, such cells may also include one or more of a polynucleotide encoding a chimeric receptor configured to bind native ligands of Natural Killer Group 2 member D (NKG2D) through an extracellular receptor domain (and comprising an effector domain comprising a transmembrane region and an intracellular signaling domain), a polynucleotide encoding membrane-bound interleukin 15 (mbIL15), a polynucleotide encoding a short hairpin RNA (shRNA) that specifically inhibits transcription or translation of native NKG2A or combinations thereof.

Also provided for herein are methods for enhancing immune cell cytotoxicity in a mammal by administering to said mammal immune cell cells, wherein said immune cell cells express an activating chimeric receptor that is either an engineered NKG2C receptor having increased affinity for antigens or an NKG2A variant that has been converted from an inhibitory receptor to an activating receptor. Various immune cells are employed depending on the embodiment. In several embodiments, NK cells are used. In some embodiments, autologous cells (e.g., NK cells) engineered to express the activating chimeric receptors are provided. Additional embodiments provide for allogeneic cells (e.g., NK cells) engineered to express the activating chimeric receptors disclosed herein. In several embodiments, the methods further comprise depleting a population of cells to be administered to a subject of cells expressing native NKG2A. In several embodiments, depletion results in a 20%, 25%, 30%, 40%, or 50% (or more) reduction in cells expression native NKG2A. In several embodiments, the enhanced immune cell-based cytotoxicity is used in treating or preventing cancer or an infectious disease.

Also provided for herein is the use of a polynucleotide encoding an activating chimeric receptor in the manufacture of a cell-based medicament for enhancing Natural Killer (NK) cell cytotoxicity. As discussed herein, in the generation of the medicament, the activating chimeric receptor can be an engineered NKG2C receptor having increased affinity for antigens or an NKG2A variant that has been converted from an inhibitory receptor to an activating receptor. In several embodiments, both engineered NKG2C and NKG2A variants are used in manufacture of a medicament for the treatment of cancer or an infectious disease.

The compositions and related methods summarized above and set forth in further detail below describe certain actions taken by a practitioner; however, it should be understood that they can also include the instruction of those actions by another party. Thus, actions such as "administering a population of NK cells expressing an activating chimeric receptor" include "instructing the administration of a population of NK cells expressing an activating chimeric receptor."

BRIEF DESCRIPTION OF THE DRAWINGS

FIGS. 1A-1B depict an engineered receptor according to several embodiments disclosed herein. FIG. 1A depicts a schematic showing an engineered Natural Killer Group 2 C (NKG2C) variant engineered for high affinity to HLA-E/peptide complex (165-168 SIIS) in a complex with CD94 and a Dap12 dimer (termed "D12(SIIS)2C94" herein), according to several embodiments disclosed herein. FIG. 1B depicts a schematic of a construct comprising NKG2C (165-168 SIIS), Dap12, and CD94 inserted into a MSCV retroviral vector containing green fluorescence protein (GFP) after an internal ribosomal entry site (IRES), according to several embodiments disclosed herein.

FIG. 3A depicts the substitution of HLA-E signal peptide with HLA-G signal peptide of HLA-E (designated as GpHLA-E; HLA-G signal peptide carrying HLA-E). FIG. 3B depicts flow cytometry data related to the exogenous expression of GpHLA-E in solid tumor cell lines HT29, U2OS, ES8, and EW8.

FIG. 5A depicts flow cytometry data related the NKG2A depletion of NK cells to generate a population of NKG2A(−) NK cells. FIG. 5B depicts data related to cytotoxicity assays, at the indicated E:T ratios, of mock transduced NKG2A(−) NK cell populations or D12 (SIIS)2C94-transduced NKG2A(−) NK cells against the genetically-modified tumor cell lines (i) HT29-GpHLA-E and (ii) U2OS-GpHLA-E, incubated with or without anti-NKG2A antibody Z199.

FIGS. 6A-6B depict schematics of an embodiment of a chimeric receptor as disclosed herein. FIG. 6A depicts a schematic showing truncated forms of Natural Killer Group 2 member A (NKG2A) and CD94 wherein there is a deletion of the N-terminus portion of the transmembrane and inhibitory cytoplasmic domain and replacement with the CD8a transmembrane domain and cytoplasmic domains of 4-1BB (CD137) and CD3zeta, according to several embodiments disclosed herein. The activating NKG2A receptor and chimeric CD94 receptor form an activating complex (termed "2A/94BBz" herein), according to several embodiments disclosed herein. FIG. 6B depicts schematics of constructs comprising chimeric CD94 and activating NKG2A receptor inserted into a MSCV retroviral vector containing green fluorescence protein (GFP) after an internal ribosomal entry site (IRES), according to several embodiments disclosed herein.

FIG. 9 provides non-limiting embodiments of constructs and portions thereof according to several embodiments of the invention.

DETAILED DESCRIPTION

General

Figure 1A:
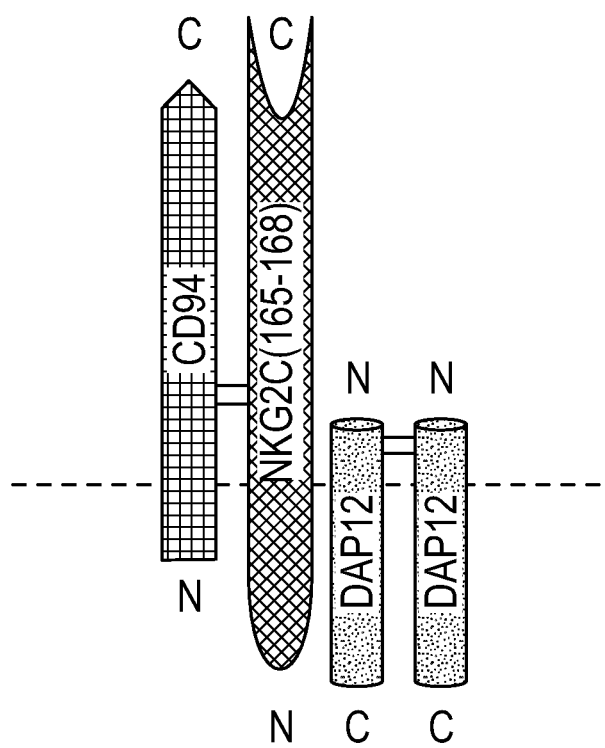
Figure 2A:
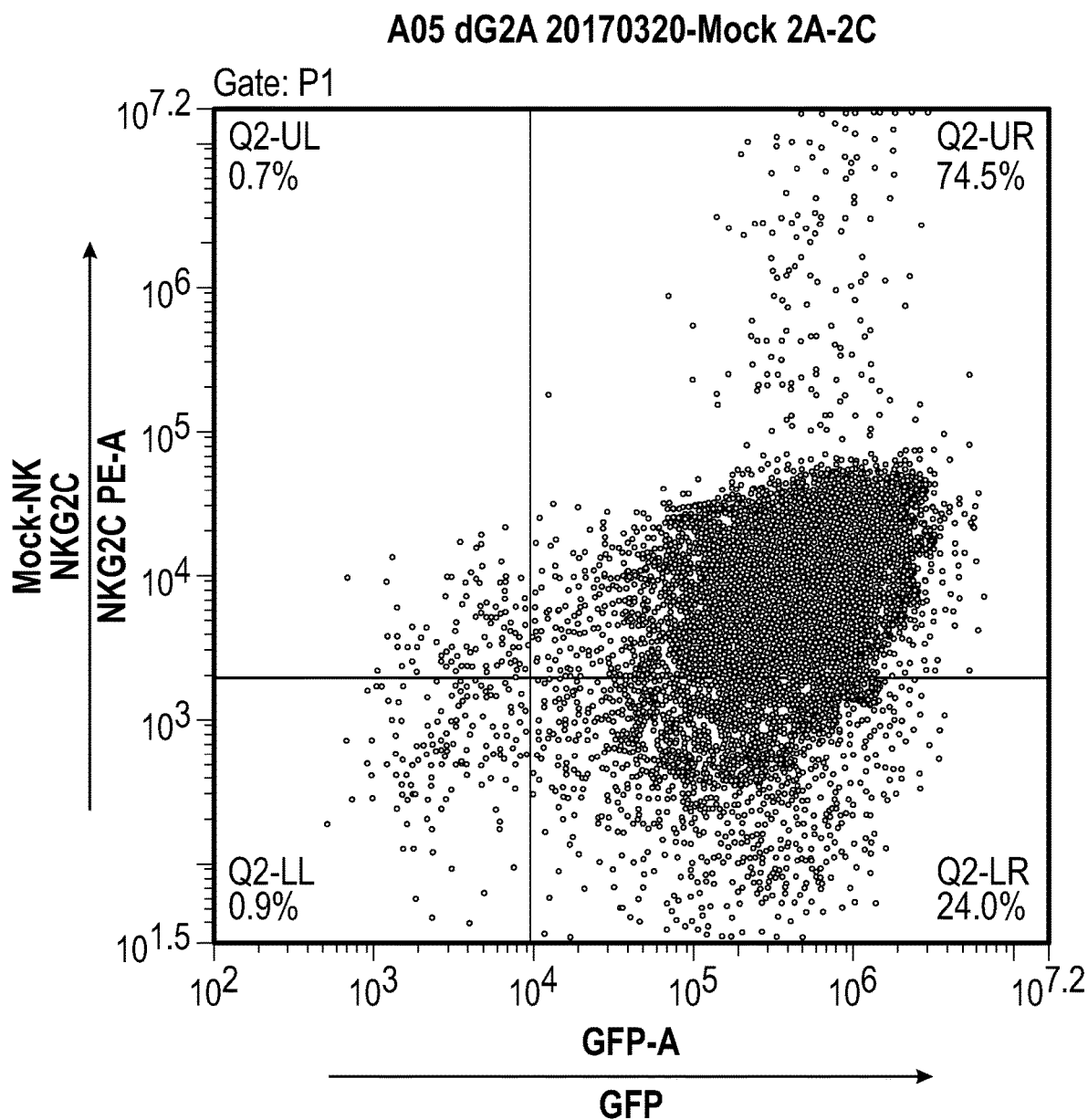
FIGS. 2A-2F depict flow cytometry data related to the expression of the high affinity activating D12(SIIS)2C94 receptor complex in purified NKG2C(+)NKG2A(−) NK cells. The D12(SIIS)2C94 expression profiles of NK cells transduced with a vector containing GFP only (FIGS. 2A-2C) and NK cells transduced with a vector containing D12(SIIS)2C94 (FIGS. 2D-2F) are depicted.
Figure 2B:
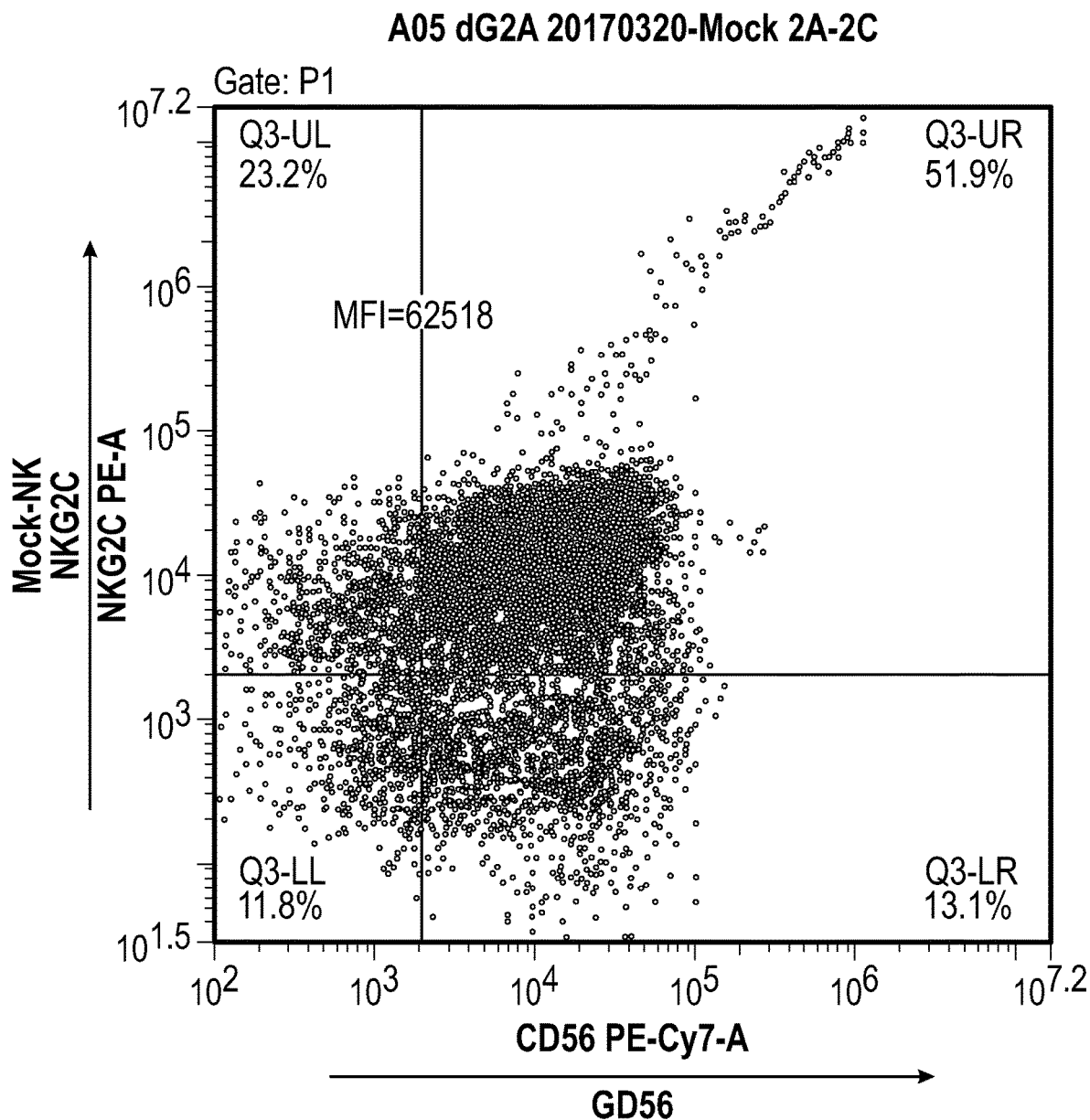
Figure 2C:
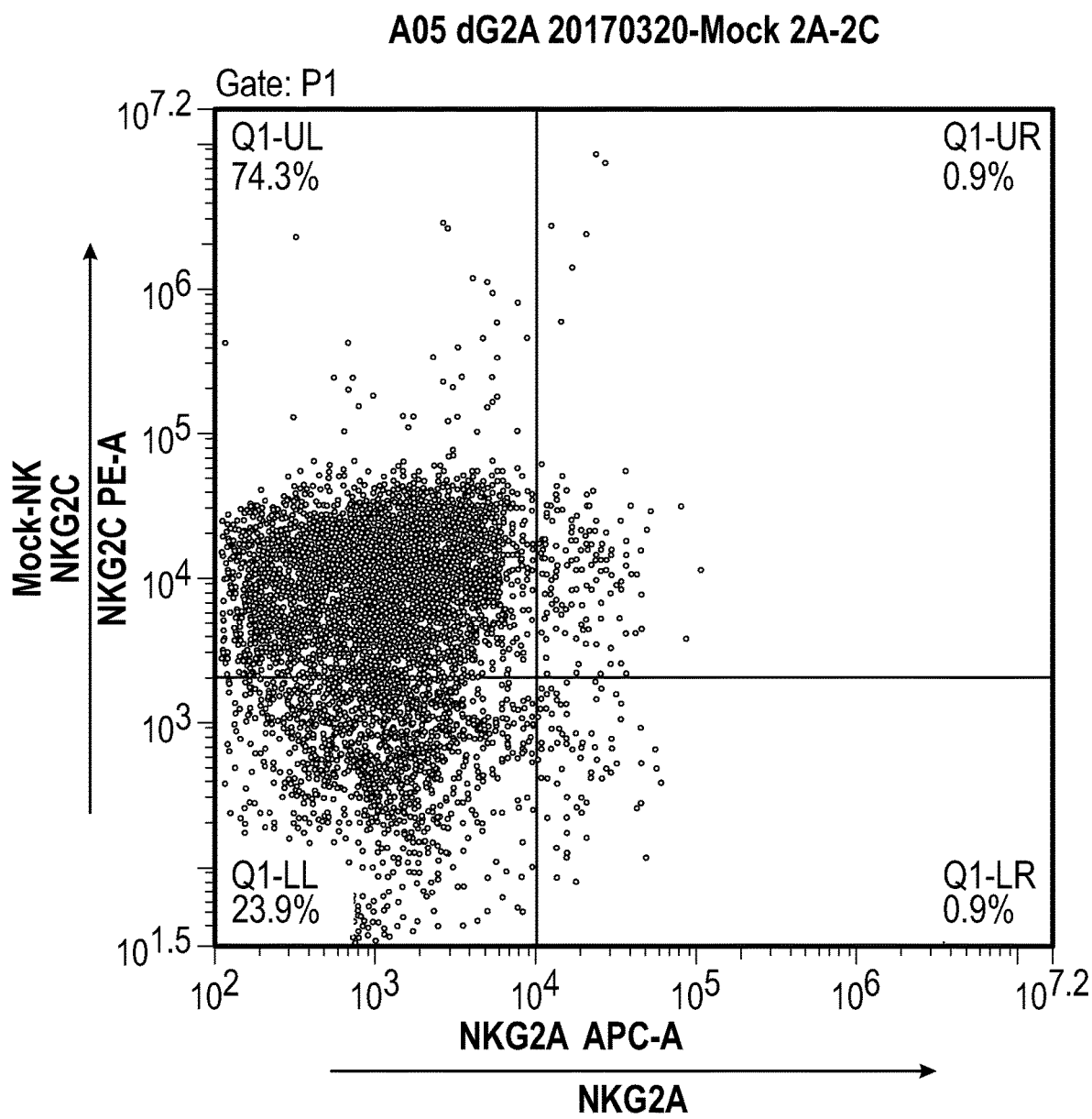
Figure 2D:
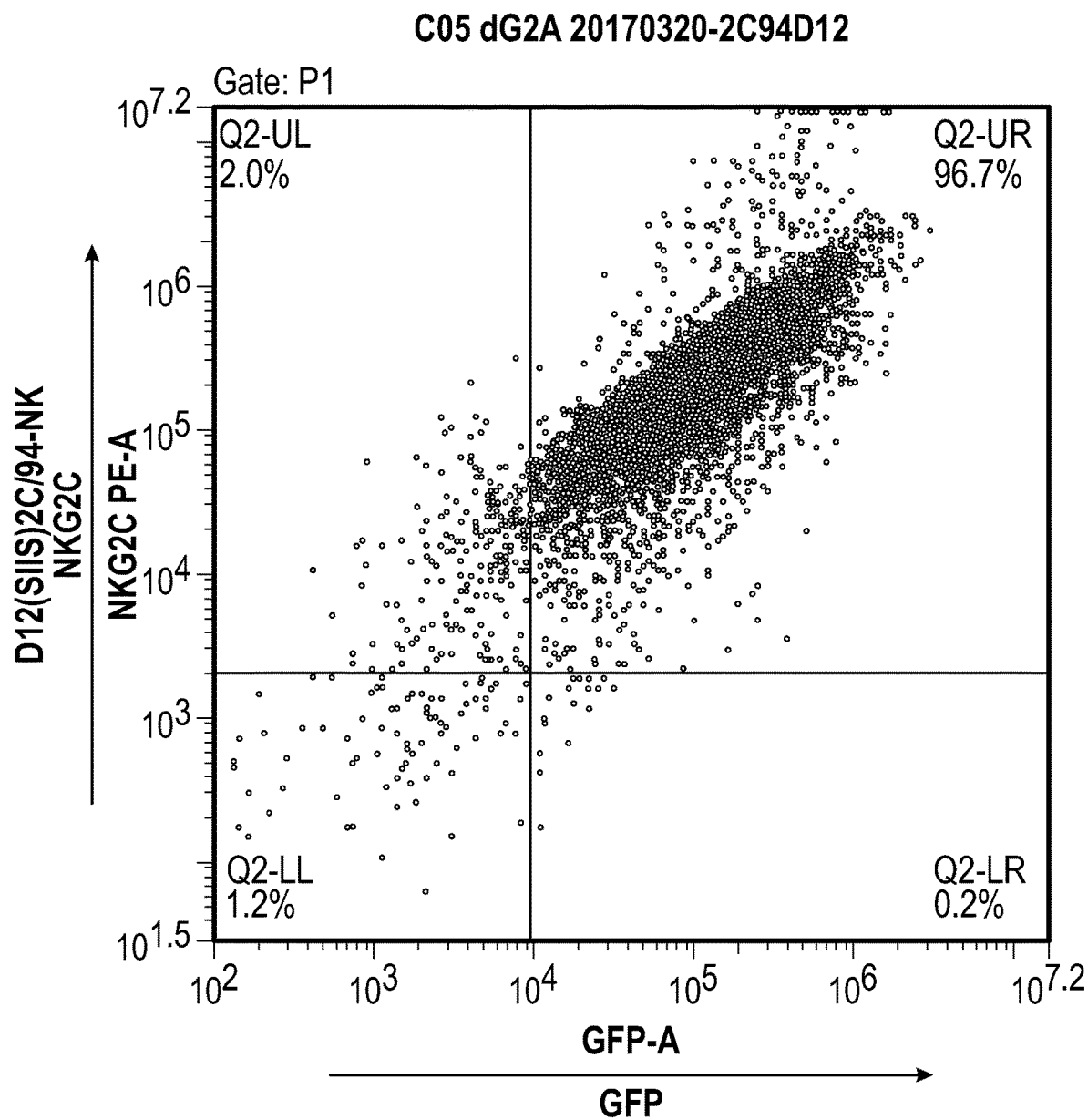
Figure 2E:
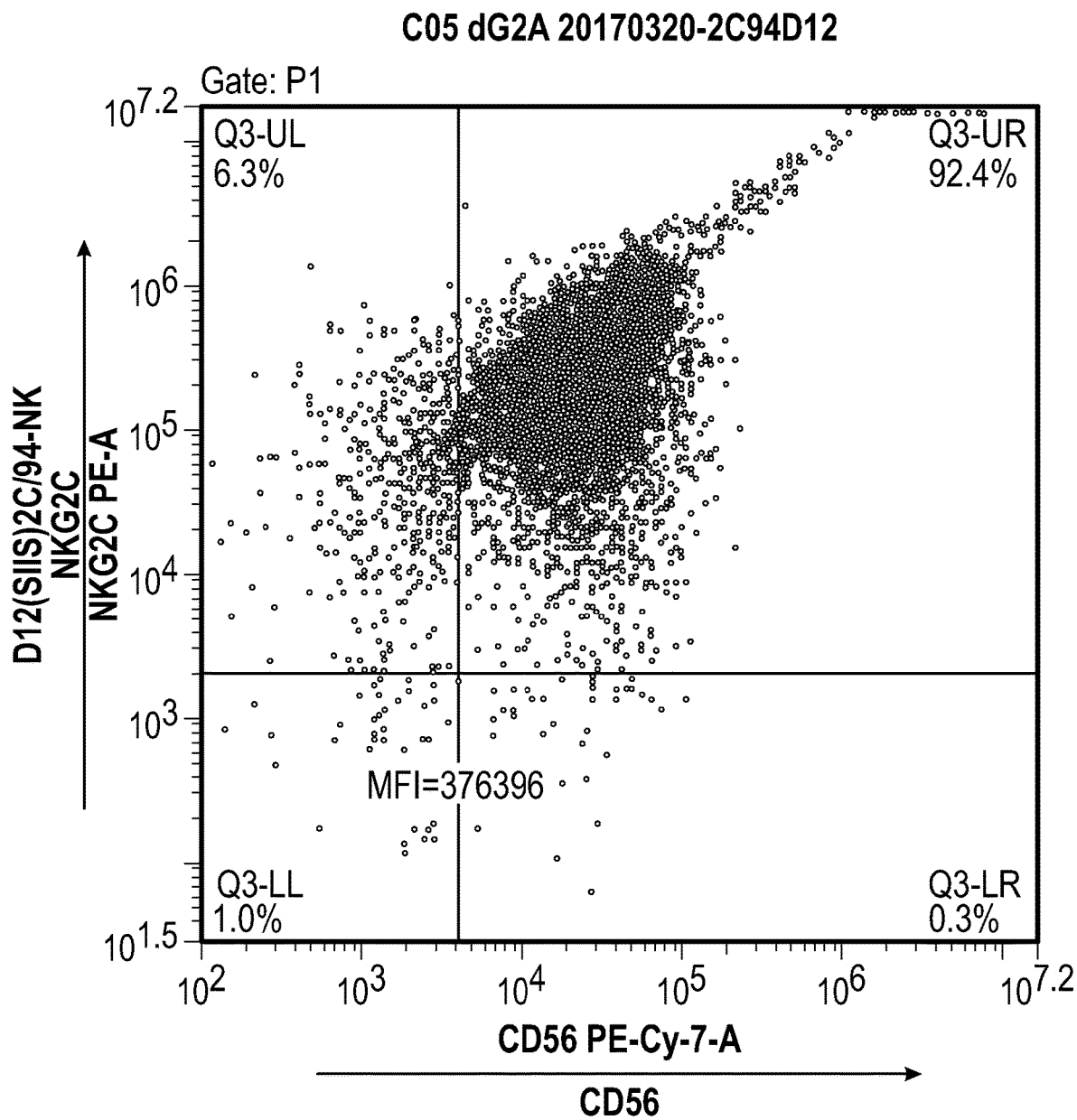
Figure 2F:
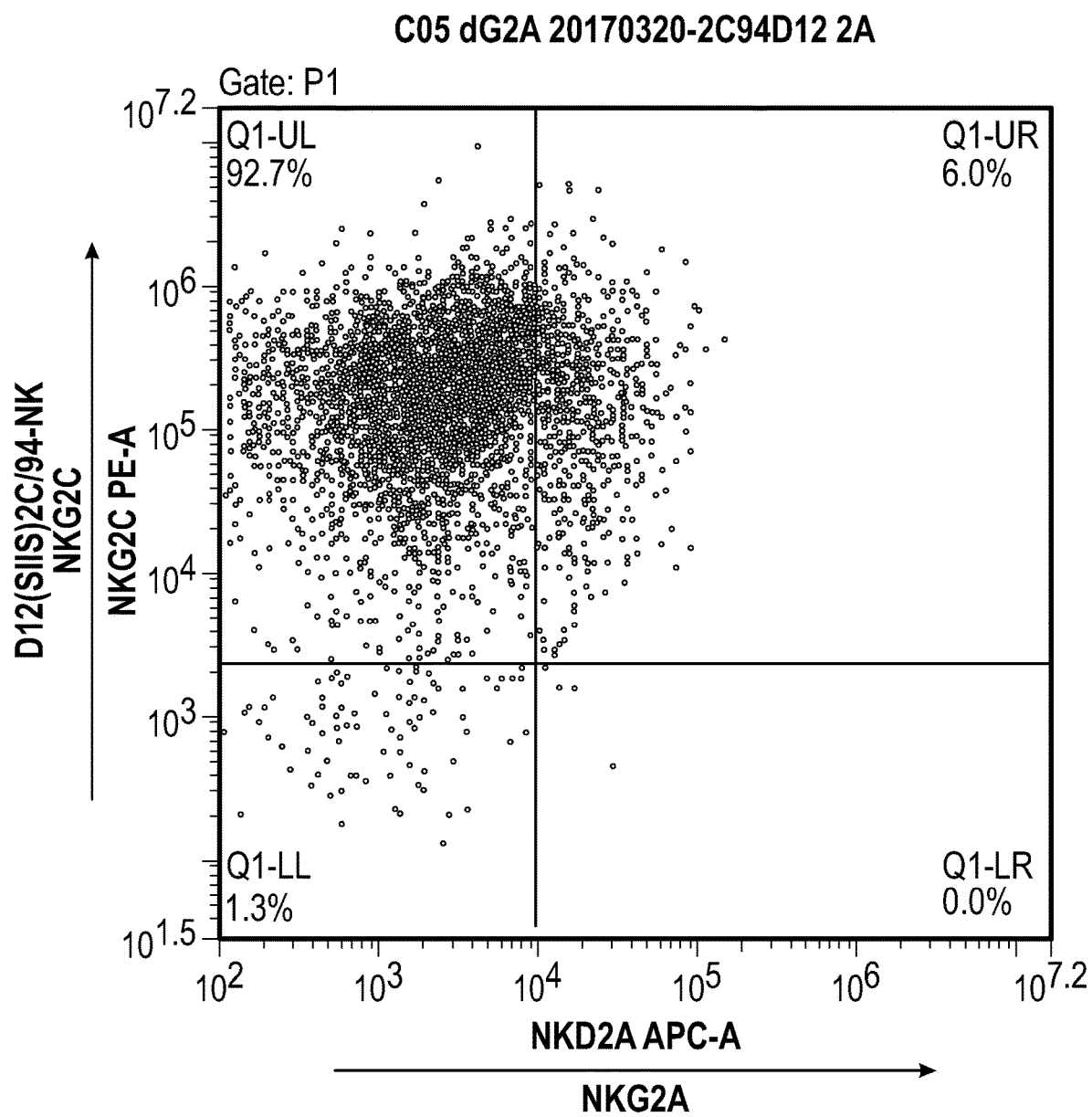

The emergence and persistence of aberrant cells (including virally infected and malignant cells) underlying many diseases is enabled by an insufficient immune response to said aberrant cells. A goal of immunotherapy is to initiate or augment the response of the patient's immune system, for example, to boost the ability of immune cells, such as Natural Killer (NK) cells to damage, kill, or otherwise inhibit damaged or diseased cells. One immunotherapy approach is the recombinant expression of activating chimeric receptors in immune cells for targeted recognition and destruction of the aberrant cells. In general, chimeric receptors comprise an extracellular receptor domain that recognizes ligands on target cells, an anchoring transmembrane domain, and an effector domain that transduces activating signals upon ligand binding. Some embodiments disclosed herein utilize activating chimeric receptors having that general structure, or having variations in that general structure. Additionally, in several embodiments, the transmembrane domain and the effector domain are separate peptides fused together. In several other embodiments, the transmembrane and the effector domain are derived from the same peptide. In some such embodiments, the transmembrane and effector domains comprise a single peptide (e.g., one peptide that passes through the membrane and is also poised to initiate a signaling cascade). As discussed in more detail below, truncations, mutations, additional linkers/spacer elements, dimers, and the like are used to generate activating chimeric receptor constructs that exhibit a desired degree of expression in an immune cell (e.g., an NK cell), induce cytotoxic activity from the NK cell, balanced with a degree of target avidity that avoids adverse effects on non-target cells. The recombinant expression of activating chimeric receptors as disclosed herein on the surface of immune cells can redirect the targeting of immune cells to aberrant cells of interest as well as augment the immune activation upon engagement.

NK Cells for Immunotherapy

One immunotherapy approach involves administering to patients T cells engineered to express activating chimeric receptors to elicit a positive immune response. However, a potential drawback of this approach is that it necessitates the use of autologous cells to prevent the induction of graft-versus-host-disease in the patient. As is provided in several embodiments disclosed herein, compositions comprising engineered NK cells enjoy several advantages. For example, either autologous or donor-derived allogeneic cells can be employed with an NK cell approach. Additionally, according to several embodiments, the engineered NK cells as provided for herein do not significantly increase cytotoxicity against normal cells. Further, NK cells have a significant cytotoxic effect, once activated. In view of this, it is unexpected that the engineered NK cells as provided for herein, are able to further elevate that cytotoxic effect, thus providing an even more effective means of selectively killing diseased target cells. Accordingly, in several embodiments, there is provided a method of treating or preventing cancer or an infectious disease, comprising administering a therapeutically effective amount of NK cells expressing the activating chimeric receptors described herein. In one embodiment, the NK cells administered are autologous cells. In a further embodiment, the NK cells administered are donor-derived (allogeneic) cells.

In several embodiments, engagement and activation of a recombinant NK cell (e.g., by binding to a ligand on a target cell) expressing an activating chimeric receptor leads to the direct killing of the stressed and/or aberrant cell (e.g., tumor cells, virally-infected cells, etc.) by cytolysis. Accordingly, in several embodiments, there is provided a method of enhancing NK cell cytotoxicity, comprising administering NK cells engineered to express the activating chimeric receptors described herein. In one embodiment, the NK cells administered are autologous cells. In a further embodiment, the NK cells are donor-derived (allogenic) cells. In several embodiments, engineered NK cells lead to indirect destruction or inhibition of stressed and/or aberrant cell (e.g., tumor cells, virally-infected cells, etc.).

Activating Chimeric Receptors that Bind HLA-E/peptide Complex

As mentioned above, in several embodiments, NK cells recognize and destroy aberrant cells, including tumor cells and/or virally-infected cells. The cytotoxic activity of these innate immune cells is regulated by the balance of signaling from inhibitory and activating receptors, respectively, that reside on the cell surface. The former bind "self"-molecules expressed on the surface of healthy cells while the latter bind ligands expressed on aberrant cells. The underlying logic is that an inhibitory receptor on an NK cell that interacts with a "self" molecule is not going to be activated and thereby spares the cell bearing the "self" molecule from destruction by the NK cell. In contrast, when an NK cell expressing an activating receptor interacts with a "non-self" ligand, for example on a diseased cell, the NK cell is activated and cytotoxic effects ensue. Thus, an increased engagement of activating receptors relative to inhibitory receptors leads to NK cell activation and target cell lysis.

Natural Killer Group 2 members A (NKG2A) and C (NKG2C) are C-type lectin receptors expressed predominantly on the surface of NK cells receptors that influence the balance of inhibitory and activating signaling. Both NKG2A and NKG2C are capable of forming heterodimers with, for example, the integral membrane glycoprotein CD94. Further, both NKG2C/CD94 and NKG2A/CD94 bind the non-classical MHC class I molecule HLA-E/peptide complex in humans. HLA-E has a specialized role in cell recognition by NK cells, as HLA-E binds a restricted subset of peptides derived from signal peptides of classical MHC class I molecules, namely HLA-A, B, C, G. Therefore, NK cells can indirectly monitor the expression of classical MHC class I molecules through the interaction of NKG2C/CD94 and NKG2A/CD94 with HLA-E. NKG2C is an activating receptor and HLA-E/peptide complex binding enables interaction between NKG2C/CD94 and ITAM-bearing adaptor protein DAP12. In contrast, NKG2A is an inhibitory receptor, and NKG2A/CD94 transmits inhibitory signals via an ITIM motif in its cytoplasmic domain.

The ability of NK cells to recognize and destroy aberrant cells, including tumor cells and/or virally-infected cells, make it a potentially useful component of immunotherapy approaches (including chimeric receptor-based immunotherapy approaches). However, complicating the use of NK cells is the fact that HLA-E is upregulated in multiple tumors and exposure of tumor cells to IFN gamma (which is secreted by immune cells) enhances expression of HLA-E. NKG2C has lower affinity for peptide complexes as compared to NKG2A, so the increased HLA-E expression on target cells can act as a "camouflage" of sorts. This is a result of the higher affinity, but inhibitory, NKG2A being able to outcompete NKG2C for binding to a target peptide, and thus invoke an overall inhibitory effect on NK cell activity.

One approach to address this is, as provided for in several embodiments, polynucleotides encoding an activating chimeric receptor that binds HLA-E/peptide complex with enhanced affinity. In some embodiments, the activating chimeric receptor comprises a NKG2C variant engineered for enhanced affinity to HLA-E/peptide complex (e.g., as compared to the affinity of a non-modified NKG2C). In some embodiments of the NKG2C variant, residues 165-168 of wild-type NKG2C are replaced with the corresponding residues of NKG2A (SIIS). In several embodiments, the NKG2C variant comprises the amino acid sequence of SEQ ID NO. 58 (SIIS), where SIIS refers to Serine-Isoleucine-Isoleucine-Serine. In such embodiments, the affinity of the original NKG2A receptor is "transplanted" such that the previously lower affinity NKG2C receptor is engineered to have enhanced affinity. In several embodiments, the affinity of mutated NKG2C (as compared to non-mutated NKG2C) is increased by about 20%, by about 30%, by about 40% by about 50%, or more, depending on the embodiment.

In some embodiments disclosed herein, polynucleotides encoding activating chimeric receptors, such as a mutated NKG2C, are provided wherein the extracellular receptor domain is a fragment of a NKG2C variant that lacks its native transmembrane and/or intracellular domains, which, in several embodiments imparts to the variant still additional enhanced affinity for the HLA-E/peptide complex. In several embodiments, the NKG2C variant fragment is encoded by SEQ ID NO. 63. In several embodiments, the fragment of the NKG2C variant is at least 70%, at least 75%, at least 80%, at least 85%, at least 90%, or at least 95% homologous with full-length wild-type NKG2C. In several embodiments, the fragment may have one or more additional mutations (e.g., insertions, deletions, and/or conservative or non-conservative substitutions) from SEQ ID NO. 63, but retains, or in some embodiments, has enhanced, ligand-binding function. In several embodiments, the NKG2C variant fragment is provided as a dimer, trimer, or other concatameric format, such embodiments providing enhanced ligand-binding activity. In several embodiments, the sequence encoding the NKG2C variant fragment is optionally fully or partially codon optimized.

Additionally, in several embodiments signal peptides are used. The species or sequence of the signal peptide can vary with the construct. However, in several embodiments, a signal peptide derived from CD8 is used. In one embodiment, the signal peptide is from CD8a and has the sequence of SEQ ID NO. 4. In some embodiments, the polynucleotide encodes a NKG2C variant receptor and DAP12. In some embodiments, the polynucleotide encodes a NKG2C variant receptor and CD94. In some embodiments, the polynucleotide encodes a NKG2C variant receptor, CD94, and DAP12. In several embodiments, wherein NKG2C is employed, the cells are further engineered to alter expression (e.g., reduce or eliminate transcription and/or reduce or eliminate translation) of native NKG2A.

In some embodiments, NKG2A is engineered to deliver activating signals upon HLA-E/peptide complex binding, as opposed to its normal delivery of inhibitory signals. As used herein, "NKG2A" refers to any variant, derivative, or isoform of the NKG2A gene or encoded protein, including, but not limited to, NKG2B. Thus, according to several embodiments disclosed herein, polynucleotides encoding activating chimeric receptors are provided wherein the extracellular receptor domain is a fragment of NKG2A that lacks its native transmembrane or intracellular domains yet advantageously retains its ability to bind HLA-E/peptide complex. Thus, in several embodiments, the chimeric receptor encoded by the polypeptides disclosed herein does not comprise an ITIM, an ITAM or a hemi-ITAM/hemi-ITAM. In several embodiments, the NKG2A fragment is encoded by SEQ ID NO. 65. In several embodiments, the fragment of NKG2A is at least 70%, at least 75%, at least 80%, at least 85%, at least 90%, or at least 95% homologous with full-length wild-type NKG2A. In several embodiments, the fragment may have one or more additional mutations (e.g., insertions, deletions, and/or conservative or non-conservative substitutions) from SEQ ID NO. 65, but retains, or in some embodiments, has enhanced, ligand-binding function. In several embodiments, the NKG2A fragment is provided as a dimer, trimer, or other concatameric format, such embodiments providing enhanced ligand-binding activity. In several embodiments, the sequence encoding the NKG2A fragment is optionally fully or partially codon optimized. Additionally, in several embodiments signal peptides are used. The species or sequence of the signal peptide can vary with the construct. However, in several embodiments, a signal peptide derived from CD8 is used. In one embodiment, the signal peptide is from CD8a and has the sequence of SEQ ID NO. 4. In some embodiments, the polynucleotide encodes an activating NKG2A receptor and a CD94 receptor.

In some embodiments, CD94 is engineered to deliver activating signals upon HLA-E/peptide complex binding. Thus, according to several embodiments disclosed herein, polynucleotides encoding activating chimeric receptors are provided wherein the extracellular receptor domain is a fragment of CD94 that lacks its native transmembrane or intracellular domains yet advantageously retains its ability to dimerize with NKG2A and NKG2C. In several embodiments, the CD94 fragment is encoded by SEQ ID NO. 67. In several embodiments, the fragment of CD94 is at least 70%, at least 75%, at least 80%, at least 85%, at least 90%, or at least 95% homologous with full-length wild-type CD94. In several embodiments, the fragment may have one or more additional mutations (e.g., insertions, deletions, and/or conservative or non-conservative substitutions) from SEQ ID NO. 67, but retains, or in some embodiments, has enhanced, ligand-binding function. In several embodiments, the CD94 fragment comprises the amino acid sequence of SEQ ID NO. 68. In several embodiments, the fragment of CD94 is at least 70%, at least 75%, at least 80%, at least 85%, at least 90%, or at least 95% homologous with full-length wild-type CD94. In several embodiments, the fragment may have one or more additional mutations (e.g., insertions, deletions, and/or conservative or non-conservative substitutions) from SEQ ID NO. 68, but retains, or in some embodiments, has enhanced, ligand-binding function. In several embodiments, the CD94 fragment is provided as a dimer, trimer, or other concatameric format, such embodiments providing enhanced ligand-binding activity. In several embodiments, the sequence encoding the CD94 fragment is optionally fully or partially codon optimized. Additionally, in several embodiments signal peptides are used. The species or sequence of the signal peptide can vary with the construct. However, in several embodiments, a signal peptide derived from CD8 is used. In one embodiment, the signal peptide is from CD8a and has the sequence of SEQ ID NO. 4. In some embodiments, the polynucleotide encodes a chimeric CD94 receptor and an activating NKG2A receptor. In some embodiments, the polynucleotide encodes an activating NKG2C variant receptor and a chimeric CD94 receptor.

In some embodiments, polynucleotides encoding the activating chimeric receptors disclosed herein are expressed in NKG2A depleted cell populations (for example a population of NK cells that is depleted, substantially depleted, or completely depleted of cells expressing NKG2A—e.g., immunodepletion methods).

Transmembrane, Signaling and Combination Domains

As mentioned above, the general activating chimeric receptor structure comprises at least one transmembrane domain, linking the ligand binding domain to a signaling domain(s). In several embodiments, however, a transmembrane domain can also serve to provide signaling function.

In several embodiments, a fragment of CD94, a fragment of NKG2A, and/or NKG2C variant retains at least a portion of its normal transmembrane domain. In several embodiments, the transmembrane domain comprises at least a portion of CD8, which is a transmembrane glycoprotein normally expressed on both T cells and NK cells. In several embodiments, the transmembrane domain comprises CD8α, while in some embodiments CD8β is used. In several embodiments, the "hinge" (e.g., the portion between the extracellular domain and the intracellular domain) of CD8α has the sequence of SEQ ID NO. 5. In several embodiments, the CD8α can be truncated or modified, such that it is at least 70%, at least 75%, at least 80%, at least 85%, at least 90%, at least 95% homologous with the CD8α having the sequence of SEQ ID NO. 5. In several embodiments, CD8β has the sequence of SEQ ID NO. 6. In several embodiments, the CD8β can be truncated or modified, such that it is at least 70%, at least 75%, at least 80%, at least 85%, at least 90%, at least 95% homologous with the CD8β having the sequence of SEQ ID NO. 6. In several embodiments, dimers, trimers, or repeated sequences of CD8α and CD8β are used.

In several embodiments, the transmembrane domain comprises CD16, which serves as a signaling domain as well, in some embodiments. CD16 exists in two isoforms, a and b (also known as Fc gamma receptor Ma and Mb, respectively). These receptors normally bind to the Fc portion of IgG antibodies that in turn activates NK cells. Accordingly, in several embodiments, the transmembrane domain comprises CD16a, while in some embodiments CD16b is used. In several embodiments, CD16a has the sequence of SEQ ID NO. 7. In several embodiments, the CD16a is truncated or modified, such that it is at least 70%, at least 75%, at least 80%, at least 85%, at least 90%, at least 95% homologous with the CD16a having the sequence of SEQ ID NO. 7. In several embodiments, CD16b has the sequence of SEQ ID NO. 8. In several embodiments, the CD16b is truncated or modified, such that it is at least 70%, at least 75%, at least 80%, at least 85%, at least 90%, at least 95% homologous with the CD16b having the sequence of SEQ ID NO. 8. In several embodiments, dimers of CD16a and CD16b are used. In several embodiments the modifications to the CD16 transmembrane domain comprise additional nucleic acid residues to increase the length of the domain. Alternatively, CD16 may be shortened. The modifications to the length of CD16 advantageously can facilitate enhanced ligand-receptor interactions.

In several embodiments, activating chimeric receptors provided for herein comprises the Natural Killer Receptor 2B4 domain (referred to herein as "2B4", and also known as CD244), which serves as a signaling domain as well. 2B4 is expressed on NK cells and regulates non-major histocompatibility complex (MHC) restricted killing through interactions between this receptor and its ligands on target cells. In several embodiments, the transmembrane domain comprises 2B4, while in several embodiments the 2B4 domain is employed as an intracellular signaling domain. In several embodiments, 2B4 has the sequence of SEQ ID NO. 9. In several embodiments, the 2B4 can be truncated or modified, such that it is at least 70%, at least 75%, at least 80%, at least 85%, at least 90%, at least 95% homologous with the 2B4 having the sequence of SEQ ID NO. 9. In several embodiments, 2B4 is used as the sole transmembrane/signaling domain in the construct, however, in several embodiments, 2B4 can be used with one or more other domains. For example, combinations of CD16, 4-1BB, and/or 2B4 are used in some embodiments.

In some embodiments, signaling is achieved through DAP10. In several embodiments, dimers of DAP10 are used. In several embodiments, the transmembrane domain comprises DAP10. In several embodiments, DAP10 has the sequence of SEQ ID NO. 10. In several embodiments, DAP10 can be truncated or modified, such that it is at least 70%, at least 75%, at least 80%, at least 85%, at least 90%, at least 95% homologous with the DAP10 having the sequence of SEQ ID NO. 10. Similarly, in some embodiments, DAP12 can be used, as it can also transduce such signals. In several embodiments, DAP12 has the sequence of SEQ ID NO. 11. In several embodiments, DAP12 can be truncated or modified, such that it is at least 70%, at least 75%, at least 80%, at least 85%, at least 90%, at least 95% homologous with the DAP12 having the sequence of SEQ ID NO. 11. In several embodiments, heterodimers of DAP10 and DAP12 are used. However, in some embodiments, neither DAP10 nor DAP12 are used, either in an NKG2A, NKG2C, or NKG2D construct.

In several embodiments, signaling is provided through 4-1BB (also known as CD137 and tumor necrosis factor receptor superfamily member 9 (TNFRSF 9)). 4-1BB is a co-stimulatory immune checkpoint molecule, typically functioning as a stimulatory molecule for activated immune cells (e.g., crosslinking of 4-1BB enhances T cell proliferation and cytolytic activity). However, in several embodiments, the function of 4-1BB is advantageously used in conjunction with NK cells. In several embodiments, 4-1BB has the sequence of SEQ ID NO. 12. In several embodiments, 4-1BB can be truncated or modified, such that it is at least 70%, at least 75%, at least 80%, at least 85%, at least 90%, at least 95% homologous with the 4-1BB having the sequence of SEQ ID NO. 12. In several embodiments, 4-1BB is the sole signaling domain, but as discussed above, in several embodiments, 4-1BB functions unexpectedly well in combination with one or more of the other transmembrane/signaling domains disclosed herein. For example, in several embodiments, CD16 in conjunction with 4-1BB provides synergistic stimulation effects, resulting in particularly effective (e.g., cytotoxic) NK cells. In several embodiments, DAP10 in conjunction with 4-1BB provides synergistic stimulation effects, resulting in particularly effective (e.g., cytotoxic) NK cells. In several embodiments, DAP10 in conjunction with 4-1BB and 2B4 provides synergistic stimulation effects, resulting in particularly effective (e.g., cytotoxic) NK cells.

In several embodiments, the signaling domain comprises at least a portion of the CD3 T cell receptor complex. The T cell receptor complex comprises multiple subunits, including the zeta, alpha, beta, gamma, delta, and epsilon subunits. In several embodiments, the NK cells engineered according to several embodiments disclosed herein comprise at least one of these subunits (or a fragment thereof). In several embodiments, the signaling domain comprises the CD3 zeta subunit. In several embodiments, CD3 zeta has the sequence of SEQ ID NO. 13. In several embodiments, CD3 zeta can be truncated or modified, such that it is at least 70%, at least 75%, at least 80%, at least 85%, at least 90%, at least 95% homologous with the CD3 zeta having the sequence of SEQ ID NO. 13. In several embodiments, the CD3 zeta is mutated (e.g., amino acid mutations, insertions, or deletions) such that the domain no longer is consistent with the canonical immunoreceptor tyrosine-based activation motif or ITAM motif. Thus, in several embodiments, the NK cells comprise an engineered receptor that does not contain an ITAM motif In some embodiments, CD3zeta is not used. In some embodiments, the resultant engineered NK cells exhibit particularly enhanced cytotoxicity against target cells, with limited or reduced adverse side effects. This, in several embodiments, results from the synergistic interactions of the various portions of the activating chimeric receptor that are used in that given embodiment. In several embodiments, CD3zeta in conjunction with 4-1BB provides synergistic stimulation effects, resulting in particularly effective (e.g., cytotoxic) NK cells. In several embodiments, CD3zeta in conjunction with 2B4 provides synergistic stimulation effects, resulting in particularly effective (e.g., cytotoxic) NK cells.

In still further embodiments, the signaling portion of the activating chimeric receptor comprises a portion of an ITAM, for example a hemi-tam. In several embodiments, these portions do not make up the canonical ITAM sequence, but rather comprise a portion that still can convey the signal required for NK cell cytotoxicity. In several embodiments, the hemi-tam has the sequence of SEQ ID NO. 14 (wherein X can be any residue). In several embodiments, the hemi-tam can be truncated or modified, such that it is at least 70%, at least 75%, at least 80%, at least 85%, at least 90%, at least 95% homologous with the hemi-tam having the sequence of SEQ ID NO. 14. In several embodiments, the activating chimeric receptor construct comprises the hemi-tam of SEQ ID NO. 14. In several embodiments, multiple hemi-tams can be used, for example in a head to tail, tail to head, head to head, or tail to tail configuration. In several embodiments, the presence of at least one hemi-tam confers enhanced signaling and cytotoxicity to the NK cells comprising an activating chimeric receptor employing the at least one hemi-tam. As discussed in more detail below, in several activating chimeric receptor comprises NKp80, which is one non-limiting example of a hemi-tam.

In several embodiments, additional signaling regions are used, including, for example, signaling regions derived from receptors of the signaling lymphocytic activation molecule (SLAM) family. These receptors include, but are not limited to 2B4 (discussed above). Receptors of the SLAM family share a consensus motif that is tyrosine-based, in their cytoplasmic tails. That motif is S/TxYxxL/I, which are referred to as immunoreceptor tyrosine-based switch motifs (ITSM) (SEQ ID NO. 15). These receptors transmit activation signals through the SLAM-associated protein (SAP, encoded by the gene SH2D1A), which recruits the tyrosine kinase Fyn. Thus, according to several embodiments, the signaling region comprise a polypeptide sequence (or the nucleic acid encoding the same) comprising an ITSM motif. In several embodiments, the ITSM motif need not be fully encoded, but the signaling region is able to transmit an activation signal through SAP (or another similar pathway). In several embodiments, the ITSM motif has the sequence of SEQ ID NO. 15 (wherein X can be any amino acid residue). In several embodiments, the ITSM motif can be truncated or modified, such that it is at least 70%, at least 75%, at least 80%, at least 85%, at least 90%, at least 95% homologous with the ITSM motif having the sequence of SEQ ID NO. 15. In several embodiments, the ITSM motif comprises the sequence of SEQ ID NO. 15.

In addition to these variations in the extracellular receptor domain, the transmembrane domain and signaling domain (and the combination transmembrane/signaling domains), additional co-activating molecules can be provided, in several embodiments. For example, in several embodiments, the NK cells are engineered to express membrane-bound interleukin 15 (mbIL15). In such embodiments, the presence of the mbIL15 on the NK cell function to further enhance the cytotoxic effects of the NK cell by synergistically enhancing the proliferation and longevity of the NK cells. In several embodiments, mbIL15 has the nucleic acid sequence of SEQ ID NO. 16. In several embodiments, mbIL15 can be truncated or modified, such that it is at least 70%, at least 75%, at least 80%, at least 85%, at least 90%, at least 95% homologous with the sequence of SEQ ID NO. 16. In several embodiments, the mbIL15 has the amino acid sequence of SEQ ID NO. 17. In conjunction with the activating chimeric receptors disclosed herein, such embodiments provide particularly effective NK cell compositions for targeting and destroying particular target cells.

Chimeric Receptor Constructs

In view of the disclosure provided herein, there are a variety of activating chimeric receptors that can be generated and expressed in NK cells in order to target and destroy particular target cells, such as diseased or cancerous cells. Non-limiting examples of such chimeric receptors are discussed in more detail below.

As discussed above, portions of the T cell receptor complex, in particular CD3zeta, serve as potent activators of immune signaling cascades. Likewise, the receptor 4-1BB, a tumor necrosis factor superfamily member, activates NK cells upon ligand binding. In several embodiments, these two signaling components act in a synergistic manner to activate NK cells upon binding of a ligand to the chimeric receptor. Thus, in several embodiments, there are provided polynucleotides encoding a NKG2A/CD8a/4-1BB/CD3zeta chimeric receptor, which comprises an NKG2A fragment extracellular receptor domain that binds HLA-E/peptide complex, a CD8 transmembrane region, and an effector domain comprising the signaling domains of 4-1BB and CD3zeta. In one embodiment, this chimeric receptor is encoded by the nucleic acid sequence of SEQ ID NO: 61. In yet another embodiment, the NKG2A/CD8a/4-1BB/CD3zeta chimeric receptor comprises the amino acid sequence of SEQ ID NO: 62. In several embodiments, this construct is particularly efficacious when the NK cells concurrently express mbIL15, the mbIL15 provides a further synergistic effect with respect to the activation and cytotoxic nature of the NK cells. In some embodiments, the sequence of the chimeric receptor may vary from SEQ ID NO. 61, but remains, depending on the embodiment, at least 70%, at least 75%, at least 80%, at least 85%, at least 90%, or at least 95% homologous with SEQ ID NO. 61. In several embodiments, while the chimeric receptor may vary from SEQ ID NO. 61, the chimeric receptor retains, or in some embodiments, has enhanced, NK cell activating and/or cytotoxic function.

Additionally, in several embodiments, there are provided polynucleotides encoding a CD94/CD8a/4-1BB/CD3zeta chimeric receptor, which comprises a CD94 fragment extracellular receptor domain, a CD8 transmembrane region, and an effector domain comprising the signaling domains of 4-1BB and CD3zeta. In one embodiment, this chimeric receptor is encoded by the nucleic acid sequence of SEQ ID NO: 59. In yet another embodiment, the CD94/CD8a/4-1BB/CD3zeta chimeric receptor comprises the amino acid sequence of SEQ ID NO: 60. In several embodiments, this construct is particularly efficacious when the NK cells concurrently express mbIL15, the mbIL15 provides a further synergistic effect with respect to the long-term activation and cytotoxic nature of the NK cells (e.g., in vivo persistence). In some embodiments, the sequence of the chimeric receptor may vary from SEQ ID NO. 59, but remains, depending on the embodiment, at least 70%, at least 75%, at least 80%, at least 85%, at least 90%, or at least 95% homologous with SEQ ID NO. 59. In several embodiments, while the chimeric receptor may vary from SEQ ID NO. 59, the chimeric receptor retains, or in some embodiments, has enhanced, NK cell activating and/or cytotoxic function.

The receptor 2B4 possesses several immunoreceptor tyrosine-based switch motifs (ITSMs) and has the potential to transduce activating signals. Likewise, signaling through the receptor 4-1BB, a tumor necrosis factor superfamily member, also activates NK cells upon ligand binding. Thus, capitalizing on the ability of these signaling molecules to cooperate to generate unexpectedly effectively cytotoxic NK cells, in several embodiments, there are provided polynucleotides encoding an activating chimeric receptor, which comprises an extracellular receptor domain that comprises a fragment of NKG2A, CD94, or NKG2C variant, a CD8a transmembrane region, and an effector domain comprising the signaling domains of 4-1BB and 2B4. Additionally, in several embodiments, this construct can optionally be co-expressed with mbIL15.

In several embodiments, combinations of 2B4 with CD3zeta are used with NK cells to generate enhanced cytotoxicity against target cells. Thus, in several embodiments, there are provided polynucleotides encoding an activating chimeric receptor which comprises an extracellular receptor domain that comprises a fragment of NKG2A, CD94, or NKG2C variant, a CD8a transmembrane region, and an effector domain comprising the signaling domains of CD3zeta and 2B4. Additionally, in several embodiments, this construct can optionally be co-expressed with mbIL15. As discussed above, 4-1BB, like CD3zeta and 2B4, is a potent activator of immune signaling cascades. In several embodiments, these three signaling components act in a synergistic manner to activate NK cells upon binding of a ligand to the chimeric receptor.

In several embodiments, there are provided polynucleotides encoding an activating chimeric receptor which comprises an extracellular receptor domain that comprises a fragment of NKG2A, CD94, or NKG2C variant, a CD8a transmembrane region, and an effector domain comprising the signaling domains of 4-1BB and DAP10. Additionally, in several embodiments, this construct can optionally be co-expressed with mbIL15.

In several additional embodiments, transmembrane and effector domains (and associated function) of the activating chimeric receptor are derived from the same peptide. CD16 is a potent activating receptor expressed on the surface of NK cells. Thus, in several embodiments, polynucleotides are provided encoding a NKG2A/CD16 chimeric receptor, NKG2C variant/CD16 chimeric receptor, or CD94/CD16 chimeric receptor, which comprises a fragment of NKG2C variant, CD94, or NKG2A, and a CD16 peptide comprising both the transmembrane region and intracellular effector domain. Additionally, in several embodiments, this construct can optionally be co-expressed with mbIL15.

In several additional embodiments, polynucleotides are provided encoding a NKG2A/CD16/4-1BB chimeric receptor, CD94/CD16/4-1BB chimeric receptor, or NKG2C variant/CD16/4-1BB chimeric receptor, wherein the signaling domain of 4-1BB acts as a second transducer of activating signals in the effector domain. Additionally, in several embodiments, this construct can optionally be co-expressed with mbIL15.

NCR1 (NKp46), NCR2 (NKp44) and NCR3 (NKp30) are receptors on NK cells that transduce activation signals upon ligand binding. Thus, in several embodiments, polynucleotides are provided encoding a NKG2A/NCR1 chimeric receptor, CD94/NCR1 chimeric receptor, or NKG2C variant/NCR1 chimeric receptor, which comprises an NKG2A, CD94, or NKG2C variant fragment, and a NCR1 peptide comprising both the transmembrane region and intracellular effector domain.

In several additional embodiments, polynucleotides are provided encoding a NKG2A/NCR1/4-1BB chimeric receptor, CD94/NCR1/4-1BB chimeric receptor, or NKG2C variant/NCR1/4-1BB chimeric receptor, wherein the signaling domain of 4-1BB acts as a second transducer of activating signals in the effector domain, leading to synergistically enhanced NK cell activation and cytotoxicity. In several additional embodiments, polynucleotides are provided encoding a NKG2A/NCR2 chimeric receptor, CD94/NCR2 chimeric receptor, NKG2C variant/NCR2 chimeric receptor, which comprises a NCR2 peptide comprising both the transmembrane region and intracellular effector domain. As with NCR1, in several embodiments these constructs are particularly amenable for use in creating NK cells expressing the chimeric receptor, due to their relatively small size and simplicity on sequence. However, they retain the ability, in several embodiments, to yield highly effective NK cells, despite the apparent simplicity of the construct. Additionally, in several embodiments, these constructs can optionally be co-expressed with mbIL15.

In several additional embodiments, polynucleotides are provided encoding a NKG2A/NCR3 chimeric receptor, CD94/NCR3 chimeric receptor, or NKG2C variant/NCR3 chimeric receptor, which comprises an NCR3 peptide comprising both the transmembrane region and intracellular effector domain. As with NCR1 and or NCR2, in several embodiments these constructs are particularly amenable for use in creating NK cells expressing the activating chimeric receptor, due to their relatively small size and simplicity on sequence. However, they retain the ability, in several embodiments, to yield highly effective NK cells, despite the apparent simplicity of the construct.

In several additional embodiments, polynucleotides are provided encoding a NKG2A/NCR2/4-1BB chimeric receptor, CD94/NCR2/4-1BB chimeric receptor, or NKG2C variant/NCR2/4-1BB chimeric receptor, wherein the signaling domain of 4-1BB acts as a second transducer of activating signals in the effector domain, thereby leading to a synergistic effect between the signaling domains, and unexpectedly effectively cytotoxic NK cells. Additionally, in several embodiments, this construct can optionally be co-expressed with mbIL15.

In several additional embodiments, polynucleotides are provided encoding a NKG2A/NCR3/4-1BB chimeric receptor, CD94/NCR3/4-1BB chimeric receptor, or NKG2C variant/NCR3/4-1BB chimeric receptor, wherein the signaling domain of 4-1BB acts as a second transducer of activating signals in the effector domain, thereby leading to a synergistic effect between the signaling domains, and unexpectedly effectively cytotoxic NK cells. Additionally, in several embodiments, this construct can optionally be co-expressed with mbIL15.

In some embodiments the surface expression and efficacy of the chimeric receptors disclosed herein are enhanced by variations in a spacer region (hinge), which, in several embodiments, are located in the extracellular domain between the transmembrane domain and any one of the CD94 fragment, NKG2A fragment, or NKG2C fragment. In some embodiments, the hinge regions can be included between other portions of the chimeric activating receptor (e.g., between intracellular and transmembrane domains, or between multiple intracellular domains). In some embodiments, domains that serve certain purposes as disclosed elsewhere herein, can serve additional functions. For example, in several embodiments, CD8a is repurposed to serve as a hinge region (encoded, in several embodiments, by the nucleic acid sequence of SEQ ID NO: 5). In yet another embodiment, the hinge region comprises an N-terminal truncated form of CD8a and/or a C-terminal truncated form of CD8a. Depending on the embodiment, these truncations can be at least about 50%, at least about 60%, at least about 70%, at least about 80%, or at least about 90% homologous to the hinge encoded by SEQ ID NO: 5. In several additional embodiments, the hinge comprises spans of Glycine and Serine residues (herein termed "GS linkers") where GSn represents the sequence (Gly-Gly-Gly-Gly-Ser)n (SEQ ID NO: 42). In one embodiment, the hinge comprises both CD8a and GS3, and is encoded by the amino acid sequence of SEQ ID NO: 32, for example, where n=3. In additional embodiments, the value of n may be equal to 1, 2, 4, 5, 6, 7, 8, 9, 10, 11, 12, 13, 14, 15 or greater depending on the embodiment. In several embodiments, the hinge could also be structured as GSn/CD8a. Alternatively, the GS linker can comprise the entire hinge region. In one such embodiment, the hinge region is encoded by the nucleic acid sequence of SEQ ID NO: 33. In another such embodiment, the hinge region is encoded by the nucleic acid sequence of SEQ ID NO: 34.

In several embodiments, the activating chimeric receptor constructs employ a 2B4 intracellular signaling domain. In several embodiments, this domain includes the amino acid sequence of SEQ ID NO. 35. In some embodiments, the 2B4 domain is encoded by the nucleic acid sequence of SEQ ID NO. 36. In some embodiments, the sequence of the 2B4 intracellular domain used in an activating chimeric receptor may vary from SEQ ID NO. 36, but remains, depending on the embodiment, at least 70%, at least 75%, at least 80%, at least 85%, at least 90%, or at least 95% homologous with SEQ ID NO. 36. In several embodiments, while the signaling domain of the activating chimeric receptor may vary from SEQ ID NO. 36, the activating chimeric receptor retains, or in some embodiments, has enhanced, NK cell activating and/or cytotoxic function. Likewise, in several embodiments an NKp80 intracellular domain is used, in several embodiments. In some embodiments, the NKp80 domain is the sole intracellular signaling domain, while in some embodiments, that domain is used in conjunction with one or more additional domains. In several embodiments, the NKp80 is encoded by the amino acid sequence of SEQ ID NO. 37. In some embodiments, the NKp80 domain is encoded by the nucleic acid sequence of SEQ ID NO. 38. In some embodiments, the sequence of the NKp80 intracellular domain used in a chimeric receptor may vary from SEQ ID NO. 38, but remains, depending on the embodiment, at least 70%, at least 75%, at least 80%, at least 85%, at least 90%, or at least 95% homologous with SEQ ID NO. 38. In several embodiments, while the signaling domain of the activating chimeric receptor may vary from SEQ ID NO. 38, the chimeric receptor retains, or in some embodiments, has enhanced, NK cell activating and/or cytotoxic function.

In several embodiments, the activating chimeric receptor uses a portion of a beta-adrenergic receptor as a transmembrane domain. In several embodiments, the portion comprises a portion of the beta-adrenergic extracellular domain. In several embodiments, the portion is a portion of the beta-adrenergic receptor transmembrane domain. In several embodiments, a combination of an extracellular domain and a transmembrane domain of the beta adrenergic receptor is used. Depending on the embodiment the portions are from the beta-1 and/or beta-2 adrenergic receptor. In several embodiments, a portion of the N-terminal extracellular region of the beta-2 adrenergic receptor is used. In several embodiments that portion has the amino acid sequence of SEQ ID NO. 39. In some embodiments, the extracellular beta-2 adrenergic domain is encoded by the nucleic acid sequence of SEQ ID NO. 40. In some embodiments, the sequence of the extracellular beta-2 adrenergic domain used in a chimeric receptor may vary from SEQ ID NO. 39, but remains, depending on the embodiment, at least 70%, at least 75%, at least 80%, at least 85%, at least 90%, or at least 95% homologous with SEQ ID NO. 39. In several embodiments, the first transmembrane helix of the beta-2 adrenergic receptor is used, optionally in conjunction with the extracellular beta-2 adrenergic domain. In several embodiments, the first transmembrane helix of the beta-2 adrenergic receptor has the amino acid sequence of SEQ ID NO. 41. In some embodiments, the first transmembrane helix of the beta-2 adrenergic receptor is encoded by the nucleic acid sequence of SEQ ID NO. 42. In some embodiments, the sequence of the first transmembrane helix of the beta-2 adrenergic receptor used in a chimeric receptor may vary from SEQ ID NO. 41, but remains, depending on the embodiment, at least 70%, at least 75%, at least 80%, at least 85%, at least 90%, or at least 95% homologous with SEQ ID NO. 41.

As discussed above, in several embodiments, codon optimized sequences are employed. For example in several embodiments, codon optimization (full or partial) is performed on the extracellular receptor domain comprising a fragment of a CD94, NKG2A, or NKG2C variant. In several embodiments, however, codon optimization is not performed. In several embodiments, a chimeric receptor construct is provided with an extracellular domain comprising a fragment of NKG2A, CD94, or NKG2C variant that is not optimized, a CD8a hinge, and a 4-1BB signaling domain. In several embodiments, a chimeric receptor construct is provided with an extracellular domain comprising a fragment of NKG2A, CD94, or NKG2C variant that is not optimized, a CD8a hinge and transmembrane domain, and a 4-1BB signaling domain.

In several embodiments, an activating chimeric receptor construct is provided with an extracellular domain comprising a fragment of NKG2A, CD94, or NKG2C variant that is not optimized, a CD8a hinge, and a NKp80 signaling domain. In several embodiments, a chimeric receptor construct is provided with an extracellular domain comprising a fragment of NKG2A, CD94, or NKG2C variant that is not optimized, a CD8a hinge and transmembrane domain, and a NKp80 signaling domain. In several embodiments, a GS linker, such as a GS3 linker joins the 4-1BB and NKp80 domains.

In several embodiments, a CD8 transmembrane domain is coupled with a 2B4 intracellular domain. In several embodiments, a CD8 transmembrane domain is replaced with a 2B4 domain that is transmembrane and intracellular. In several embodiments, the CD8 transmembrane domain is replaced with 2B4 and 4-1BB is expressed in a proximal configuration.

In several embodiments, a CD16 intracellular signaling domain is coupled with a CD3zeta or gamma subunit which are exogenously expressed in trans to the activating chimeric receptors described herein. As discussed above, such constructs can result in unexpectedly enhanced signal transduction, and thus an unexpected increase in cytotoxic effects of the NK cells.

In several embodiments, the activating chimeric receptors are configured to dimerize, as discussed in additional detail herein. In several embodiments a receptor comprising a fragment of CD94, NKG2A, or NKG2C variant according to several embodiments disclosed herein is optionally dimerized. Dimerization may comprise homodimers or heterodimers, depending on the embodiment. In several embodiments, dimerization results in a shift of avidity of the activating chimeric receptor (and hence the NK cells expressing the receptor) to better ligand recognition with a coordinate balance in reduced (or lack) of adverse toxic effects. In still further embodiments, the extracellular receptor domain further comprises a CD8a signal peptide. In several embodiments, the activating chimeric receptors employ internal dimers, or repeats of one or more component subunits. For example, in several embodiments, the chimeric receptor comprises a NKG2C variant extracellular domain coupled to a second NKG2C variant extracellular domain, and a transmembrane/signaling region (or a separate transmembrane region along with a separate signaling region). In several embodiments, one or more of the extracellular domains are codon optimized. In several embodiments, the two extracellular domains are separated by a linker, for example a GSn linker. In one embodiment, a GS3 linker is used. In several embodiments, the transmembrane domain comprises an extracellular region of the beta-adrenergic receptor. In several embodiments, the transmembrane domain transmembrane domain comprises an extracellular region of the beta-2 adrenergic receptor and further comprises the first transmembrane domain of the beta-2 adrenergic receptor. In several embodiments, the signaling region comprises 4-1BB. In several embodiments, the signaling region comprises NKp80. In several embodiments, the signaling region comprises a CD16 transmembrane-intracellular domain. In several embodiments, the signaling region comprises 4-1BB in conjunction with NKp80 or a CD16 transmembrane-intracellular domain.

According to several embodiments disclosed herein, additional chimeric receptors employing codon optimized extracellular receptor domains are provided for (optionally, these constructs can also be replicated with non-optimized or partially optimized domains). For example, in several embodiments, a codon optimized extracellular domain is coupled with a hinge and at least two domains (e.g. a transmembrane domain and a signaling domain). In several embodiments, the multiple signaling domains provide enhanced cytotoxic efficacy of the NK cells because multiple, non-redundant signal cascades are set in motion. While in some embodiments these multiple pathways may converge on a single signaling molecule (e.g., IFNγ), the overall cytotoxic effect is unexpectedly increased because of the overall magnitude of signaling molecules driving a cytotoxic endpoint.

In still additional embodiments, certain components of an activating chimeric receptor can be replaced with one or more additional subunits that lead to enhanced efficacy (e.g., activation or cytotoxicity of NK cells). For example, in one embodiment, a CD16 intracellular signaling domain can be replaced with a quad-repeat of DAP10 (e.g., 4×DAP10). In an additional embodiment, a CD16 intracellular signaling domain can be replaced with a Zap70 subunit. Certain such embodiments lead to unexpectedly enhanced NK cell cytotoxicity.

In several additional embodiments, the effector domain comprises one or more consensus hemi-ITAM sequences to enhance the transduction of activation signaling upon ligand binding. In additional embodiments, the inclusion of a GS linker between the signaling domains of 4-1BB, CD16, NCR1, NCR2 and/or NCR3 enhances signal transduction. Moreover, in several embodiments one or both of CD3zeta and FcRγ are additionally expressed along with the chimeric receptors described herein (either on the same or a separate construct), which results in unexpectedly enhanced signal transduction, and thus an unexpected increase in cytotoxic effects of the NK cells. Depending on the embodiment, the engineered expression of one or more of CD3zeta and FcRγ supplements endogenous expression of these molecules by NK cells, thereby further enhancing the signaling and ultimate cytotoxic potency of the NK cells.

Optionally, depending on the embodiment, any of the polynucleotides disclosed herein may also encode truncations and/or variants of one or more of the constituent subunits of an activating chimeric receptor, yet retain their ability to direct NK cells to target cells and in several embodiments unexpectedly enhance cytotoxicity upon binding. In addition, any of the polynucleotides disclosed herein may also optionally include codon-optimized nucleotide sequences encoding the various constituent subunits of a chimeric receptor. As used herein, the terms "fragment" and "truncated" shall be given their ordinary meaning and shall also include N- and C-terminal deletion variants of proteins.

The polynucleotides encoding the activating chimeric receptors described herein may be inserted into vectors to achieve recombinant protein expression in NK cells. In one embodiment, the polynucleotide is operably linked to at least one regulatory element for the expression of the activating chimeric receptor. In specific embodiments, transcriptional regulatory elements heterologous, such as, for example an internal ribosome entry site (IRES) or enhancer element, to the peptides disclosed herein are employed to direct the transcription of the activating chimeric receptor. Depending on the embodiment, the various constituent parts of a activating chimeric receptor can be delivered to an NK cell in a single vector, or alternatively in multiple vectors. In some embodiments, an activating chimeric receptor construct is delivered in a single vector, while another factor that enhances efficacy of the activating chimeric receptor, such as mbIL15, is delivered in a separate vector. In several embodiments, an activating chimeric receptor and a factor that enhances efficacy of the activating chimeric receptor (e.g., mbIL15), is delivered in a single vector. Regardless of the number of vectors used, any polynucleotide may optionally include a tag sequence, allowing identification of the presence of NK cells expressing the construct. For example, in several embodiments a FLAG tag (DYKDDDDK, SEQ ID NO. 55) is used. Also available are other tag sequences, such as a polyhistidine tag (His-tag) (HHHHHH, SEQ ID NO. 56), HA-tag or myc-tag (EQKLISEEDL; SEQ ID NO: 57). Alternatively, green fluorescent protein, or other fluorescent moiety, is used. Combinations of tag types can also be used, to individually recognize sub-components of an activating chimeric receptor.

In several embodiments, the polynucleotide encoding the activating chimeric receptor is an mRNA that may be introduced into NK cells by electroporation. In another embodiment, the vector is a virus, preferably a retrovirus, which may be introduced into NK cells by transduction. In several embodiments, the vector is a Murine Stem Cell Virus (MSCV). In additional embodiments, other vectors may be used, for example lentivirus, adenovirus, adeno-associated virus, and the like may be used. In several embodiments, non-HIV-derived retroviruses are used. The vector chosen will depend upon a variety of factors, including, without limitation, the strength of the transcriptional regulatory elements and the cell to be used to express a protein. The vector can be a plasmid, phagemid, cosmid, viral vector, phage, artificial chromosome, and the like. In additional embodiments, the vectors can be episomal, non-homologously, or homologously integrating vectors, which can be introduced into the appropriate cells by any suitable means (transformation, transfection, conjugation, protoplast fusion, electroporation, calcium phosphate-precipitation, direct microinjection, etc.) to transform them. Other approaches to induce expression of activating chimeric receptors in NK cells are used in several embodiments, including for example, the SV40 early promoter region, the promoter contained in the 3' long terminal repeat of Rous sarcoma virus, the herpes thymidine kinase promoter, the regulatory sequences of the metallothionein gene, an adenovirus (ADV) promoter, a cytomegalovirus (CMV) promoter, the bovine papilloma virus (BPV) promoter, the parovirus B 19p6 promoter, the beta-lactamase promoter, the tac promoter, the nopaline synthetase promoter region or the cauliflower mosaic virus 35S RNA promoter, the promoter of ribulose biphosphate carboxylase, the Gal 4 promoter, the ADC (alcohol dehydrogenase) promoter, the PGK (phosphoglycerol kinase) promoter, the synthetic MND promoter containing the U3 region of a modified MoMuLV LTR with the myeloproliferative sarcoma virus enhancer, and the alkaline phosphatase promoter.

Natural killer cells may be engineered to express the activating chimeric receptors disclosed herein. Activating chimeric receptor expression constructs may be introduced into NK cells using any of the techniques known to one of skill in the art. In one embodiment, the activating chimeric receptors are transiently expressed in the NK cells. In another embodiment, the activating chimeric receptors are stably expressed in NK cells. In an additional embodiment, the NK cells are autologous cells. In yet another embodiment, the NK cells are donor-derived (allogeneic) cells.

Further provided herein are methods of treating a subject having cancer or an infectious disease comprising administering to the subject a composition comprising NK cells engineered to express an activating chimeric receptor as disclosed herein, the activating chimeric receptor designed to target a marker or ligand expressed differentially on the damaged or diseased cells or tissue (e.g., expressed to a different degree as compared to a normal cell or tissue). As used herein, the terms "express", "expressed" and "expression" be given their ordinary meaning and shall refer to allowing or causing the information in a gene or polynucleotide sequence to become manifest, for example producing a protein by activating the cellular functions involved in transcription and translation of a corresponding gene or DNA sequence. The expression product itself, e.g., the resulting protein, may also be said to be "expressed" by the cell. An expression product may be characterized as intracellular, extracellular or transmembrane. The term "intracellular" shall be given its ordinary meaning and shall refer to inside a cell. The term "extracellular" shall be given its ordinary meaning and shall refer to outside a cell. The term "transmembrane" shall be given its ordinary meaning and shall refer to at least a portion of a polypeptide is embedded in a cell membrane. The term "cytoplasmic" shall be given its ordinary meaning and shall refer to residing within the cell membrane, outside the nucleus. As used herein, the terms "treat," "treating," and "treatment" in the context of the administration of a therapy to a subject shall be given their ordinary meaning and shall refer to the beneficial effects that a subject derives from a therapy. In certain embodiments, treatment of a subject with a genetically engineered cell(s) described herein achieves one, two, three, four, or more of the following effects, including, for example: (i) reduction or amelioration the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy. Administration can be by a variety of routes, including, without limitation, intravenous, intraarterial, subcutaneous, intramuscular, intrahepatic, intraperitoneal and/or local delivery to an affected tissue. Doses of NK cells can be readily determined for a given subject based on their body mass, disease type and state, and desired aggressiveness of treatment, but range, depending on the embodiments, from about 105 cells per kg to about 1012 cells per kg (e.g., 105-107, 107-1010, 1010-1012 and overlapping ranges therein). In one embodiment, a dose escalation regimen is used. In several embodiments, a range of NK cells is administered, for example between about 1×106 cells/kg to about 1×108 cells/kg. Depending on the embodiment, various types of cancer or infection disease can be treated. Various embodiments provided for herein include treatment or prevention of the following non-limiting examples of cancers including, but not limited to, acute lymphoblastic leukemia (ALL), acute myeloid leukemia (AML), adrenocortical carcinoma, Kaposi sarcoma, lymphoma, gastrointestinal cancer, appendix cancer, central nervous system cancer, basal cell carcinoma, bile duct cancer, bladder cancer, bone cancer, brain tumors (including but not limited to astrocytomas, spinal cord tumors, brain stem glioma, craniopharyngioma, ependymoblastoma, ependymoma, medulloblastoma, medulloepithelioma), breast cancer, bronchial tumors, Burkitt lymphoma, cervical cancer, colon cancer, chronic lymphocytic leukemia (CLL), chronic myelogenous leukemia (CIVIL), chronic myeloproliferative disorders, ductal carcinoma, endometrial cancer, esophageal cancer, gastric cancer, Hodgkin lymphoma, non-Hodgkin lymphoma, hairy cell leukemia, renal cell cancer, leukemia, oral cancer, nasopharyngeal cancer, liver cancer, lung cancer (including but not limited to, non-small cell lung cancer, (NSCLC) and small cell lung cancer), pancreatic cancer, bowel cancer, lymphoma, melanoma, ocular cancer, ovarian cancer, pancreatic cancer, prostate cancer, pituitary cancer, uterine cancer, and vaginal cancer.

Further, various embodiments provided for herein include treatment or prevention of the following non-limiting examples of infectious diseases including, but not limited to, infections of bacterial origin may include, for example, infections with bacteria from one or more of the following genera: *Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia,* and mutants or combinations thereof. In several embodiments, methods are provided to treat a variety to treat fungal infections, and such as infections of fungal origin may include, for example, infections with fungi from one or more of the following genera: *Aspergillus, Blastomyces, Candida, Coccidioides, Cryptococcus,* and *Histoplasma,* and mutants or combinations thereof. In several embodiments, methods are provided to treat a variety to treat viral infections, such as those caused by one or more viruses, such as adenovirus, Coxsackievirus, Epstein-Barr virus, hepatitis a virus, hepatitis b virus, hepatitis c virus, herpes simplex virus, type 1, herpes simplex virus, type 2, cytomegalovirus, ebola virus, human herpesvirus, type 8, HIV, influenza virus, measles virus, mumps virus, human papillomavirus, parainfluenza virus, poliovirus, rabies virus, respiratory syncytial virus, rubella virus, and varicella-zoster virus.

In some embodiments, also provided herein are nucleic acid and amino acid sequences that have homology of at least 80%, 85%, 90%, 95%, 96%, 97%, 98%, 99% (and ranges therein) as compared with the respective nucleic acid or amino acid sequences of SEQ ID NOS. 1-68 and that also exhibit one or more of the functions as compared with the respective SEQ ID NOS. 1-68: including but not limited to, (i) enhanced proliferation, (ii) enhanced activation, (iii) enhanced cytotoxic activity against cells presenting ligands to which NK cells harboring receptors encoded by the nucleic acid and amino acid sequences bind, (iv) enhanced homing to tumor or infected sites, (v) reduced off target cytotoxic effects, (vi) enhanced secretion of immunostimulatory cytokines and chemokines (including, but not limited to IFNg, TNFa, IL-22, CCL3, CCL4, and CCL5), (vii) enhanced ability to stimulate further innate and adaptive immune responses, and (viii) combinations thereof.

Additionally, in several embodiments, there are provided amino acid sequences that correspond to any of the nucleic acids disclosed herein, while accounting for degeneracy of the nucleic acid code. Furthermore, those sequences (whether nucleic acid or amino acid) that vary from those expressly disclosed herein, but have functional similarity or equivalency are also contemplated within the scope of the present disclosure. The foregoing includes mutants, truncations, substitutions, or other types of modifications.

There are provided for herein, according to several embodiments, polynucleotides encoding activating chimeric receptors, comprising an extracellular receptor domain, wherein the extracellular receptor domain comprises a fragment of CD94, NKG2A, or NKG2C variant, an effector domain comprising a transmembrane region and an intracellular signaling domain. In several embodiments, the polynucleotide encodes an effector domain comprising CD16. In several embodiments, the polynucleotide encodes an effector domain comprising NCR1. In several embodiments, the polynucleotide encodes an effector domain comprising NCR2. In several embodiments, the polynucleotide encodes an effector domain comprising NCR3. In some embodiments, the polynucleotide encodes an additional effector domain portion comprising 4-1BB. In several embodiments, the polynucleotide encodes a chimeric receptor made up of CD16 and a fragment of CD94, NKG2A, or NKG2C variant. In several embodiments, the polynucleotide encodes a chimeric receptor made up of NCR1 and fragment of CD94, NKG2A, or NKG2C variant. In several embodiments, the polynucleotide encodes a chimeric receptor made up of NCR2 and a fragment of CD94, NKG2A, or NKG2C variant. In additional embodiments, the polynucleotide encodes a chimeric receptor made up of a fragment of CD94, NKG2A, or NKG2C variant coupled to CD16 and optionally 4-1BB. In several embodiments, CD16 is replaced by NCR1, and in some embodiments, by NCR2, or even NCR3, depending on the embodiment. In several embodiments, the effector domain further comprises a GS linker between, for example, 4-1BB and one of CD16, NCR1, NCR2, or NCR3.

In several embodiments, the extracellular receptor domain further comprises a hinge region. In several embodiments, the hinge region comprises CD8a. However, in additional embodiments, the hinge region further comprises one or more linkers, which in some embodiments, comprise GS9, CD8a/GS3, truncated CD8a, GS3, and the like.

In several embodiments, the extracellular receptor domain further comprises a CD8a signal peptide. In several embodiments, the effector domain comprises one or more hemi-ITAM sequences. In several embodiments, the chimeric receptor does not comprise DNAX-activating protein 10 (DAP10). In several embodiments, the chimeric receptor does not comprise an ITAM motif, but rather employs an alternative signaling region, such as an ITSM, hemi-tam or other co-stimulatory region.

In several embodiments, the activating chimeric receptors described herein are co-expressed with a chimeric receptor targeting cells that express natural ligands of Natural Killer Group 2 member D (NKG2D), leading to synergistically enhanced NK cell activation and cytotoxicity. Thus, in several embodiments, there is provided also provided a polynucleotide encoding a NKGD chimeric receptor comprising an extracellular receptor domain, wherein the extracellular receptor domain comprises a peptide that binds native NKG2D, wherein the peptide that binds native ligands of NKG2D is a fragment of NKG2D, a transmembrane region, and an effector domain. In several embodiments, the fragment of NKG2D is encoded by a polynucleotide comprising a fragment of the sequence of SEQ ID NO: 1. In several embodiments, the fragment of NKG2D comprises the sequence of SEQ ID NO: 2, while in additional embodiments, the fragment encoding NKG2D is codon optimized, and comprises, for example, the sequence of SEQ ID NO: 3. In several embodiments, the effector domain comprises one or more of CD16, NCR1, NCR2, NCR3, 4-1BB, CD28, NKp80, DAP10, CD3zeta and 2B4. In several embodiments, these effector domains are coupled to CD8 alpha. In several embodiments, the NKG2D domain is not full-length or wild-type NKG2D and in some such embodiments, DAP10 is not used in the chimeric receptor construct. In still further embodiments, CD3Zeta or an ITAM is not used. As discussed herein, combinations of transmembrane and intracellular domains are used in several embodiments and provide for synergistic interactions between the components of the NKG2D chimeric receptor and yield enhanced cytotoxic effects. In several embodiments, linkers, hinges, or other "spacing" elements are provided for in the NKG2D chimeric receptor constructs. For example, in several embodiments, the effector domain comprises a linker. In several embodiments, the polynucleotides encode a GS linker between the portions of the NKG2D chimeric receptor construct, such as between any of 4-1BB, CD28, CD16, NCR1, NCR3, CD3zeta, DAP10, 2B4 or NKp80. In several embodiments, the NKG2D chimeric receptor effector domain comprises a linker. In several embodiments, the polynucleotides encode a GS linker between the portions of the NKG2D chimeric receptor construct, such as between any of 4-1BB, CD28, CD16, NCR1, NCR3, 2B4 or NKp80. In several embodiments, there is provided for a chimeric receptor comprising a hinge region. In several embodiments, the NKG2D chimeric receptor effector domain comprises one or more hemi-ITAM sequences. Additionally, any of chimeric receptors disclosed herein can also be co-expressed with membrane-bound interleukin 15 (mbIL15).

In several embodiments, the provided polynucleotide is an mRNA. In some embodiments, the polynucleotide is operably linked to at least one regulatory element for the expression of the activating chimeric receptor. As used herein, the terms "nucleic acid," "nucleotide," and "polynucleotide" shall be given their ordinary meanings and shall include deoxyribonucleotides, deoxyribonucleic acids, ribonucleotides, and ribonucleic acids, and polymeric forms thereof, and includes either single- or double-stranded forms. Nucleic acids include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleic acid analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), locked-nucleic acids (LNAs), and the like. As used herein, the term "operably linked," for example in the context of a regulatory nucleic acid sequence being "operably linked" to a heterologous nucleic acid sequence, shall be given its ordinary meaning and shall mean that the regulatory nucleic acid sequence is placed into a functional relationship with the heterologous nucleic acid sequence. In the context of an IRES, "operably linked to" refers to a functional linkage between a nucleic acid sequence containing an internal ribosome entry site and a heterologous coding sequence initiation in the middle of an mRNA sequence resulting in translation of the heterologous coding sequence. As used herein, the term "vector" shall be given its ordinary meaning and shall refer to a vehicle by which a DNA or RNA sequence (e.g., a foreign gene) can be introduced into a genetically engineered cell, so as to transform the genetically engineered cell and promote expression (e.g., transcription and/or translation) of the introduced sequence. Vectors include viruses, plasmids, phages, etc. The term "chimeric receptor" as used herein shall be given its ordinary meaning and shall refer to a cell-surface receptor comprising at least two polypeptide domains not naturally found together on a single protein or comprising one or more regions or portions from a different receptor or signaling molecule (e.g., another subtype or type of receptor). The term "chimeric receptor complex" as used herein refers to a first polypeptide, which may comprise at least two polypeptide domains in a combination that are not naturally found together on a single protein, which first polypeptide is associated with a second polypeptide, for example, an adaptor polypeptide, a signaling molecule, or a stimulatory molecule. Additional terms relating to generation and use of chimeric receptors as disclosed here are readily understood by one of ordinary skill in the art and can also be found in International Publication WO 2014/117121 and U.S. Pat. No. 7,994,298, each of which are incorporated by reference in their entirety herein.

Additionally provided, according to several embodiments, is a vector comprising the polynucleotide encoding any of the polynucleotides provided for herein, wherein the polynucleotides are optionally operatively linked to at least one regulatory element for expression of an activating chimeric receptor. In several embodiments, the vector is a retrovirus.

Further provided herein are engineered natural killer cells comprising the polynucleotide, vector, or chimeric activating receptors as disclosed herein. In several embodiments, these NK cells are suitable for use in the treatment of prevention of disease, such as, for example, cancer and/or infectious disease.

In several embodiments, the polynucleotides disclosed herein further encode a short hairpin RNA (shRNA) that specifically inhibits transcription or translation of native NKG2A, wherein the shRNA comprises a nucleotide sequence that hybridizes under stringent conditions to the native NKG2A gene, wherein the shRNA comprises a sense fragment, which comprises a nucleotide sequence substantially identical to a target sequence in the NKG2A gene that is absent in the NKG2A fragment, and an antisense fragment, wherein the sense and antisense fragments are separated by a loop fragment. In several embodiments, the polynucleotide is co-expressed with an additional construct encoding membrane-bound interleukin 15 (mbIL15). In several embodiments, the polynucleotide is an mRNA. In several embodiments, the polynucleotide is operably linked to at least one regulatory element for the expression of the activating chimeric receptor.

Also provided for herein in several embodiments, in several embodiments is a vector comprising a polynucleotide of the present disclosure, wherein the polynucleotide is operatively linked to at least one regulatory element for expression of the activating chimeric receptor. In several embodiments, the vector is a retrovirus.

In several embodiments, there is provided a method for treating or preventing cancer or an infectious disease in a mammal in need thereof, said method comprising administering to said mammal a therapeutically effective amount of NK cells, wherein said NK cells express a activating chimeric receptor encoded by a polynucleotide according to the present disclosure. In several embodiments, the NK cells are autologous cells isolated from a patient having a cancer or an infectious disease. In several embodiments, the NK cells are allogenic cells isolated from a donor. In several embodiments, the NK cells lack surface expression of native NKG2A.

In several embodiments, there is provided the use of a polynucleotide according to the present disclosure in the manufacture of a medicament for treating or preventing cancer or an infectious disease in a mammal in need thereof. In several embodiments, there is provided the use of a vector according the present disclosure in the manufacture of a medicament for enhancing NK cell cytotoxicity in a mammal in need thereof. In several embodiments the vector is used in the manufacture of a medicament for treating or preventing cancer or an infectious disease in a mammal in need thereof.

In several embodiments, there is provided the use of an isolated genetically engineered natural killer cell according to the present disclosure for enhancing NK cell cytotoxicity in a mammal in need thereof. In several embodiments, there is also provided the use of an isolated genetically engineered natural killer cell according to the present disclosure for treating or preventing cancer or an infectious disease in a mammal in need thereof.

In several embodiments, there is provided a chimeric Natural Killer Group 2 member C (NKG2C) comprising an extracellular receptor domain, a transmembrane domain, and a cytoplasmic domain, wherein the extracellular receptor domain comprises SEQ ID NO. 58. In several embodiments, there is provided a chimeric receptor comprising a Natural Killer Group 2 member A (NKG2A) extracellular receptor domain, a transmembrane region, and a cytoplasmic domain. In several embodiments, the transmembrane region comprises a CD8 transmembrane region. In several embodiments, the cytoplasmic domain comprises one or more of a 4-1BB cytoplasmic domain and a CD3zeta cytoplasmic domain.

In several embodiments, there is provided a polynucleotide encoding a chimeric receptor, the chimeric receptor comprising an extracellular domain, a transmembrane domain, and a cytoplasmic domain, wherein the extracellular domain comprises a Natural Killer Group 2 member C (NKG2C) and SEQ ID NO. 58.

In several embodiments, there is provided a polynucleotide encoding a chimeric receptor, the chimeric receptor comprising a Natural Killer Group 2 member A (NKG2A) extracellular receptor domain, a transmembrane region, and a cytoplasmic domain. In several embodiments, the transmembrane region comprises a CD8 transmembrane region. In several embodiments, the cytoplasmic domain comprises one or more of a 4-1BB cytoplasmic domain and a CD3zeta cytoplasmic domain.

EXAMPLES

Methods

The following experimental methods and materials were used in the non-limiting experimental examples disclosed below.

Cell Lines and Culture Conditions

The human tumor cell lines SKBR3, HT-29, U2-OS were purchased from the American Type Culture Collection (ATCC; Rockville, MD). The Ewing sarcoma cell line ES8 and EW8 were from the tissue repository of St. Jude Research Hospital (Memphis, TN). Cell lines were maintained in RPMI-1640 (ThermoFisher, Waltham, MA); media were supplemented with 10% fetal bovine serum (FBS; GE Healthcare, Chicago, IL) and antibiotics. The cell lines were transduced with a murine stem cell virus (MSCV) retroviral vector (from the Vector Development and Production Shared Resource of St. Jude Children's Research Hospital, Memphis, TN) containing either green fluorescence protein (GFP) and luciferase.

Expansion of Human NK Cells and Selection of NK Cell Subsets

Peripheral blood samples were obtained from discarded anonymized by-products of platelet donations from healthy adult donors at the National University Hospital Blood Bank, Singapore.

Mononucleated cells were separated by centrifugation on a Lymphoprep density step (Nycomed, Oslo, Norway) and washed twice in RPMI-1640. To expand NK cells, mononucleated cells were co-cultured with the genetically-modified K562-mb15-41BBL cell line. Briefly, peripheral blood mononucleated cells ($3 \times 10^6$) were cultured in a 6-well tissue culture plate with $2 \times 10^6$ irradiated (100 Gy)K562-mb15-41BBL cells in SCGM medium (CellGenix, Freiburg, Germany) containing 10% FBS and 40 IU/mL human interleukin (IL)-2 (Novartis, Basel, Switzerland). Every 2-3 days, fresh tissue culture medium and IL-2 was added. After 7 days of co-culture, residual T cells were removed using Dynabeads CD3 (Thermo Fisher), producing cell populations containing >90% CD56+CD3−NK cells. Expanded NK cells were maintained in SCGM with FBS, antibiotics, and 400 IU/mL IL2 before the experiments.

To deplete NKG2A+NK cells, expanded NK cells were labeled with anti-NKG2A antibody conjugated to allophycocyanin (APC) and anti-APC microbeads and separated on LD column (all from Miltenyi Biotech).

DNA Plasmids, Production of Retrovirus and Transduction of NK Cells

Plasmids encoding all constructs were synthesized by Genescript (Nanjing, China). A RD114-pseudotyped MSCV retrovirus containing the constructs was used to transduce NK cells. Retroviral vector-conditioned medium was added to RetroNectin (Takara, Otsu, Japan)-coated polypropylene tubes; after centrifugation and removal of the supernatant, expanded NK cells ($3 \times 10^5$) were added to the tubes and left at 37° C. for 12 hours; fresh viral supernatant was added every 12 hours for a total of 6 times. Cells were then maintained in RPMI with FBS, antibiotics and 400 IU/ml of IL-2 until the time of the experiments.

Detection of Activating Receptor Expression by Flow Cytometry

Surface expression of the anti-NKG2C was detected with an anti-NKG2C-phycoerythrin (PE) antibody (Miltenyi Biotech). Expression of NKG2A was detected with anti-NKG2A antibodies conjugated to PE or APC (Miltenyi Biotech). Expression of CD94 was detected with anti-CD94-APC (BD Biosciences).

Cytotoxicity Assays

Target cells transduced with GFP/luciferase were suspended in RPMI-1640 with 10% FBS, and plated into 96-well flat bottom plates (Costar, Corning, NY). The plates were placed in an incubator for at least 4 hours to allow for cell attachment before adding NK cells. Expanded NK cells expressing various receptors or GFP alone, suspended in RPMI-1640 with 10% FBS were then added at various effector-to-target (E:T) ratios, and co-cultured with target cells for 4 hours. At the end of the cultures, number of viable cells were measured, after adding BrightGlo (Promega, Fitchburg, WI) to the wells, using a Flx 800 plate reader (BioTek, Winooski, VT).

Example 1—Activating High Affinity NKG2C Receptor Constructs

As disclosed herein, various activating chimeric receptor constructs comprising an extracellular receptor domain coupled with various transmembrane domains are provided. The present experiment was conducted to evaluate the expression and cytotoxic activity of an activating Natural Killer Group 2 member C (NKG2C) variant engineered for high affinity to HLA-E/peptide complex. The activating NKG2C receptor construct was prepared and tested according to the methods and materials described above. Depending on the construct, the methods used can be readily adjusted to account for variations required for generating, expressing and testing a construct.

FIG. 1A depicts a schematic showing an engineered NKG2C variant (165-168 SIIS) engineered for high affinity to HLA-E/peptide complex in a complex with CD94 and a Dap12 dimer (termed "D12(SIIS)2C94" herein). FIG. 1B depicts a schematic of a construct comprising NKG2C (165-168 SIIS), Dap12, and CD94 inserted into a MSCV retroviral vector containing green fluorescence protein (GFP) after an internal ribosomal entry site (IRES).

The ability of NK cells to effectively express this construct was first assessed. FIG. 2 depicts flow cytometry data demonstrating the robust expression of the high affinity activating D12(SIIS)2C94 receptor complex in purified NKG2C(+)NKG2A(−) NK cells relative to NK cells transduced with a vector containing GFP only. Collectively, these data demonstrate that, in accordance with several embodiments disclosed herein, engineered activating chimeric receptor constructs can successfully be expressed on NK cells.

In several embodiments, enhanced expression of the construct can be achieved by repeated transduction of the NK cells with a particular construct. In several embodiments, the components of the constructs can be delivered to a cell in a single vector, or alternatively using multiple vectors. Depending on the embodiment, the construct itself may lead to enhanced expression, for example a linear or head to tail construct may yield increased expression because of a lesser degree of in-cell assembly that a multiple subunit construct requires.

Figure 3A:
FIGS. 3A-3B depict the design and generation of a HLA-G signal peptide containing HLA-E molecule.
Figure 3B:
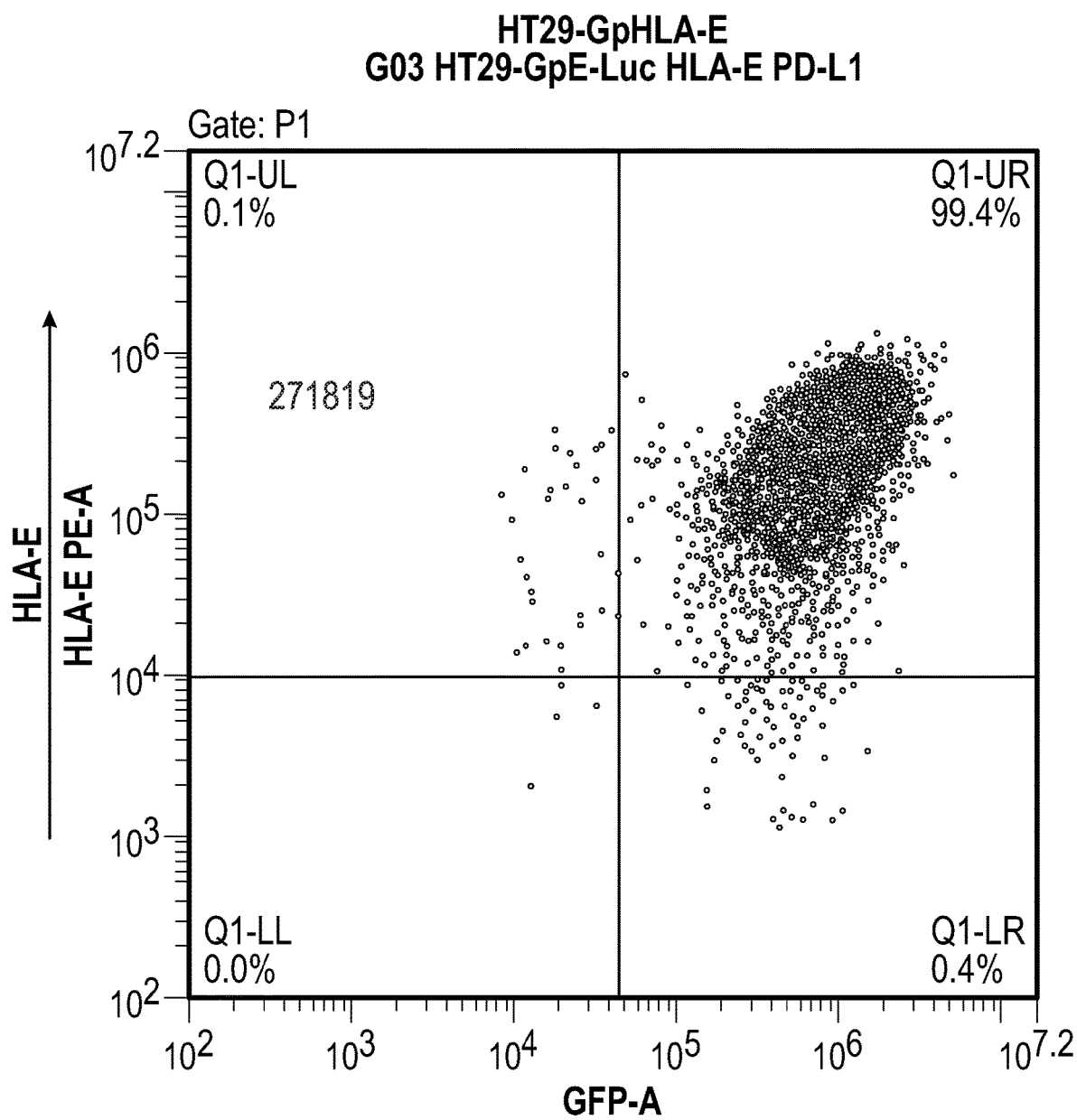
Figure 3B:
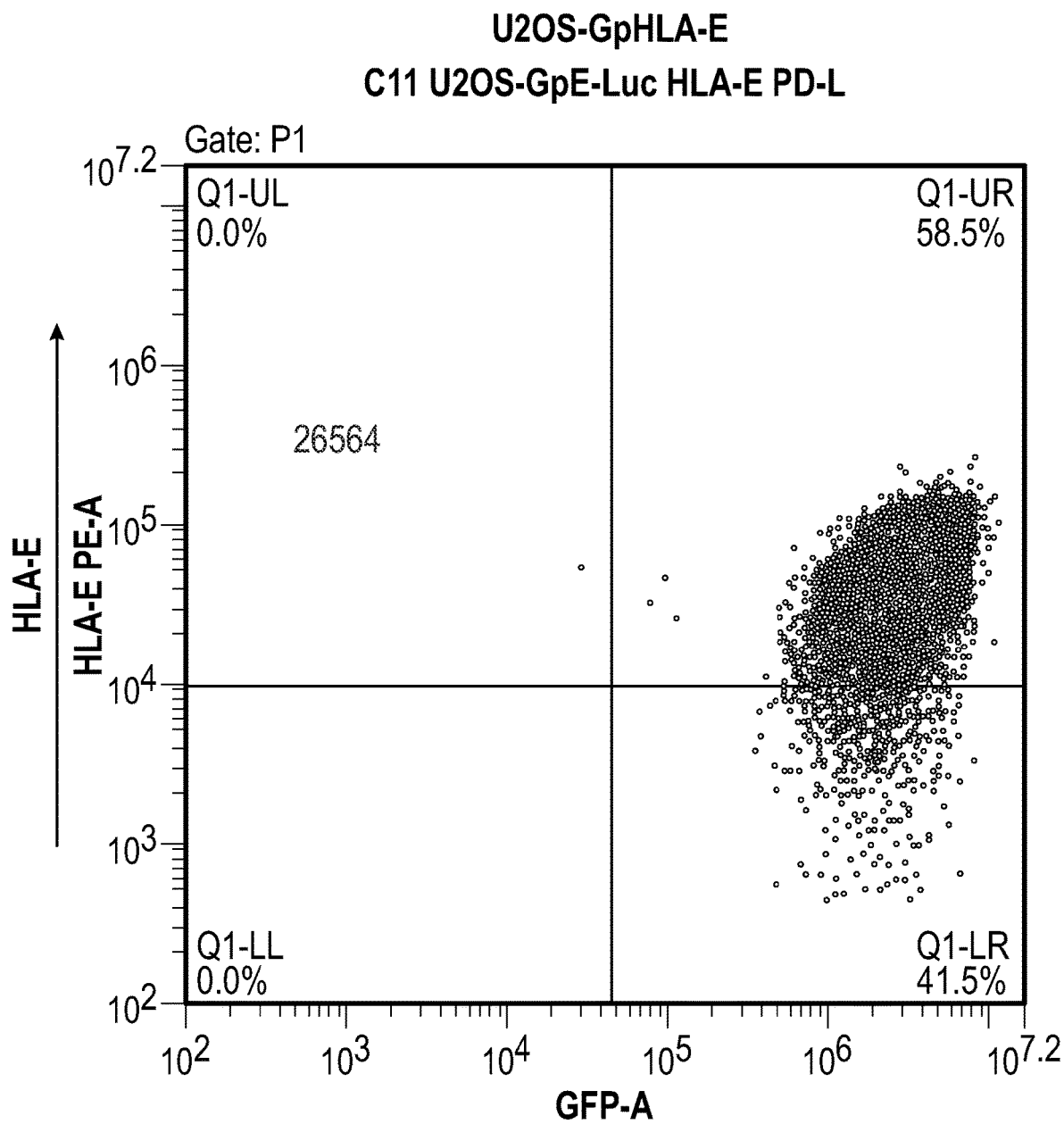
Figure 3B:
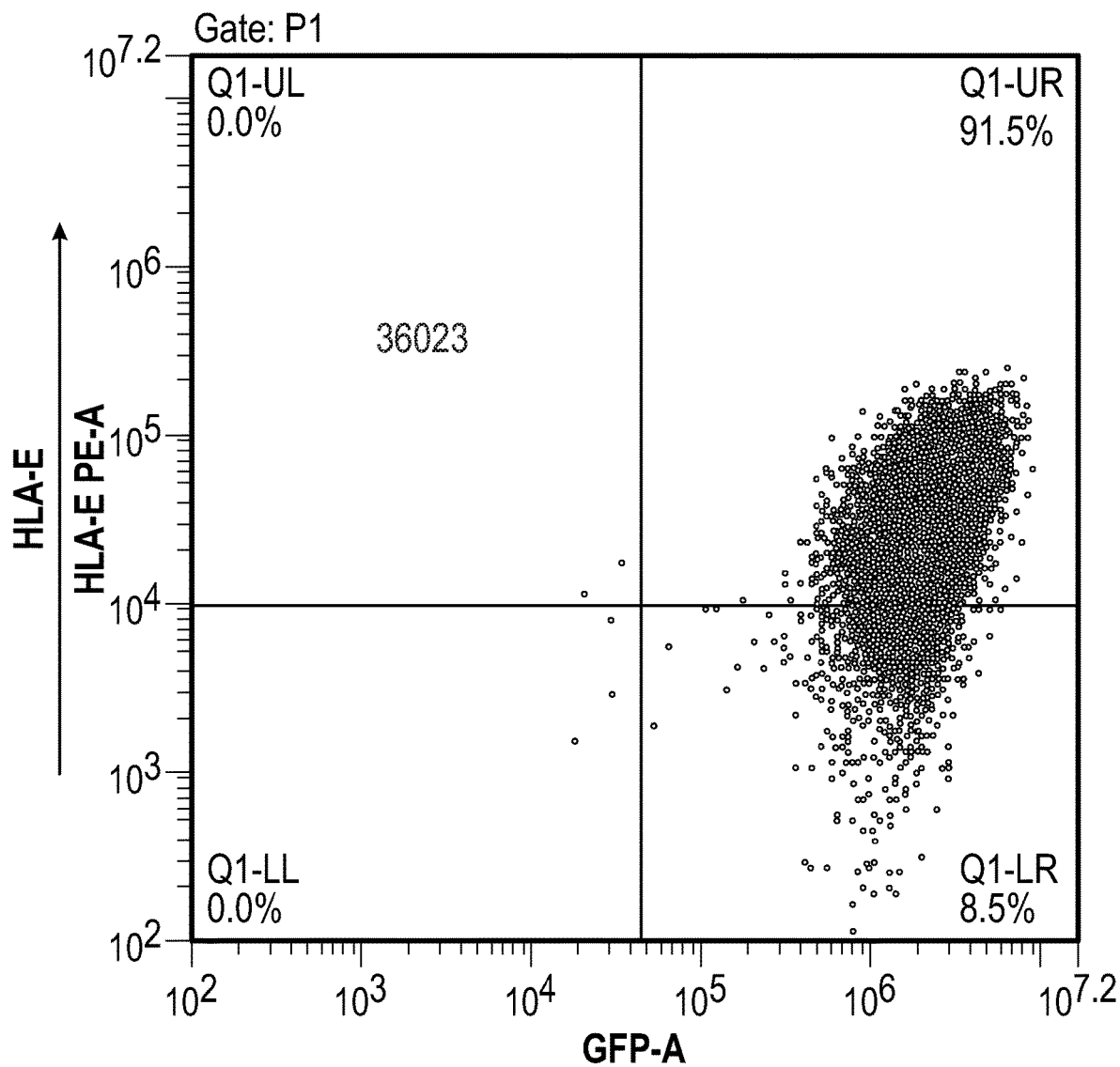
Figure 3B:
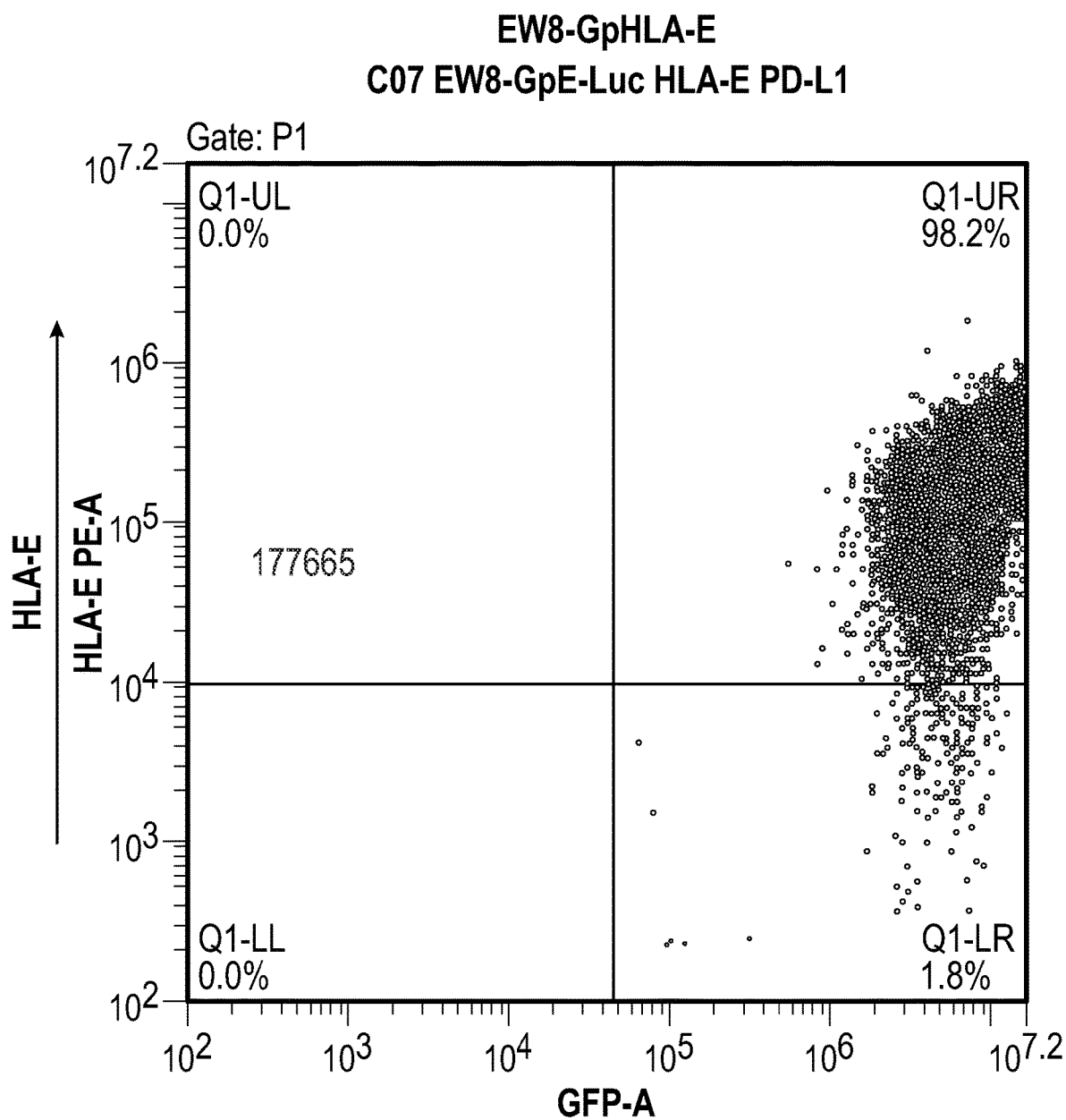

NKG2C/CD94 and NKG2A/CD94 bind the nonclassical MEW class I molecule HLA-E/peptide complex in humans. HLA-E has a very specialized role in cell recognition by NK cells, and HLA-E binds a restricted subset of peptides derived from signal peptides of classical MEW class I molecules, namely HLA-A, B, C, G. Therefore NK cells can indirectly monitor the expression of classical MEW class I molecules through the interaction of NKG2C/CD94 and NKG2A/CD94 with HLA-E/peptide complex. To evaluate the efficacy of the activating NKG2C receptor constructs and activating NKG2A receptor constructs described herein, cancer cells were engineered to express HLA-E containing the HLA-G signal peptide. FIG. 3 depicts the design and generation of a HLA-G signal peptide containing HLA-E molecule. FIG. 3A depicts the substitution of HLA-E signal peptide (SEQ ID NO. 69) with HLA-G signal peptide (SEQ ID NO. 70) of HLA-E (designated as GpHLA-E; HLA-G signal peptide carrying HLA-E). FIG. 3B depicts flow cytometry data verifying the exogenous expression of GpHLA-E in solid tumor cell lines HT29, U2OS, ES8, and EW8.

Figure 4A:
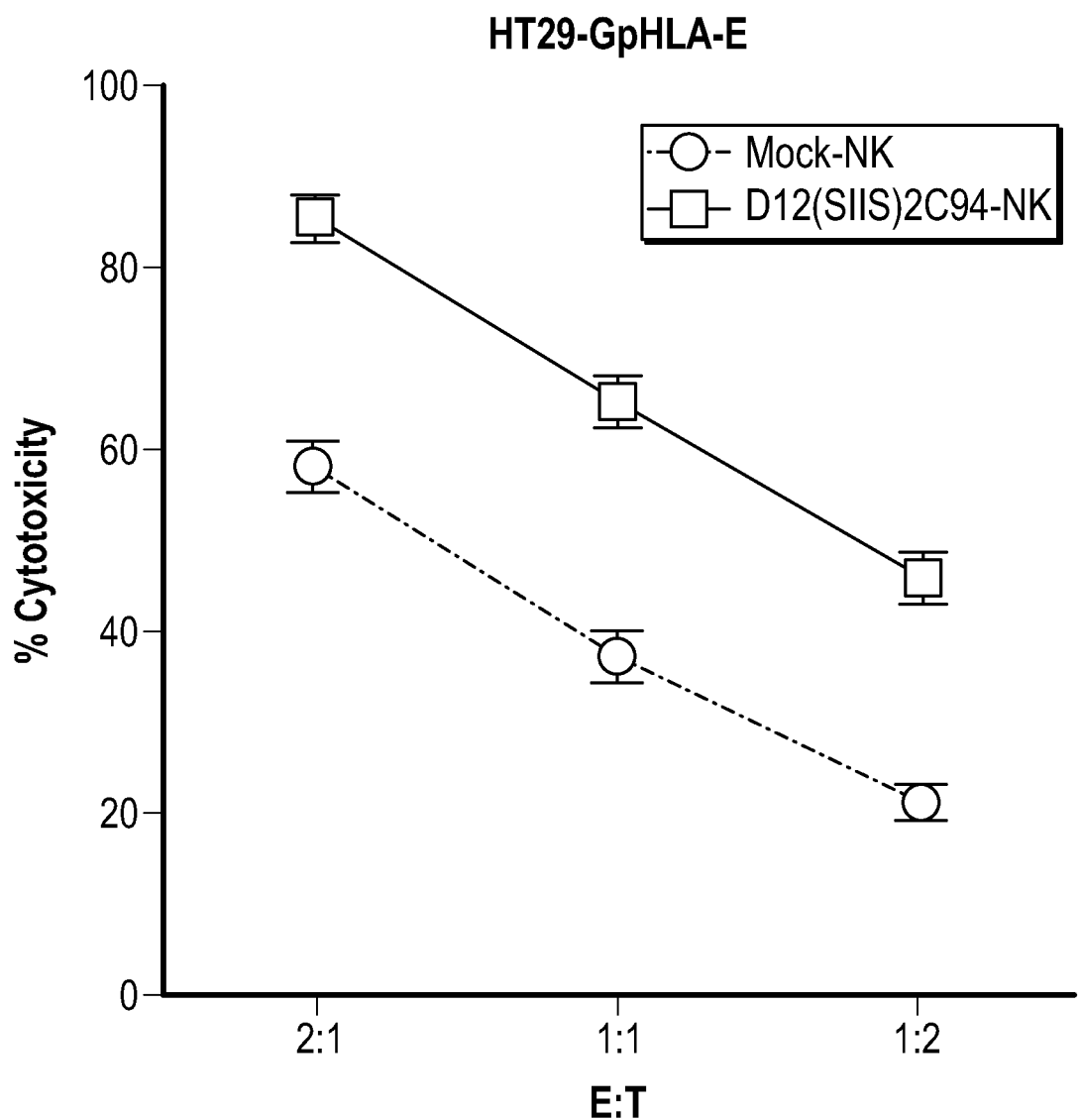
FIGS. 4A-4C depicts data related to 4-hour cytotoxicity assays at the indicated E:T ratios of purified NKG2C(+) NKG2A(−) NK cells that are transduced with D12(SIIS) 2C94 against the genetically-modified tumor cell lines HT29-GpHLA-E (FIG. 4A), U2OS-GpHLA-E (FIG. 4B), and SKBR3-GpHLA-E (FIG. 4C).
Figure 4B:
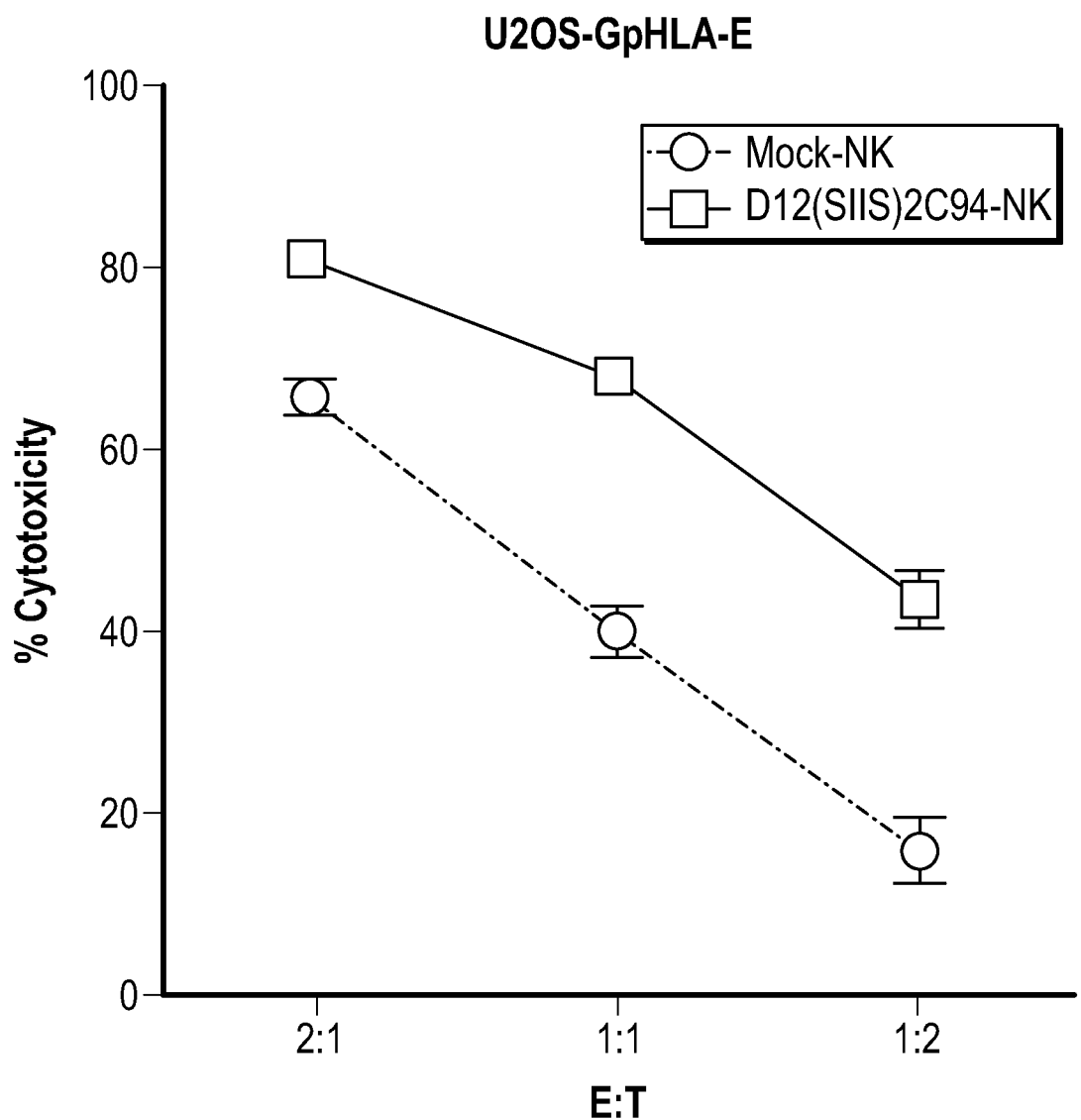
Figure 4C:
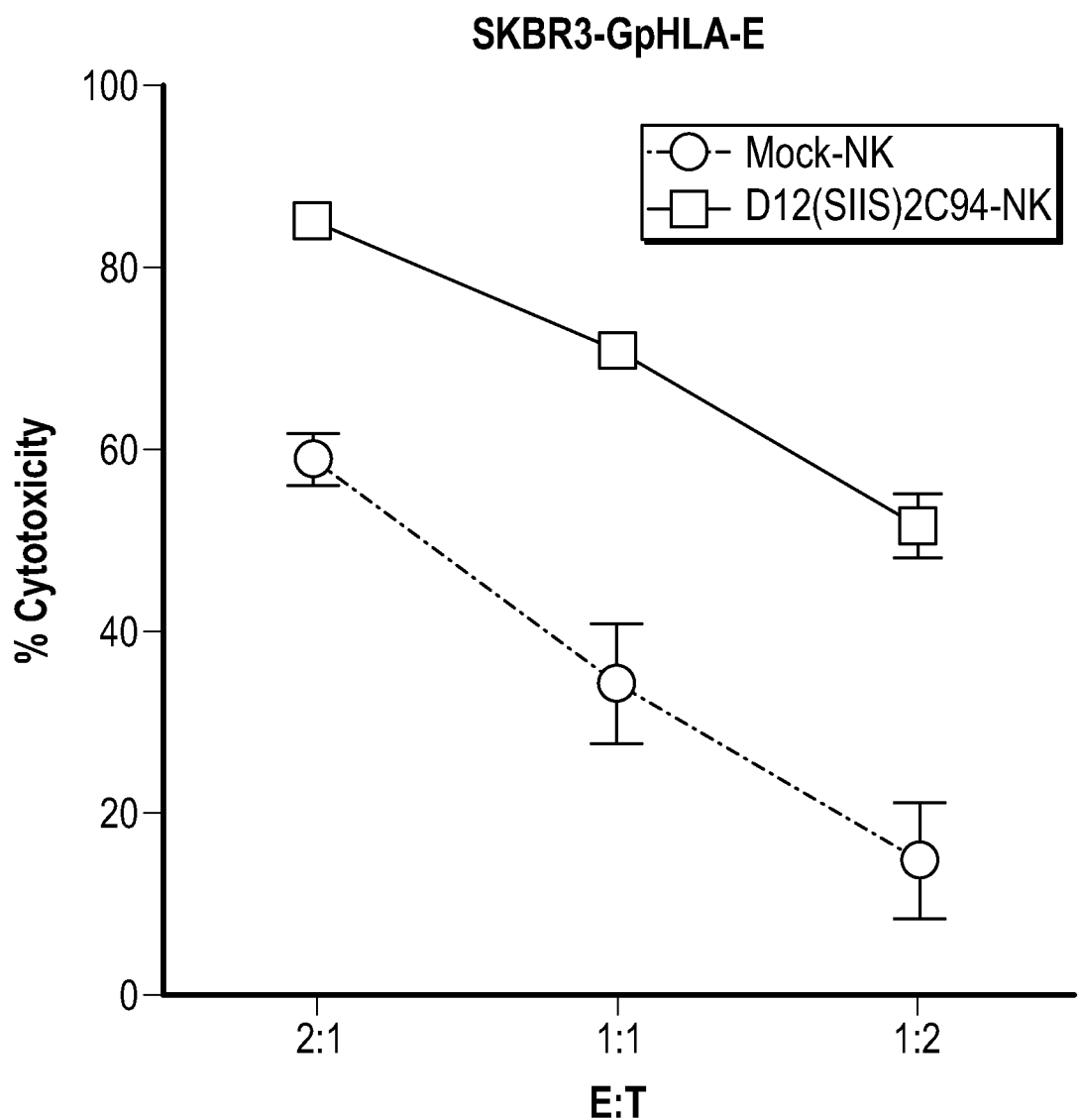
Figure 5A:
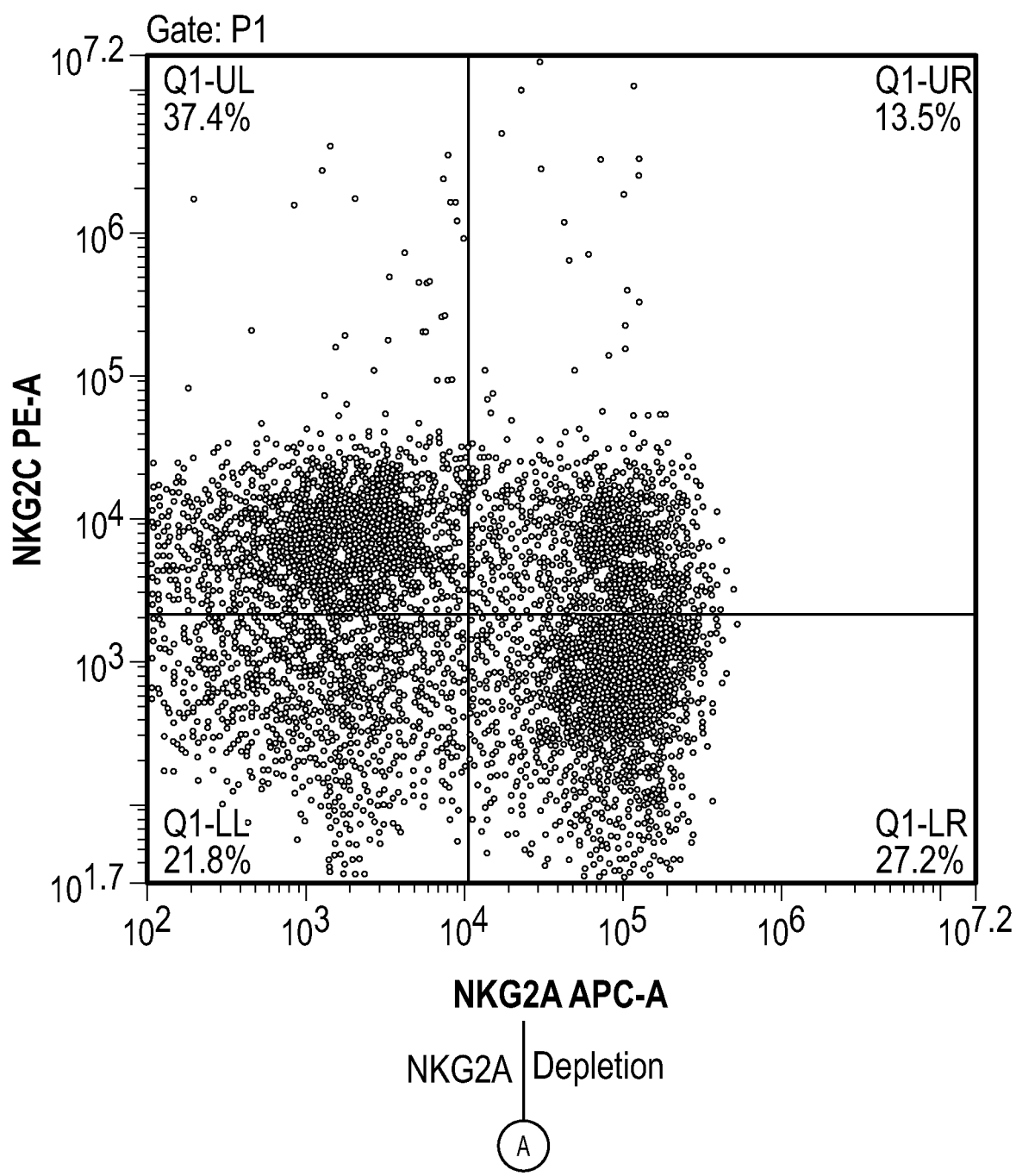
FIGS. 5A-5B depict data related to characterization of transduced NK cells.
Figure 5A:
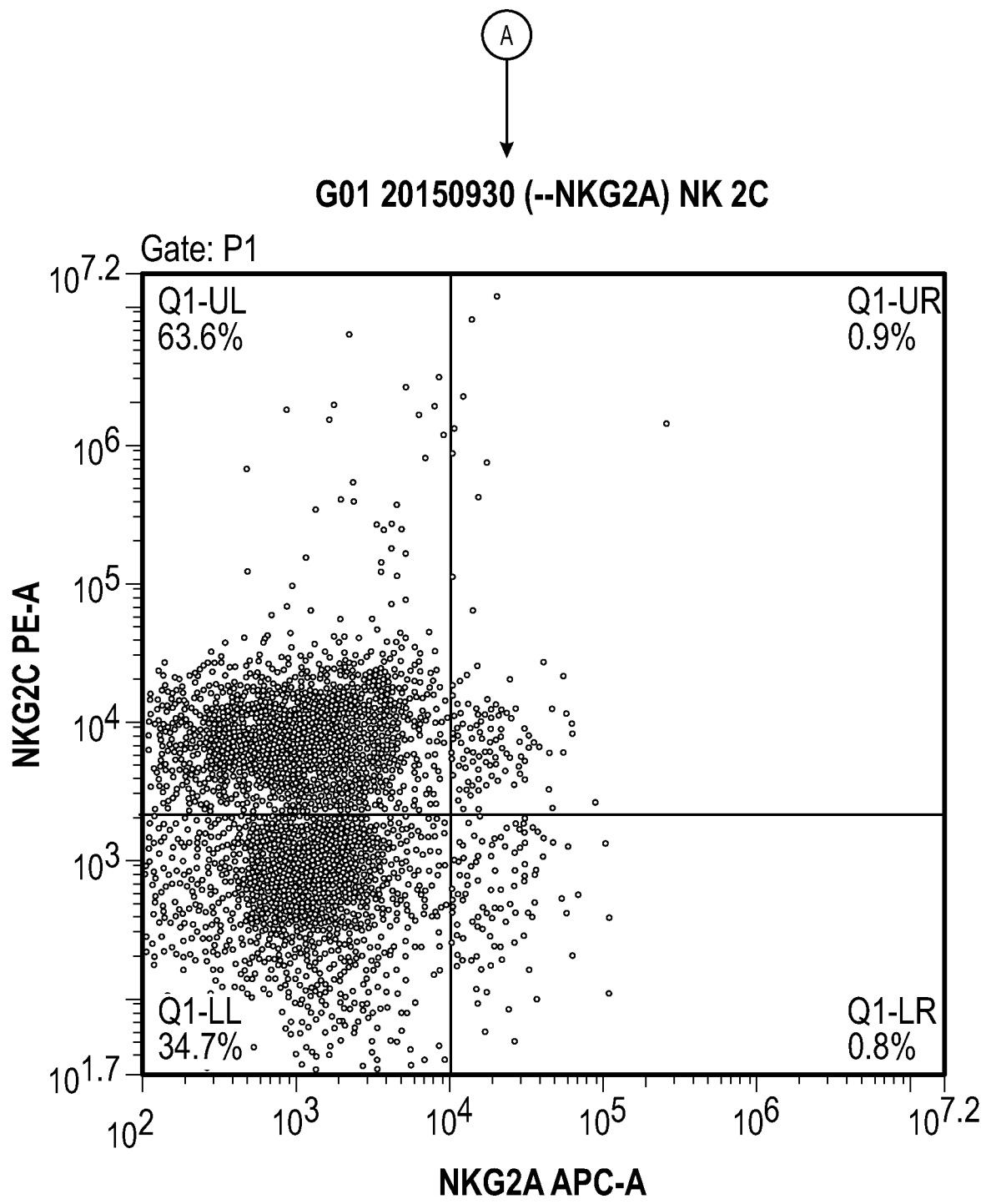
Figure 5B:
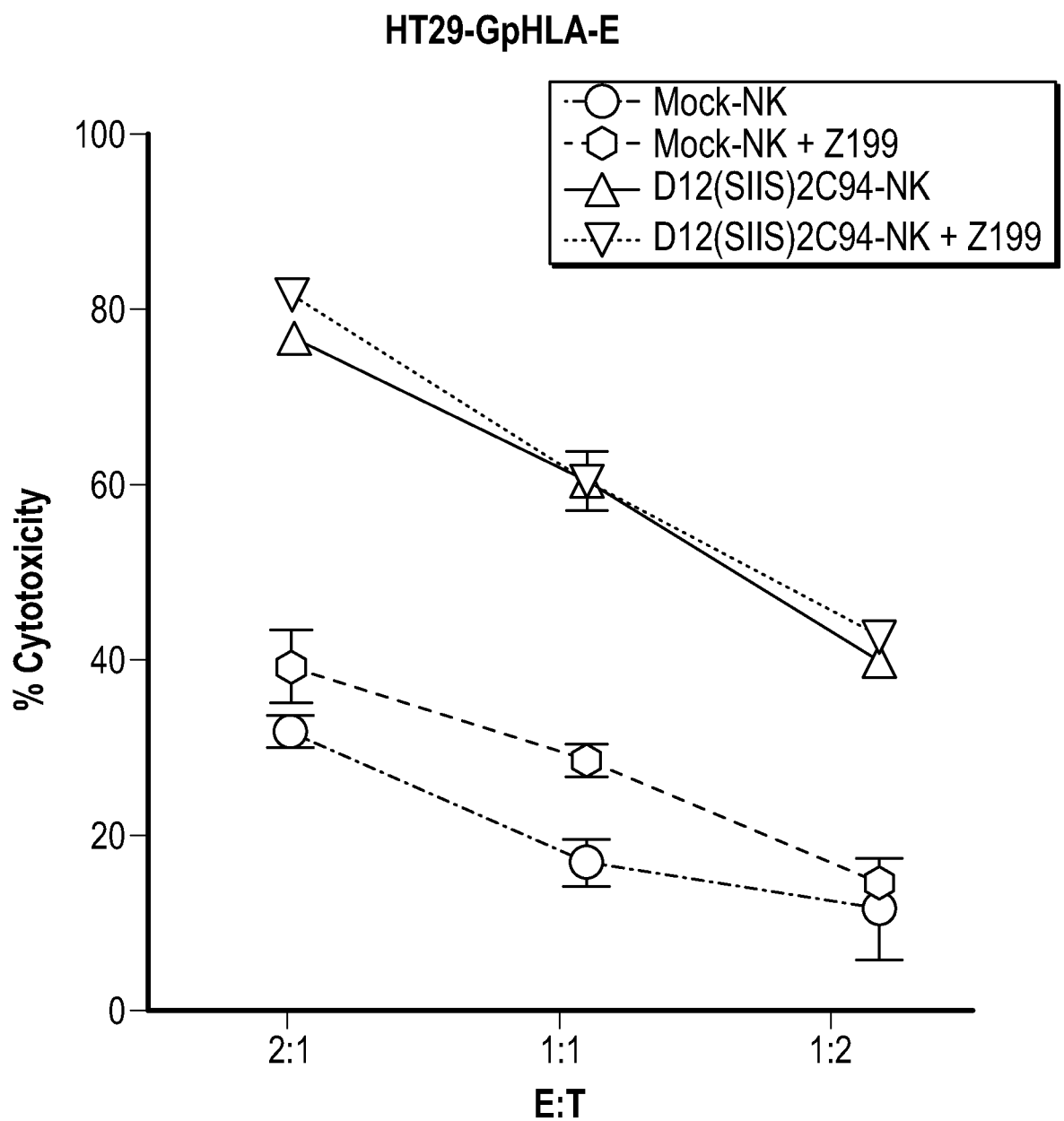
Figure 5B:
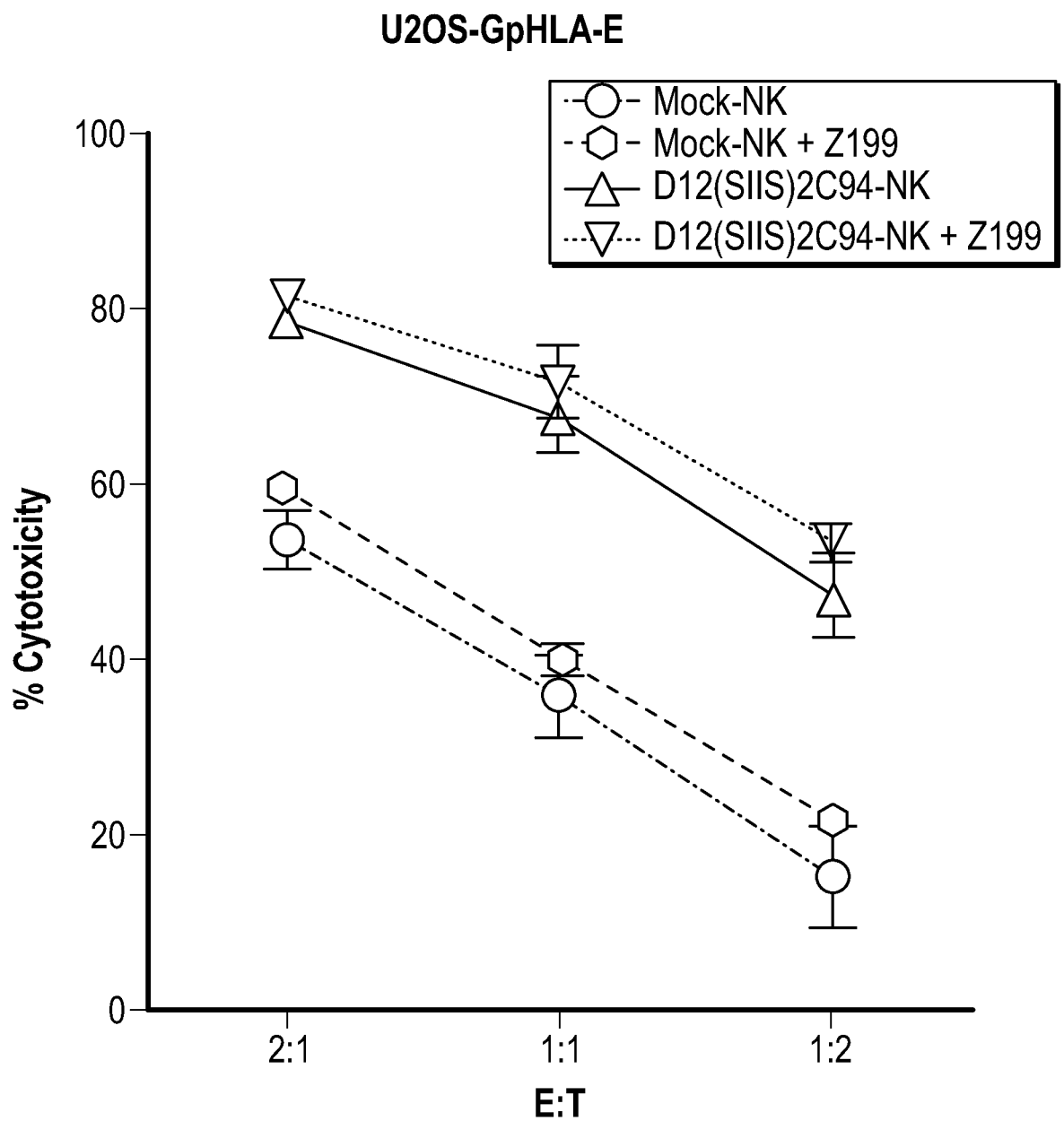

To evaluate the potency of the populations of transduced NK cells, cytotoxicity assays were performed using cancer cell lines that express GpHLA-E. Purified NKG2C(+) NKG2A(−) NK cells expressing D12(SIIS)2C94 displayed significantly higher cytotoxicity against U2O5-GpHLA-E, SKBR3-GpHLA-E, and HT29-GpHLA-E cells than the control NK cells at all of the E:T ratios tested (FIG. 4). These data provide evidence that NK cells can not only be engineered to express activating chimeric receptor constructs, but those cells that express the activating chimeric receptor are able to be activated and successfully generate enhanced cytotoxic effects against target cells.

To confirm the depletion of NKG2A(+) cells, presence of which could potentially confound the results of these studies and NK cell-based therapies, flow cytometry analysis was conducted. Following NKG2A depletion, we confirmed that the cell population was comprised of NKG2C(+)NKG2A(−) NK cells. Further, cytotoxicity assays of mock transduced NK cell populations or D12(SIIS)2C94-transduced NKG2C (+)NKG2A(−) NK cells against the genetically-modified tumor cell lines demonstrated the enhanced cytotoxicity of the latter NK cell population, regardless of whether or not cells were incubated with anti-NKG2A antibody Z199 (FIG. 5).

Example 2—Activating Chimeric NKG2A/CD94 Receptor Constructs

As disclosed herein, various activating chimeric receptor constructs comprising an extracellular receptor domain coupled with various transmembrane domains are provided. The present experiment was conducted to evaluate the expression and cytotoxic activity of an activating Natural Killer Group 2 member A (NKG2A)/CD94 receptor construct. The activating NKG2A/CD94 receptor construct was prepared and tested according to the methods and materials described above. Depending on the construct, the methods used can be readily adjusted to account for variations required for generating, expressing and testing a construct.

Figure 6A:
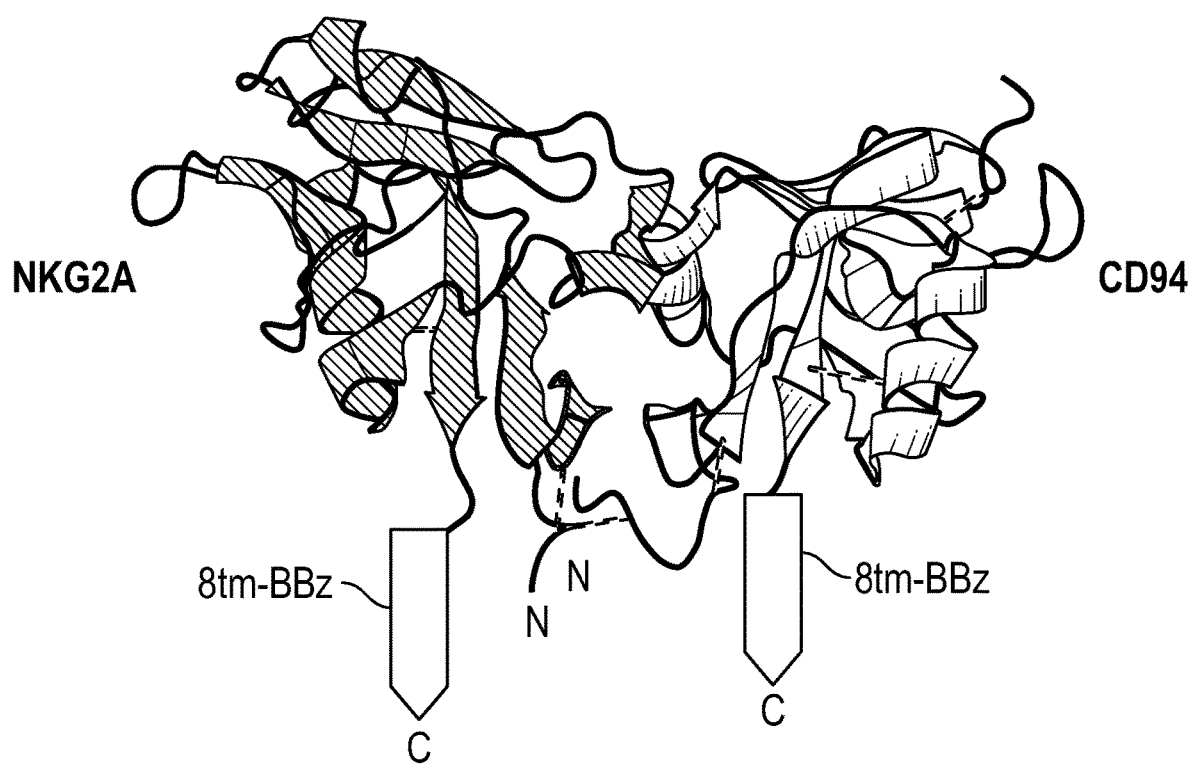
Figure 7A:
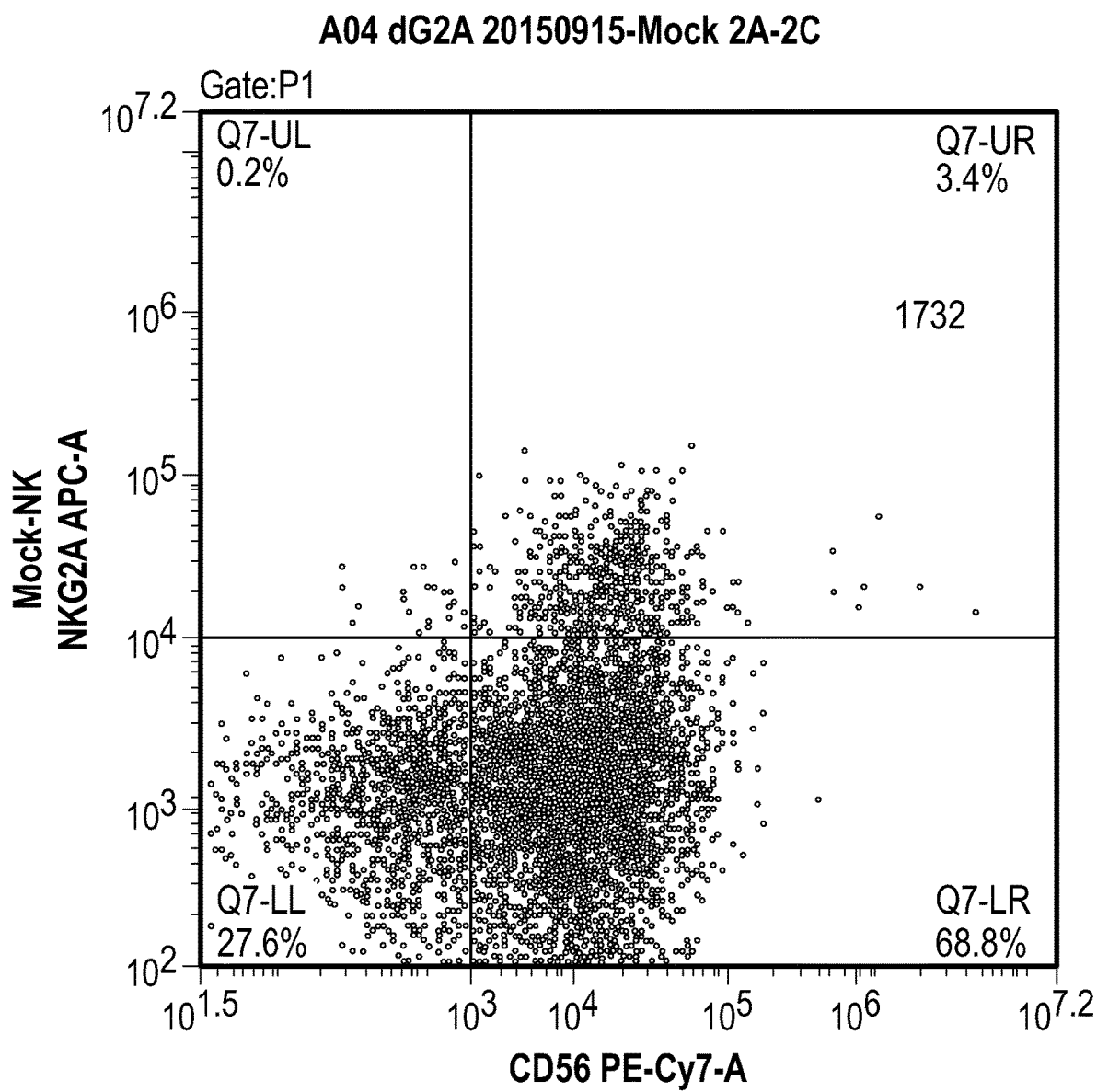
FIGS. 7A-7C depict flow cytometry data related to the expression of activating NKG2A/CD94-41BB-CD3z receptor in transduced NKG2A-depleted NK cells (bottom row) and in mock transduced NK cell populations (top row).
Figure 7A:
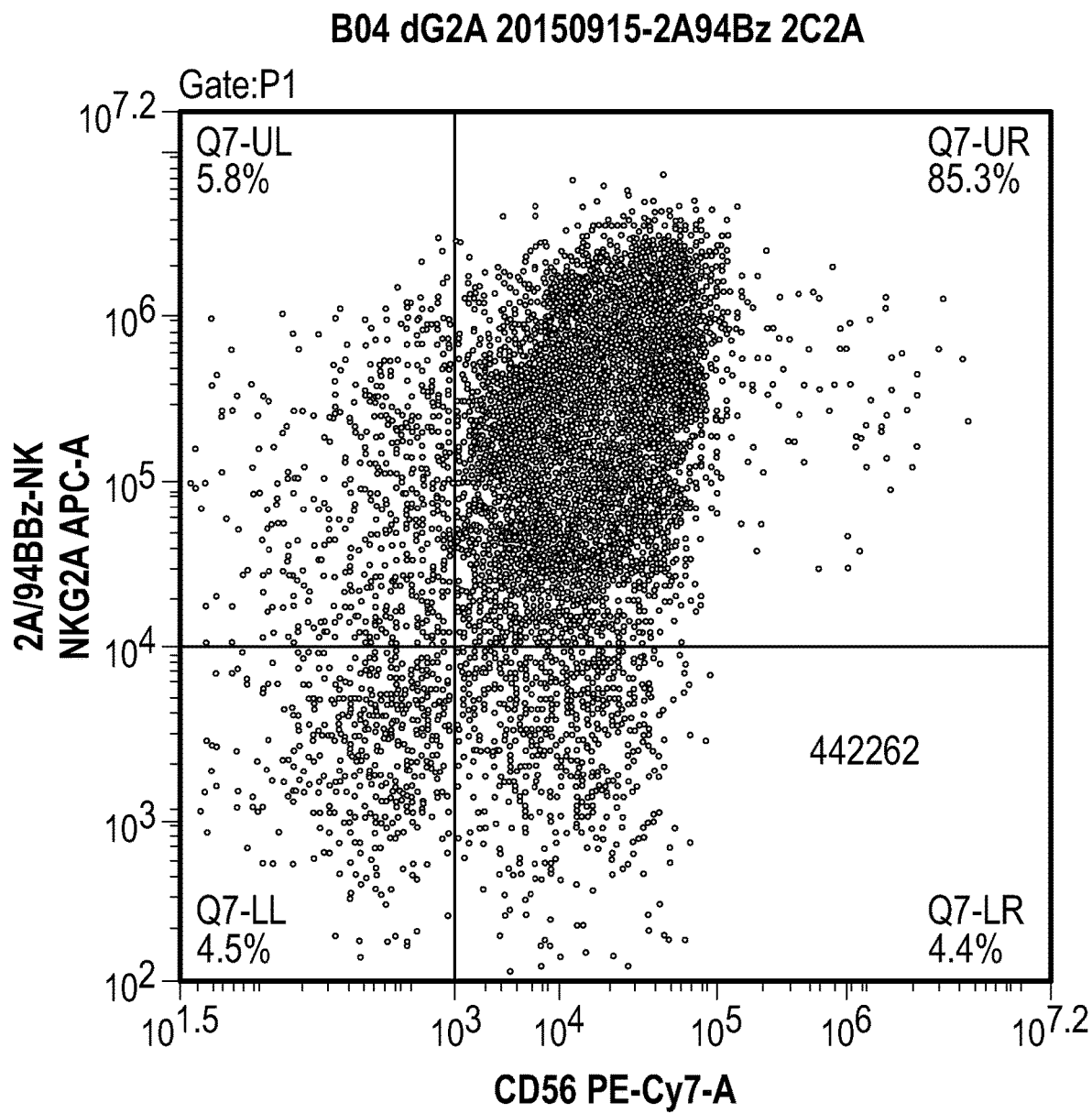
Figure 7A:
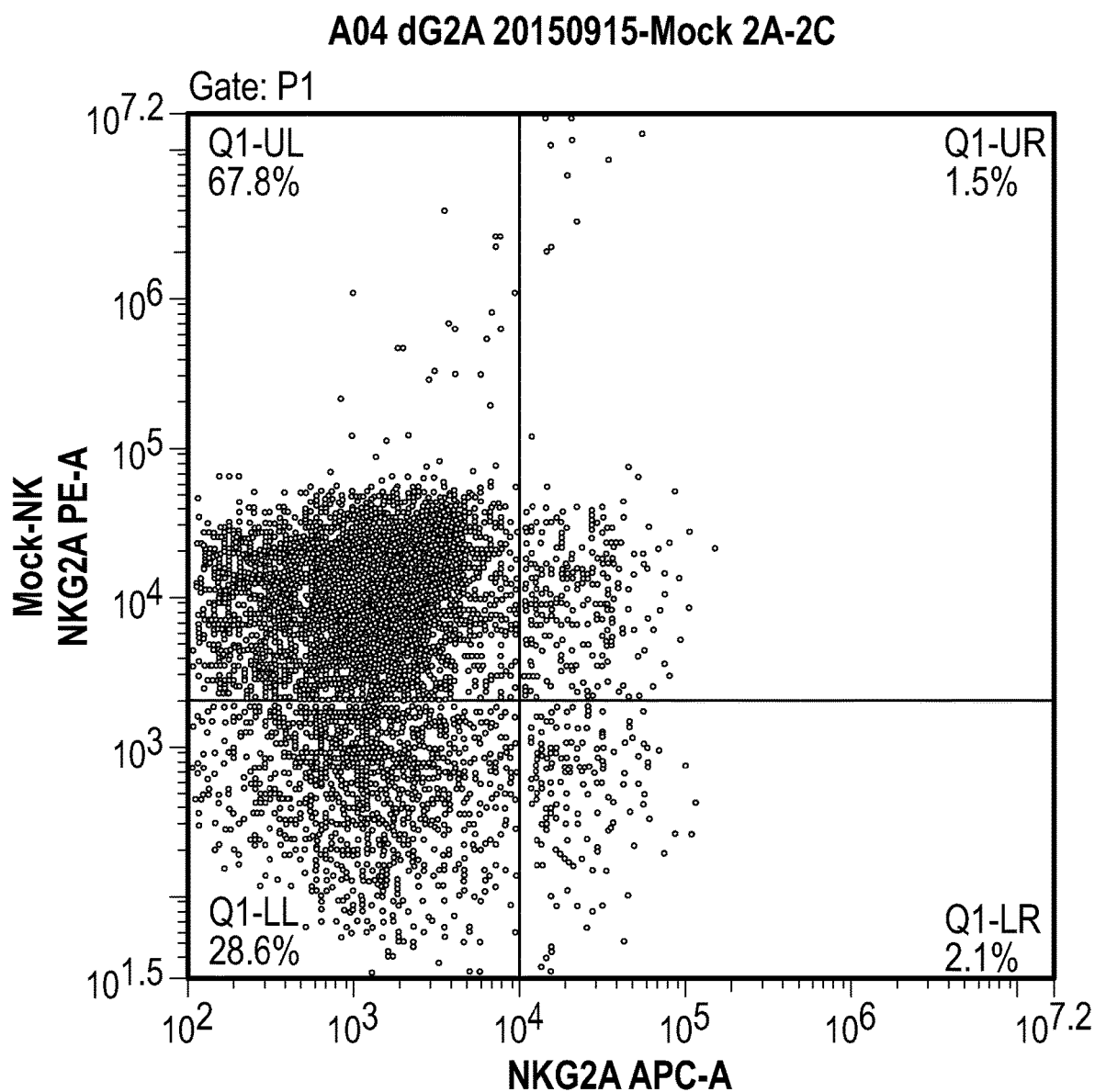
Figure 7A:
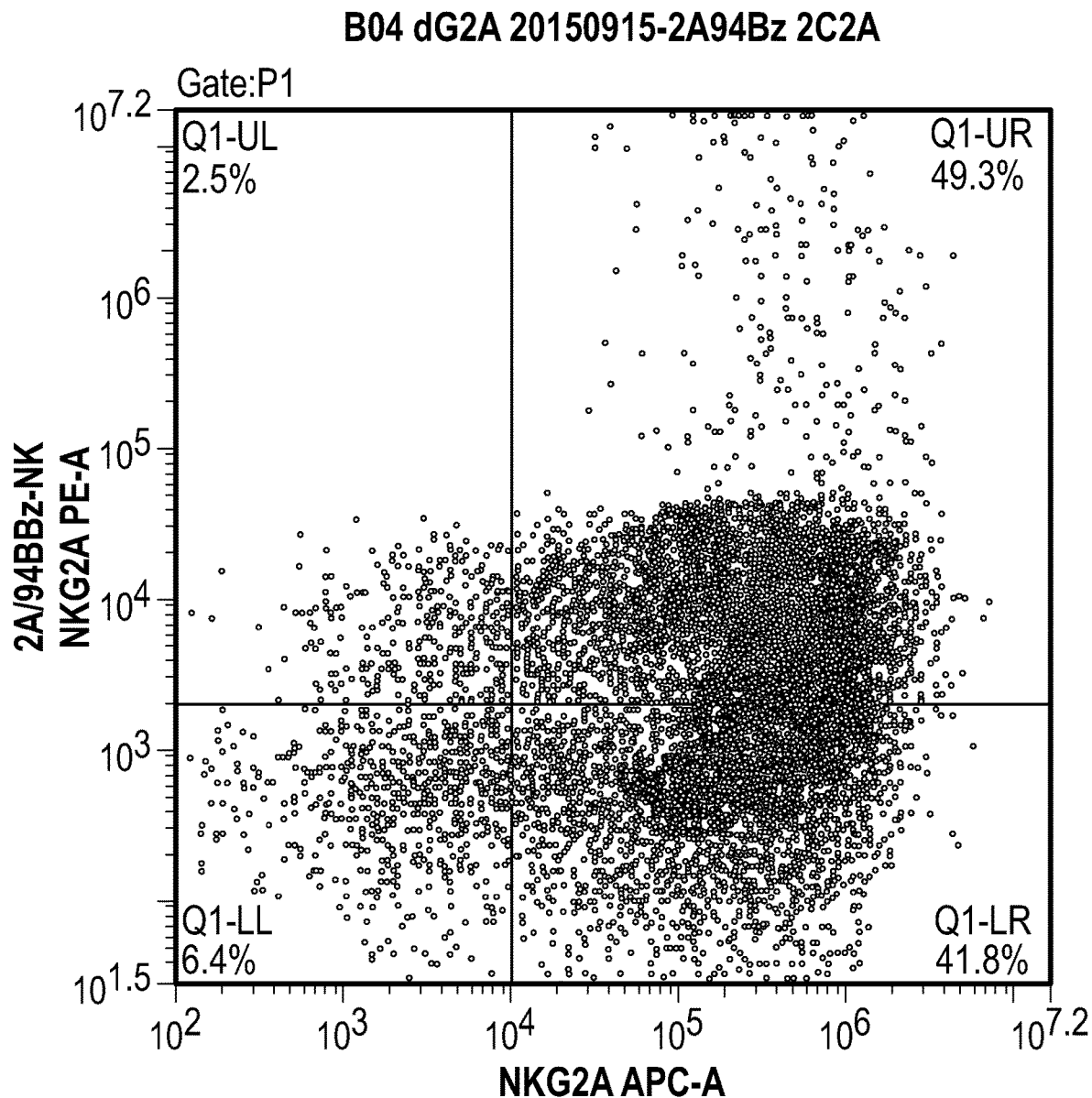
Figure 7B:
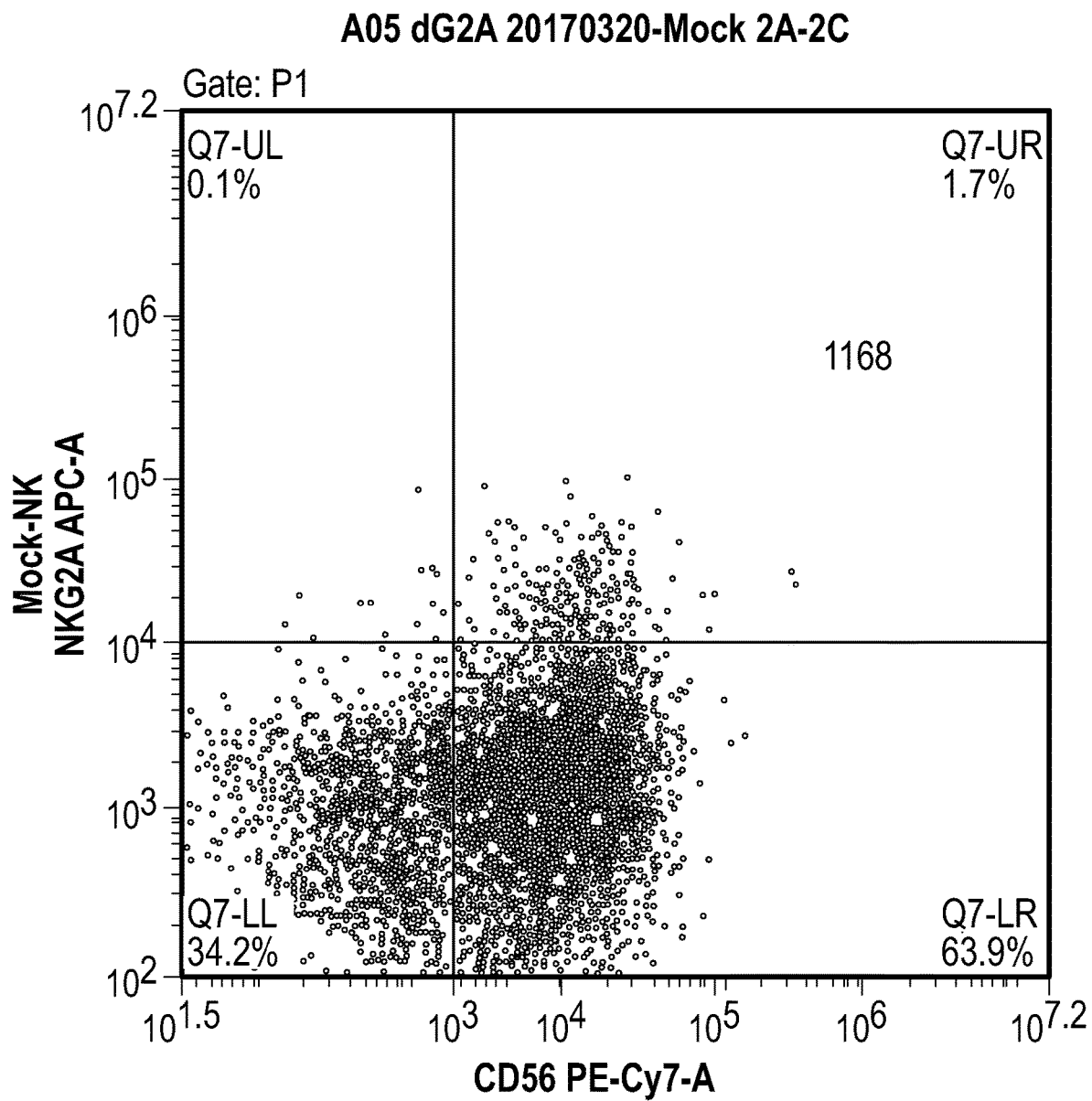
Figure 7B:
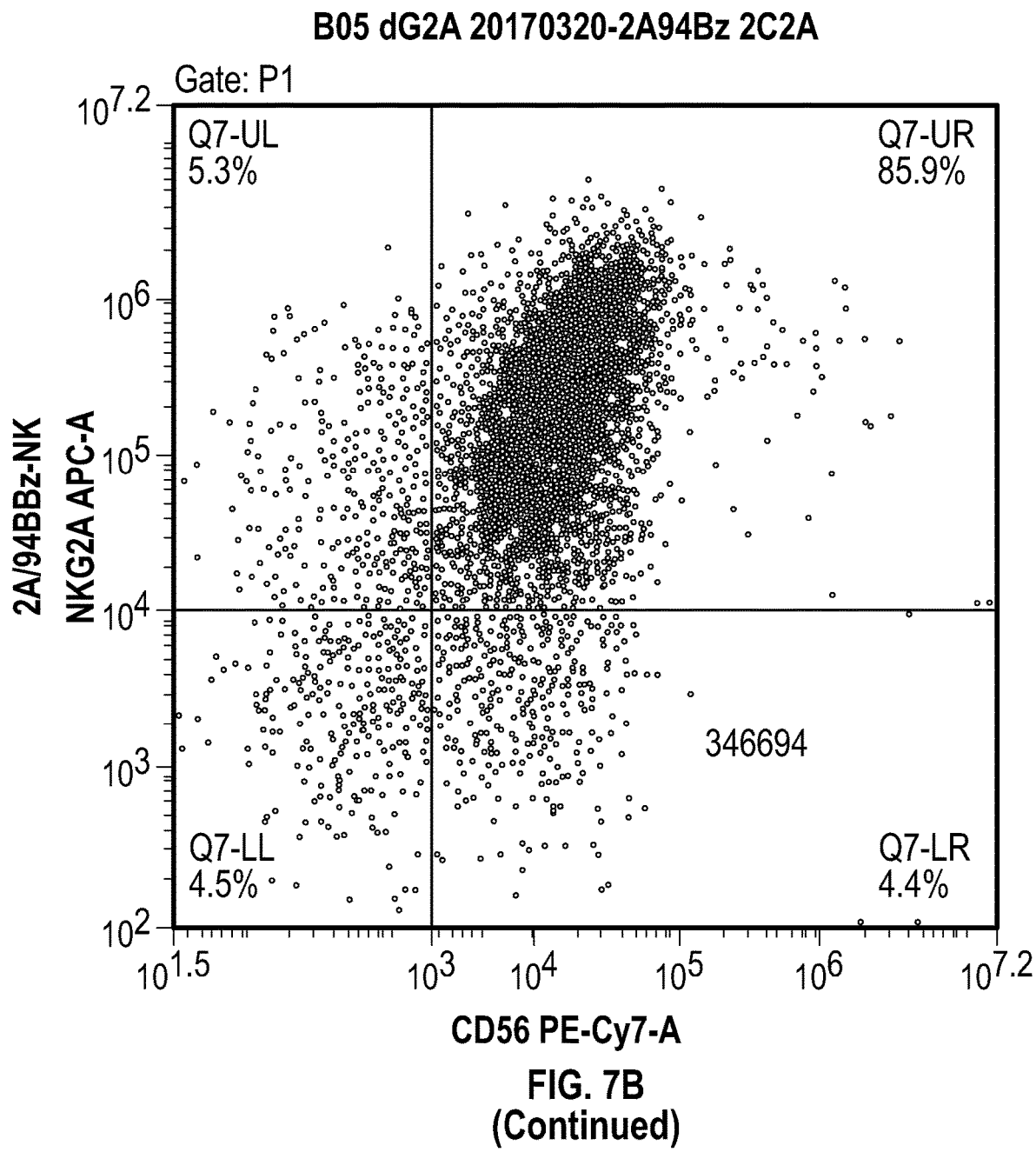
Figure 7B:
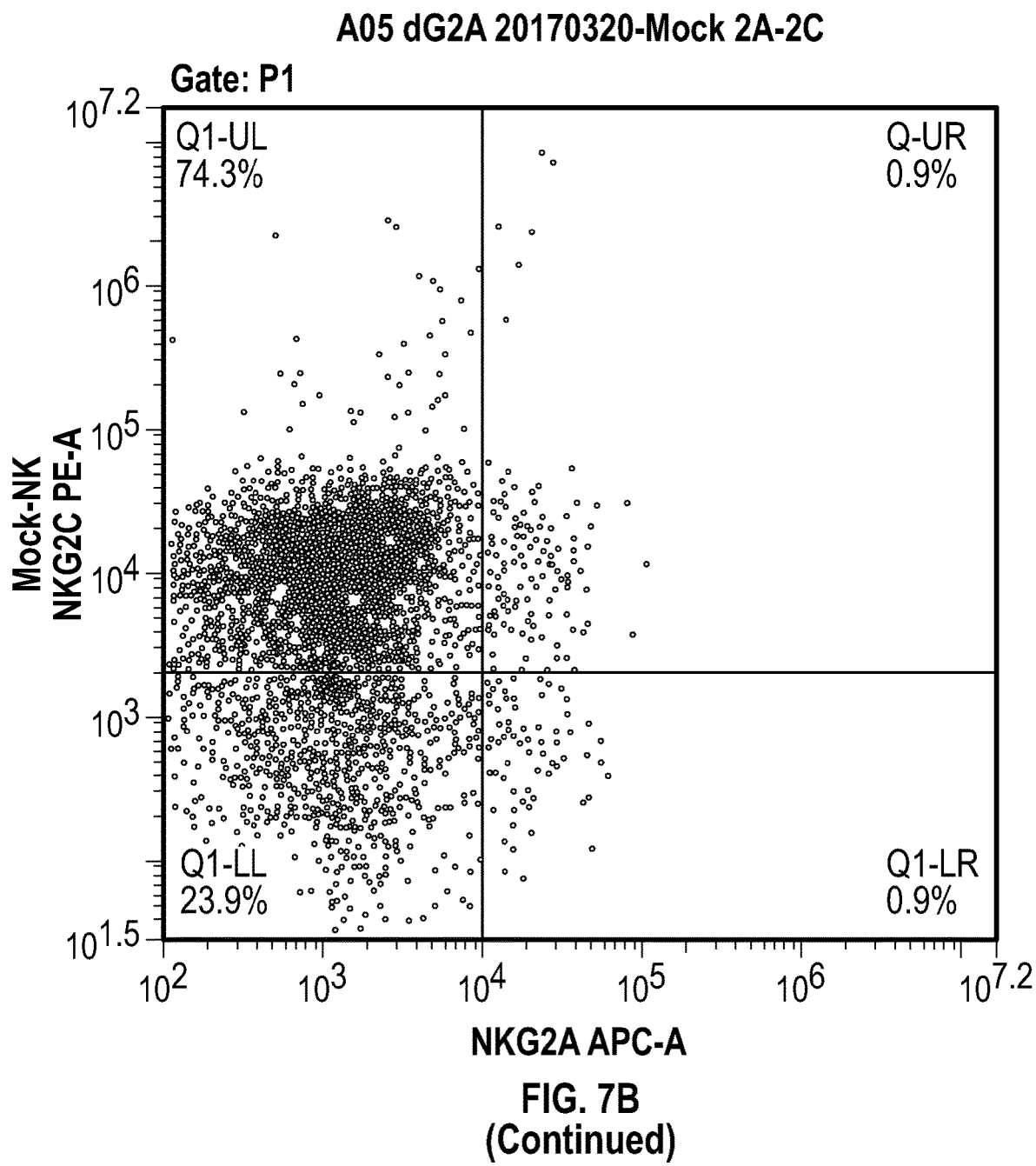
Figure 7B:
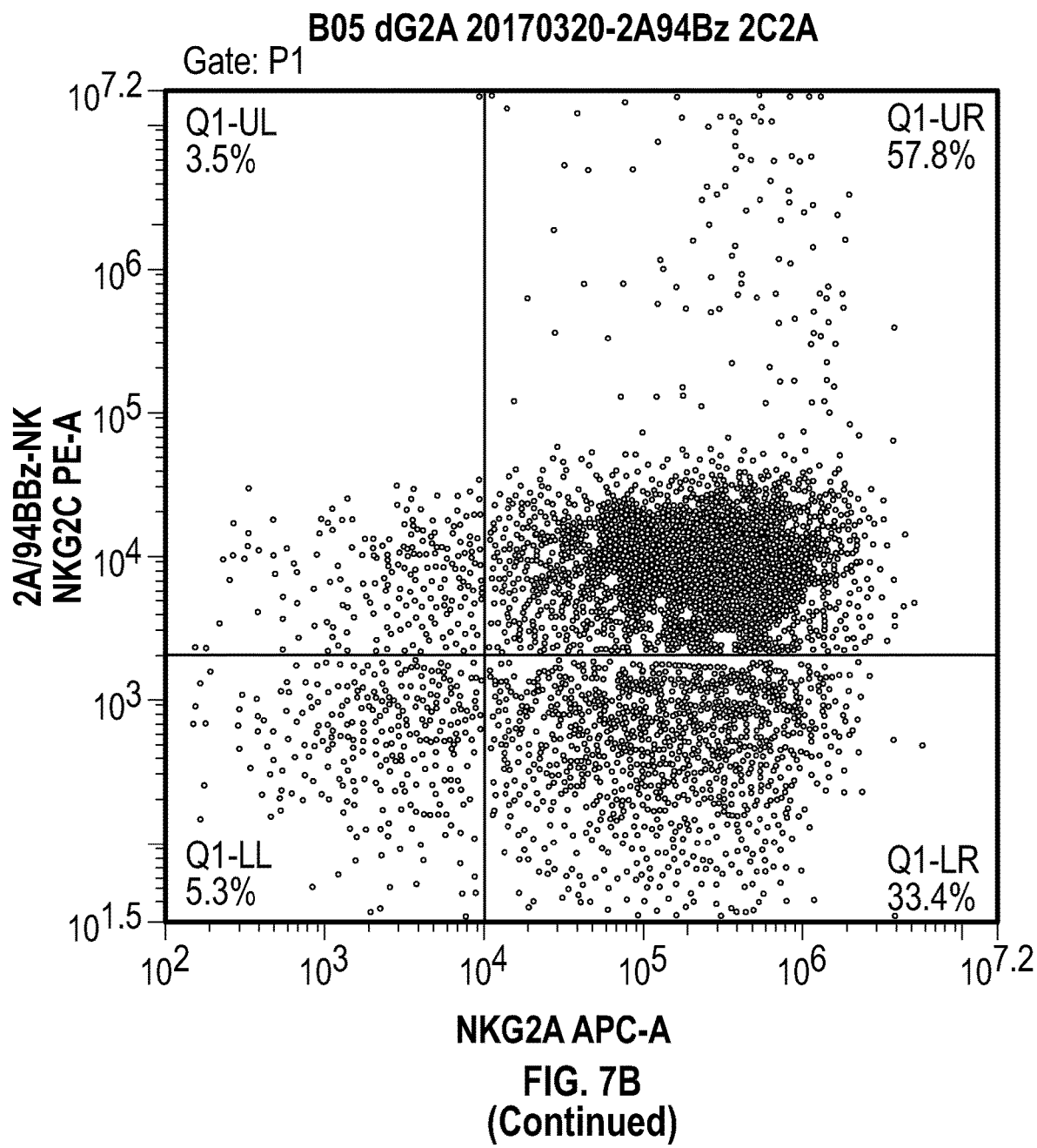
Figure 7C:
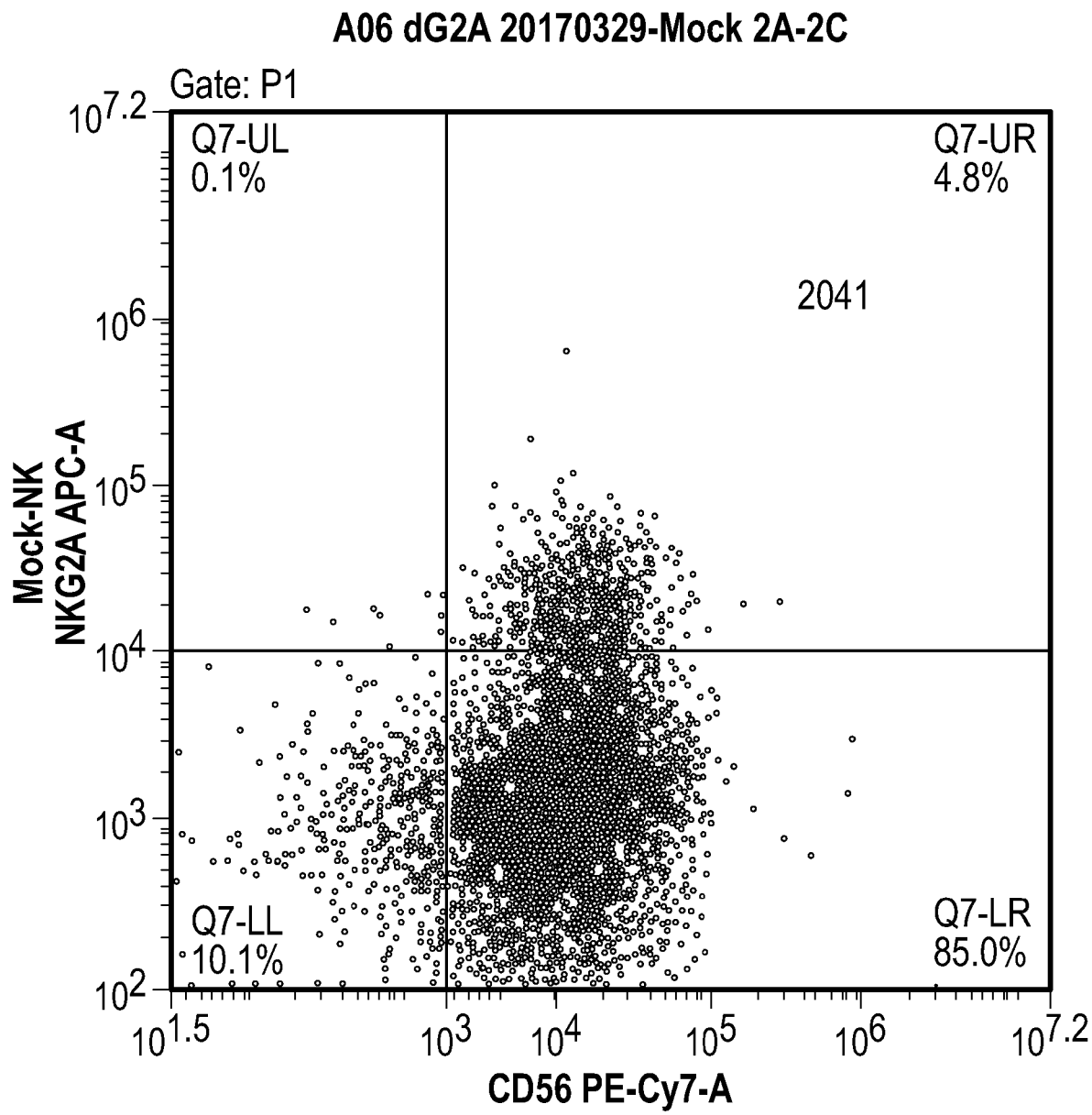
Figure 7C:
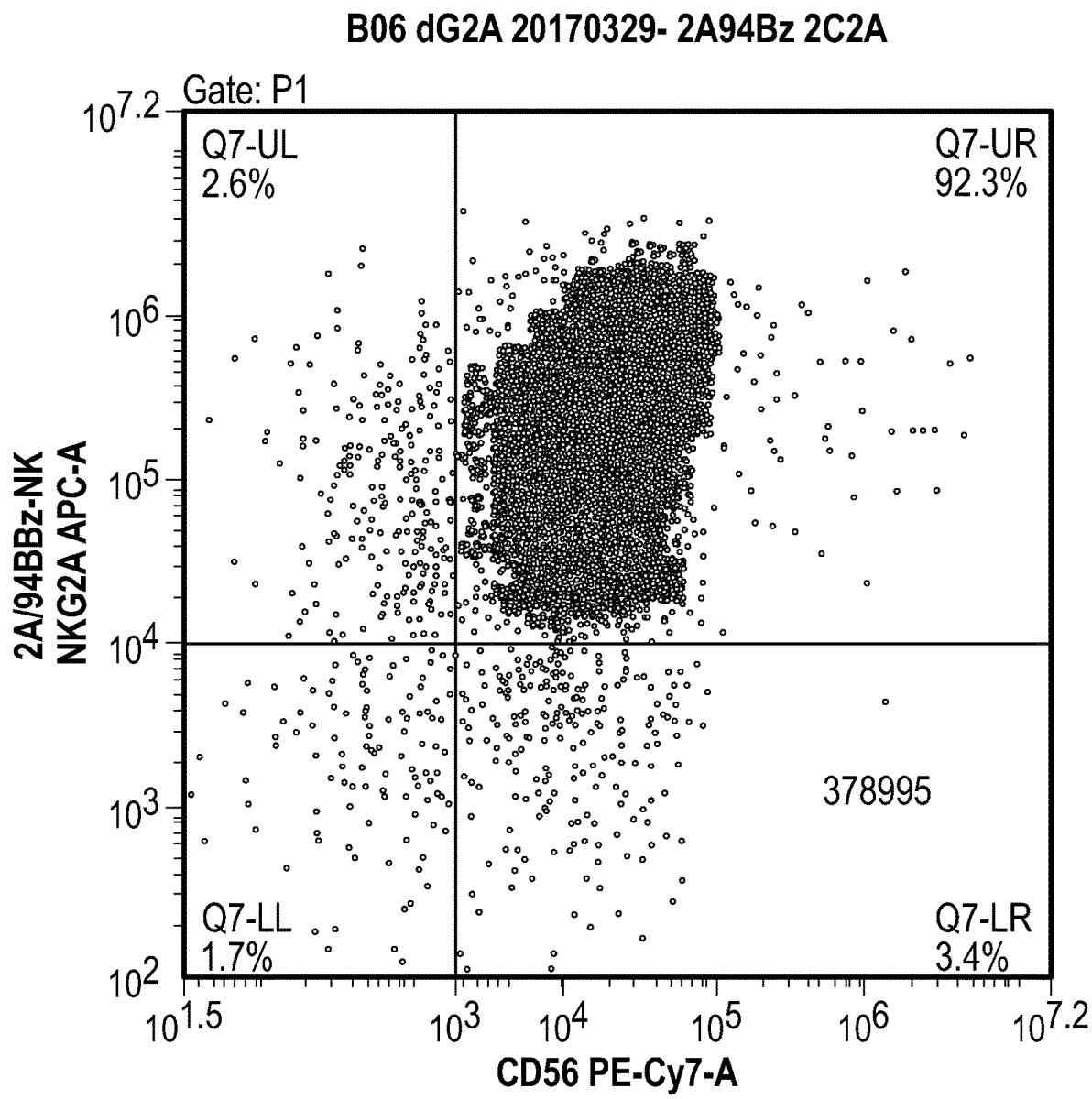
Figure 7C:
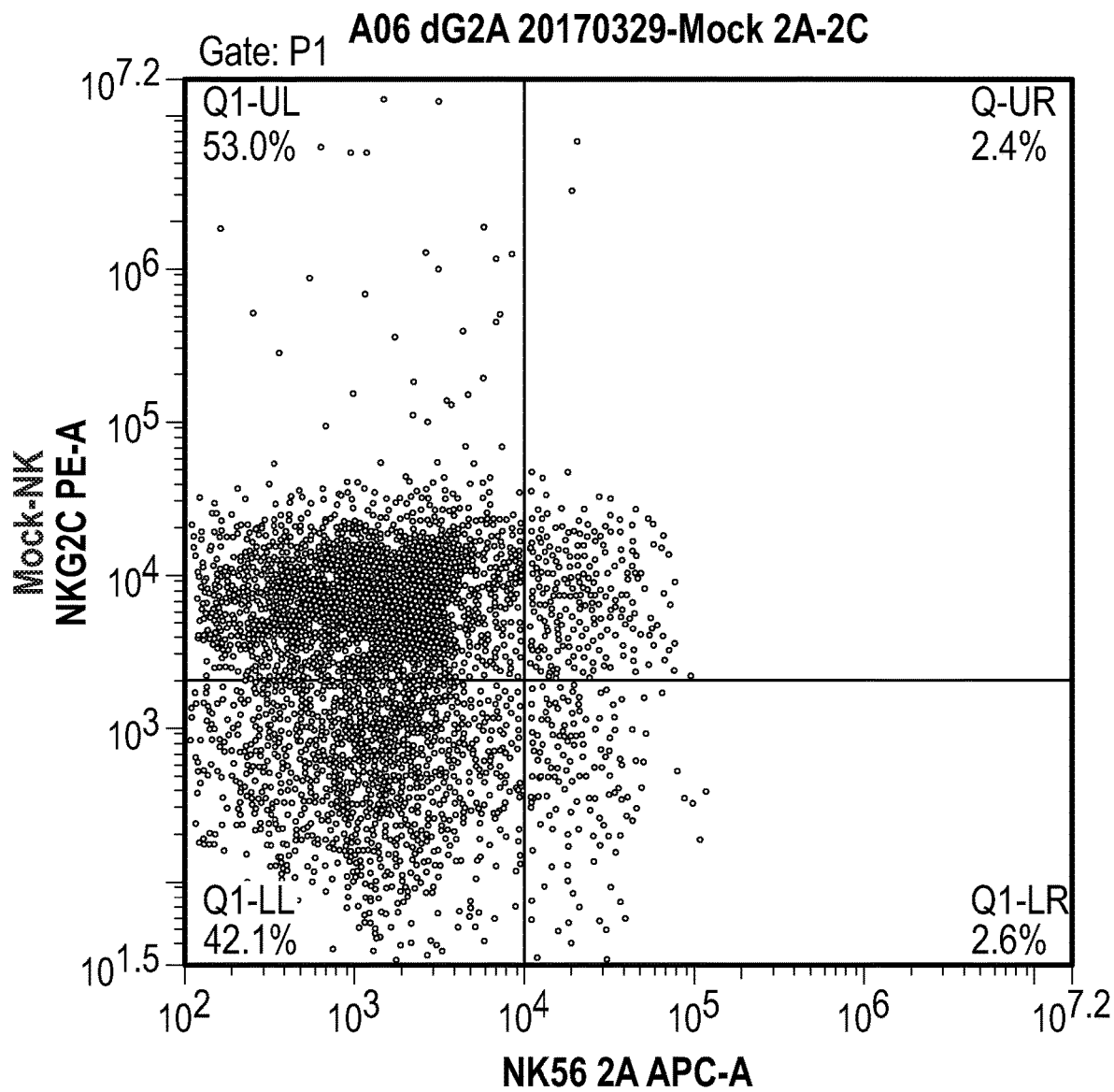
Figure 7C:
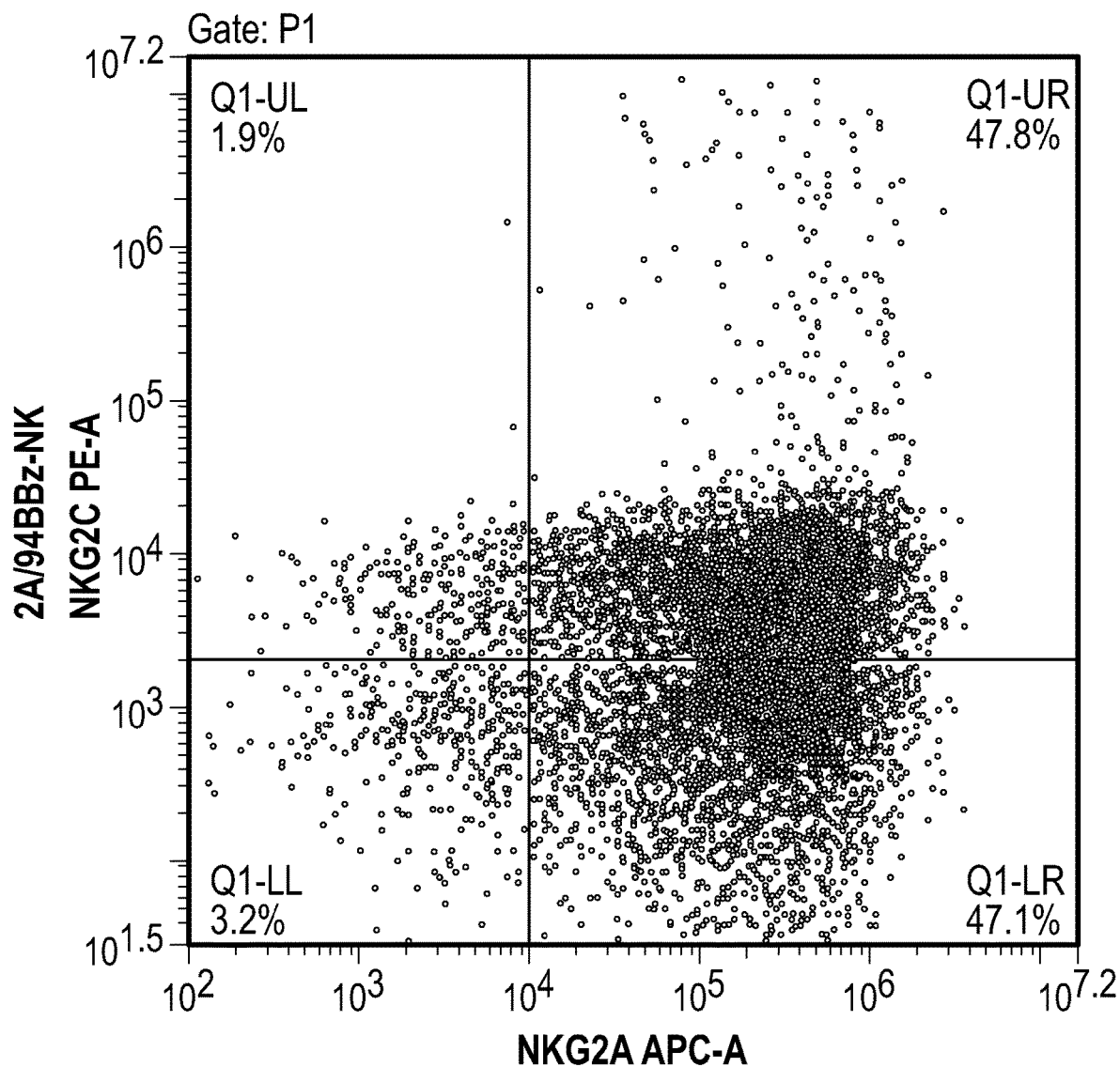
Figure 8A:
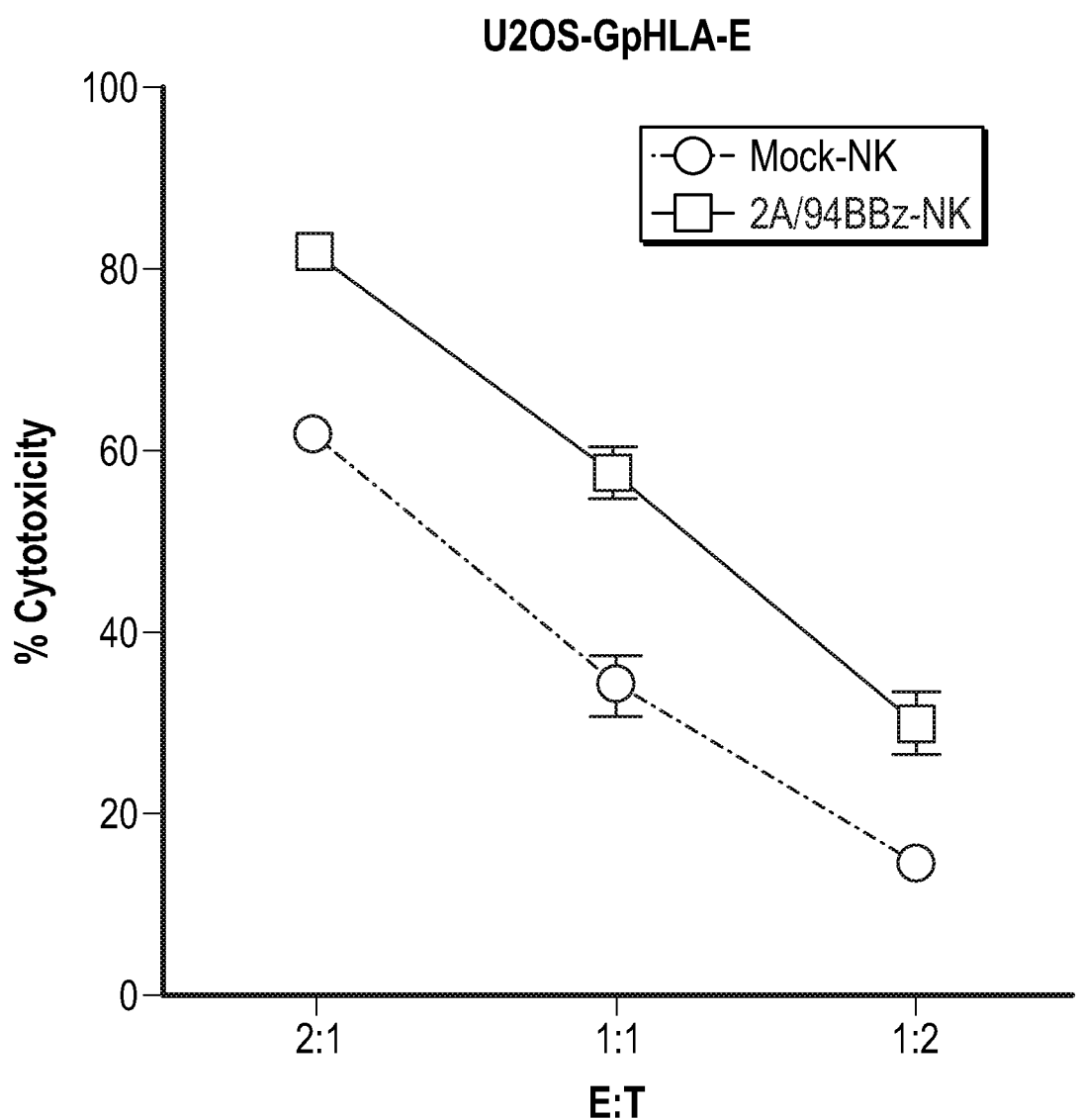
FIGS. 8A-8B depict data related to 4-hour cytotoxicity assays at the indicated E:T ratios of mock transduced NK cell populations or expanded NK cells expressing activating NKG2A/CD94-41BB-CD3z receptor against (a) U2OS-GpHLA-E cells (FIG. 8A) and HT29-GpHLA-E cells (FIG. 8B).
Figure 8B:
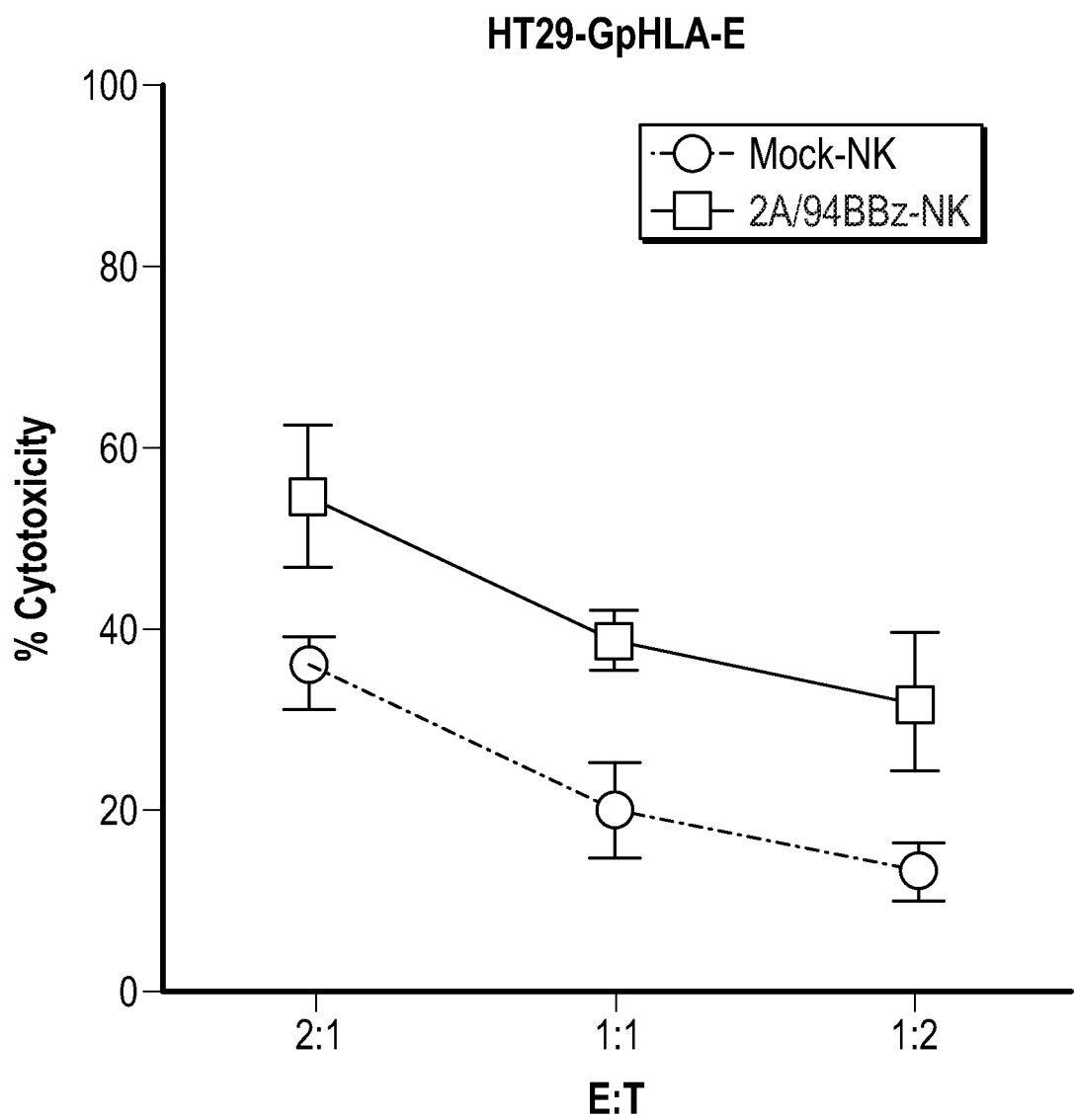

FIG. 6A depicts a schematic showing a complex comprised of truncated forms of Natural Killer Group 2 member A (NKG2A) and CD94 wherein there is a deletion of the N-terminus portion of the transmembrane and inhibitory cytoplasmic domain. These domains have been replaced with the CD8a transmembrane domain and cytoplasmic domains of 4-1BB (CD137) and CD3zeta. The activating NKG2A receptor and chimeric CD94 receptor form an activating complex (termed "2A/94BBz" herein). FIG. 6B depicts schematics of constructs comprising chimeric CD94 receptor and activating NKG2A receptor inserted into a MSCV retroviral vector containing green fluorescence protein (GFP) after an internal ribosomal entry site (IRES).

The ability of NK cells to effectively express these constructs was first assessed. FIG. 7 depicts flow cytometry data demonstrating the robust expression of activating NKG2A/CD94-41BB-CD3z receptor in NKG2A-depleted NK cells relative to mock transduced NK cell populations. Collectively, these data demonstrate that, in accordance with several embodiments disclosed herein, engineered activating chimeric receptor constructs can successfully be expressed on NK cells.

To evaluate the potency of the populations of transduced NK cells, cytotoxicity assays were performed using cancer cell lines that express GpHLA-E. Expression of activating NKG2A/CD94-41BB-CD3z receptor on expanded NK cells significantly increased cytotoxicity against U2OS-GpHLA-E and HT29-GpHLA-E cells in 4-hour cytotoxicity assays relative to control NK cells. These data provide evidence that NK cells can not only be engineered to express activating chimeric receptor constructs, but those cells that express the activating chimeric receptors are able to be activated and successfully generate enhanced cytotoxic effects against target cells.

Example 3—Anti-Tumor Activity of Activating Chimeric Receptor Constructs

In order to demonstrate the ability of the activating NK receptor constructs disclosed herein to exert cytotoxic effects against target cells (e.g., tumor cells), a xenograft model of colorectal adenocarcinoma was used. HT-29 cells are an immortalized colorectal adenocarcinoma cell line. HT-29 cells were transduced with both GpHLA-E and luciferase, such that the HT-29 cells express HLA-E, which is a portion of the target recognized by the engineered activating receptors used in this example (the D12(SIIS)2C/94 construct is engineered for high affinity to an HLA-E/peptide complex (165-168 SIIS)). The transduced HT-29 cells were injected intraperitoneally at a dose of $1 \times 10^5$ cells per mouse into each of 12 NOD-SCID IL2RGnull mice. Subsequently, NK cells ($1 \times 10^7$ cells) were injected on day 3, 6, 10 and 13. NK cells were either transduced with GFP only ("Control") or the D12(SIIS)2C/94 construct. Mice also received IL-2 (20,000 IU) three times per week by intraperitoneal injection. Ventral and dorsal bioluminescence was measured to assess tumor burden using a Xenogen Spectrum instrument (each symbol is the average of ventral and dorsal readings).

Figure 10:
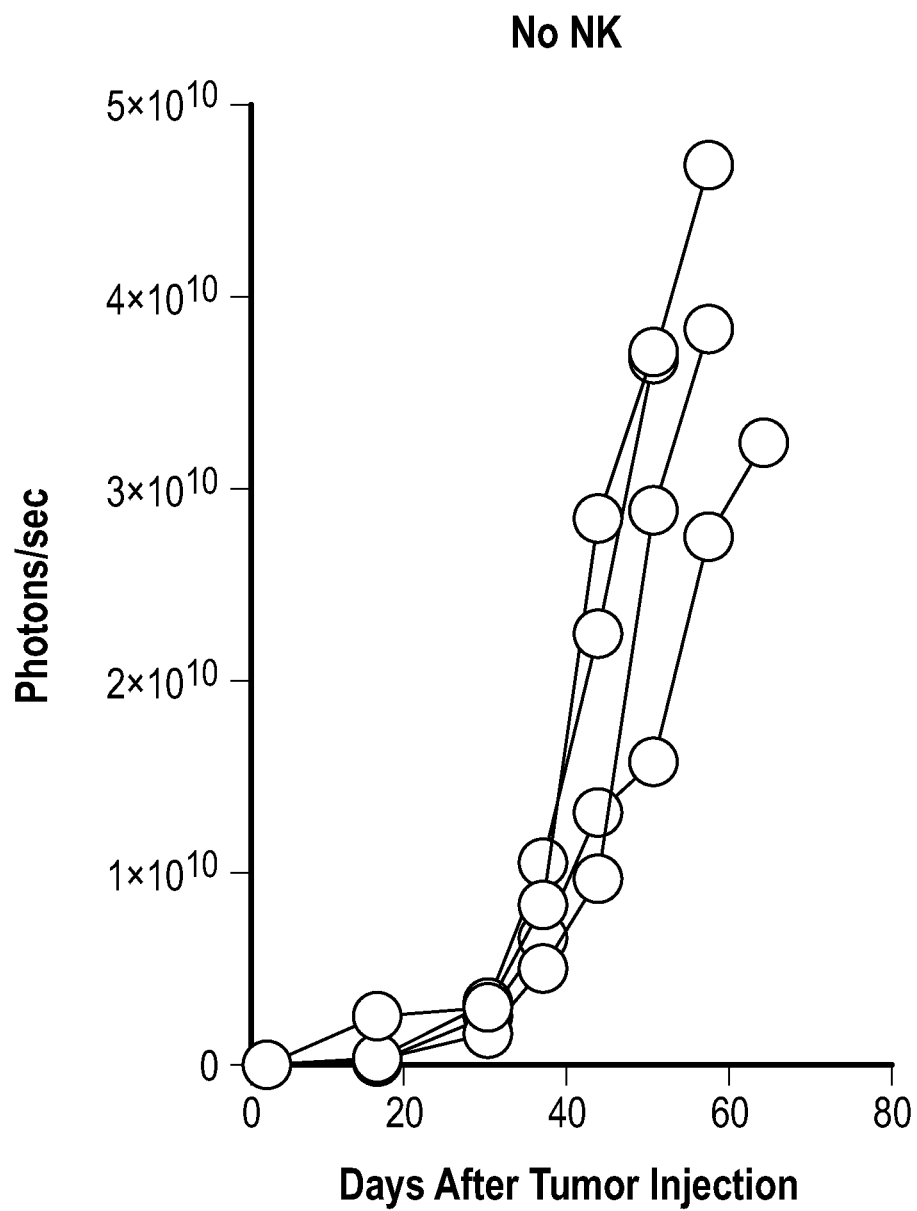
FIG. 10 depicts data related to a xenograft model of colorectal adenocarcinoma and the anti-tumor activity of NK-cell constructs according to several embodiments disclosed herein.
Figure 10:
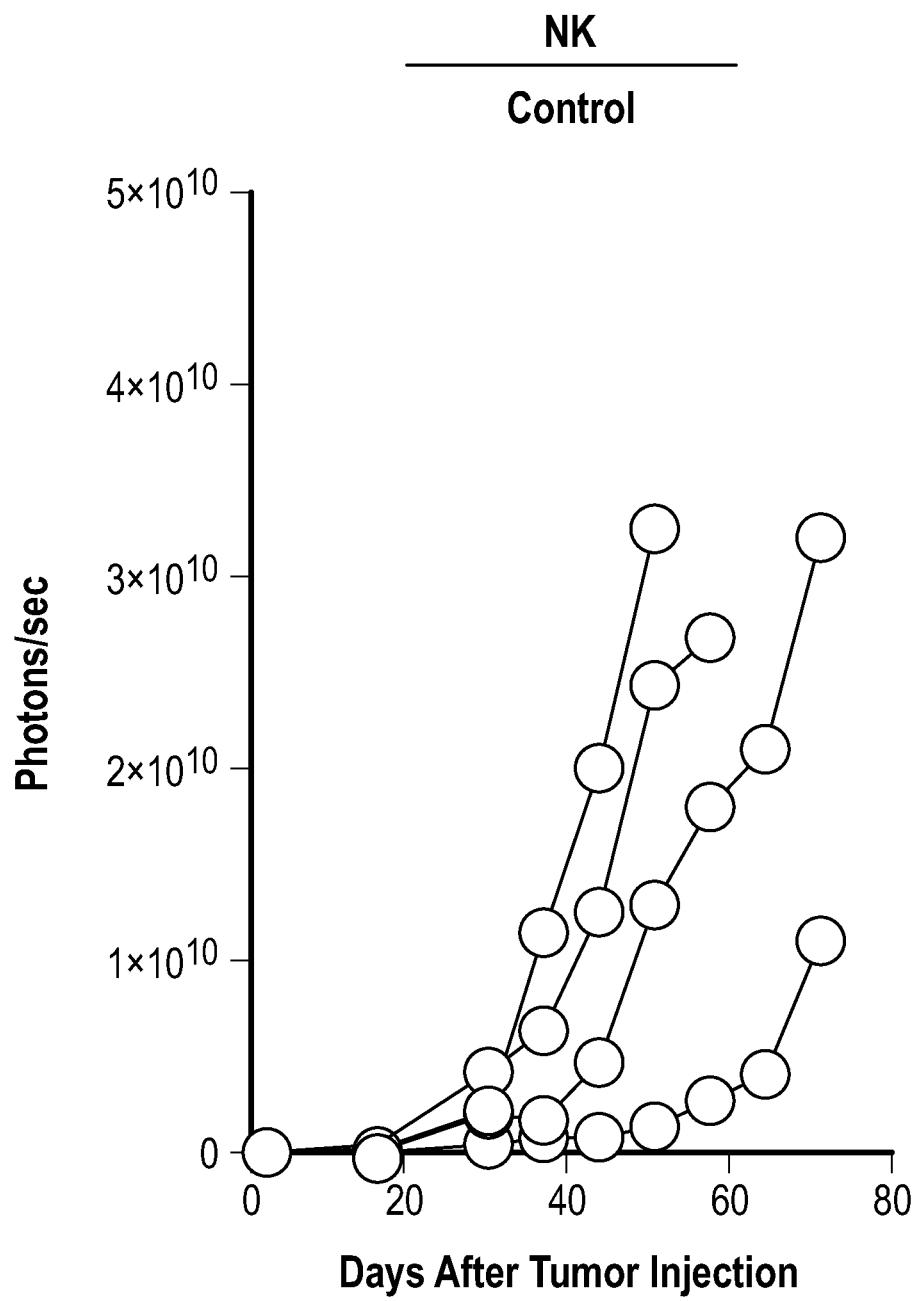
Figure 10:
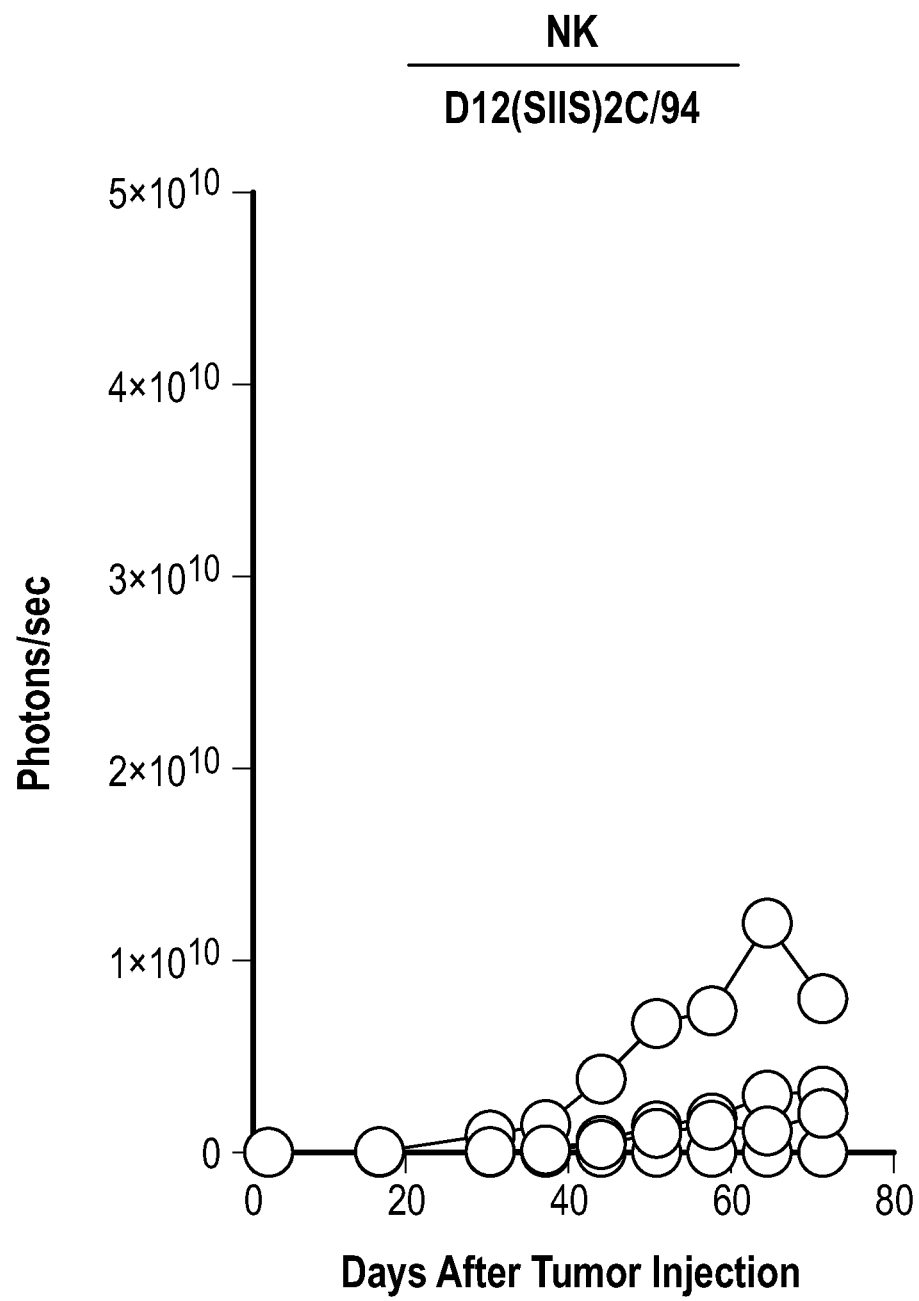

As can be seen in the left panel of FIG. 10 (no NK cells) the average bioluminescence increased in each mouse over time, which is indicative of increasing tumor burden from the growth/proliferation of the injected HT-29 cells. The central panel (mice injected with NK cells expressing GFP) exhibited generally increasing average bioluminescence, though to a lesser degree than the "No NK" group. In stark contrast, the average bioluminescence in the D12(SIIS)2C/94 shows very limited increase, even to the ~75 day timepoint at which the experiments were concluded. A single mouse had a modest elevation of average bioluminescence between ~40 and 75 days of the experiment. These data indicate that the engineered NK cells expressing an activating chimeric receptor have significant anti-tumor activity, even when compared to NK cells, which have a relatively robust anti-tumor effect on their own.

Figure 11:
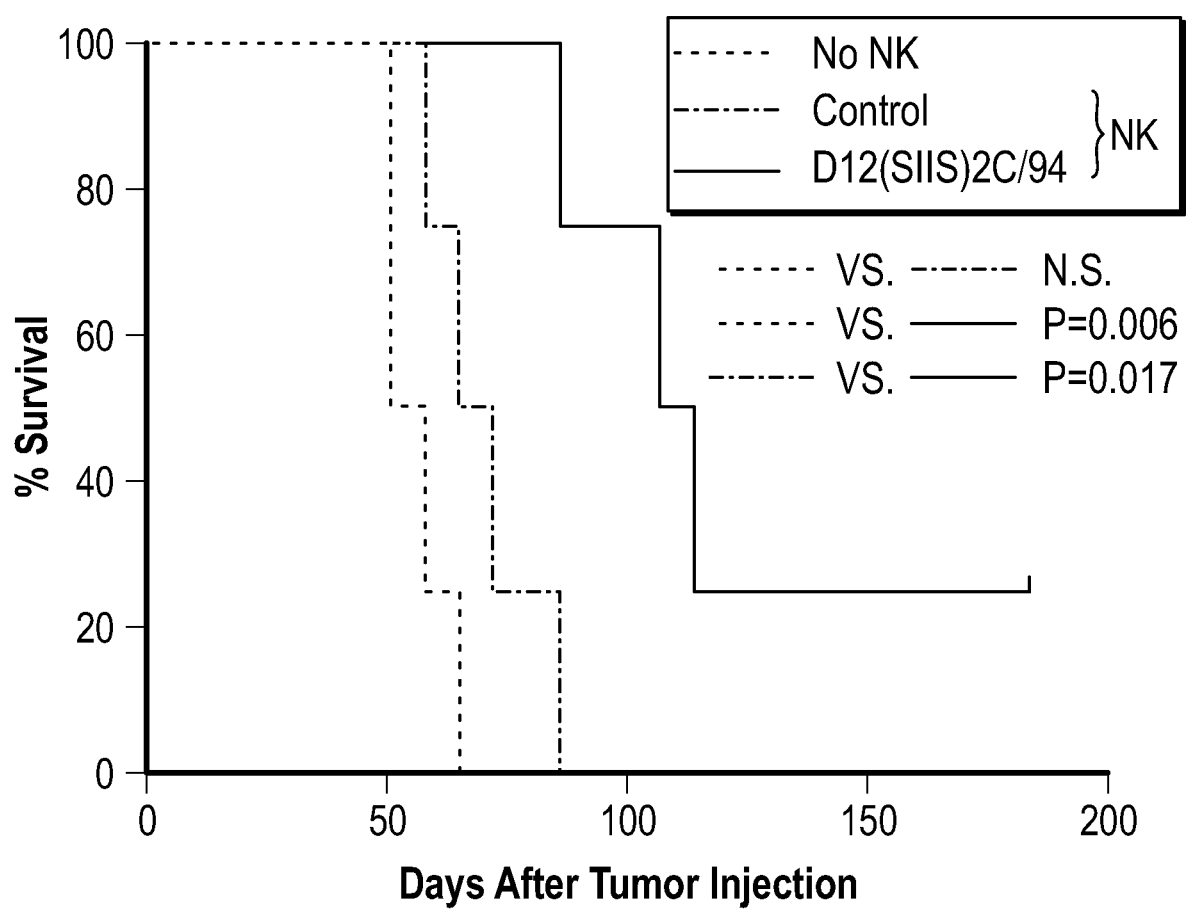
FIG. 11 depicts survival data from a xenograft model of colorectal adenocarcinoma after administration of NK-cell constructs according to several embodiments disclosed herein.

Further investigating the effects of the engineered activating receptors disclosed herein, survival curves were generated to determine survival rates of the mice in the various groups. Kaplan Meier survival curves analyzed by log rank test are shown in FIG. 11, with the same experimental groups as described above. As shown (dashed line) the mice receiving HT-29 cells but no NK cells reached 0% survival at ~60 days. Similarly, the mice receiving NK cells expressing GFP (solid gray line) showed a similar survival pattern, reaching 0% survival by ~80 days. Statistical evaluation of these groups showed no statistical difference between the No NK and Control groups (Kaplan Meier survival curve, log rank test, FIG. 11). In contrast to the first two groups (similar to the average bioluminescence data above), the D12(SIIS)2C/94 group showed significantly enhanced survival. Not only did one of the four D12(SIIS)2C/94 mice survive the entire duration of the experiment, the duration of survival of all of the mice in the D12(SIIS)2C/94 was enhanced. Statistical evaluation shows that survival in the D12(SIIS)2C/94 was significant in comparison to the No NK group as well as the NK cell-receiving Control group (Kaplan Meier survival curves, log rank test, p values depicted in FIG. 11). Thus, these data demonstrate that, even in comparison to NK cells (which exhibit relatively high natural cytotoxicity) NK cells engineered to express activating chimeric receptors have unexpectedly elevated cytotoxic effects against target cells. In several embodiments, the expression of activating chimeric receptors on NK cells allows one or more of a reduced frequency of treatment, reduced duration of treatment, reduced required dose of NK cells, and an overall improved outcome (e.g., reduced tumor burden and/or increased survival) of a NK-based cancer immunotherapy regimen (e.g., for example as compared to treatment frequency, duration etc. using NK cells not engineered to express the high affinity domains as disclosed herein).

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a population of expanded NK cells" include "instructing the administration of a population of expanded NK cells." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

What is claimed is:

1. A population of Natural Killer (NK) cells expressing a first chimeric receptor and a second chimeric receptor, wherein:
   a) the first chimeric receptor comprises an extracellular receptor domain, wherein said extracellular receptor domain comprises an engineered Natural Killer Group 2 member C (NKG2C) variant that comprises the amino acid sequence of SEQ ID NO. 64; and
   b) the second chimeric receptor comprises an extracellular receptor domain, wherein said extracellular receptor domain comprises an engineered variant of Natural Killer Group 2 member A (NKG2A),
   wherein the engineered variant of NKG2A is coupled to an effector domain comprising a transmembrane region and an intracellular signaling domain,
   wherein the engineered NKG2A variant consists of the amino acid sequence of SEQ ID NO. 66.

2. The population of NK cells of claim 1, wherein NK cells of the population further express a chimeric CD94 receptor.

3. The population of NK cells of claim 2, wherein the chimeric CD94 receptor comprises a fragment of CD94 coupled to a CD8a transmembrane domain and an effector domain comprising 4-1BB and CD3zeta, wherein the fragment of CD94 comprises the amino acid sequence of SEQ ID NO. 68.

4. The population of NK cells of claim 1, wherein the effector domain comprises a CD8a transmembrane domain and the intracellular signaling domain comprises 4-1BB and CD3zeta.

5. The population of NK cells of claim 1, wherein NK cells of the population further express a short hairpin RNA (shRNA) that specifically inhibits transcription or translation of native NKG2A.

6. The population of NK cells of claim 1, wherein the population further expresses a chimeric CD94 receptor, wherein the chimeric CD94 receptor comprises an extracellular receptor domain, wherein said extracellular receptor domain comprises a CD94 fragment comprising the amino acid sequence of SEQ ID NO. 68.

7. The population of NK cells of claim 1, wherein NK cells of the population further express a membrane-bound interleukin 15 (mbIL15).

8. The population of NK cells of claim 7, wherein the mbIL15 comprises the amino acid sequence of SEQ ID NO. 17.

9. The population of NK cells of claim 7, wherein the mbIL15 is encoded by the nucleic acid sequence of SEQ ID NO. 16.

10. The population of NK cells of claim 1, wherein the second chimeric receptor is encoded by a nucleic acid sequence of SEQ ID NO. 61.

11. The population of NK cells of claim 1, wherein the second chimeric receptor comprises the amino acid sequence of SEQ ID NO. 62.

12. The population of NK cells claim 1, wherein the second chimeric receptor further comprises a hinge region.

13. The population of NK cells of claim 12, wherein the hinge region is encoded by the nucleic acid sequence of SEQ ID NO. 5.

14. The population of NK cells of claim 1, wherein NK cells of the population further express a chimeric receptor comprising: (a) an extracellular receptor domain, wherein said extracellular receptor domain binds native ligands of Natural Killer Group 2 member D (NKG2D); and (b) an effector domain comprising a transmembrane region and an intracellular signaling domain.

15. The population of NK cells of claim 1, wherein the first chimeric receptor further comprises a transmembrane region that is a native NKG2C transmembrane region and an intracellular signaling domain that is a native NKG2C intracellular signaling domain.

16. The population of NK cells of claim 1, wherein NK cells of the population further express DNAX-activating protein 12 (DAP12).

17. The population of NK cells of claim 2, wherein NK cells of the population further express DNAX-activating protein 12 (DAP12).

* * * * *

SEQUENCE LISTING

<160> NUMBER OF SEQ ID NOS: 70

<210> SEQ ID NO 1
<211> LENGTH: 645
<212> TYPE: DNA
<213> ORGANISM: Homo sapiens
<220> FEATURE:
<221> NAME/KEY: misc_feature
<223> OTHER INFORMATION: Full length NKG2D

<400> SEQUENCE: 1
gggtggattc gtggtcggag gtctcgacac agctgggaga tgagtgaatt tcataattat      60
aacttggatc tgaagaagag tgatttttca acacgatggc aaaagcaaag atgtccagta    120
gtcaaaagca aatgtagaga aaatgcatct ccatttttt tctgctgctt catcgctgta     180
gccatgggaa tccgtttcat tattatggta acaatatgga gtgctgtatt cctaaactca    240
ttattcaacc aagaagttca aattcccttg accgaaagtt actgtggccc atgtcctaaa    300
aactggatat gttacaaaaa taactgctac caattttttg atgagagtaa aaactggtat    360
gagagccagg cttcttgtat gtctcaaaat gccagccttc tgaaagtata cagcaaagag    420
gaccaggatt tacttaaact ggtgaagtca tatcattgga tgggactagt acacattcca    480
acaaatggat cttggcagtg gaagatggc tccattctct cacccaacct actaacaata     540
attgaaatgc agaagggaga ctgtgcactc tatgcctcga gctttaaagg ctatatagaa    600
aactgttcaa ctccaaatac gtacatctgc atgcaaagga ctgtg                     645

<210> SEQ ID NO 2
<211> LENGTH: 405
<212> TYPE: DNA
<213> ORGANISM: Homo sapiens
<220> FEATURE:
<221> NAME/KEY: misc_feature
<223> OTHER INFORMATION: Truncated NKG2D

<400> SEQUENCE: 2
ttattcaacc aagaagttca aattcccttg accgaaagtt actgtggccc atgtcctaaa      60
aactggatat gttacaaaaa taactgctac caattttttg atgagagtaa aaactggtat    120
gagagccagg cttcttgtat gtctcaaaat gccagccttc tgaaagtata cagcaaagag    180
gaccaggatt tacttaaact ggtgaagtca tatcattgga tgggactagt acacattcca    240
acaaatggat cttggcagtg gaagatggc tccattctct cacccaacct actaacaata     300
attgaaatgc agaagggaga ctgtgcactc tatgcctcga gctttaaagg ctatatagaa    360
aactgttcaa ctccaaatac gtacatctgc atgcaaagga ctgtg                     405

<210> SEQ ID NO 3
<211> LENGTH: 405
<212> TYPE: DNA
<213> ORGANISM: Homo sapiens
<220> FEATURE:
<221> NAME/KEY: misc_feature
<223> OTHER INFORMATION: Codon Optimized Truncated NKG2D

<400> SEQUENCE: 3
ctgttcaatc aggaagtcca gatcccctg acagagtctt actgcggccc atgtcccaag      60
aactggatct gctacaagaa caattgttat cagttctttg acgagagcaa gaactggtat    120
gagtcccagg cctcttgcat gagccagaat gcctctctgc tgaaggtgta cagcaaggag    180
gaccaggatc tgctgaagct ggtgaagtcc tatcactgga tgggcctggt gcacatccct    240

```
acaaacggct cttggcagtg ggaggacggc tccatcctgt ctccaaatct gctgaccatc    300
atcgagatgc agaagggcga ttgcgccctg tacgccagct ccttcaaggg ctatatcgag    360
aactgctcca cacccaatac ctacatctgt atgcagagga ccgtg                    405
```

<210> SEQ ID NO 4
<211> LENGTH: 63
<212> TYPE: DNA
<213> ORGANISM: Homo sapiens
<220> FEATURE:
<221> NAME/KEY: misc_feature
<223> OTHER INFORMATION: CD8 Signaling Sequence

<400> SEQUENCE: 4

```
atggctctgc ccgtcaccgc actgctgctg cctctggctc tgctgctgca cgccgcacga     60
cca                                                                   63
```

<210> SEQ ID NO 5
<211> LENGTH: 135
<212> TYPE: DNA
<213> ORGANISM: Homo sapiens
<220> FEATURE:
<221> NAME/KEY: misc_feature
<223> OTHER INFORMATION: CD8 alpha hinge

<400> SEQUENCE: 5

```
accacaaccc ctgcaccacg ccccctaca ccagcaccta ccatcgcaag ccagcctctg      60
tccctgcggc cagaggcatg tagaccagca gcaggaggag cagtgcacac aagaggcctg    120
gacttcgcct gcgat                                                     135
```

<210> SEQ ID NO 6
<211> LENGTH: 1722
<212> TYPE: DNA
<213> ORGANISM: Homo sapiens
<220> FEATURE:
<221> NAME/KEY: misc_feature
<223> OTHER INFORMATION: CD8 beta
<220> FEATURE:
<221> NAME/KEY: misc_feature
<222> LOCATION: (674)..(773)
<223> OTHER INFORMATION: n is a, c, g, or t
<220> FEATURE:
<221> NAME/KEY: misc_feature
<222> LOCATION: (859)..(958)
<223> OTHER INFORMATION: n is a, c, g, or t

<400> SEQUENCE: 6

```
atctaggtct tgctgcaccc gcacaaccta caaacagcgt cggggccttc tctgcacctc     60
cagttcccag ctcacctccc tcagtgtcac agccggttac ctttccttcc tccctgggg    120 agggcaagac ttgggggcttg ctgactccag gcccagccca gccgggggca cccaggagcc   180
cctcaattgc tactcaaaca gacaagaagc ggcccgagtt agtggccagc tccaccatgc   240
actacacatc ctgacctctc tgagcctcta ctgtcactcg gggtcacaac ccttttcctga  300 gcacctcccg ggggcagggggg cgatgacaca catgcagctg cctggggggag gccggcggtg 360 tccccctcctt tctggaacgc ggagggtcct ggtgggctct ggaaacgcag cccagacctt  420
tgcaatgcta ggaggatgag ggcggagacc tcgcggtccc caacaccaga ctcccgcagc   480
caccgcgccc ggtcccgccc tccccactgc cccccagct cccgaccca ggcgccccgc     540 ccggccagct cctcacccac cccagccgcg actgtctccg ccgagccccc ggggccaggt   600 gtccccgggcg cgccacgatg cggccgcggc tgtggctcct cctggccgcg cagctgacag  660
```

```
gtaaggcggc ggcnnnnnnn nnnnnnnnnn nnnnnnnnnn nnnnnnnnnn nnnnnnnnnn      720
nnnnnnnnnn nnnnnnnnnn nnnnnnnnnn nnnnnnnnnn nnnnnnnnnn nnnttgcttt      780
cctcttccag gccggcggag gagagcccgg cttcgtttca tgaaacagta agtgtataac      840
ctgggtgtgg ccttgggann nnnnnnnnnn nnnnnnnnnn nnnnnnnnnn nnnnnnnnnn      900
nnnnnnnnnn nnnnnnnnnn nnnnnnnnnn nnnnnnnnnn nnnnnnnnnn nnnnnnnnct      960
tgctgttgtt ttcagatttt acaaatgagc agagaatacg gttttggtgt cctgctacaa     1020
aaagacatcg gtcagtaacg agcacgatgt ggaaaaatga gagaagggac acattcaacc     1080
ctggagagtt caatggctgc tgaagctgcc tgcttttcac tgctgcaagg cctttctgtg     1140
tgtgacgtgc atgggagcaa cttgttcgtg ggtcatcggg aatactaggg agaaggtttc     1200
attgccccca gggcacttca cagagtgtgc tggaggactg agtaagaaat gctgcccatg     1260
ccaccgcttc cggctcctgt gctttccctg aactgggacc tttagtggtg gccatttagc     1320
caccatcttt gcaggttgct ttgccctggt agggcagtaa cattgggtcc tgggtctttc     1380
atggggtgat gctgggctgg ctccctgttg gtcttcccag gctggggctg accttcctcg     1440
cagagaggcc aggtgcaggt tgggaatgag gcttgctgag aggggctgtc cagttcccag     1500
aaggcatatc agtctctgag ggcttccttt ggggccggga acttgcgggt ttgaggatag     1560
gagttcactt catcttctca gctcccattt ctactcttaa gtttctcagc tcccatttct     1620
actctcccat ggcttaatgc ttctttcatt ttctgtttgt tttatacaaa tgtcttagtt     1680
gtaaaaataa agtcccaggt taaagataac aaacgggtcc tg                       1722

<210> SEQ ID NO 7
<211> LENGTH: 2415
<212> TYPE: DNA
<213> ORGANISM: Homo sapiens
<220> FEATURE:
<221> NAME/KEY: misc_feature
<223> OTHER INFORMATION: CD16 alpha

<400> SEQUENCE: 7
attcttggtg ctgggtggat ccaaatccag gagatggggc aagcatcctg ggatggctga       60
gggcacactc tggcagattc tgtgtgtgtc ctcagatgct cagccacaga cctttgaggg      120
agtaaagggg gcagacccac ccaccttgcc tccaggctct ttccttcctg gtcctgttct      180
atggtggggc tcccttgcca gacttcagac tgagaagtca gatgaagttt caagaaaagg      240
aaattggtgg gtgacagaga tgggtggagg ggctggggaa aggctgttta cttcctcctg      300
tctagtcggt ttggtcccct tagggctccg gatatctttg gtgacttgtc cactccagtg      360
tggcatcatg tggcagctgc tcctcccaac tgctctgcta cttctagttt cagctggcat      420
gcggactgaa gatctcccaa aggctgtggt gttcctggag cctcaatggt acaggggtgct     480
cgagaaggac agtgtgactc tgaagtgcca gggagcctac tcccctgagg acaattccac      540
acagtggttt cacaatgaga gcctcatctc aagccaggcc tcgagctact tcattgacgc      600
tgccacagtc gacgacagtg gagagtacag gtgccagaca aacctctcca ccctcagtga      660
cccggtgcag ctagaagtcc atatcggctg gctgttgctc caggcccctc ggtgggtgtt      720
caaggaggaa gaccctattc acctgaggtg tcacagctgg aagaacactg ctctgcataa      780
ggtcacatat ttacagaatg gcaaaggcag gaagtatttt catcataatt ctgacttcta      840
cattccaaaa gccacactca aagacagcgg ctcctacttc tgcaggggc ttttttggga      900
taaaaatgtg tcttcagaga ctgtgaacat caccatcact caaggtttgg cagtgtcaac      960
```

| | |
|---|---|
| catctcatca ttctttccac ctgggtacca agtctctttc tgcttggtga tggtactcct | 1020 |
| ttttgcagtg gacacaggac tatatttctc tgtgaagaca acattcgaa gctcaacaag | 1080 |
| agactggaag gaccataaat ttaaatggag aaaggaccct caagacaaat gaccccatc | 1140 |
| ccatggggt aataagagca gtagcagcag catctctgaa catttctctg gatttgcaac | 1200 |
| cccatcatcc tcaggcctct ctacaagcag caggaaacat agaactcaga gccagatccc | 1260 |
| ttatccaact ctcgactttt ccttggtctc cagtggaagg gaaaagccca tgatcttcaa | 1320 |
| gcagggaagc cccagtgagt agctgcattc ctagaaattg aagtttcaga gctacacaaa | 1380 |
| cactttttct gtcccaaccg ttccctcaca gcaaagcaac aatacaggct agggatggta | 1440 |
| atccttaaa catacaaaaa ttgctcgtgt tataaattac ccagtttaga ggggaaaaaa | 1500 |
| aaacaattat tcctaaataa atggataagt agaattaatg gttgaggcag gaccatacag | 1560 |
| agtgtgggaa ctgctgggga tctagggaat tcagtgggac caatgaaagc atggctgaga | 1620 |
| aatagcaggt agtccaggat agtctaaggg aggtgttccc atctgagccc agagataagg | 1680 |
| gtgtcttcct agaacattag ccgtagtgga attaacagga atcatgagg gtgacgtaga | 1740 |
| attgagtctt ccaggggact ctatcagaac tggaccatct ccaagtatat aacgatgagt | 1800 |
| cctcttaatg ctaggagtag aaaatggtcc taggaagggg actgaggatt gcggtggggg | 1860 |
| gtggggtgga aaagaaagta cagaacaaac cctgtgtcac tgtcccaagt tgctaagtga | 1920 |
| acagaactat ctcagcatca gaatgagaaa gcctgagaag aaagaaccaa ccacaagcac | 1980 |
| acaggaagga aagcgcagga ggtgaaaatg cttctcttggc cagggtagta agaattagag | 2040 |
| gttaatgcag ggactgtaaa accacctttt ctgcttcaat atctaattcc tgtgtagctt | 2100 |
| tgttcattgc atttattaaa caaatgttgt ataaccaata ctaaatgtac tactgagctt | 2160 |
| cgctgagtta agttatgaaa ctttcaaatc cttcatcatg tcagttccaa tgaggtgggg | 2220 |
| atggagaaga caattgttgc ttatgaaaga aagctttagc tgtctctgtt ttgtaagctt | 2280 |
| taagcgcaac atttcttggt tccaataaag cattttacaa gatcttgcat gctactctta | 2340 |
| gatagaagat gggaaaacca tggtaataaa atatgaatga taaaaaaaaa aaaaaaaaaa | 2400 |
| aaaaaaaaaa aaaaa | 2415 |

```
<210> SEQ ID NO 8
<211> LENGTH: 2473
<212> TYPE: DNA
<213> ORGANISM: Homo sapiens
<220> FEATURE:
<221> NAME/KEY: misc_feature
<223> OTHER INFORMATION: CD16 beta
<220> FEATURE:
<221> NAME/KEY: misc_feature
<222> LOCATION: (211)..(310)
<223> OTHER INFORMATION: n is a, c, g, or t
<220> FEATURE:
<221> NAME/KEY: misc_feature
<222> LOCATION: (537)..(636)
<223> OTHER INFORMATION: n is a, c, g, or t
<220> FEATURE:
<221> NAME/KEY: misc_feature
<222> LOCATION: (968)..(1067)
<223> OTHER INFORMATION: n is a, c, g, or t

<400> SEQUENCE: 8
```

| | |
|---|---|
| aaagatgggt ggagggactg gggaaaggct gtttactccc tcctgtctag tcggcttggt | 60 |
| cccctttaggg gtccggatat ctttggtgac ttgtccactc cagtgtggca tcatgtggca | 120 |
| gctgctcctc ccaactgctc tgctacttct aggtaagtag gatctccctg gttgagggag | 180 |

```
aagtttgaga tgccttgggt tcagcagaga nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn aagaggcatg aacagtggaa gaccagagag caggtagcaa ggtttccacc    360
agaaacatcc tgattcttgg gaaaattggg ctcctgggc agaggagggc aggggagttt    420
taaactcact ctatgttcta atcactctga tctctgcccc tactcaatat ttgatttact    480
cttttttctt gcagtttcag ctggcatgcg gactggtgag tcagcttcat ggtcttnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnncact gagagctgag ctcccgggcc    660
tggggtgtct ctgtgtcttt caggctggct gttgctccag gcccctcggt gggtgttcaa    720
ggaggaagac cctattcacc tgaggtgtca cagctggaag aacactgctc tgcataaggt    780
cacatattta cagaatggca agacaggaa gtattttcat cataattctg acttccacat    840
tccaaaagcc acactcaaag atagcggctc ctacttctgc aggggcttg ttgggagtaa    900
aaatgtgtct tcagagactg tgaacatcac catcactcaa ggtgagacat gtgccaccct    960
ggaatgcnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnntttt ttcatctctc   1080
cacttctcct aataggtttg gcagtgtcaa ccatctcatc attctctcca cctgggtacc   1140
aagtctcttt ctgcttggtg atggtactcc tttttgcagt ggacacagga ctatatttct   1200
ctgtgaagac aaacatttga agctcaacaa gagactggaa ggaccataaa cttaaatgga   1260
gaaaggaccc tcaagacaaa tgaccccat cccatgggaa taataagagc agtggcagca   1320
gcatctctga acatttctct ggatttgcaa ccccatcatc ctcaggcctc tctacaagca   1380
gcaggaaaca tagaactcag agccagatcc tttatccaac tctcgatttt tccttggtct   1440
ccagtggaag ggaaaagccc atgatcttca agcagggaag ccccagtgag tagctgcatt   1500
cctagaaatt gaagtttcag agctacacaa acactttttc tgtcccaacc attccctcac   1560
agtaaaacaa caatacaggc tagggatggt aatcctttaa acatacaaaa attgctcgta   1620
ttataaatta cccagtttag accggaaaaa agaaaataat tattcctaaa caaatggata   1680
agtagaatta atgattgagg caggaccta cagagtgtgg gaactgctgg ggatctagag   1740
aattcagtgg gaccaatgaa agcatggctg agaaatagca gggtagtcca ggagagtcta   1800
agggaggtgt tcccatctga gcccagagat aagggtgtct tcctagaaca ttagccgtag   1860
tggaattaac aggaaatcat gagggtgacg tagaattgag tcttccaggg gactctatca   1920
gaactggacc atttccaagt atataacgat gagccctcta atgctaggag tagcaaatgg   1980
tcctaggaag gggactgagg attggggtgg ggtgggtg gaaagaaag tacagaacaa   2040
accctgtgtc actgtcccaa gttaagctaa gtgaacagaa ctatctcagc atcagaatga   2100
gaaagcctga gaagaaagaa ccaaccacaa gcacacagga aggaaagcgc aggaggtgaa   2160
aatgctttct tggccagggt agtaagaatt agaggttaat gcaggactg taaaaccacc   2220
ttttctgctt caatgtctag ttcctgtata gctttgttca ttgcatttat taaacaaatg   2280
ttgtataacc aatactaaat gtactactga gcttcactga gttacgctgt gaaactttca   2340
aatccttctt catgtcagtt ccaatgaggt ggggatggag aagacaattg ttgcttatga   2400
aaaaaagctt tagctgtctc tgttttgtaa gctttcagtg caacatttct tggttccaat   2460
aaagcatttt aca                                                      2473
```

```
<210> SEQ ID NO 9
<211> LENGTH: 370
<212> TYPE: PRT
<213> ORGANISM: Homo sapiens
<220> FEATURE:
<221> NAME/KEY: MISC_FEATURE
<223> OTHER INFORMATION: 2B4

<400> SEQUENCE: 9

Met Leu Gly Gln Val Val Thr Leu Ile Leu Leu Leu Leu Lys Val
1               5                   10                  15

Tyr Gln Gly Lys Gly Cys Gln Gly Ser Ala Asp His Val Val Ser Ile
            20                  25                  30

Ser Gly Val Pro Leu Gln Leu Gln Pro Asn Ser Ile Gln Thr Lys Val
            35                  40                  45

Asp Ser Ile Ala Trp Lys Lys Leu Leu Pro Ser Gln Asn Gly Phe His
    50                  55                  60

His Ile Leu Lys Trp Glu Asn Gly Ser Leu Pro Ser Asn Thr Ser Asn
65                  70                  75                  80

Asp Arg Phe Ser Phe Ile Val Lys Asn Leu Ser Leu Leu Ile Lys Ala
                85                  90                  95

Ala Gln Gln Gln Asp Ser Gly Leu Tyr Cys Leu Glu Val Thr Ser Ile
                100                 105                 110

Ser Gly Lys Val Gln Thr Ala Thr Phe Gln Val Phe Val Phe Glu Ser
            115                 120                 125

Leu Leu Pro Asp Lys Val Glu Lys Pro Arg Leu Gln Gly Gln Gly Lys
    130                 135                 140

Ile Leu Asp Arg Gly Arg Cys Gln Val Ala Leu Ser Cys Leu Val Ser
145                 150                 155                 160

Arg Asp Gly Asn Val Ser Tyr Ala Trp Tyr Arg Gly Ser Lys Leu Ile
                165                 170                 175

Gln Thr Ala Gly Asn Leu Thr Tyr Leu Asp Glu Glu Val Asp Ile Asn
            180                 185                 190

Gly Thr His Thr Tyr Thr Cys Asn Val Ser Asn Pro Val Ser Trp Glu
            195                 200                 205

Ser His Thr Leu Asn Leu Thr Gln Asp Cys Gln Asn Ala His Gln Glu
    210                 215                 220

Phe Arg Phe Trp Pro Phe Leu Val Ile Ile Val Ile Leu Ser Ala Leu
225                 230                 235                 240

Phe Leu Gly Thr Leu Ala Cys Phe Cys Val Trp Arg Arg Lys Arg Lys
                245                 250                 255

Glu Lys Gln Ser Glu Thr Ser Pro Lys Glu Phe Leu Thr Ile Tyr Glu
                260                 265                 270

Asp Val Lys Asp Leu Lys Thr Arg Arg Asn His Glu Gln Glu Gln Thr
            275                 280                 285

Phe Pro Gly Gly Gly Ser Thr Ile Tyr Ser Met Ile Gln Ser Gln Ser
    290                 295                 300

Ser Ala Pro Thr Ser Gln Glu Pro Ala Tyr Thr Leu Tyr Ser Leu Ile
305                 310                 315                 320

Gln Pro Ser Arg Lys Ser Gly Ser Arg Lys Asn His Ser Pro Ser
                325                 330                 335

Phe Asn Ser Thr Ile Tyr Glu Val Ile Gly Lys Ser Gln Pro Lys Ala
            340                 345                 350

Gln Asn Pro Ala Arg Leu Ser Arg Lys Glu Leu Glu Asn Phe Asp Val
    355                 360                 365
```

Tyr Ser
    370

<210> SEQ ID NO 10
<211> LENGTH: 279
<212> TYPE: DNA
<213> ORGANISM: Homo sapiens
<220> FEATURE:
<221> NAME/KEY: misc_feature
<223> OTHER INFORMATION: DAP10

<400> SEQUENCE: 10
atgatccatc tgggtcacat cctcttcctg cttttgctcc cagtggctgc agctcagacg      60
actccaggag agagatcatc actccctgcc ttttaccctg gcacttcagg ctcttgttcc     120
ggatgtgggt ccctctctct gccgctcctg gcaggcctcg tggctgctga tgcggtggca     180
tcgctgctca tcgtgggggc ggtgttcctg tgcgcacgcc cacgccgcag ccccgcccaa     240
gatggcaaag tctacatcaa catgccaggc aggggctga                            279

<210> SEQ ID NO 11
<211> LENGTH: 575
<212> TYPE: DNA
<213> ORGANISM: Homo sapiens
<220> FEATURE:
<221> NAME/KEY: misc_feature
<223> OTHER INFORMATION: DAP12

<400> SEQUENCE: 11
agacttcctc cttcacttgc ctggacgctg cgccacatcc caccggccct tacactgtgg      60
tgtccagcag catccggctt catggggggga cttgaaccct gcagcaggct cctgctcctg    120
cctctcctgc tggctgtaag tgattgcagt tgctctacgg tgagcccggg cgtgctggca    180
gggatcgtga tgggagacct ggtgctgaca gtgctcattg ccctggccgt gtacttcctg    240
ggccggctgg tccctcgggg gcgaggggct gcggaggcag cgacccggaa acagcgtatc    300
actgagaccg agtcgcctta tcaggagctc caggggtcaga ggtcggatgt ctacagcgac    360
ctcaacacac agaggccgta ttacaaatga gcccgaatca tgacagtcag caacatgata    420
cctggatcca gccattcctg aagcccaccc tgcacctcat tccaactcct accgcgatac    480
agacccacag agtgccatcc ctgagagacc agaccgctcc ccaatactct cctaaaataa    540
acatgaagca caaaaacaaa aaaaaaaaaa aaaaa                                575

<210> SEQ ID NO 12
<211> LENGTH: 126
<212> TYPE: DNA
<213> ORGANISM: Homo sapiens
<220> FEATURE:
<221> NAME/KEY: misc_feature
<223> OTHER INFORMATION: 4-1BB

<400> SEQUENCE: 12
aaacggggca gaaagaaact cctgtatata ttcaaacaac catttatgag accagtacaa      60
actactcaag aggaagatgg ctgtagctgc cgatttccag aagaagaaga aggaggatgt    120
gaactg                                                                126

<210> SEQ ID NO 13
<211> LENGTH: 339
<212> TYPE: DNA
<213> ORGANISM: Homo sapiens
<220> FEATURE:
<221> NAME/KEY: misc_feature
<223> OTHER INFORMATION: CD3-zeta

<400> SEQUENCE: 13

```
agagtgaagt tcagcaggag cgcagacgcc ccgcgtacc agcagggcca gaaccagctc    60
tataacgagc tcaatctagg acgaagagag gagtacgatg ttttggacaa gagacgtggc   120
cgggaccctg agatggggg aaagccgaga aggaagaacc ctcaggaagg cctgtacaat   180
gaactgcaga agataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgctaa                         339
```

<210> SEQ ID NO 14
<211> LENGTH: 6
<212> TYPE: PRT
<213> ORGANISM: Homo sapiens
<220> FEATURE:
<221> NAME/KEY: MISC_FEATURE
<223> OTHER INFORMATION: Canonical hemi-tam
<220> FEATURE:
<221> NAME/KEY: MISC_FEATURE
<222> LOCATION: (4)..(5)
<223> OTHER INFORMATION: X = any amino acid

<400> SEQUENCE: 14

```
Asp Gly Tyr Xaa Xaa Leu
1               5
```

<210> SEQ ID NO 15
<211> LENGTH: 6
<212> TYPE: PRT
<213> ORGANISM: Homo sapiens
<220> FEATURE:
<221> NAME/KEY: MISC_FEATURE
<223> OTHER INFORMATION: ITSM Motif
<220> FEATURE:
<221> NAME/KEY: MISC_FEATURE
<222> LOCATION: (1)..(1)
<223> OTHER INFORMATION: N = S or T
<220> FEATURE:
<221> NAME/KEY: MISC_FEATURE
<222> LOCATION: (2)..(2)
<223> OTHER INFORMATION: x = any amino acid
<220> FEATURE:
<221> NAME/KEY: MISC_FEATURE
<222> LOCATION: (4)..(5)
<223> OTHER INFORMATION: x = any amino acid
<220> FEATURE:
<221> NAME/KEY: MISC_FEATURE
<222> LOCATION: (6)..(6)
<223> OTHER INFORMATION: N = L or I

<400> SEQUENCE: 15

```
Asn Xaa Tyr Xaa Xaa Asn
1               5
```

<210> SEQ ID NO 16
<211> LENGTH: 614
<212> TYPE: DNA
<213> ORGANISM: Homo sapiens
<220> FEATURE:
<221> NAME/KEY: misc_feature
<223> OTHER INFORMATION: Membrane-bound IL15

<400> SEQUENCE: 16

```
atggccttac cagtgaccgc cttgctcctg ccgctggcct tgctgctcca cgccgccagg    60
ccgaactggg tgaatgtaat aagtgatttg aaaaaaattg aagatcttat tcaatctatg   120
```

```
catattgatg ctactttata tacggaaagt gatgttcacc ccagttgcaa agtaacagca        180
atgaagtgct ttctcttgga gttacaagtt atttcacttg agtccggaga tgcaagtatt        240
catgatacag tagaaaatct gatcatccta gcaaacaaca gtttgtcttc taatgggaat        300
gtaacagaat ctggatgcaa agaatgtgag gaactggagg aaaaaaatat taaagaattt        360
ttgcagagtt ttgtacatat tgtccaaatg ttcatcaaca cttctaccac gacgccagcg        420
ccgcgaccac caacaccggc gcccaccatc gcgtcgcagc ccctgtccct gcgcccagag        480
gcgtgccggc cagcggcggg gggcgcagtg cacacgaggg ggctggactt cgcctgtgat        540
atctacatct gggcgccctt ggccgggact tgtggggtcc ttctcctgtc actggtatca        600 cccttactg ctaa                                                           614
```

```
<210> SEQ ID NO 17
<211> LENGTH: 204
<212> TYPE: PRT
<213> ORGANISM: Homo sapiens
<220> FEATURE:
<221> NAME/KEY: MISC_FEATURE
<223> OTHER INFORMATION: Membrane-bound IL15

<400> SEQUENCE: 17
```

```
Met Ala Leu Pro Val Thr Ala Leu Leu Leu Pro Leu Ala Leu Leu Leu
 1               5                  10                  15

His Ala Ala Arg Pro Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser Thr Thr Thr Pro Ala Pro Arg Pro Pro
    130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175

Phe Ala Cys Asp Ile Tyr Ile Trp Ala Pro Leu Ala Gly Thr Cys Gly
            180                 185                 190

Val Leu Leu Leu Ser Leu Val Ile Thr Leu Tyr Cys
        195                 200
```

```
<210> SEQ ID NO 18
<211> LENGTH: 1140
<212> TYPE: DNA
<213> ORGANISM: Homo sapiens
<220> FEATURE:
<221> NAME/KEY: misc_feature
<223> OTHER INFORMATION: NKG2D/CD8a/4-1BB/CD3z

<400> SEQUENCE: 18
```

```
atggccttac cagtgaccgc cttgctcctg ccgctggcct tgctgctcca cgccgccagg      60
ccgttattca accaagaagt tcaaattccc ttgaccgaaa gttactgtgg cccatgtcct     120
aaaaactgga tatgttacaa aaataactgc taccaatttt ttgatgagag taaaaactgg     180
tatgagagcc aggcttcttg tatgtctcaa aatgccagcc ttctgaaagt atacagcaaa     240
gaggaccagg atttacttaa actggtgaag tcatatcatt ggatgggact agtacacatt     300
ccaacaaatg gatcttggca gtgggaagat ggctccattc tctcacccaa cctactaaca     360
ataattgaaa tgcagaaggg agactgtgca ctctatgcct cgagctttaa aggctatata     420
gaaaactgtt caactccaaa tacatacatc tgcatgcaaa ggactgtgac cacgacgcca     480
gcgccgcgac caccaacacc ggcgcccacc atcgcgtcgc agcccctgtc cctgcgccca     540
gaggcgtgcc ggccagcggc gggggcgca gtgcacacga gggggctgga cttcgcctgt     600
gatatctaca tctgggcgcc cttggccggg acttgtgggg tccttctcct gtcactggtt     660
atcacccttt actgcaaacg gggcagaaag aaactcctgt atatattcaa acaaccattt     720
atgagaccag tacaaactac tcaagaggaa gatggctgta gctgccgatt tccagaagaa     780
gaagaaggag gatgtgaact gagagtgaag ttcagcagga gcgcagacgc ccccgcgtac     840
cagcagggcc agaaccagct ctataacgag ctcaatctag acgaagaga ggagtacgat     900
gttttggaca gagacgtggc ccgggaccct gagatggggg aaagccgag aaggaagaac     960
cctcaggaag cctgtacaa tgaactgcag aaagataaga tggcggaggc ctacagtgag    1020
attgggatga aggcgagcg ccggagggggc aaggggcacg atggccttta ccagggtctc    1080
agtacagcca ccaaggacac ctacgacgcc cttcacatgc aggccctgcc ccctcgctaa    1140
```

<210> SEQ ID NO 19
<211> LENGTH: 379
<212> TYPE: PRT
<213> ORGANISM: Homo sapiens
<220> FEATURE:
<221> NAME/KEY: MISC_FEATURE
<223> OTHER INFORMATION: Amino acid sequence of NKG2D/CD8a/4-1BB/CD3z

<400> SEQUENCE: 19

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
                20                  25                  30

Glu Ser Tyr Cys Gly Pro Cys Pro Lys Asn Trp Ile Cys Tyr Lys Asn
            35                  40                  45

Asn Cys Tyr Gln Phe Phe Asp Glu Ser Lys Asn Trp Tyr Glu Ser Gln
        50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
                100                 105                 110

Ile Leu Ser Pro Asn Leu Leu Thr Ile Ile Glu Met Gln Lys Gly Asp
            115                 120                 125

Cys Ala Leu Tyr Ala Ser Ser Phe Lys Gly Tyr Ile Glu Asn Cys Ser
        130                 135                 140

Thr Pro Asn Thr Tyr Ile Cys Met Gln Arg Thr Val Thr Thr Thr Pro
145                 150                 155                 160

```
Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Ser Leu Val Ile Thr Leu Tyr
    210                 215                 220

Cys Lys Arg Gly Arg Lys Leu Leu Tyr Ile Phe Lys Gln Pro Phe
225                 230                 235                 240

Met Arg Pro Val Gln Thr Thr Gln Glu Glu Asp Gly Cys Ser Cys Arg
                245                 250                 255

Phe Pro Glu Glu Glu Glu Gly Gly Cys Glu Leu Arg Val Lys Phe Ser
                260                 265                 270

Arg Ser Ala Asp Ala Pro Ala Tyr Gln Gln Gly Gln Asn Gln Leu Tyr
            275                 280                 285

Asn Glu Leu Asn Leu Gly Arg Arg Glu Glu Tyr Asp Val Leu Asp Lys
        290                 295                 300

Arg Arg Gly Arg Asp Pro Glu Met Gly Gly Lys Pro Arg Arg Lys Asn
305                 310                 315                 320

Pro Gln Glu Gly Leu Tyr Asn Glu Leu Gln Lys Asp Lys Met Ala Glu
                325                 330                 335

Ala Tyr Ser Glu Ile Gly Met Lys Gly Glu Arg Arg Arg Gly Lys Gly
                340                 345                 350

His Asp Gly Leu Tyr Gln Gly Leu Ser Thr Ala Thr Lys Asp Thr Tyr
            355                 360                 365

Asp Ala Leu His Met Gln Ala Leu Pro Pro Arg
        370                 375

<210> SEQ ID NO 20
<211> LENGTH: 46
<212> TYPE: PRT
<213> ORGANISM: Homo sapiens
<220> FEATURE:
<221> NAME/KEY: MISC_FEATURE
<223> OTHER INFORMATION: Amino acid for NCR1 TM/IC

<400> SEQUENCE: 20

Met Gly Leu Ala Phe Leu Val Leu Val Ala Leu Val Trp Phe Leu Val
1               5                   10                  15

Glu Asp Trp Leu Ser Arg Lys Arg Thr Arg Glu Arg Ala Ser Arg Ala
            20                  25                  30

Ser Thr Trp Glu Gly Arg Arg Arg Leu Asn Thr Gln Thr Leu
        35                  40                  45

<210> SEQ ID NO 21
<211> LENGTH: 276
<212> TYPE: PRT
<213> ORGANISM: Homo sapiens
<220> FEATURE:
<221> NAME/KEY: MISC_FEATURE
<223> OTHER INFORMATION: Full length NCR2

<400> SEQUENCE: 21

Met Ala Trp Arg Ala Leu His Pro Leu Leu Leu Leu Leu Leu Leu Phe
1               5                   10                  15

Pro Gly Ser Gln Ala Gln Ser Lys Ala Gln Val Leu Gln Ser Val Ala
            20                  25                  30
```

-continued

Gly Gln Thr Leu Thr Val Arg Cys Gln Tyr Pro Pro Thr Gly Ser Leu
            35                  40                  45

Tyr Glu Lys Lys Gly Trp Cys Lys Glu Ala Ser Ala Leu Val Cys Ile
 50                  55                  60

Arg Leu Val Thr Ser Ser Lys Pro Arg Thr Met Ala Trp Thr Ser Arg
 65                  70                  75                  80

Phe Thr Ile Trp Asp Asp Pro Asp Ala Gly Phe Phe Thr Val Thr Met
                85                  90                  95

Thr Asp Leu Arg Glu Glu Asp Ser Gly His Tyr Trp Cys Arg Ile Tyr
            100                 105                 110

Arg Pro Ser Asp Asn Ser Val Ser Lys Ser Val Arg Phe Tyr Leu Val
            115                 120                 125

Val Ser Pro Ala Ser Ala Ser Thr Gln Thr Ser Trp Thr Pro Arg Asp
 130                 135                 140

Leu Val Ser Ser Gln Thr Gln Thr Gln Ser Cys Val Pro Pro Thr Ala
 145                 150                 155                 160

Gly Ala Arg Gln Ala Pro Glu Ser Pro Ser Thr Ile Pro Val Pro Ser
            165                 170                 175

Gln Pro Gln Asn Ser Thr Leu Arg Pro Gly Pro Ala Ala Pro Ile Ala
            180                 185                 190

Leu Val Pro Val Phe Cys Gly Leu Leu Val Ala Lys Ser Leu Val Leu
            195                 200                 205

Ser Ala Leu Leu Val Trp Trp Gly Asp Ile Trp Trp Lys Thr Met Met
 210                 215                 220

Glu Leu Arg Ser Leu Asp Thr Gln Lys Ala Thr Cys His Leu Gln Gln
225                 230                 235                 240

Val Thr Asp Leu Pro Trp Thr Ser Val Ser Ser Pro Val Glu Arg Glu
            245                 250                 255

Ile Leu Tyr His Thr Val Ala Arg Thr Lys Ile Ser Asp Asp Asp Asp
            260                 265                 270

Glu His Thr Leu
            275

<210> SEQ ID NO 22
<211> LENGTH: 66
<212> TYPE: PRT
<213> ORGANISM: Homo sapiens
<220> FEATURE:
<221> NAME/KEY: MISC_FEATURE
<223> OTHER INFORMATION: NCR3 TM/IC domains

<400> SEQUENCE: 22

Ala Gly Thr Val Leu Leu Arg Ala Gly Phe Tyr Ala Val Ser Phe
 1                5                  10                  15

Leu Ser Val Ala Val Gly Ser Thr Val Tyr Tyr Gln Gly Lys Cys Leu
            20                  25                  30

Thr Trp Lys Gly Pro Arg Arg Gln Leu Pro Ala Val Val Pro Ala Pro
            35                  40                  45

Leu Pro Pro Pro Cys Gly Ser Ser Ala His Leu Leu Pro Pro Val Pro
 50                  55                  60

Gly Gly
 65

<210> SEQ ID NO 23
<211> LENGTH: 741
<212> TYPE: DNA
<213> ORGANISM: Homo sapiens
<220> FEATURE:
<221> NAME/KEY: misc_feature
<223> OTHER INFORMATION: NKG2D/CD16

<400> SEQUENCE: 23

```
atggccttac cagtgaccgc cttgctcctg ccgctggcct tgctgctcca cgccgcccgc      60
cccctgttca accaggaagt gcagatcccc ctgaccgagt cctattgtgg cccttgccct     120
aagaattgga tttgctataa aaacaactgc taccagttct ttgacgagtc taagaattgg     180
tatgagtccc aggcctcttg tatgagccag aacgcctctc tgctgaaggt gtacagcaag     240
gaggaccagg atctgctgaa gctggtgaag tcctatcact ggatgggcct ggtgcacatc     300
cccacaaacg gctcttggca gtgggaggac ggctccatcc tgtctcctaa tctgctgacc     360
atcatcgaga tgcagaaggg cgattgcgcc ctgtacgcca gctccttcaa gggctatatc     420
gagaactgca gcacacccaa tacctacatc tgtatgcagc ggacagtgac cacaacccca     480
gcacccaggc cccctacacc tgcaccaacc atcgcaagcc agccactgtc cctgaggcct     540
gaggcatgta ggccagcagc aggaggagca gtgcacacac ggggcctgga cttcgcctgc     600
gatgtgagct ttgtctctgg catggtgctg ctgttcgccg tggataccgg cctgtatttt     660
tccgtgaaga caaatatccg gtctagcacc agagactgga aggatcacaa gttcaaatgg     720
aggaaggacc cacaggacaa g                                                741
```

<210> SEQ ID NO 24
<211> LENGTH: 247
<212> TYPE: PRT
<213> ORGANISM: Homo sapiens
<220> FEATURE:
<221> NAME/KEY: MISC_FEATURE
<223> OTHER INFORMATION: NKG2D/CD16

<400> SEQUENCE: 24

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190
```

```
Thr Arg Gly Leu Asp Phe Ala Cys Asp Val Ser Phe Cys Leu Val Met
        195                 200                 205

Val Leu Leu Phe Ala Val Asp Thr Gly Leu Tyr Phe Ser Val Lys Thr
        210                 215                 220

Asn Ile Arg Ser Ser Thr Arg Asp Trp Lys Asp His Lys Phe Lys Trp
225                 230                 235                 240

Arg Lys Asp Pro Gln Asp Lys
                245
```

<210> SEQ ID NO 25
<211> LENGTH: 870
<212> TYPE: DNA
<213> ORGANISM: Homo sapiens
<220> FEATURE:
<221> NAME/KEY: misc_feature
<223> OTHER INFORMATION: CD8/NKG2DOpt/CD8a/CD16 TM/IC/4-1BB

<400> SEQUENCE: 25

```
atggctctgc cgtcaccgc actgctgctg cctctggctc tgctgctgca cgccgcacga      60
ccactgttca atcaggaagt ccagatcccc ctgacagagt cttactgcgg cccatgtccc    120
aagaactgga tctgctacaa gaacaattgt tatcagttct ttgacgagag caagaactgg    180
tatgagtccc aggcctcttg catgagccag aatgcctctc tgctgaaggt gtacagcaag    240
gaggaccagg atctgctgaa gctggtgaag tcctatcact ggatgggcct ggtgcacatc    300
cctacaaacg gctcttggca gtgggaggac ggctccatcc tgtctccaaa tctgctgacc    360
atcatcgaga tgcagaaggg cgattgcgcc ctgtacgcca gctccttcaa gggctatatc    420
gagaactgct ccacacccaa tacctacatc tgtatgcaga ggaccgtgac cacaaccccct   480
gcaccacgcc ccctacacc agcacctacc atcgcaagcc agcctctgtc cctgcggcca    540
gaggcatgta gaccagcagc aggaggagca gtgcacacaa gaggcctgga cttcgcctgc    600
gatgtgagct tttgtctggt catggtgctg ctgttcgccg tggataccgg cctgtacttt    660
tccgtgaaga caaatatcag gtctagcacc cgcgactgga aggatcacaa gtttaagtgg    720
cggaaggacc ctcaggataa gaagcggggc agaaagaagc tgctgtatat cttcaagcag    780
cccttcatgc ggcccgtgca gacaacccag gaggaagacg gctgctcatg tagatttcct    840
gaagaagaag aagggggctg tgaactgtaa                                      870
```

<210> SEQ ID NO 26
<211> LENGTH: 289
<212> TYPE: PRT
<213> ORGANISM: Homo sapiens
<220> FEATURE:
<221> NAME/KEY: MISC_FEATURE
<223> OTHER INFORMATION: CD8/NKG2DOpt/CD8a/CD16 TM/IC/4-1BB

<400> SEQUENCE: 26

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
                20                  25                  30

Glu Ser Tyr Cys Gly Pro Cys Pro Lys Asn Trp Ile Cys Tyr Lys Asn
            35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80
```

Glu Asp Gln Asp Leu Leu Lys Leu Val Lys Ser Tyr His Trp Met Gly
            85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
            115                 120                 125

Cys Ala Leu Tyr Ala Ser Ser Phe Lys Gly Tyr Ile Glu Asn Cys Ser
            130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
            165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Val Ser Phe Cys Leu Val Met
            195                 200                 205

Val Leu Leu Phe Ala Val Asp Thr Gly Leu Tyr Phe Ser Val Lys Thr
            210                 215                 220

Asn Ile Arg Ser Ser Thr Arg Asp Trp Lys Asp His Lys Phe Lys Trp
225                 230                 235                 240

Arg Lys Asp Pro Gln Asp Lys Arg Gly Arg Lys Lys Leu Leu Tyr
            245                 250                 255

Ile Phe Lys Gln Pro Phe Met Arg Pro Val Gln Thr Thr Gln Glu Glu
            260                 265                 270

Asp Gly Cys Ser Cys Arg Phe Pro Glu Glu Glu Gly Gly Cys Glu
            275                 280                 285

Leu

```
<210> SEQ ID NO 27
<211> LENGTH: 741
<212> TYPE: DNA
<213> ORGANISM: Homo sapiens
<220> FEATURE:
<221> NAME/KEY: misc_feature
<223> OTHER INFORMATION: NKG2D/NCR1

<400> SEQUENCE: 27
atggccttac cagtgaccgc cttgctcctg ccgctggcct tgctgctcca cgccgcccgc    60
cctctgttca accaggaagt gcagatccct ctgaccgaaa gctattgcgg accttgccct   120
aagaattgga tttgctataa aaacaactgc taccagttct ttgacgagtc taagaattgg   180
tatgagtctc aggccagctg tatgtcccag aacgcctctc tgctgaaggt gtacagcaag   240
gaggaccagg atctgctgaa gctggtgaag tcctatcact ggatgggcct ggtgcacatc   300
cccacaaacg gctcttggca gtgggaggac ggctctatcc tgagccctaa tctgctgacc   360
atcatcgaga tgcagaaggg cgattgcgcc ctgtacgcca gctccttcaa gggctatatc   420
gagaactgca gcacacccaa tacctacatc tgtatgcaga ggacagtgac cacaaccccaa  480 gcacccccgc ccctacacc tgcaccaacc atcgcaagcc agccactgtc cctgcggcct   540
gaggcctgca gaccagcagc aggaggagca gtgcacaccc ggggcctgga cttcgcctgt   600
gatatgggcc tggcctttct ggtgctggtg ccctggtgt ggtttctggt ggaggattgg   660
ctgtcccgga agaaccaag ggagagggcc tcccgggcct ctacctggga aggaagaagg   720
agactgaaca cccagacact g                                            741
```

<210> SEQ ID NO 28
<211> LENGTH: 247
<212> TYPE: PRT
<213> ORGANISM: Homo sapiens
<220> FEATURE:
<221> NAME/KEY: MISC_FEATURE
<223> OTHER INFORMATION: NKG2D/NCR1

<400> SEQUENCE: 28

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Met Gly Leu Ala Phe Leu Val
        195                 200                 205

Leu Val Ala Leu Val Trp Phe Leu Val Glu Asp Trp Leu Ser Arg Lys
    210                 215                 220

Arg Thr Arg Glu Arg Ala Ser Arg Ala Ser Thr Trp Glu Gly Arg Arg
225                 230                 235                 240

Arg Leu Asn Thr Gln Thr Leu
                245
```

<210> SEQ ID NO 29
<211> LENGTH: 801
<212> TYPE: DNA
<213> ORGANISM: Homo sapiens
<220> FEATURE:
<221> NAME/KEY: misc_feature
<223> OTHER INFORMATION: NKG2D/NCR3

<400> SEQUENCE: 29

| atggccttac | cagtgaccgc | cttgctcctg | ccgctggcct | tgctgctcca | cgccgccaga | 60  |
| cccctgttca | accaggaggt | gcagattccc | ctgacagaaa | gctattgtgg | cccttgccct | 120 |
| aaaaattgga | tttgctataa | aaacaactgc | taccagttct | ttgacgagtc | taagaattgg | 180 |
| tatgagtctc | aggccagctg | tatgtcccag | aacgcctctc | tgctgaaggt | gtacagcaag | 240 |
| gaggaccagg | atctgctgaa | gctggtgaag | tcctatcact | ggatgggcct | ggtgcacatc | 300 |

```
cctacaaacg gctcttggca gtgggaggac ggctctatcc tgagcccaaa tctgctgacc    360
atcatcgaga tgcagaaggg cgattgcgcc ctgtacgcca gctccttcaa gggctatatc    420
gagaactgca gcacacccaa tacctacatc tgtatgcagc ggacagtgac cacaaccccca   480 gcacccagac cccctacacc tgcaccaacc atcgccagcc agccactgtc cctgaggccc    540
gaggcatgca ggcctgcagc aggaggcgcc gtgcacacaa ggggcctgga ctttgcctgt    600
gatgcaggaa ccgtgctgct gctgagagca ggcttctatg ccgtgtcctt tctgtctgtg    660
gccgtgggct ccacagtgta ctatcagggc aagtgcctga cctggaaggg cccacggaga    720
cagctgcccg ccgtggtgcc cgcccctctg ccaccccctt gtggcagtag cgcccacctg    780
ctgccacccg tgcccggagg a                                              801
```

<210> SEQ ID NO 30
<211> LENGTH: 267
<212> TYPE: PRT
<213> ORGANISM: Homo sapiens
<220> FEATURE:
<221> NAME/KEY: MISC_FEATURE
<223> OTHER INFORMATION: NKG2D/NCR3

<400> SEQUENCE: 30

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ala Gly Thr Val Leu Leu Leu
        195                 200                 205

Arg Ala Gly Phe Tyr Ala Val Ser Phe Leu Ser Val Ala Val Gly Ser
    210                 215                 220

Thr Val Tyr Tyr Gln Gly Lys Cys Leu Thr Trp Lys Gly Pro Arg Arg
225                 230                 235                 240

Gln Leu Pro Ala Val Val Pro Ala Pro Leu Pro Pro Cys Gly Ser
                245                 250                 255

Ser Ala His Leu Leu Pro Pro Val Pro Gly Gly
            260                 265
```

```
<210> SEQ ID NO 31
<211> LENGTH: 6
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: N is an integer indicating the number of GGGGS
      repeated

<400> SEQUENCE: 31

Gly Gly Gly Gly Ser Asn
1               5

<210> SEQ ID NO 32
<211> LENGTH: 60
<212> TYPE: PRT
<213> ORGANISM: Homo sapiens
<220> FEATURE:
<221> NAME/KEY: MISC_FEATURE
<223> OTHER INFORMATION: GS3/CD8a

<400> SEQUENCE: 32

Gly Gly Gly Gly Ser Gly Gly Gly Gly Ser Gly Gly Gly Gly Ser Thr
1               5                   10                  15

Thr Thr Pro Ala Pro Arg Pro Pro Thr Pro Ala Pro Thr Ile Ala Ser
            20                  25                  30

Gln Pro Leu Ser Leu Arg Pro Glu Ala Cys Arg Pro Ala Ala Gly Gly
        35                  40                  45

Ala Val His Thr Arg Gly Leu Asp Phe Ala Cys Asp
    50                  55                  60

<210> SEQ ID NO 33
<211> LENGTH: 45
<212> TYPE: PRT
<213> ORGANISM: Homo sapiens
<220> FEATURE:
<221> NAME/KEY: MISC_FEATURE
<223> OTHER INFORMATION: GS9

<400> SEQUENCE: 33

Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 34
<211> LENGTH: 15
<212> TYPE: PRT
<213> ORGANISM: Homo sapiens
<220> FEATURE:
<221> NAME/KEY: MISC_FEATURE
<223> OTHER INFORMATION: GS3

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 120
<212> TYPE: PRT
<213> ORGANISM: Homo sapiens
```

<220> FEATURE:
<221> NAME/KEY: MISC_FEATURE
<223> OTHER INFORMATION: 2B4 ICR

<400> SEQUENCE: 35

Trp Arg Arg Lys Arg Lys Glu Lys Gln Ser Glu Thr Ser Pro Lys Glu
1               5                   10                  15

Phe Leu Thr Ile Tyr Glu Asp Val Lys Asp Leu Lys Thr Arg Arg Asn
            20                  25                  30

His Glu Gln Glu Gln Thr Phe Pro Gly Gly Gly Ser Thr Ile Tyr Ser
        35                  40                  45

Met Ile Gln Ser Gln Ser Ser Ala Pro Thr Ser Gln Glu Pro Ala Tyr
50                  55                  60

Thr Leu Tyr Ser Leu Ile Gln Pro Ser Arg Lys Ser Gly Ser Arg Lys
65                  70                  75                  80

Arg Asn His Ser Pro Ser Phe Asn Ser Thr Ile Tyr Glu Val Ile Gly
                85                  90                  95

Lys Ser Gln Pro Lys Ala Gln Asn Pro Ala Arg Leu Ser Arg Lys Glu
            100                 105                 110

Leu Glu Asn Phe Asp Val Tyr Ser
        115                 120

<210> SEQ ID NO 36
<211> LENGTH: 360
<212> TYPE: DNA
<213> ORGANISM: Homo sapiens
<220> FEATURE:
<221> NAME/KEY: misc_feature
<223> OTHER INFORMATION: 2B4 ICR

<400> SEQUENCE: 36
tggaggagga aaaggaagga gaaacagagc gagacctccc ctaaggagtt cctgaccatc    60
tacgaggacg tgaaggacct gaagaccagg aggaaccacg agcaggaaca gacctttcct   120
ggcggaggca gcaccatcta cagcatgatc cagagccaga gcagcgcccc taccagccaa   180
gagcctgcct acaccctgta cagcctgatc cagcccagca ggaaaagcgg ctccaggaag   240
aggaaccaca gccccagctt caacagcacc atctatgagg tgatcggcaa gagccagccc   300
aaggcccaga ccctgccag gctgtccagg aaggagctgg agaacttcga cgtgtacagc    360

<210> SEQ ID NO 37
<211> LENGTH: 38
<212> TYPE: PRT
<213> ORGANISM: Homo sapiens
<220> FEATURE:
<221> NAME/KEY: MISC_FEATURE
<223> OTHER INFORMATION: NKp80 ICR

<400> SEQUENCE: 37

Met Gln Asp Glu Asp Gly Tyr Met Thr Leu Asn Val Gln Ser Lys Lys
1               5                   10                  15

Arg Ser Ser Ala Gln Thr Ser Gln Leu Thr Phe Lys Asp Tyr Ser Val
            20                  25                  30

Thr Leu His Trp Tyr Lys
        35

<210> SEQ ID NO 38
<211> LENGTH: 114
<212> TYPE: DNA
<213> ORGANISM: Homo sapiens
<220> FEATURE:

<221> NAME/KEY: misc_feature
<223> OTHER INFORMATION: NKp80 ICR

<400> SEQUENCE: 38
atgcaggatg aggacggcta tatgaccctg aacgtccagt ccaagaagag gtccagcgct    60
cagaccagcc agctgacctt caaggactac tccgtgaccc tgcactggta caag         114

<210> SEQ ID NO 39
<211> LENGTH: 30
<212> TYPE: PRT
<213> ORGANISM: Homo sapiens
<220> FEATURE:
<221> NAME/KEY: MISC_FEATURE
<223> OTHER INFORMATION: B2Ad N-term ECD

<400> SEQUENCE: 39

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu
            20                  25                  30

<210> SEQ ID NO 40
<211> LENGTH: 90
<212> TYPE: DNA
<213> ORGANISM: Homo sapiens
<220> FEATURE:
<221> NAME/KEY: misc_feature
<223> OTHER INFORMATION: B2 AdR N-term ECD

<400> SEQUENCE: 40
atggggcaac ccgggaacgg cagcgccttc ttgctggcac ccaatagaag ccatgcgccg    60
gaccacgacg tcacgcagca aagggacgag                                    90

<210> SEQ ID NO 41
<211> LENGTH: 33
<212> TYPE: PRT
<213> ORGANISM: Homo sapiens
<220> FEATURE:
<221> NAME/KEY: MISC_FEATURE
<223> OTHER INFORMATION: B2 AdR TM helix

<400> SEQUENCE: 41

Val Trp Val Val Gly Met Gly Ile Val Met Ser Leu Ile Val Leu Ala
1               5                   10                  15

Ile Val Phe Gly Asn Val Leu Val Ile Thr Ala Ile Ala Lys Phe Glu
            20                  25                  30

Arg

<210> SEQ ID NO 42
<211> LENGTH: 99
<212> TYPE: DNA
<213> ORGANISM: Homo sapiens
<220> FEATURE:
<221> NAME/KEY: misc_feature
<223> OTHER INFORMATION: B2AdR TM helix

<400> SEQUENCE: 42
gtgtgggtgg tgggcatggg catcgtcatg tctctcatcg tcctggccat cgtgtttggc    60
aatgtgctgg tcatcacagc cattgccaag ttcgagcgt                          99

<210> SEQ ID NO 43
<211> LENGTH: 924
<212> TYPE: DNA

<213> ORGANISM: Homo sapiens
<220> FEATURE:
<221> NAME/KEY: misc_feature
<223> OTHER INFORMATION: NK15_1

<400> SEQUENCE: 43

| | | | | | |
|---|---|---|---|---|---|
| gccgccacca | tggctctgcc | cgtcaccgca | ctgctgctgc | ctctggctct | gctgctgcac | 60 |
| gccgcacgac | cactgttcaa | tcaggaagtc | cagatccccc | tgacagagtc | ttactgcggc | 120 |
| ccatgtccca | agaactggat | ctgctacaag | aacaattgtt | atcagttctt | tgacgagagc | 180 |
| aagaactggt | atgagtccca | ggcctcttgc | atgagccaga | atgcctctct | gctgaaggtg | 240 |
| tacagcaagg | aggaccagga | tctgctgaag | ctggtgaagt | cctatcactg | gatgggcctg | 300 |
| gtgcacatcc | ctacaaacgg | ctcttggcag | tgggaggacg | gctccatcct | gtctccaaat | 360 |
| ctgctgacca | tcatcgagat | gcagaagggc | gattgcgccc | tgtacgccag | ctcccttcaag | 420 |
| ggctatatcg | agaactgctc | cacacccaat | acctacatct | gtatgcagag | gaccgtgggt | 480 |
| ggcggtggct | cgggcggtgg | tgggtcgggt | ggcggcggat | ctaccacaac | ccctgcacca | 540 |
| cgcccccta | caccagcacc | taccatcgca | agccagcctc | tgtccctgcg | gccagaggca | 600 |
| tgtagaccag | cagcaggagg | agcagtgcac | acaagaggcc | tggacttcgc | ctgcgatgtg | 660 |
| agcttttgtc | tggtcatggt | gctgctgttc | gccgtggata | ccggcctgta | cttttccgtg | 720 |
| aagacaaata | tcaggtctag | cacccgcgac | tggaaggatc | acaagtttaa | gtggcggaag | 780 |
| gaccctcagg | ataagaagcg | gggcagaaag | aagctgctgt | atatcttcaa | gcagcccttc | 840 |
| atgcggcccg | tgcagacaac | ccaggaggaa | gacggctgct | catgtagatt | tcctgaagaa | 900 |
| gaagaagggg | gctgtgaact | gtaa | | | | 924 |

<210> SEQ ID NO 44
<211> LENGTH: 789
<212> TYPE: DNA
<213> ORGANISM: Homo sapiens
<220> FEATURE:
<221> NAME/KEY: misc_feature
<223> OTHER INFORMATION: NK15_2

<400> SEQUENCE: 44

| | | | | | |
|---|---|---|---|---|---|
| gccgccacca | tggctctgcc | cgtcaccgca | ctgctgctgc | ctctggctct | gctgctgcac | 60 |
| gccgcacgac | cactgttcaa | tcaggaagtc | cagatccccc | tgacagagtc | ttactgcggc | 120 |
| ccatgtccca | agaactggat | ctgctacaag | aacaattgtt | atcagttctt | tgacgagagc | 180 |
| aagaactggt | atgagtccca | ggcctcttgc | atgagccaga | atgcctctct | gctgaaggtg | 240 |
| tacagcaagg | aggaccagga | tctgctgaag | ctggtgaagt | cctatcactg | gatgggcctg | 300 |
| gtgcacatcc | ctacaaacgg | ctcttggcag | tgggaggacg | gctccatcct | gtctccaaat | 360 |
| ctgctgacca | tcatcgagat | gcagaagggc | gattgcgccc | tgtacgccag | ctcccttcaag | 420 |
| ggctatatcg | agaactgctc | cacacccaat | acctacatct | gtatgcagag | gaccgtgggt | 480 |
| ggcggtggct | cgggcggtgg | tgggtcgggt | ggcggcggat | ctgtgagctt | ttgtctggtc | 540 |
| atggtgctgc | tgttcgccgt | ggataccggc | ctgtactttt | ccgtgaagac | aaatatcagg | 600 |
| tctagcaccc | gcgactggaa | ggatcacaag | tttaagtggc | ggaaggaccc | tcaggataag | 660 |
| aagcggggca | gaaagaagct | gctgtatatc | ttcaagcagc | ccttcatgcg | gcccgtgcag | 720 |
| acaacccagg | aggaagacgg | ctgctcatgt | agatttcctg | aagaagaaga | agggggctgt | 780 |
| gaactgtaa | | | | | | 789 |

```
<210> SEQ ID NO 45
<211> LENGTH: 744
<212> TYPE: DNA
<213> ORGANISM: Homo sapiens
<220> FEATURE:
<221> NAME/KEY: misc_feature
<223> OTHER INFORMATION: NK15_3

<400> SEQUENCE: 45
gccgccacca tggctctgcc cgtcaccgca ctgctgctgc ctctggctct gctgctgcac      60
gccgcacgac cactgttcaa tcaggaagtc cagatccccc tgacagagtc ttactgcggc     120
ccatgtccca gaactggat ctgctacaag aacaattgtt atcagttctt tgacgagagc      180
aagaactggt atgagtccca ggcctcttgc atgagccaga atgcctctct gctgaaggtg     240
tacagcaagg aggaccagga tctgctgaag ctggtgaagt cctatcactg gatgggcctg     300
gtgcacatcc ctacaaacgg ctcttggcag tgggaggacg gctccatcct gtctccaaat     360
ctgctgacca tcatcgagat gcagaagggc gattgcgccc tgtacgccag ctccttcaag     420
ggctatatcg agaactgctc cacacccaat acctacatct gtatgcagag gaccgtggtg     480
agcttttgtc tggtcatggt gctgctgttc gccgtggata ccggcctgta cttttccgtg     540
aagacaaata tcaggtctag cacccgcgac tggaaggatc acaagtttaa gtggcggaag     600
gaccctcagg ataagaagcg gggcagaaag aagctgctgt atatcttcaa gcagcccttc     660
atgcggcccg tgcagacaac ccaggaggaa gacggctgct catgtagatt tcctgaagaa     720
gaagaagggg gctgtgaact gtaa                                            744

<210> SEQ ID NO 46
<211> LENGTH: 1164
<212> TYPE: DNA
<213> ORGANISM: Homo sapiens
<220> FEATURE:
<221> NAME/KEY: misc_feature
<223> OTHER INFORMATION: NK15_4

<400> SEQUENCE: 46
gccgccacca tggccctgcc tgtgacagcc ctgctgctgc ctctggctct gctgctgcac      60
gctgccagac ccttattcaa ccaagaagtt caaattccct tgaccgaaag ttactgtggc     120
ccatgtccta aaaactggat atgttacaaa aataactgct accaatttt tgatgagagt      180 aaaaactggt atgagagcca ggcttcttgt atgtctcaaa atgccagcct tctgaaagta     240
tacagcaaag aggaccagga tttacttaaa ctggtgaagt catatcattg gatgggacta     300
gtacacattc caacaaatgg atcttggcag tgggaagatg gctccattct ctcacccaac     360
ctactaacaa taattgaaat gcagaaggga gactgtgcac tctatgcctc gagctttaaa     420
ggctatatag aaaactgttc aactccaaat acgtacatct gcatgcaaag gactgtgacc     480
acaaccccgc ctcccagacc tcctaccct gccctacaa tcgccagcca gccctgagc       540 ctgagacccg aagcctgtag acctgctgcc ggaggcgctg tgcacacaag aggcctggac     600
ttcgcctgcg atatctatat ctgggcccct ctggctggaa cctgtggcgt gctgctgctg     660
agcctggtga ttaccaagag gggcaggaag aagctgctgt acatcttcaa gcagcctttc     720
atgaggcccg tgcaaaccac ccaggaggag gacggctgca gctgcagatt ccctgaggag     780
gaggagggcg gatgcgagct gtggaggagg aaaaggaagg agaaacagag cgagacctcc     840
cctaaggagt tcctgaccat ctacgaggac gtgaaggacc tgaagaccag gaggaaccac     900
gagcaggaac agaccttcc tggcggaggc agcaccatct acagcatgat ccagagccag     960
```

| | |
|---|---|
| agcagcgccc ctaccagcca agagcctgcc tacaccctgt acagcctgat ccagcccagc | 1020 |
| aggaaaagcg gctccaggaa gaggaaccac agccccagct tcaacagcac catctatgag | 1080 |
| gtgatcggca agagccagcc caaggcccag aaccctgcca ggctgtccag gaaggagctg | 1140 |
| gagaacttcg acgtgtacag ctga | 1164 |

<210> SEQ ID NO 47
<211> LENGTH: 1155
<212> TYPE: DNA
<213> ORGANISM: Homo sapiens
<220> FEATURE:
<221> NAME/KEY: misc_feature
<223> OTHER INFORMATION: NK15_5

<400> SEQUENCE: 47

| | |
|---|---|
| gccgccacca tggccctgcc tgtgacagcc ctgctgctgc ctctggctct gctgctgcac | 60 |
| gctgccagac ccttattcaa ccaagaagtt caaattccct tgaccgaaag ttactgtggc | 120 |
| ccatgtccta aaaactggat atgttacaaa ataactgct accaattttt tgatgagagt | 180 |
| aaaaactggt atgagagcca ggcttcttgt atgtctcaaa atgccagcct tctgaaagta | 240 |
| tacagcaaag aggaccagga tttacttaaa ctggtgaagt catatcattg atgggacta | 300 |
| gtacacattc aacaaatgg atcttggcag tgggaagatg gctccattct ctcacccaac | 360 |
| ctactaacaa taattgaaat gcagaaggga gactgtgcac tctatgcctc gagctttaaa | 420 |
| ggctatatag aaaactgttc aactccaaat acgtacatct gcatgcaaag gactgtgatg | 480 |
| ggacagcctg gaaacggcag cgccttcctg ctggccccta acagaagcca cgcccccgat | 540 |
| cacgatgtga cccagcagag ggacgaggtg tgggtggtgg gcatgggcat cgtgatgagc | 600 |
| ctgatcgtgc tggctatcgt gttcggcaac gtgctggtga tcaccgccat cgccaagttc | 660 |
| gagaggaaga ggggcaggaa aaagctgctc tacatcttca gcagcccctt catgaggccc | 720 |
| gtgcagacca cccaggaaga ggatggctgc tcctgtaggt ttcccgagga ggaggagggc | 780 |
| ggctgtgagc tgtggaggag aaaaaggaag gagaagcaga gcgagaccag ccccaaggag | 840 |
| ttcctgacca tctacgagga cgtgaaggac ctgaagacca ggaggaacca cgagcaggaa | 900 |
| cagaccttcc ccggcggagg cagcaccatc tacagcatga tccagagcca gtccagcgcc | 960 |
| cccacaagcc aggaacccgc ctacacactg tatagcctga tccagccctc caggaagagc | 1020 |
| ggcagcagga agaggaacca cagccccagc ttcaacagca ccatttacga ggtgatcgga | 1080 |
| aagagccagc ccaaggctca gaaccccgcc aggctgagca ggaaggagct cgaaaacttc | 1140 |
| gacgtgtaca gctga | 1155 |

<210> SEQ ID NO 48
<211> LENGTH: 1349
<212> TYPE: DNA
<213> ORGANISM: Homo sapiens
<220> FEATURE:
<221> NAME/KEY: misc_feature
<223> OTHER INFORMATION: NK15_6

<400> SEQUENCE: 48

| | |
|---|---|
| ggatccgaat cgccgccac catggccctg cctgtgacag ccctgctgct gcctctggct | 60 |
| ctgctgctgc acgctgccag acccttattc aaccaagaag ttcaaattcc cttgaccgaa | 120 |
| agttactgtg gcccatgtcc taaaaactgg atatgttaca aaaataactg ctaccaattt | 180 |
| tttgatgaga gtaaaaactg gtatgagagc caggcttctt gtatgtctca aaatgccagc | 240 |
| cttctgaaag tatacagcaa agaggaccag gatttactta aactggtgaa gtcatatcat | 300 |

```
tggatgggac tagtacacat tccaacaaat ggatcttggc agtgggaaga tggctccatt    360
ctctcaccca acctactaac aataattgaa atgcagaagg gagactgtgc actctatgcc    420
tcgagcttta aaggctatat agaaaactgt tcaactccaa atacgtacat ctgcatgcaa    480
aggactgtga ccacaacccc tgctcccaga cctcccacac ccgcccctac aatcgcctcc    540
cagcctctga gcctgagacc cgaagcctgt agacctgccg ccggcggagc tgtgcataca    600
agaggcctgg acttcgcctg cgacatctac atctgggccc ctctggctgg cacatgcgga    660
gtcctgctgc tgagcctggt gatcaccaag aggggcagga agaagctgct gtacatcttc    720
aagcagccct tcatgaggcc tgtgcagacc acacaggagg aggacggctg ctcctgcagg    780
ttccctgagg aggaggaggg aggctgcgag ctgtggagga ggaagagaaa ggagaagcag    840
tccgagaccc cccccaagga gttcctcacc atttacgagg acgtgaagga cctgaagacc    900
aggagaaacc acgagcagga acaaaccttc cccggcggcg gcagcaccat ctacagcatg    960
atccagagcc agtcctccgc ccctacaagc caggagcctg cctacacccct gtacagcctg   1020 atccagccta gcaggaagag cggctccagg aagaggaacc actcccccag cttcaacagc   1080
accatttatg aggtgatcgg caagtcccag cccaaggccc agaaccctgc cagactgtcc   1140
aggaaggagc tggagaactt cgacgtctac tccggcggcg gcggcagcgg cggaggaggc   1200
tccggaggag gcggcagcat gcaggatgag gacggctata tgaccctgaa cgtccagtcc   1260
aagaagaggt ccagcgctca gaccagccag ctgaccttca aggactactc cgtgaccctg   1320
cactggtaca agtgagcggc cgcgtcgac                                     1349

<210> SEQ ID NO 49
<211> LENGTH: 989
<212> TYPE: DNA
<213> ORGANISM: Homo sapiens
<220> FEATURE:
<221> NAME/KEY: misc_feature
<223> OTHER INFORMATION: NK15_7

<400> SEQUENCE: 49
ggatccgaat cgccgccac catggccctg cctgtgacag ccctgctgct gcctctggct     60
ctgctgctgc atgccgccag acccttattc aaccaagaag ttcaaattcc cttgaccgaa   120
agttactgtg gcccatgtcc taaaaactgg atatgttaca aaataactg ctaccaattt    180 tttgatgaga gtaaaaactg gtatgagagc caggcttctt gtatgtctca aaatgccagc   240
cttctgaaag tatacagcaa agaggaccag gatttactta aactggtgaa gtcatatcat   300
tggatgggac tagtacacat tccaacaaat ggatcttggc agtgggaaga tggctccatt   360
ctctcaccca acctactaac aataattgaa atgcagaagg gagactgtgc actctatgcc   420
tcgagcttta aaggctatat agaaaactgt tcaactccaa atacgtacat ctgcatgcaa   480
aggactgtga ccaccacccc tgctcccaga ccccctacac ctgcccctac aatcgccagc   540
cagcccctga gcctgagacc tgaggcctgc agacctgctg ctggaggcgc tgtgcacaca   600
aggggcctcg acttcgcctg cgacatctac atctgggccc ctctggccgg cacatgtgga   660
gtgctgctgc tgtccctggt gatcaccaag aggggcagga agaagctgct gtacatcttc   720
aagcagccct tcatgaggcc cgtgcagacc acccaggagg aggacggctg ctcctgcaga   780
ttccccgagg aggaggaggg cggatgtgaa ctgggcggag gaggcagcgg cggcggcggc   840
agcggcggcg gcggcagcat gcaggatgag gacggctaca tgaccctgaa cgtgcagagc   900
aagaagagga gcagcgccca gaccagccag ctgaccttca aggactacag cgtgaccctg   960
```

-continued cactggtaca agtgagcggc cgcgtcgac                                       989

<210> SEQ ID NO 50
<211> LENGTH: 1430
<212> TYPE: DNA
<213> ORGANISM: Homo sapiens
<220> FEATURE:
<221> NAME/KEY: misc_feature
<223> OTHER INFORMATION: NK15_8

<400> SEQUENCE: 50
ggatccgaat tcgccgccac catggccctg cccgtgacag ctctgctgct gcctctggcc      60
ctgctgctgc atgccgctag acccctgttc aaccaggagg tgcagatccc cctgaccgaa    120
agctactgcg gccctgccc caagaactgg atctgttaca agaacaactg ctatcagttc      180
ttcgacgaga gcaagaactg gtacgagagc caggccagct gtatgagcca gaacgccagc    240
ctgctgaaag tgtatagcaa ggaggaccag gacctgctga agctggtgaa gagctaccac    300
tggatgggcc tggtgcacat ccccaccaac ggaagctggc agtgggagga cggcagcatc    360
ctgagcccca acctgctgac catcatcgag atgcagaagg gcgactgcgc cctgtatgcc    420
agcagcttca gggctacat cgagaactgt agcacccccca acacctacat ctgcatgcag    480
aggaccgtgg gcggcggcgg cagcggcgga ggcggctccg gcggcggcgg cagcttattc    540
aaccaagaag ttcaaattcc cttgaccgaa agttactgtg gccatgtcc taaaaactgg    600 atatgttaca aaataactg ctaccaattt tttgatgaga gtaaaaactg gtatgagagc      660
caggcttctt gtatgtctca aaatgccagc cttctgaaag tatacagcaa agaggaccag    720
gatttactta aactggtgaa gtcatatcat tggatgggac tagtacacat tccaacaaat    780
ggatcttggc agtgggaaga tggctccatt ctctcaccca acctactaac aataattgaa    840
atgcagaagg gagactgtgc actctatgcc tcgagcttta aaggctatat agaaaactgt    900
tcaactccaa atacgtacat ctgcatgcaa aggactgtga tgggccagcc tggcaacggc    960
agcgcctttc tgctggcccc caacaggagc catgcccctg accacgacgt gacccagcag   1020
agggacgagg tgtgggtggt gggcatgggc atcgtgatga gcctgatcgt gctggccatc   1080
gtgttcggca acgtgctggt gatcaccgcc atcgccaagt tcgagaggaa gaggggcagg   1140
aagaagctgc tgtacatctt caagcagccc ttcatgagac ccgtgcaaac cacccaggag   1200
gaggacggct gcagctgcag gtttcccgag gaggaggagg gcggatgcga actgggaggc   1260
ggaggaagcg gaggaggagg atccggagga ggcggaagca tgcaggacga ggacggctac   1320
atgaccctga acgtccagag caagaagagg agcagcgccc agacctccca gctgacctt c  1380 aaggactact ccgtgaccct gcactggtac aagtgagcgg ccgcgtcgac               1430

<210> SEQ ID NO 51
<211> LENGTH: 1439
<212> TYPE: DNA
<213> ORGANISM: Homo sapiens
<220> FEATURE:
<221> NAME/KEY: misc_feature
<223> OTHER INFORMATION: NK15_9

<400> SEQUENCE: 51
ggatccgaat tcgccgccac catggccctg cccgtgacag ctctgctgct gcctctggcc      60
ctgctgctgc atgccgctag acccctgttc aaccaggagg tgcagatccc cctgaccgaa    120
agctactgcg gccctgccc caagaactgg atctgttaca agaacaactg ctatcagttc      180

```
ttcgacgaga gcaagaactg gtacgagagc caggccagct gtatgagcca gaacgccagc      240
ctgctgaaag tgtatagcaa ggaggaccag gacctgctga agctggtgaa gagctaccac      300
tggatgggcc tggtgcacat ccccaccaac ggaagctggc agtgggagga cggcagcatc      360
ctgagcccca acctgctgac catcatcgag atgcagaagg gcgactgcgc cctgtatgcc      420
agcagcttca agggctacat cgagaactgt agcaccccca cacctacat ctgcatgcag       480 aggaccgtgg gcggcggcgg cagcggcgga ggcggctccg gcggcggcgg cagcttattc      540
aaccaagaag ttcaaattcc cttgaccgaa agttactgtg gcccatgtcc taaaaactgg      600
atatgttaca aaataactg ctaccaattt tttgatgaga gtaaaaactg gtatgagagc       660
caggcttctt gtatgtctca aaatgccagc cttctgaaag tatacagcaa agaggaccag      720
gatttactta aactggtgaa gtcatatcat tggatgggac tagtacacat tccaacaaat      780
ggatcttggc agtgggaaga tggctccatt ctctcaccca acctactaac aataattgaa      840
atgcagaagg gagactgtgc actctatgcc tcgagcttta aaggctatat agaaaactgt      900
tcaactccaa atacgtacat ctgcatgcaa aggactgtga ccaccacccc tgctcccaga      960
ccccctacac ctgcccctac aatcgccagc cagcccctga gcctgagacc tgaggcctgc     1020
agacctgctg ctggaggcgc tgtgcacaca aggggcctcg acttcgcctg cgacatctac     1080
atctgggccc ctctggccgg cacatgtgga gtgctgctgc tgtccctggt gatcaccaag     1140
aggggcagga agaagctgct gtacatcttc aagcagccct tcatgaggcc cgtgcagacc     1200
acccaggagg aggacggctg ctcctgcaga ttccccgagg aggaggaggg cggatgtgaa     1260
ctgggcggag gaggcagcgg cggcggcggc agcggcggcg cgcggcagcat gcaggatgag     1320 gacggctaca tgaccctgaa cgtgcagagc aagaagagga gcagcgccca gaccagccag     1380
ctgaccttca aggactacag cgtgacccctg cactggtaca gtgagcggc gcgtcgac      1439
```

<210> SEQ ID NO 52
<211> LENGTH: 1329
<212> TYPE: DNA
<213> ORGANISM: Homo sapiens
<220> FEATURE:
<221> NAME/KEY: misc_feature
<223> OTHER INFORMATION: NK15_10

<400> SEQUENCE: 52

```
gccgccacaa tggccctgcc tgtgacagcc ctgctgctgc tctggcccct gctgctgcat       60
gctgccaggc tctgttcaa ccaggaggtg cagatccctc tgaccgagag ctactgcggc      120
ccctgcccca gaactggat ctgctacaag aacaactgct accagttctt cgacgagagc      180
aagaactggt acgagagcca ggccagctgc atgtcccaga acgctagcct gctgaaggtg     240
tatagcaagg aggaccagga cctgctgaag ctggtgaaga gctaccactg gatgggcctg     300
gtgcacatcc ccaccaacgg ctcctggcag tgggaggacg gcagcatcct gagccctaac     360
ctgctgacca tcatcgagat gcagaaggga gactgcgccc tgtacgccag ctccttaag    420 ggctacatcg agaactgcag cacccccaac acctacatct gtatgcagag gaccgtggga     480
ggcggcggca gcggcggcgg cggcagcggc ggcggcggca gcttattcaa ccaagaagtt     540
caaattccct tgaccgaaag ttactgtggc ccatgtccta aaaactggat atgttacaaa     600
aataactgct accaattttt tgatgagagt aaaaactggt atgagagcca ggcttcttgt     660
atgtctcaaa atgccagcct tctgaaagta tacagcaaag aggaccagga tttacttaaa     720
ctggtgaagt catatcattg gatgggacta gtacacattc aacaaatgg atcttggcag     780
```

| | | | | |
|---|---|---|---|---|
| tgggaagatg | gctccattct | ctcacccaac | ctactaacaa | taattgaaat gcagaaggga | 840 |
| gactgtgcac | tctatgcctc | gagctttaaa | ggctatatag | aaaactgttc aactccaaat | 900 |
| acgtacatct | gcatgcaaag | gactgtgacc | accaccctg | ccctagacc ccctacacct | 960 |
| gccctacca | tcgccagcca | gcctctgagc | ctgagaccg | aggcctgtag acctgctgcc | 1020 |
| ggaggagccg | tgcacacaag | aggcctggac | ttcgcctgcg | acgtgagctt ctgcctggtg | 1080 |
| atggtgctgc | tgttcgccgt | ggacaccggc | ctgtacttca | gcgtgaagac caacatcagg | 1140 |
| agcagcacca | gggactggaa | ggaccacaaa | ttcaagtgga | ggaaggaccc ccaggacaag | 1200 |
| aagaggggca | ggaagaagct | gctgtacatc | ttcaagcagc | ccttcatgag gcctgtgcag | 1260 |
| accacccagg | aggaggacgg | ctgcagctgc | aggttccctg | aggaggaaga gggcggctgc | 1320 |
| gagctgtga | | | | | 1329 |

<210> SEQ ID NO 53
<211> LENGTH: 1239
<212> TYPE: DNA
<213> ORGANISM: Homo sapiens
<220> FEATURE:
<221> NAME/KEY: misc_feature
<223> OTHER INFORMATION: NK15_11

<400> SEQUENCE: 53

| | | | | |
|---|---|---|---|---|
| gccgccacca | tggctctgcc | cgtcaccgca | ctgctgctgc | tctggctct gctgctgcac | 60 |
| gccgcacgac | cactgttcaa | tcaggaagtc | cagatccccc | tgacagagtc ttactgcggc | 120 |
| ccatgtccca | agaactggat | ctgctacaag | aacaattgtt | atcagttctt tgacgagagc | 180 |
| aagaactggt | atgagtccca | ggcctcttgc | atgagccaga | atgcctctct gctgaaggtg | 240 |
| tacagcaagg | aggaccagga | tctgctgaag | ctggtgaagt | cctatcactg gatgggcctg | 300 |
| gtgcacatcc | ctacaaacgg | ctcttggcag | tgggaggacg | gctccatcct gtctccaaat | 360 |
| ctgctgacca | tcatcgagat | gcagaagggc | gattgcgccc | tgtacgccag ctcccttcaag | 420 |
| ggctatatcg | agaactgctc | cacacccaat | acctacatct | gtatgcagag gaccgtgacc | 480 |
| acaaccccctg | caccacgccc | cctacacca | gcacctacca | tcgcaagcca gcctctgtcc | 540 |
| ctgcggccag | aggcatgtag | accagcagca | ggaggagcag | tgcacacaag aggcctggac | 600 |
| ttcgcctgcg | atgtgagctt | tgtctggtc | atggtgctgc | tgttcgccgt ggataccggc | 660 |
| ctgtactttt | ccgtgaagac | aaatatcagg | tctagcaccc | gcgactggaa ggatcacaag | 720 |
| tttaagtggc | ggaaggaccc | tcaggataag | aagcggggca | gaaagaagct gctgtatatc | 780 |
| ttcaagcagc | ccttcatgcg | gcccgtgcag | acaacccagg | aggaagacgg ctgctcatgt | 840 |
| agatttcctg | aagaagaaga | aggggctgt | gaactgtgga | ggaggaaaag gaaggagaaa | 900 |
| cagagcgaga | cctccctaa | ggagttcctg | accatctacg | aggacgtgaa ggacctgaag | 960 |
| accaggagga | accacgagca | ggaacagacc | tttcctggcg | gaggcagcac catctacagc | 1020 |
| atgatccaga | gccagagcag | cgcccctacc | agccaagagc | ctgcctacac cctgtacagc | 1080 |
| ctgatccagc | ccagcaggaa | aagcggctcc | aggaagagga | accacagccc cagcttcaac | 1140 |
| agcaccatct | atgaggtgat | cggcaagagc | cagcccaagg | cccagaaccc tgccaggctg | 1200 |
| tccaggaagg | agctggagaa | cttcgacgtg | tacagctga | | 1239 |

<210> SEQ ID NO 54
<211> LENGTH: 1064
<212> TYPE: DNA
<213> ORGANISM: Homo sapiens
<220> FEATURE:

```
<221> NAME/KEY: misc_feature
<223> OTHER INFORMATION: NK15_12

<400> SEQUENCE: 54
ggatccgaat cgccgccac catggctctg cccgtcaccg cactgctgct gcctctggct      60
ctgctgctgc acgccgcacg accactgttc aatcaggaag tccagatccc cctgacagag     120
tcttactgcg gcccatgtcc caagaactgg atctgctaca gaacaattg ttatcagttc      180
tttgacgaga gcaagaactg gtatgagtcc caggcctctt gcatgagcca gaatgcctct     240
ctgctgaagg tgtacagcaa ggaggaccag gatctgctga agctggtgaa gtcctatcac     300
tggatgggcc tggtgcacat ccctacaaac ggctcttggc agtgggagga cggctccatc     360
ctgtctccaa atctgctgac catcatcgag atgcagaagg gcgattgcgc cctgtacgcc     420
agctccttca agggctatat cgagaactgc tccacaccca atacctacat ctgtatgcag     480
aggaccgtga ccacaacccc tgcaccacgc cccctacac cagcacctac catcgcaagc     540
cagcctctgt ccctgcggcc agaggcatgt agaccagcag caggaggagc agtgcacaca     600
agaggcctgg acttcgcctg cgatgtgagc ttttgtctgg tcatggtgct gctgttcgcc     660
gtggataccg gcctgtactt ttccgtgaag acaaatatca ggtctagcac ccgcgactgg     720
aaggatcaca gtttaagtg gcggaaggac cctcaggata agaagcgggg cagaaagaag     780
ctgctgtata tcttcaagca gcccttcatg cggcccgtgc agacaaccca ggaggaagac     840
ggctgctcat gtagatttcc tgaagaagaa gaaggggct gtgaactggg cggaggaggc      900
agcggcggcg gcggcagcgg cggcggcggc agcatgcagg atgaggacgg ctacatgacc     960
ctgaacgtgc agagcaagaa gaggagcagc gcccagacca gccagctgac cttcaaggac    1020
tacagcgtga ccctgcactg gtacaagtga gcggccgcgt cgac                     1064

<210> SEQ ID NO 55
<211> LENGTH: 8
<212> TYPE: PRT
<213> ORGANISM: Homo sapiens
<220> FEATURE:
<221> NAME/KEY: MISC_FEATURE
<223> OTHER INFORMATION: FLAG tag

<400> SEQUENCE: 55

Asp Tyr Lys Asp Asp Asp Asp Lys
1               5

<210> SEQ ID NO 56
<211> LENGTH: 6
<212> TYPE: PRT
<213> ORGANISM: Homo sapiens
<220> FEATURE:
<221> NAME/KEY: MISC_FEATURE
<223> OTHER INFORMATION: His tag

<400> SEQUENCE: 56

His His His His His His
1               5

<210> SEQ ID NO 57
<211> LENGTH: 10
<212> TYPE: PRT
<213> ORGANISM: Homo sapiens
<220> FEATURE:
<221> NAME/KEY: MISC_FEATURE
<223> OTHER INFORMATION: Myc tag

<400> SEQUENCE: 57
```

Glu Gln Lys Leu Ile Ser Glu Glu Asp Leu
1               5                   10

<210> SEQ ID NO 58
<211> LENGTH: 4
<212> TYPE: PRT
<213> ORGANISM: Homo sapiens
<220> FEATURE:
<221> NAME/KEY: MISC_FEATURE
<223> OTHER INFORMATION: Amino Acid NKG2C high affinity modification

<400> SEQUENCE: 58

Ser Ile Ile Ser
1

<210> SEQ ID NO 59
<211> LENGTH: 1137
<212> TYPE: DNA
<213> ORGANISM: Homo sapiens
<220> FEATURE:
<221> NAME/KEY: misc_feature
<223> OTHER INFORMATION: DNA Sequence Chimeric CD94-CD8a
      TM-4-1BB/CD3zeta

<400> SEQUENCE: 59

| | | | | | |
|---|---|---|---|---|---|
| atggccttac | cagtgaccgc | cttgctcctg | ccgctggcct | tgctgctcca | cgccgccagg | 60 |
| ccgccaggac | ccaacataga | actccagaaa | gactctgact | gctgttcttg | ccaagaaaaa | 120 |
| tgggttgggt | accggtgcaa | ctgttacttc | atttccagtg | aacagaaaac | ttggaacgaa | 180 |
| agtcggcatc | tctgtgcttc | tcagaaatcc | agcctgcttc | agcttcaaaa | cacagatgaa | 240 |
| ctggatttta | tgagctccag | tcaacaattt | tactggattg | gactctctta | cagtgaggag | 300 |
| cacaccgcct | ggttgtggga | gaatggctct | gcactctccc | agtatctatt | tccatcattt | 360 |
| gaaactttta | atacaaagaa | ctgcatagcg | tataatccaa | atggaaatgc | tttagatgaa | 420 |
| tcctgtgaag | ataaaaatcg | ttatatctgt | aagcaacagc | tcattaccac | gacgccagcg | 480 |
| ccgcgaccac | caacaccggc | gcccaccatc | gcgtcgcagc | ccctgtccct | gcgcccagag | 540 |
| gcgtgccggc | cagcggcggg | gggcgcagtg | cacacgaggg | gctggacttc | gcctgtgat | 600 |
| atctacatct | gggcgccctt | ggccgggact | tgtgggggtcc | ttctcctgtc | actggttatc | 660 |
| accctttact | gcaaacgggg | cagaaagaaa | ctcctgtata | tattcaaaca | accatttatg | 720 |
| agaccagtac | aaactactca | agaggaagat | ggctgtagct | gccgatttcc | agaagaagaa | 780 |
| gaaggaggat | gtgaactgag | agtgaagttc | agcaggagcg | cagacgcccc | cgcgtaccag | 840 |
| cagggccaga | accagctcta | taacgagctc | aatctaggac | gaagagagga | gtacgatgtt | 900 |
| ttggacaaga | gacgtggccg | ggaccctgag | atggggggaa | agccgagaag | gaagaaccct | 960 |
| caggaaggcc | tgtacaatga | actgcagaaa | gataagatgg | cggaggccta | cagtgagatt | 1020 |
| gggatgaaag | gcgagcgccg | gaggggcaag | gggcacgatg | cctttacca | gggtctcagt | 1080 |
| acagccacca | aggacaccta | cgacgccctt | cacatgcagg | ccctgccccc | tcgctaa | 1137 |

<210> SEQ ID NO 60
<211> LENGTH: 378
<212> TYPE: PRT
<213> ORGANISM: Homo sapiens
<220> FEATURE:
<221> NAME/KEY: MISC_FEATURE
<223> OTHER INFORMATION: Amino Acid Sequence Chimeric CD94-CD8a
      TM-4-1BB/CD3zeta

<400> SEQUENCE: 60

-continued

```
Met Ala Leu Pro Val Thr Ala Leu Leu Leu Pro Leu Ala Leu Leu Leu
 1               5                  10                  15

His Ala Ala Arg Pro Pro Gly Pro Asn Ile Glu Leu Gln Lys Asp Ser
            20                  25                  30

Asp Cys Cys Ser Cys Gln Glu Lys Trp Val Gly Tyr Arg Cys Asn Cys
        35                  40                  45

Tyr Phe Ile Ser Ser Glu Gln Lys Thr Trp Asn Glu Ser Arg His Leu
    50                  55                  60

Cys Ala Ser Gln Lys Ser Ser Leu Leu Gln Leu Gln Asn Thr Asp Glu
 65                  70                  75                  80

Leu Asp Phe Met Ser Ser Gln Gln Phe Tyr Trp Ile Gly Leu Ser
                85                  90                  95

Tyr Ser Glu Glu His Thr Ala Trp Leu Trp Glu Asn Gly Ser Ala Leu
            100                 105                 110

Ser Gln Tyr Leu Phe Pro Ser Phe Glu Thr Phe Asn Thr Lys Asn Cys
        115                 120                 125

Ile Ala Tyr Asn Pro Asn Gly Asn Ala Leu Asp Glu Ser Cys Glu Asp
    130                 135                 140

Lys Asn Arg Tyr Ile Cys Lys Gln Gln Leu Ile Thr Thr Thr Pro Ala
145                 150                 155                 160

Pro Arg Pro Pro Thr Pro Ala Pro Thr Ile Ala Ser Gln Pro Leu Ser
                165                 170                 175

Leu Arg Pro Glu Ala Cys Arg Pro Ala Ala Gly Gly Ala Val His Thr
            180                 185                 190

Arg Gly Leu Asp Phe Ala Cys Asp Ile Tyr Ile Trp Ala Pro Leu Ala
        195                 200                 205

Gly Thr Cys Gly Val Leu Leu Leu Ser Leu Val Ile Thr Leu Tyr Cys
    210                 215                 220

Lys Arg Gly Arg Lys Lys Leu Leu Tyr Ile Phe Lys Gln Pro Phe Met
225                 230                 235                 240

Arg Pro Val Gln Thr Thr Gln Glu Glu Asp Gly Cys Ser Cys Arg Phe
                245                 250                 255

Pro Glu Glu Glu Glu Gly Gly Cys Glu Leu Arg Val Lys Phe Ser Arg
            260                 265                 270

Ser Ala Asp Ala Pro Ala Tyr Gln Gln Gly Gln Asn Gln Leu Tyr Asn
        275                 280                 285

Glu Leu Asn Leu Gly Arg Arg Glu Glu Tyr Asp Val Leu Asp Lys Arg
    290                 295                 300

Arg Gly Arg Asp Pro Glu Met Gly Gly Lys Pro Arg Arg Lys Asn Pro
305                 310                 315                 320

Gln Glu Gly Leu Tyr Asn Glu Leu Gln Lys Asp Lys Met Ala Glu Ala
                325                 330                 335

Tyr Ser Glu Ile Gly Met Lys Gly Glu Arg Arg Arg Gly Lys Gly His
            340                 345                 350

Asp Gly Leu Tyr Gln Gly Leu Ser Thr Ala Thr Lys Asp Thr Tyr Asp
        355                 360                 365

Ala Leu His Met Gln Ala Leu Pro Pro Arg
    370                 375

<210> SEQ ID NO 61
<211> LENGTH: 1119
<212> TYPE: DNA
<213> ORGANISM: Homo sapiens
<220> FEATURE:
```

```
<221> NAME/KEY: misc_feature
<223> OTHER INFORMATION: DNA Sequence chimeric NKG2A Receptor - CD8a
      TM-4-1BB/CD3zeta

<400> SEQUENCE: 61
atggccttac cagtgaccgc cttgctcctg ccgctggcct tgctgctcca cgccgccagg     60
ccgctgaata caagaactca gaaagcacgt cattgtggcc attgtcctga ggagtggatt    120
acatattcca acagttgtta ctacattggt aaggaaagaa gaacttggga agagagtttg    180
ctggcctgta cttcgaagaa ctccagtctg ctttctatag ataatgaaga agaaatgaaa    240
tttctgtcca tcatttcacc atcctcatgg attggtgtgt tcgtaacag cagtcatcat    300 ccatgggtga caatgaatgg tttggctttc aaacatgaga taaaagactc agataatgct    360
gaacttaact gtgcagtgct acaagtaaat cgacttaaat cagcccagtg tggatcttca    420
ataatatatc attgtaagca taagcttacc acgacgccag cgccgcgacc accaacaccg    480
gcgcccacca tcgcgtcgca gccctgtcc ctgcgcccag aggcgtgccg gccagcggcg    540
gggggcgcag tgcacacgag ggggctggac ttcgcctgtg atatctacat ctgggcgccc    600
ttggccggga cttgtggggt ccttctcctg tcactggtta tcacccttta ctgcaaacgg    660
ggcagaaaga aactcctgta tatattcaaa caaccatta tgagaccagt acaaactact    720
caagaggaag atggctgtag ctgccgattt ccagaagaag aagaaggag atgtgaactg    780 agagtgaagt tcagcaggag cgcagacgcc ccgcgtacc agcagggcca gaaccagctc    840
tataacgagc tcaatctagg acgaagagag gagtacgatg ttttggacaa gagacgtggc    900
cgggaccctg atgggggg aaagccgaga aggaagaacc tcaggaagg cctgtacaat    960 gaactgcaga aagataagat ggcggaggcc tacagtgaga ttgggatgaa aggcgagcgc   1020
cggaggggca aggggcacga tggcctttac cagggtctca gtacagccac caaggacacc   1080
tacgacgccc ttcacatgca ggccctgccc cctcgctaa                          1119

<210> SEQ ID NO 62
<211> LENGTH: 372
<212> TYPE: PRT
<213> ORGANISM: Homo sapiens
<220> FEATURE:
<221> NAME/KEY: MISC_FEATURE
<223> OTHER INFORMATION: Amino Acid Sequence chimeric NKG2A Receptor -
      CD8a TM-4-1BB/CD3zeta

<400> SEQUENCE: 62

Met Ala Leu Pro Val Thr Ala Leu Leu Leu Pro Leu Ala Leu Leu Leu
1               5                   10                  15

His Ala Ala Arg Pro Leu Asn Thr Arg Thr Gln Lys Ala Arg His Cys
            20                  25                  30

Gly His Cys Pro Glu Glu Trp Ile Thr Tyr Ser Asn Ser Cys Tyr Tyr
        35                  40                  45

Ile Gly Lys Glu Arg Arg Thr Trp Glu Glu Ser Leu Leu Ala Cys Thr
    50                  55                  60

Ser Lys Asn Ser Ser Leu Leu Ser Ile Asp Asn Glu Glu Glu Met Lys
65                  70                  75                  80

Phe Leu Ser Ile Ile Ser Pro Ser Ser Trp Ile Gly Val Phe Arg Asn
                85                  90                  95

Ser Ser His His Pro Trp Val Thr Met Asn Gly Leu Ala Phe Lys His
            100                 105                 110

Glu Ile Lys Asp Ser Asp Asn Ala Glu Leu Asn Cys Ala Val Leu Gln
        115                 120                 125
```

Val Asn Arg Leu Lys Ser Ala Gln Cys Gly Ser Ser Ile Ile Tyr His
            130                 135                 140
Cys Lys His Lys Leu Thr Thr Thr Pro Ala Pro Arg Pro Pro Thr Pro
145                 150                 155                 160
Ala Pro Thr Ile Ala Ser Gln Pro Leu Ser Leu Arg Pro Glu Ala Cys
                165                 170                 175
Arg Pro Ala Ala Gly Gly Ala Val His Thr Arg Gly Leu Asp Phe Ala
            180                 185                 190
Cys Asp Ile Tyr Ile Trp Ala Pro Leu Ala Gly Thr Cys Gly Val Leu
        195                 200                 205
Leu Leu Ser Leu Val Ile Thr Leu Tyr Cys Lys Arg Gly Arg Lys Lys
    210                 215                 220
Leu Leu Tyr Ile Phe Lys Gln Pro Phe Met Arg Pro Val Gln Thr Thr
225                 230                 235                 240
Gln Glu Glu Asp Gly Cys Ser Cys Arg Phe Pro Glu Glu Glu Glu Gly
                245                 250                 255
Gly Cys Glu Leu Arg Val Lys Phe Ser Arg Ser Ala Asp Ala Pro Ala
            260                 265                 270
Tyr Gln Gln Gly Gln Asn Gln Leu Tyr Asn Glu Leu Asn Leu Gly Arg
        275                 280                 285
Arg Glu Glu Tyr Asp Val Leu Asp Lys Arg Arg Gly Arg Asp Pro Glu
    290                 295                 300
Met Gly Gly Lys Pro Arg Arg Lys Asn Pro Gln Glu Gly Leu Tyr Asn
305                 310                 315                 320
Glu Leu Gln Lys Asp Lys Met Ala Glu Ala Tyr Ser Glu Ile Gly Met
                325                 330                 335
Lys Gly Glu Arg Arg Arg Gly Lys Gly His Asp Gly Leu Tyr Gln Gly
            340                 345                 350
Leu Ser Thr Ala Thr Lys Asp Thr Tyr Asp Ala Leu His Met Gln Ala
        355                 360                 365
Leu Pro Pro Arg
    370

<210> SEQ ID NO 63
<211> LENGTH: 690
<212> TYPE: DNA
<213> ORGANISM: Homo sapiens
<220> FEATURE:
<221> NAME/KEY: misc_feature
<223> OTHER INFORMATION: DNA Sequence Engineered NKG2C

<400> SEQUENCE: 63
aataaacaaa gaggaacctt ctcagaagtg agtctggccc aggacccaaa gcggcagcaa      60
aggaaaccta aaggcaataa aagctccatt tcaggaaccg aacaggaaat attccaagta     120
gaattaaatc ttcaaaatcc ttccctgaat catcaaggga ttgataaaat atatgactgc     180
caaggtttac tgccacctcc agagaagctc actgccgagg tcctaggaat catttgcatt     240
gtcctgatgg ccactgtgtt aaaaacaata gttcttattc ctttcctgga gcagaacaat     300
ttttccccga atacaagaac gcagaaagca cgtcattgtg gccattgtcc tgaggagtgg     360
attacatatt ccaacagttg ttattacatt ggtaaggaaa gaagaacttg ggaagagagt     420
ttgctggcct gtacttcgaa gaactccagt ctgctttcta tagataatga agaagaaatg     480
aaatttctgt ccatcatttc accttcctca tggattggtg tgtttcgtaa cagcagtcat     540
catccatggg tgacaataaa tggtttggct ttcaaacata agataaaaga ctcagataat     600

```
gctgaactta actgtgcagt gctacaagta aatcgactta aatcagccca gtgtggatct    660
tcaatgatat atcattgtaa gcataagctt                                    690
```

<210> SEQ ID NO 64
<211> LENGTH: 231
<212> TYPE: PRT
<213> ORGANISM: Homo sapiens
<220> FEATURE:
<221> NAME/KEY: MISC_FEATURE
<223> OTHER INFORMATION: Amino acid sequence engineered NKG2C
<400> SEQUENCE: 64

```
Met Asn Lys Gln Arg Gly Thr Phe Ser Glu Val Ser Leu Ala Gln Asp
1               5                   10                  15

Pro Lys Arg Gln Gln Arg Lys Pro Lys Gly Asn Lys Ser Ser Ile Ser
            20                  25                  30

Gly Thr Glu Gln Glu Ile Phe Gln Val Glu Leu Asn Leu Gln Asn Pro
        35                  40                  45

Ser Leu Asn His Gln Gly Ile Asp Lys Ile Tyr Asp Cys Gln Gly Leu
    50                  55                  60

Leu Pro Pro Pro Glu Lys Leu Thr Ala Glu Val Leu Gly Ile Ile Cys
65                  70                  75                  80

Ile Val Leu Met Ala Thr Val Leu Lys Thr Ile Val Leu Ile Pro Phe
                85                  90                  95

Leu Glu Gln Asn Asn Phe Ser Pro Asn Thr Arg Thr Gln Lys Ala Arg
            100                 105                 110

His Cys Gly His Cys Pro Glu Glu Trp Ile Thr Tyr Ser Asn Ser Cys
        115                 120                 125

Tyr Tyr Ile Gly Lys Glu Arg Arg Thr Trp Glu Glu Ser Leu Leu Ala
    130                 135                 140

Cys Thr Ser Lys Asn Ser Ser Leu Leu Ser Ile Asp Asn Glu Glu Glu
145                 150                 155                 160

Met Lys Phe Leu Ser Ile Ile Ser Pro Ser Ser Trp Ile Gly Val Phe
                165                 170                 175

Arg Asn Ser Ser His His Pro Trp Val Thr Ile Asn Gly Leu Ala Phe
            180                 185                 190

Lys His Lys Ile Lys Asp Ser Asp Asn Ala Glu Leu Asn Cys Ala Val
        195                 200                 205

Leu Gln Val Asn Arg Leu Lys Ser Ala Gln Cys Gly Ser Ser Met Ile
    210                 215                 220

Tyr His Cys Lys His Lys Leu
225                 230
```

<210> SEQ ID NO 65
<211> LENGTH: 384
<212> TYPE: DNA
<213> ORGANISM: Homo sapiens
<220> FEATURE:
<221> NAME/KEY: misc_feature
<223> OTHER INFORMATION: DNA sequence NKG2A fragment
<400> SEQUENCE: 65

```
ctgaatacaa gaactcagaa agcacgtcat tgtggccatt gtcctgagga gtggattaca     60
tattccaaca gttgttacta cattggtaag gaaagaagaa cttgggaaga gagtttgctg    120
gcctgtactt cgaagaactc cagtctgctt tctatagata atgaagaaga aatgaaattt    180
ctgtccatca tttcaccatc ctcatggatt ggtgtgtttc gtaacagcag tcatcatcca    240
```
tgggtgacaa tgaatggttt ggctttcaaa catgagataa aagactcaga taatgctgaa    300
cttaactgtg cagtgctaca agtaaatcga cttaaatcag cccagtgtgg atcttcaata    360
atatatcatt gtaagcataa gctt    384

<210> SEQ ID NO 66
<211> LENGTH: 128
<212> TYPE: PRT
<213> ORGANISM: Homo sapiens
<220> FEATURE:
<221> NAME/KEY: MISC_FEATURE
<223> OTHER INFORMATION: Amino Acid sequence NKG2A fragment

<400> SEQUENCE: 66

Leu Asn Thr Arg Thr Gln Lys Ala Arg His Cys Gly His Cys Pro Glu
1               5                   10                  15

Glu Trp Ile Thr Tyr Ser Asn Ser Cys Tyr Tyr Ile Gly Lys Glu Arg
            20                  25                  30

Arg Thr Trp Glu Glu Ser Leu Leu Ala Cys Thr Ser Lys Asn Ser Ser
        35                  40                  45

Leu Leu Ser Ile Asp Asn Glu Glu Glu Met Lys Phe Leu Ser Ile Ile
    50                  55                  60

Ser Pro Ser Ser Trp Ile Gly Val Phe Arg Asn Ser Ser His His Pro
65                  70                  75                  80

Trp Val Thr Met Asn Gly Leu Ala Phe Lys His Glu Ile Lys Asp Ser
                85                  90                  95

Asp Asn Ala Glu Leu Asn Cys Ala Val Leu Gln Val Asn Arg Leu Lys
            100                 105                 110

Ser Ala Gln Cys Gly Ser Ser Ile Ile Tyr His Cys Lys His Lys Leu
        115                 120                 125

<210> SEQ ID NO 67
<211> LENGTH: 402
<212> TYPE: DNA
<213> ORGANISM: Homo sapiens
<220> FEATURE:
<221> NAME/KEY: misc_feature
<223> OTHER INFORMATION: DNA sequence CD94 fragment

<400> SEQUENCE: 67
ccaggaccca acatagaact ccagaaagac tctgactgct gttcttgcca agaaaaatgg     60
gttgggtacc ggtgcaactg ttacttcatt tccagtgaac agaaaacttg gaacgaaagt    120
cggcatctct gtgcttctca gaaatccagc ctgcttcagc ttcaaaacac agatgaactg    180
gattttatga gctccagtca acaatttttac tggattggac tctcttacag tgaggagcac    240
accgcctggt gtgggagaa tggctctgca ctctcccagt atctatttcc atcatttgaa    300
acttttaata caaagaactg catagcgtat aatccaaatg gaaatgcttt agatgaatcc    360
tgtgaagata aaaatcgtta tatctgtaag caacagctca tt                      402

<210> SEQ ID NO 68
<211> LENGTH: 134
<212> TYPE: PRT
<213> ORGANISM: Homo sapiens
<220> FEATURE:
<221> NAME/KEY: MISC_FEATURE
<223> OTHER INFORMATION: Amino acid sequence CD94 fragment

<400> SEQUENCE: 68

Pro Gly Pro Asn Ile Glu Leu Gln Lys Asp Ser Asp Cys Cys Ser Cys

```
1               5                   10                  15
Gln Glu Lys Trp Val Gly Tyr Arg Cys Asn Cys Tyr Phe Ile Ser Ser
            20                  25                  30

Glu Gln Lys Thr Trp Asn Glu Ser Arg His Leu Cys Ala Ser Gln Lys
            35              40                  45

Ser Ser Leu Leu Gln Leu Gln Asn Thr Asp Glu Leu Asp Phe Met Ser
        50              55                  60

Ser Ser Gln Gln Phe Tyr Trp Ile Gly Leu Ser Tyr Ser Glu Glu His
65              70                  75                  80

Thr Ala Trp Leu Trp Glu Asn Gly Ser Ala Leu Ser Gln Tyr Leu Phe
            85                  90                  95

Pro Ser Phe Glu Thr Phe Asn Thr Lys Asn Cys Ile Ala Tyr Asn Pro
            100                 105                 110

Asn Gly Asn Ala Leu Asp Glu Ser Cys Glu Asp Lys Asn Arg Tyr Ile
            115                 120                 125

Cys Lys Gln Gln Leu Ile
            130

<210> SEQ ID NO 69
<211> LENGTH: 21
<212> TYPE: PRT
<213> ORGANISM: Homo sapiens
<220> FEATURE:
<221> NAME/KEY: MISC_FEATURE
<223> OTHER INFORMATION: HLA-E Signal Peptide

<400> SEQUENCE: 69

Met Val Asp Gly Thr Leu Leu Leu Leu Ser Glu Ala Leu Ala Leu
1               5                   10                  15

Thr Gln Thr Trp Ala
            20

<210> SEQ ID NO 70
<211> LENGTH: 24
<212> TYPE: PRT
<213> ORGANISM: Homo sapiens
<220> FEATURE:
<221> NAME/KEY: MISC_FEATURE
<223> OTHER INFORMATION: HLA-G Signal Peptide

<400> SEQUENCE: 70

Met Val Val Met Ala Pro Arg Thr Leu Phe Leu Leu Leu Ser Gly Ala
1               5                   10                  15

Leu Thr Leu Thr Glu Thr Trp Ala
            20
```